United States Patent
Masignani et al.

(10) Patent No.: US 7,618,636 B1
(45) Date of Patent: Nov. 17, 2009

(54) ANTIGENIC MENINGOCOCCAL PEPTIDES

(75) Inventors: Vega Masignani, Siena (IT); Vincenzo Scarlato, Colle di Val d'Elsa (IT); Maria Scarselli, Siena (IT); Cesira L. Galeotti, Poggibonsi (IT); Marirosa Mora, Siena (IT)

(73) Assignee: Novartis Vaccines And Diagnostics SRL, Siena (IT)

( * ) Notice: Subject to any disclaimer, the term of this patent is extended or adjusted under 35 U.S.C. 154(b) by 0 days.

(21) Appl. No.: 10/031,289

(22) PCT Filed: Jul. 13, 2000

(86) PCT No.: PCT/IB00/01026

§ 371 (c)(1),
(2), (4) Date: May 31, 2002

(87) PCT Pub. No.: WO01/04316

PCT Pub. Date: Jan. 18, 2001

(30) Foreign Application Priority Data

Jul. 14, 1999 (GB) .................................. 9916529.2

(51) Int. Cl.
*A61K 39/02* (2006.01)
*A61K 39/00* (2006.01)
*A61K 39/095* (2006.01)
*A61K 38/00* (2006.01)
*C07K 2/00* (2006.01)
*C07K 14/00* (2006.01)
*C07K 16/00* (2006.01)

(52) U.S. Cl. .............. 424/190.1; 424/234.1; 424/249.1; 424/185.1; 424/250.1; 514/2; 530/300; 530/350; 530/825; 530/328

(58) Field of Classification Search ................ 530/300, 530/350, 825, 326, 328; 514/2; 424/234.1, 424/185.1, 190.1, 250.1, 249.1
See application file for complete search history.

(56) References Cited

U.S. PATENT DOCUMENTS 7,029,845 B2   4/2006   Nassif et al. .................... 435/6

FOREIGN PATENT DOCUMENTS

| WO | WO 90/06696 A2 | 6/1990 |
| WO | WO-98/02547 A2 | 1/1998 |
| WO | WO 99/36544 A2 | 7/1999 |

OTHER PUBLICATIONS

Relf et al. J. Clin. Microbiol. 30: 3190-3194, 1992.*
Burgess et al. J. Cell Biol. 111: 2129-2138, 1990.*
Bowie et al. Science 247: 1306-1310, 1990.*
Lazar et al. Mol. Cellualr Biol. 8: 1247-1252, 1988.*
McGuinnes et al. Mol. Microbiol. 7 (4): 505-514, 1993.*
McGuinnes et al. Lancet 337: 514-517, 1991.*
Rudinger et al. In: Peptide Hormones. (Ed) JA Parsons, University Park Press, Jun. 1976.*
Houghten et al. Vaccines86. Cold Spring Harbor Laboratory, pp. 21-25, 1986.*
Glick DM. Glossary of Biochemistry and Molecular Biology. Revised Edition, Portland Press, London, p. 75, 1997.*
Cruse et al. Illustrated Dictionary of Immunology. p. 18, 1997.*
Herbert et al. The Dictionary of Immunology, Academic Press, 3rd Edition, London, pp. 58 and 59, 1985.*
Malorny et al. J. Bacteriol. 180: 1323-1330, 1998.*
Gomez et al. Vaccine 14: 1340-1346, 1996, abstract.*
Teerlink et al. J. Exp. Med. 166: 63-76, 1987, abstract.*
Forest et al. Gene 192: 165-169, 1997, abstract.*
Ala'Aldeen et al. Vaccine 12: 535-541, 1994.*
Cruse et al. Illustrated Dictionary of Immunology, 2nd Edn., CRC Press, 2003.*
McGuiness et al. Mol. Microbiol. 7:505-514, Feb. 1993.*
Ala'Aldeen et al. (1996) "The meningococcal transferrin-binding proteins 1 and 2 are both surface exposed and generate bactericidal antibodies capable of killing homologous and heterologous strains," *Vaccine*, 14(1):49-53.
Biegel Carson et al. (1999) "Ferric enterobactin binding and utilization by *Neisseria gonorrhoeae*", *Journal of Bacteriology*, 181(9): 2895-2901.
Christodoulides et al. (1994) "Immunization with a multiple antigen peptide containing defined B- and T-cell epitopes: production of bacterial antibodies against group B *Neisseria meningitidis*", *Microbiology*, 140(11): 2951-2960.
Delvig et al. (1996) "Immune responses to linear epitopes on the porB protein of *Neisseria meningitidis* in patients with systemic meningococcal disease", *Microbiology*, 142(9): 2491-2498.
Poolman et al. (1995) "Development of a Meningococcal Vaccine," *Infect. Agents and Dis.*, 4: 13-28.
Rokbi et al. (1995) "Variable sequences in a mosaic-like domain of meningococcal tbp2 encode immunoreactive epitopes", *FEMS Microbiology Letters*, 132: 277-283.
Tinsley et al. (Oct. 1996). "Analysis of the genetic differences between *Neisseria meningitidis* and *Neisseria gonorrhoeae*: Two closely related bacteria expressing two different pathogenicities," *Proccedings of the National Academy of Science, USA*, 93(20):11109-11114.
EMBL Accession No. U56741, last updated Oct. 22, 1996, located at <http://www.ebi.ac.uk/cgi-bin/dbfetch?db=embl&id=U56741&style=raw> visted on Aug. 15, 2008. 2 pages.
European Examination Report mailed Mar. 16, 2004, for EP Application No. 00944161.9 filed Jan. 29, 2002, 9 pages.
European Examination Report mailed Apr. 5, 2005, for EP Application No. 00944161.9 filed Jan. 29, 2002, 9 pages.

* cited by examiner

*Primary Examiner*—S. Devi
(74) *Attorney, Agent, or Firm*—Amy Hessler; Helen Lee; Robert Corman

(57) ABSTRACT

WO99/36544 discloses a large number of proteins from *Neisseria Meningitidis*. The present invention relates to fragments of those proteins which comprise at least one antigenic determinant. Homologous sequences and proteins comprising these fragments are also disclosed.

8 Claims, No Drawings

SEQUENCE LISTING

<160> NUMBER OF SEQ ID NOS: 1859

<210> SEQ ID NO 1
<211> LENGTH: 9
<212> TYPE: PRT
<213> ORGANISM: Neisseria meningitidis

<400> SEQUENCE: 1

Ala Leu Ala Val Cys Thr Ala Leu Ala
1               5

```
<210> SEQ ID NO 2

<400> SEQUENCE: 2

000

<210> SEQ ID NO 3
<211> LENGTH: 10
<212> TYPE: PRT
<213> ORGANISM: Neisseria meningitidis

<400> SEQUENCE: 3

Leu Gly Met Leu Asp Thr Leu Ser Lys Leu
1               5                   10

<210> SEQ ID NO 4
<211> LENGTH: 9
<212> TYPE: PRT
<213> ORGANISM: Neisseria meningitidis

<400> SEQUENCE: 4

Leu Glu Glu Tyr Phe Lys Thr Thr Lys
1               5

<210> SEQ ID NO 5
<211> LENGTH: 11
<212> TYPE: PRT
<213> ORGANISM: Neisseria meningitidis

<400> SEQUENCE: 5

Ala Ala Lys Ala Phe Asp Lys Leu Asn Glu Ile
1               5                   10

<210> SEQ ID NO 6
<211> LENGTH: 18
<212> TYPE: PRT
<213> ORGANISM: Neisseria meningitidis

<400> SEQUENCE: 6

Asn Leu Lys Glu Ser Ala Lys Glu Arg Ile Asp Ala Leu Ala Gln Ile
1               5                   10                  15

Phe Gly

<210> SEQ ID NO 7
<211> LENGTH: 6
<212> TYPE: PRT
<213> ORGANISM: Neisseria meningitidis

<400> SEQUENCE: 7

Pro Ser Ser Arg Leu Gly
1               5

<210> SEQ ID NO 8
<211> LENGTH: 6
<212> TYPE: PRT
<213> ORGANISM: Neisseria meningitidis

<400> SEQUENCE: 8

Ile Lys Glu Gly Ser His
1               5
```

```
<210> SEQ ID NO 9

<400> SEQUENCE: 9

000

<210> SEQ ID NO 10
<211> LENGTH: 18
<212> TYPE: PRT
<213> ORGANISM: Neisseria meningitidis

<400> SEQUENCE: 10

Ala Gln Glu Leu Leu Asn Ala Ser Lys Gln Val Ala Asp Ala Phe Asn
1               5                   10                  15

Ala Ala

<210> SEQ ID NO 11
<211> LENGTH: 19
<212> TYPE: PRT
<213> ORGANISM: Neisseria meningitidis

<400> SEQUENCE: 11

Gly Ala Cys Ser Pro Gln Asn Ser Asp Ser Ala Pro Gln Ala Lys Glu
1               5                   10                  15

Gln Ala Val

<210> SEQ ID NO 12
<211> LENGTH: 6
<212> TYPE: PRT
<213> ORGANISM: Neisseria meningitidis

<400> SEQUENCE: 12

Ala Gln Thr Glu Gly Ala
1               5

<210> SEQ ID NO 13
<211> LENGTH: 19
<212> TYPE: PRT
<213> ORGANISM: Neisseria meningitidis

<400> SEQUENCE: 13

Val Lys Thr Ala Arg Gly Asp Val Gln Ile Pro Gln Asn Pro Glu Arg
1               5                   10                  15

Ile Ala Val

<210> SEQ ID NO 14
<211> LENGTH: 20
<212> TYPE: PRT
<213> ORGANISM: Neisseria meningitidis

<400> SEQUENCE: 14

Thr Leu Ser Lys Leu Gly Val Lys Thr Gly Leu Ser Val Asp Lys Asn
1               5                   10                  15

Arg Leu Pro Tyr
            20

<210> SEQ ID NO 15
<211> LENGTH: 19
<212> TYPE: PRT
<213> ORGANISM: Neisseria meningitidis
```

-continued

```
<400> SEQUENCE: 15

Glu Tyr Phe Lys Thr Thr Lys Pro Ala Gly Thr Leu Phe Glu Pro Asp
1               5                   10                  15

Tyr Glu Thr

<210> SEQ ID NO 16
<211> LENGTH: 4
<212> TYPE: PRT
<213> ORGANISM: Neisseria meningitidis

<400> SEQUENCE: 16

Asn Ala Tyr Lys
1

<210> SEQ ID NO 17
<211> LENGTH: 13
<212> TYPE: PRT
<213> ORGANISM: Neisseria meningitidis

<400> SEQUENCE: 17

Gly Ser Arg Ala Ala Lys Ala Phe Asp Lys Leu Asn Glu
1               5                   10

<210> SEQ ID NO 18
<211> LENGTH: 4
<212> TYPE: PRT
<213> ORGANISM: Neisseria meningitidis

<400> SEQUENCE: 18

Met Thr Ala Asp
1

<210> SEQ ID NO 19
<211> LENGTH: 13
<212> TYPE: PRT
<213> ORGANISM: Neisseria meningitidis

<400> SEQUENCE: 19

Ala Asn Leu Lys Glu Ser Ala Lys Glu Arg Ile Asp Ala
1               5                   10

<210> SEQ ID NO 20
<211> LENGTH: 29
<212> TYPE: PRT
<213> ORGANISM: Neisseria meningitidis

<400> SEQUENCE: 20

Lys Gln Ala Glu Ala Asp Lys Leu Lys Ala Glu Ile Asp Ala Ser Phe
1               5                   10                  15

Glu Ala Ala Lys Thr Ala Ala Gln Gly Lys Gly Lys Gly
            20                  25

<210> SEQ ID NO 21
<211> LENGTH: 16
<212> TYPE: PRT
<213> ORGANISM: Neisseria meningitidis

<400> SEQUENCE: 21

Asn Gly Gly Lys Met Ser Ala Phe Gly Pro Ser Ser Arg Leu Gly Gly
1               5                   10                  15
```

<210> SEQ ID NO 22
<211> LENGTH: 23
<212> TYPE: PRT
<213> ORGANISM: Neisseria meningitidis

<400> SEQUENCE: 22

Leu His Lys Asp Ile Gly Val Pro Ala Val Asp Glu Ser Ile Lys Glu
1               5                   10                  15

Gly Ser His Gly Gln Pro Ile
            20

<210> SEQ ID NO 23
<211> LENGTH: 9
<212> TYPE: PRT
<213> ORGANISM: Neisseria meningitidis

<400> SEQUENCE: 23

Tyr Leu Lys Glu Lys Asn Pro Asp Trp
1               5

<210> SEQ ID NO 24
<211> LENGTH: 22
<212> TYPE: PRT
<213> ORGANISM: Neisseria meningitidis

<400> SEQUENCE: 24

Asp Arg Ser Ala Ala Ile Gly Glu Glu Gly Gln Ala Ala Lys Asp Val
1               5                   10                  15

Leu Asp Asn Pro Leu Val
            20

<210> SEQ ID NO 25
<211> LENGTH: 9
<212> TYPE: PRT
<213> ORGANISM: Neisseria meningitidis

<400> SEQUENCE: 25

Thr Ala Trp Lys Lys Gly Gln Val Val
1               5

<210> SEQ ID NO 26
<211> LENGTH: 7
<212> TYPE: PRT
<213> ORGANISM: Neisseria meningitidis

<400> SEQUENCE: 26

Asn Ala Ser Lys Gln Val Ala
1               5

<210> SEQ ID NO 27
<211> LENGTH: 14
<212> TYPE: PRT
<213> ORGANISM: Neisseria meningitidis

<400> SEQUENCE: 27

Gln Asn Ser Asp Ser Ala Pro Gln Ala Lys Glu Gln Ala Val
1               5                   10

<210> SEQ ID NO 28
<211> LENGTH: 6
<212> TYPE: PRT
<213> ORGANISM: Neisseria meningitidis

```
<400> SEQUENCE: 28

Ala Gln Thr Glu Gly Ala
1               5

<210> SEQ ID NO 29
<211> LENGTH: 9
<212> TYPE: PRT
<213> ORGANISM: Neisseria meningitidis

<400> SEQUENCE: 29

Lys Thr Ala Arg Gly Asp Val Gln Ile
1               5

<210> SEQ ID NO 30
<211> LENGTH: 5
<212> TYPE: PRT
<213> ORGANISM: Neisseria meningitidis

<400> SEQUENCE: 30

Gln Asn Pro Glu Arg
1               5

<210> SEQ ID NO 31

<400> SEQUENCE: 31

000

<210> SEQ ID NO 32

<400> SEQUENCE: 32

000

<210> SEQ ID NO 33
<211> LENGTH: 10
<212> TYPE: PRT
<213> ORGANISM: Neisseria meningitidis

<400> SEQUENCE: 33

Leu Ser Val Asp Lys Asn Arg Leu Pro Tyr
1               5                   10

<210> SEQ ID NO 34
<211> LENGTH: 8
<212> TYPE: PRT
<213> ORGANISM: Neisseria meningitidis

<400> SEQUENCE: 34

Glu Tyr Phe Lys Thr Thr Lys Pro
1               5

<210> SEQ ID NO 35
<211> LENGTH: 5
<212> TYPE: PRT
<213> ORGANISM: Neisseria meningitidis

<400> SEQUENCE: 35

Pro Asp Tyr Glu Thr
1               5

<210> SEQ ID NO 36
<211> LENGTH: 11
<212> TYPE: PRT
<213> ORGANISM: Neisseria meningitidis
```

```
<400> SEQUENCE: 36

Arg Ala Ala Lys Ala Phe Asp Lys Leu Asn Glu
1               5                   10

<210> SEQ ID NO 37
<211> LENGTH: 4
<212> TYPE: PRT
<213> ORGANISM: Neisseria meningitidis

<400> SEQUENCE: 37

Met Thr Ala Asp
1

<210> SEQ ID NO 38
<211> LENGTH: 13
<212> TYPE: PRT
<213> ORGANISM: Neisseria meningitidis

<400> SEQUENCE: 38

Ala Asn Leu Lys Glu Ser Ala Lys Glu Arg Ile Asp Ala
1               5                   10

<210> SEQ ID NO 39
<211> LENGTH: 29
<212> TYPE: PRT
<213> ORGANISM: Neisseria meningitidis

<400> SEQUENCE: 39

Lys Gln Ala Glu Ala Asp Lys Leu Lys Ala Glu Ile Asp Ala Ser Phe
1               5                   10                  15

Glu Ala Ala Lys Thr Ala Ala Gln Gly Lys Gly Lys Gly
            20                  25

<210> SEQ ID NO 40

<400> SEQUENCE: 40

000

<210> SEQ ID NO 41
<211> LENGTH: 11
<212> TYPE: PRT
<213> ORGANISM: Neisseria meningitidis

<400> SEQUENCE: 41

Ala Val Asp Glu Ser Ile Lys Glu Gly Ser His
1               5                   10

<210> SEQ ID NO 42
<211> LENGTH: 7
<212> TYPE: PRT
<213> ORGANISM: Neisseria meningitidis

<400> SEQUENCE: 42

Tyr Leu Lys Glu Lys Asn Pro
1               5

<210> SEQ ID NO 43
<211> LENGTH: 18
<212> TYPE: PRT
<213> ORGANISM: Neisseria meningitidis
```

<400> SEQUENCE: 43

Asp Arg Ser Ala Ala Ile Gly Glu Glu Gly Gln Ala Ala Lys Asp Val
1               5                   10                  15

Leu Asp

<210> SEQ ID NO 44
<211> LENGTH: 5
<212> TYPE: PRT
<213> ORGANISM: Neisseria meningitidis

<400> SEQUENCE: 44

Thr Ala Trp Lys Lys
1               5

<210> SEQ ID NO 45
<211> LENGTH: 4
<212> TYPE: PRT
<213> ORGANISM: Neisseria meningitidis

<400> SEQUENCE: 45

Lys Gln Val Ala
1

<210> SEQ ID NO 46
<211> LENGTH: 9
<212> TYPE: PRT
<213> ORGANISM: Neisseria meningitidis

<400> SEQUENCE: 46

Ala Leu Ala Val Cys Thr Ala Leu Ala
1               5

<210> SEQ ID NO 47

<400> SEQUENCE: 47

000

<210> SEQ ID NO 48
<211> LENGTH: 10
<212> TYPE: PRT
<213> ORGANISM: Neisseria meningitidis

<400> SEQUENCE: 48

Leu Gly Met Leu Asp Thr Leu Ser Lys Leu
1               5                   10

<210> SEQ ID NO 49
<211> LENGTH: 9
<212> TYPE: PRT
<213> ORGANISM: Neisseria meningitidis

<400> SEQUENCE: 49

Leu Glu Glu Tyr Phe Lys Thr Thr Lys
1               5

<210> SEQ ID NO 50
<211> LENGTH: 11
<212> TYPE: PRT
<213> ORGANISM: Neisseria meningitidis

<400> SEQUENCE: 50

Ala Ala Lys Ala Phe Asp Lys Leu Asn Glu Ile
1               5                   10

```
<210> SEQ ID NO 51
<211> LENGTH: 18
<212> TYPE: PRT
<213> ORGANISM: Neisseria meningitidis

<400> SEQUENCE: 51

Asn Leu Lys Glu Ser Ala Lys Glu Arg Ile Asp Ala Leu Ala Gln Ile
1               5                   10                  15

Phe Gly

<210> SEQ ID NO 52
<211> LENGTH: 6
<212> TYPE: PRT
<213> ORGANISM: Neisseria meningitidis

<400> SEQUENCE: 52

Pro Ser Ser Arg Leu Gly
1               5

<210> SEQ ID NO 53

<400> SEQUENCE: 53

000

<210> SEQ ID NO 54
<211> LENGTH: 6
<212> TYPE: PRT
<213> ORGANISM: Neisseria meningitidis

<400> SEQUENCE: 54

Ile Lys Glu Gly Ser His
1               5

<210> SEQ ID NO 55

<400> SEQUENCE: 55

000

<210> SEQ ID NO 56
<211> LENGTH: 18
<212> TYPE: PRT
<213> ORGANISM: Neisseria meningitidis

<400> SEQUENCE: 56

Ala Gln Glu Leu Leu Asn Ala Ser Lys Gln Val Ala Asp Ala Phe Asn
1               5                   10                  15

Ala Ala

<210> SEQ ID NO 57
<211> LENGTH: 19
<212> TYPE: PRT
<213> ORGANISM: Neisseria meningitidis

<400> SEQUENCE: 57

Gly Ala Cys Ser Pro Gln Asn Ser Asp Ser Ala Pro Gln Ala Lys Glu
1               5                   10                  15

Gln Ala Val

<210> SEQ ID NO 58
<211> LENGTH: 6
<212> TYPE: PRT
<213> ORGANISM: Neisseria meningitidis
```

```
<400> SEQUENCE: 58

Ala Gln Ser Glu Gly Val
1               5

<210> SEQ ID NO 59
<211> LENGTH: 19
<212> TYPE: PRT
<213> ORGANISM: Neisseria meningitidis

<400> SEQUENCE: 59

Val Lys Thr Ala Arg Gly Asp Val Gln Ile Pro Gln Asn Pro Glu Arg
1               5                   10                  15

Ile Ala Val

<210> SEQ ID NO 60
<211> LENGTH: 20
<212> TYPE: PRT
<213> ORGANISM: Neisseria meningitidis

<400> SEQUENCE: 60

Thr Leu Ser Lys Leu Gly Val Lys Thr Gly Leu Ser Val Asp Lys Asn
1               5                   10                  15

Arg Leu Pro Tyr
            20

<210> SEQ ID NO 61
<211> LENGTH: 19
<212> TYPE: PRT
<213> ORGANISM: Neisseria meningitidis

<400> SEQUENCE: 61

Glu Tyr Phe Lys Thr Thr Lys Pro Ala Gly Thr Leu Phe Glu Pro Asp
1               5                   10                  15

Tyr Glu Thr

<210> SEQ ID NO 62
<211> LENGTH: 4
<212> TYPE: PRT
<213> ORGANISM: Neisseria meningitidis

<400> SEQUENCE: 62

Asn Ala Tyr Lys
1

<210> SEQ ID NO 63
<211> LENGTH: 13
<212> TYPE: PRT
<213> ORGANISM: Neisseria meningitidis

<400> SEQUENCE: 63

Gly Ser Arg Ala Ala Lys Ala Phe Asp Lys Leu Asn Glu
1               5                   10

<210> SEQ ID NO 64
<211> LENGTH: 4
<212> TYPE: PRT
<213> ORGANISM: Neisseria meningitidis

<400> SEQUENCE: 64

Met Thr Ala Asp
1
```

```
<210> SEQ ID NO 65
<211> LENGTH: 13
<212> TYPE: PRT
<213> ORGANISM: Neisseria meningitidis

<400> SEQUENCE: 65

Ala Asn Leu Lys Glu Ser Ala Lys Glu Arg Ile Asp Ala
1               5                   10

<210> SEQ ID NO 66
<211> LENGTH: 31
<212> TYPE: PRT
<213> ORGANISM: Neisseria meningitidis

<400> SEQUENCE: 66

Phe Gly Lys Lys Ala Glu Ala Asp Lys Leu Lys Ala Glu Ile Asp Ala
1               5                   10                  15

Ser Phe Glu Ala Ala Lys Thr Ala Ala Gln Gly Lys Gly Lys Gly
            20                  25                  30

<210> SEQ ID NO 67
<211> LENGTH: 16
<212> TYPE: PRT
<213> ORGANISM: Neisseria meningitidis

<400> SEQUENCE: 67

Asn Gly Gly Lys Met Ser Ala Phe Gly Pro Ser Ser Arg Leu Gly Gly
1               5                   10                  15

<210> SEQ ID NO 68
<211> LENGTH: 23
<212> TYPE: PRT
<213> ORGANISM: Neisseria meningitidis

<400> SEQUENCE: 68

Leu His Lys Asp Ile Gly Val Pro Ala Val Asp Glu Ala Ile Lys Glu
1               5                   10                  15

Gly Ser His Gly Gln Pro Ile
            20

<210> SEQ ID NO 69
<211> LENGTH: 9
<212> TYPE: PRT
<213> ORGANISM: Neisseria meningitidis

<400> SEQUENCE: 69

Tyr Leu Lys Glu Lys Asn Pro Asp Trp
1               5

<210> SEQ ID NO 70
<211> LENGTH: 22
<212> TYPE: PRT
<213> ORGANISM: Neisseria meningitidis

<400> SEQUENCE: 70

Asp Arg Ser Ala Ala Ile Gly Glu Glu Gly Gln Ala Ala Lys Asp Val
1               5                   10                  15

Leu Asn Asn Pro Leu Val
            20

<210> SEQ ID NO 71
<211> LENGTH: 9
<212> TYPE: PRT
<213> ORGANISM: Neisseria meningitidis
```

```
-continued

<400> SEQUENCE: 71

Thr Ala Trp Lys Lys Gly Gln Val Val
1               5

<210> SEQ ID NO 72
<211> LENGTH: 7
<212> TYPE: PRT
<213> ORGANISM: Neisseria meningitidis

<400> SEQUENCE: 72

Asn Ala Ser Lys Gln Val Ala
1               5

<210> SEQ ID NO 73
<211> LENGTH: 14
<212> TYPE: PRT
<213> ORGANISM: Neisseria meningitidis

<400> SEQUENCE: 73

Gln Asn Ser Asp Ser Ala Pro Gln Ala Lys Glu Gln Ala Val
1               5                   10

<210> SEQ ID NO 74
<211> LENGTH: 6
<212> TYPE: PRT
<213> ORGANISM: Neisseria meningitidis

<400> SEQUENCE: 74

Ala Gln Ser Glu Gly Val
1               5

<210> SEQ ID NO 75
<211> LENGTH: 9
<212> TYPE: PRT
<213> ORGANISM: Neisseria meningitidis

<400> SEQUENCE: 75

Lys Thr Ala Arg Gly Asp Val Gln Ile
1               5

<210> SEQ ID NO 76
<211> LENGTH: 5
<212> TYPE: PRT
<213> ORGANISM: Neisseria meningitidis

<400> SEQUENCE: 76

Gln Asn Pro Glu Arg
1               5

<210> SEQ ID NO 77

<400> SEQUENCE: 77

000

<210> SEQ ID NO 78

<400> SEQUENCE: 78

000

<210> SEQ ID NO 79
<211> LENGTH: 10
<212> TYPE: PRT
<213> ORGANISM: Neisseria meningitidis
```

-continued

```
<400> SEQUENCE: 79

Leu Ser Val Asp Lys Asn Arg Leu Pro Tyr
1               5                   10

<210> SEQ ID NO 80
<211> LENGTH: 8
<212> TYPE: PRT
<213> ORGANISM: Neisseria meningitidis

<400> SEQUENCE: 80

Glu Tyr Phe Lys Thr Thr Lys Pro
1               5

<210> SEQ ID NO 81
<211> LENGTH: 5
<212> TYPE: PRT
<213> ORGANISM: Neisseria meningitidis

<400> SEQUENCE: 81

Pro Asp Tyr Glu Thr
1               5

<210> SEQ ID NO 82
<211> LENGTH: 11
<212> TYPE: PRT
<213> ORGANISM: Neisseria meningitidis

<400> SEQUENCE: 82

Arg Ala Ala Lys Ala Phe Asp Lys Leu Asn Glu
1               5                   10

<210> SEQ ID NO 83
<211> LENGTH: 4
<212> TYPE: PRT
<213> ORGANISM: Neisseria meningitidis

<400> SEQUENCE: 83

Met Thr Ala Asp
1

<210> SEQ ID NO 84
<211> LENGTH: 13
<212> TYPE: PRT
<213> ORGANISM: Neisseria meningitidis

<400> SEQUENCE: 84

Ala Asn Leu Lys Glu Ser Ala Lys Glu Arg Ile Asp Ala
1               5                   10

<210> SEQ ID NO 85
<211> LENGTH: 31
<212> TYPE: PRT
<213> ORGANISM: Neisseria meningitidis

<400> SEQUENCE: 85

Phe Gly Lys Lys Ala Glu Ala Asp Lys Leu Lys Ala Glu Ile Asp Ala
1               5                   10                  15

Ser Phe Glu Ala Ala Lys Thr Ala Ala Gln Gly Lys Gly Lys Gly
            20                  25                  30
```

```
<210> SEQ ID NO 86

<400> SEQUENCE: 86

000

<210> SEQ ID NO 87
<211> LENGTH: 11
<212> TYPE: PRT
<213> ORGANISM: Neisseria meningitidis

<400> SEQUENCE: 87

Ala Val Asp Glu Ala Ile Lys Glu Gly Ser His
1               5                   10

<210> SEQ ID NO 88
<211> LENGTH: 7
<212> TYPE: PRT
<213> ORGANISM: Neisseria meningitidis

<400> SEQUENCE: 88

Tyr Leu Lys Glu Lys Asn Pro
1               5

<210> SEQ ID NO 89
<211> LENGTH: 17
<212> TYPE: PRT
<213> ORGANISM: Neisseria meningitidis

<400> SEQUENCE: 89

Asp Arg Ser Ala Ala Ile Gly Glu Glu Gly Gln Ala Ala Lys Asp Val
1               5                   10                  15

Leu

<210> SEQ ID NO 90
<211> LENGTH: 5
<212> TYPE: PRT
<213> ORGANISM: Neisseria meningitidis

<400> SEQUENCE: 90

Thr Ala Trp Lys Lys
1               5

<210> SEQ ID NO 91
<211> LENGTH: 4
<212> TYPE: PRT
<213> ORGANISM: Neisseria meningitidis

<400> SEQUENCE: 91

Lys Gln Val Ala
1

<210> SEQ ID NO 92
<211> LENGTH: 8
<212> TYPE: PRT
<213> ORGANISM: Neisseria meningitidis

<400> SEQUENCE: 92

Ala Pro Leu Pro Ala Leu Ser Ala
1               5

<210> SEQ ID NO 93
<211> LENGTH: 4
<212> TYPE: PRT
<213> ORGANISM: Neisseria meningitidis
```

```
<400> SEQUENCE: 93

His Gly Ile Ala
1

<210> SEQ ID NO 94
<211> LENGTH: 4
<212> TYPE: PRT
<213> ORGANISM: Neisseria meningitidis

<400> SEQUENCE: 94

Ser Ala Gln Ser
1

<210> SEQ ID NO 95
<211> LENGTH: 16
<212> TYPE: PRT
<213> ORGANISM: Neisseria meningitidis

<400> SEQUENCE: 95

Val Val Arg Gln Pro Ile Lys Arg Leu Ala Met Ala Thr Leu Pro Ala
1               5                   10                  15

<210> SEQ ID NO 96
<211> LENGTH: 5
<212> TYPE: PRT
<213> ORGANISM: Neisseria meningitidis

<400> SEQUENCE: 96

Ser Asn Arg Tyr Ser
1               5

<210> SEQ ID NO 97
<211> LENGTH: 6
<212> TYPE: PRT
<213> ORGANISM: Neisseria meningitidis

<400> SEQUENCE: 97

Val Leu Gly Ser Leu Ala
1               5

<210> SEQ ID NO 98
<211> LENGTH: 19
<212> TYPE: PRT
<213> ORGANISM: Neisseria meningitidis

<400> SEQUENCE: 98

Val Val Leu Gln Leu Phe Ala Leu Ile Thr Pro Leu Phe Phe Gln Val
1               5                   10                  15

Val Met Asp

<210> SEQ ID NO 99
<211> LENGTH: 4
<212> TYPE: PRT
<213> ORGANISM: Neisseria meningitidis

<400> SEQUENCE: 99

Ser Thr Leu Asp
1

<210> SEQ ID NO 100
<211> LENGTH: 9
<212> TYPE: PRT
<213> ORGANISM: Neisseria meningitidis
```

```
<400> SEQUENCE: 100

Arg Leu Phe Arg His Leu Leu Ser Leu
1               5

<210> SEQ ID NO 101
<211> LENGTH: 21
<212> TYPE: PRT
<213> ORGANISM: Neisseria meningitidis

<400> SEQUENCE: 101

Glu His Arg Arg Val Gly Asp Thr Val Ala Arg Val Arg Glu Leu Glu
1               5                   10                  15

Gln Ile Arg Asn Phe
            20

<210> SEQ ID NO 102

<400> SEQUENCE: 102

000

<210> SEQ ID NO 103
<211> LENGTH: 10
<212> TYPE: PRT
<213> ORGANISM: Neisseria meningitidis

<400> SEQUENCE: 103

Val Val Leu Ala Ser Leu Pro Ala Tyr Ala
1               5                   10

<210> SEQ ID NO 104
<211> LENGTH: 10
<212> TYPE: PRT
<213> ORGANISM: Neisseria meningitidis

<400> SEQUENCE: 104

Trp Ser Ala Phe Ile Ser Pro Ile Leu Arg
1               5                   10

<210> SEQ ID NO 105
<211> LENGTH: 9
<212> TYPE: PRT
<213> ORGANISM: Neisseria meningitidis

<400> SEQUENCE: 105

Leu Asn Asp Lys Phe Ala Arg Asn Ala
1               5

<210> SEQ ID NO 106
<211> LENGTH: 10
<212> TYPE: PRT
<213> ORGANISM: Neisseria meningitidis

<400> SEQUENCE: 106

Glu Ser Ile Thr Ala Val Gly Thr Val Lys
1               5                   10

<210> SEQ ID NO 107
<211> LENGTH: 7
<212> TYPE: PRT
<213> ORGANISM: Neisseria meningitidis
```

```
<400> SEQUENCE: 107

Arg Trp Asp Asn Gln Leu Ala
1               5

<210> SEQ ID NO 108

<400> SEQUENCE: 108

000

<210> SEQ ID NO 109

<400> SEQUENCE: 109

000

<210> SEQ ID NO 110
<211> LENGTH: 8
<212> TYPE: PRT
<213> ORGANISM: Neisseria meningitidis

<400> SEQUENCE: 110

Gln Leu Ile Gln Lys Leu Val Thr
1               5

<210> SEQ ID NO 111
<211> LENGTH: 4
<212> TYPE: PRT
<213> ORGANISM: Neisseria meningitidis

<400> SEQUENCE: 111

Leu Ile Ala Phe
1

<210> SEQ ID NO 112
<211> LENGTH: 4
<212> TYPE: PRT
<213> ORGANISM: Neisseria meningitidis

<400> SEQUENCE: 112

Gly Gln Val Ala
1

<210> SEQ ID NO 113
<211> LENGTH: 10
<212> TYPE: PRT
<213> ORGANISM: Neisseria meningitidis

<400> SEQUENCE: 113

Arg Leu Ala Gln Leu Trp Gln Asp Phe Gln
1               5                   10

<210> SEQ ID NO 114
<211> LENGTH: 10
<212> TYPE: PRT
<213> ORGANISM: Neisseria meningitidis

<400> SEQUENCE: 114

Ala Arg Leu Gly Asp Ile Leu Asn Ala Pro
1               5                   10
```

```
<210> SEQ ID NO 115

<400> SEQUENCE: 115

000

<210> SEQ ID NO 116

<400> SEQUENCE: 116

000

<210> SEQ ID NO 117
<211> LENGTH: 8
<212> TYPE: PRT
<213> ORGANISM: Neisseria meningitidis

<400> SEQUENCE: 117

Ser Thr Leu Thr Lys Leu Val Gln
1               5

<210> SEQ ID NO 118
<211> LENGTH: 12
<212> TYPE: PRT
<213> ORGANISM: Neisseria meningitidis

<400> SEQUENCE: 118

Glu Arg Ile Ile Glu Ala Ala Lys Leu Ala Gly Ala
1               5                   10

<210> SEQ ID NO 119
<211> LENGTH: 12
<212> TYPE: PRT
<213> ORGANISM: Neisseria meningitidis

<400> SEQUENCE: 119

Glu Phe Ile Met Glu Leu Pro Glu Gly Tyr Gly Thr
1               5                   10

<210> SEQ ID NO 120

<400> SEQUENCE: 120

000

<210> SEQ ID NO 121
<211> LENGTH: 5
<212> TYPE: PRT
<213> ORGANISM: Neisseria meningitidis

<400> SEQUENCE: 121

Val Lys Thr Ala His
1               5

<210> SEQ ID NO 122
<211> LENGTH: 7
<212> TYPE: PRT
<213> ORGANISM: Neisseria meningitidis

<400> SEQUENCE: 122

Asn Pro Ala Asp Ile Gln His
1               5
```

```
<210> SEQ ID NO 123
<211> LENGTH: 11
<212> TYPE: PRT
<213> ORGANISM: Neisseria meningitidis

<400> SEQUENCE: 123

Cys Thr Ser Ala Gln Ser Asp Leu Asn Glu Thr
1               5                   10

<210> SEQ ID NO 124
<211> LENGTH: 16
<212> TYPE: PRT
<213> ORGANISM: Neisseria meningitidis

<400> SEQUENCE: 124

Leu Gly Leu Lys Ala Lys Val Val Arg Gln Pro Ile Lys Arg Leu Ala
1               5                   10                  15

<210> SEQ ID NO 125
<211> LENGTH: 6
<212> TYPE: PRT
<213> ORGANISM: Neisseria meningitidis

<400> SEQUENCE: 125

Cys Asp Asp Gly Asn His
1               5

<210> SEQ ID NO 126
<211> LENGTH: 9
<212> TYPE: PRT
<213> ORGANISM: Neisseria meningitidis

<400> SEQUENCE: 126

Ala Lys Thr Asp Gly Glu Gly Glu His
1               5

<210> SEQ ID NO 127
<211> LENGTH: 6
<212> TYPE: PRT
<213> ORGANISM: Neisseria meningitidis

<400> SEQUENCE: 127

Val Thr Asn Lys Ser Ala
1               5

<210> SEQ ID NO 128
<211> LENGTH: 8
<212> TYPE: PRT
<213> ORGANISM: Neisseria meningitidis

<400> SEQUENCE: 128

Phe Ser Asn Arg Tyr Ser Gly Lys
1               5

<210> SEQ ID NO 129

<400> SEQUENCE: 129

000

<210> SEQ ID NO 130

<400> SEQUENCE: 130

000
```

<210> SEQ ID NO 131
<211> LENGTH: 10
<212> TYPE: PRT
<213> ORGANISM: Neisseria meningitidis

<400> SEQUENCE: 131

Thr Thr Ser Arg Ile Asp Val Glu Leu Gly
1               5                   10

<210> SEQ ID NO 132
<211> LENGTH: 20
<212> TYPE: PRT
<213> ORGANISM: Neisseria meningitidis

<400> SEQUENCE: 132

Phe Glu His Arg Arg Val Gly Asp Thr Val Ala Arg Val Arg Glu Leu
1               5                   10                  15

Glu Gln Ile Arg
            20

<210> SEQ ID NO 133
<211> LENGTH: 4
<212> TYPE: PRT
<213> ORGANISM: Neisseria meningitidis

<400> SEQUENCE: 133

Tyr Ser Ser Thr
1

<210> SEQ ID NO 134
<211> LENGTH: 18
<212> TYPE: PRT
<213> ORGANISM: Neisseria meningitidis

<400> SEQUENCE: 134

Leu Arg Thr Arg Leu Asn Asp Lys Phe Ala Arg Asn Ala Asp Asn Gln
1               5                   10                  15

Ser Phe

<210> SEQ ID NO 135
<211> LENGTH: 10
<212> TYPE: PRT
<213> ORGANISM: Neisseria meningitidis

<400> SEQUENCE: 135

Pro Gln Met Thr Gln Arg Trp Asp Asn Gln
1               5                   10

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

```
<210> SEQ ID NO 139

<400> SEQUENCE: 139

000

<210> SEQ ID NO 140
<211> LENGTH: 4
<212> TYPE: PRT
<213> ORGANISM: Neisseria meningitidis

<400> SEQUENCE: 140

Arg Leu Gly Asp
1

<210> SEQ ID NO 141
<211> LENGTH: 8
<212> TYPE: PRT
<213> ORGANISM: Neisseria meningitidis

<400> SEQUENCE: 141

Ala Pro Thr Glu Asn Ala Ser Ser
1               5

<210> SEQ ID NO 142
<211> LENGTH: 5
<212> TYPE: PRT
<213> ORGANISM: Neisseria meningitidis

<400> SEQUENCE: 142

Pro Asp Ile Arg Gly
1               5

<210> SEQ ID NO 143
<211> LENGTH: 12
<212> TYPE: PRT
<213> ORGANISM: Neisseria meningitidis

<400> SEQUENCE: 143

Val Asp Phe Arg Tyr Lys Ala Asp Gly Arg Leu Ile
1               5                   10

<210> SEQ ID NO 144
<211> LENGTH: 9
<212> TYPE: PRT
<213> ORGANISM: Neisseria meningitidis

<400> SEQUENCE: 144

Leu Asn Leu Arg Ile Arg Ala Gly Glu
1               5

<210> SEQ ID NO 145
<211> LENGTH: 10
<212> TYPE: PRT
<213> ORGANISM: Neisseria meningitidis

<400> SEQUENCE: 145

Gly Arg Ser Gly Ser Gly Lys Ser Thr Leu
1               5                   10

<210> SEQ ID NO 146
<211> LENGTH: 15
<212> TYPE: PRT
<213> ORGANISM: Neisseria meningitidis
```

```
<400> SEQUENCE: 146

Tyr Val Pro Glu Gln Gly Arg Val Leu Val Asp Gly Asn Asp Leu
1               5                   10                  15

<210> SEQ ID NO 147
<211> LENGTH: 11
<212> TYPE: PRT
<213> ORGANISM: Neisseria meningitidis

<400> SEQUENCE: 147

Leu Leu Asn Arg Ser Ile Arg Asp Asn Ile Ala
1               5                   10

<210> SEQ ID NO 148
<211> LENGTH: 7
<212> TYPE: PRT
<213> ORGANISM: Neisseria meningitidis

<400> SEQUENCE: 148

Thr Asp Thr Gly Met Pro Leu
1               5

<210> SEQ ID NO 149
<211> LENGTH: 4
<212> TYPE: PRT
<213> ORGANISM: Neisseria meningitidis

<400> SEQUENCE: 149

Arg Ile Ile Glu
1

<210> SEQ ID NO 150
<211> LENGTH: 7
<212> TYPE: PRT
<213> ORGANISM: Neisseria meningitidis

<400> SEQUENCE: 150

Glu Leu Pro Glu Gly Tyr Gly
1               5

<210> SEQ ID NO 151
<211> LENGTH: 17
<212> TYPE: PRT
<213> ORGANISM: Neisseria meningitidis

<400> SEQUENCE: 151

Gly Glu Gln Gly Ala Gly Leu Ser Gly Gly Gln Arg Gln Arg Ile Ala
1               5                   10                  15

Ile

<210> SEQ ID NO 152

<400> SEQUENCE: 152

000

<210> SEQ ID NO 153
<211> LENGTH: 4
<212> TYPE: PRT
<213> ORGANISM: Neisseria meningitidis

<400> SEQUENCE: 153

Glu Ala Thr Ser
1
```

```
<210> SEQ ID NO 154
<211> LENGTH: 9
<212> TYPE: PRT
<213> ORGANISM: Neisseria meningitidis

<400> SEQUENCE: 154

Leu Asp Tyr Glu Ser Glu Arg Ala Ile
1               5

<210> SEQ ID NO 155
<211> LENGTH: 4
<212> TYPE: PRT
<213> ORGANISM: Neisseria meningitidis

<400> SEQUENCE: 155

Cys Ala Asn Arg
1

<210> SEQ ID NO 156

<400> SEQUENCE: 156

000

<210> SEQ ID NO 157
<211> LENGTH: 10
<212> TYPE: PRT
<213> ORGANISM: Neisseria meningitidis

<400> SEQUENCE: 157

Ile Ala Met Asp Lys Gly Arg Ile Val Glu
1               5                   10

<210> SEQ ID NO 158
<211> LENGTH: 4
<212> TYPE: PRT
<213> ORGANISM: Neisseria meningitidis

<400> SEQUENCE: 158

Gly Thr Gln Gln
1

<210> SEQ ID NO 159
<211> LENGTH: 7
<212> TYPE: PRT
<213> ORGANISM: Neisseria meningitidis

<400> SEQUENCE: 159

Leu Leu Ala Lys Pro Asn Gly
1               5

<210> SEQ ID NO 160
<211> LENGTH: 4
<212> TYPE: PRT
<213> ORGANISM: Neisseria meningitidis

<400> SEQUENCE: 160

Leu Gln Asn Gly
1

<210> SEQ ID NO 161
<211> LENGTH: 5
<212> TYPE: PRT
<213> ORGANISM: Neisseria meningitidis
```

```
<400> SEQUENCE: 161

Ala Asp Ile Gln His
1               5

<210> SEQ ID NO 162
<211> LENGTH: 7
<212> TYPE: PRT
<213> ORGANISM: Neisseria meningitidis

<400> SEQUENCE: 162

Ala Gln Ser Asp Leu Asn Glu
1               5

<210> SEQ ID NO 163
<211> LENGTH: 16
<212> TYPE: PRT
<213> ORGANISM: Neisseria meningitidis

<400> SEQUENCE: 163

Leu Gly Leu Lys Ala Lys Val Val Arg Gln Pro Ile Lys Arg Leu Ala
1               5                   10                  15

<210> SEQ ID NO 164
<211> LENGTH: 4
<212> TYPE: PRT
<213> ORGANISM: Neisseria meningitidis

<400> SEQUENCE: 164

Asp Asp Gly Asn
1

<210> SEQ ID NO 165
<211> LENGTH: 8
<212> TYPE: PRT
<213> ORGANISM: Neisseria meningitidis

<400> SEQUENCE: 165

Lys Thr Asp Gly Glu Gly Glu His
1               5

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169
<211> LENGTH: 8
<212> TYPE: PRT
<213> ORGANISM: Neisseria meningitidis
```

```
<400> SEQUENCE: 169

Ser Arg Ile Asp Val Glu Leu Gly
1               5

<210> SEQ ID NO 170
<211> LENGTH: 19
<212> TYPE: PRT
<213> ORGANISM: Neisseria meningitidis

<400> SEQUENCE: 170

Glu His Arg Arg Val Gly Asp Thr Val Ala Arg Val Arg Glu Leu Glu
1               5                   10                  15

Gln Ile Arg

<210> SEQ ID NO 171
<211> LENGTH: 15
<212> TYPE: PRT
<213> ORGANISM: Neisseria meningitidis

<400> SEQUENCE: 171

Leu Arg Thr Arg Leu Asn Asp Lys Phe Ala Arg Asn Ala Asp Asn
1               5                   10                  15

<210> SEQ ID NO 172
<211> LENGTH: 5
<212> TYPE: PRT
<213> ORGANISM: Neisseria meningitidis

<400> SEQUENCE: 172

Gln Arg Trp Asp Asn
1               5

<210> SEQ ID NO 173

<400> SEQUENCE: 173

000

<210> SEQ ID NO 174

<400> SEQUENCE: 174

000

<210> SEQ ID NO 175
<211> LENGTH: 4
<212> TYPE: PRT
<213> ORGANISM: Neisseria meningitidis

<400> SEQUENCE: 175

Arg Leu Gly Asp
1

<210> SEQ ID NO 176
<211> LENGTH: 6
<212> TYPE: PRT
<213> ORGANISM: Neisseria meningitidis

<400> SEQUENCE: 176

Pro Thr Glu Asn Ala Ser
1               5
```

```
<210> SEQ ID NO 177
<211> LENGTH: 5
<212> TYPE: PRT
<213> ORGANISM: Neisseria meningitidis

<400> SEQUENCE: 177

Pro Asp Ile Arg Gly
1               5

<210> SEQ ID NO 178
<211> LENGTH: 12
<212> TYPE: PRT
<213> ORGANISM: Neisseria meningitidis

<400> SEQUENCE: 178

Val Asp Phe Arg Tyr Lys Ala Asp Gly Arg Leu Ile
1               5                   10

<210> SEQ ID NO 179
<211> LENGTH: 9
<212> TYPE: PRT
<213> ORGANISM: Neisseria meningitidis

<400> SEQUENCE: 179

Leu Asn Leu Arg Ile Arg Ala Gly Glu
1               5

<210> SEQ ID NO 180
<211> LENGTH: 9
<212> TYPE: PRT
<213> ORGANISM: Neisseria meningitidis

<400> SEQUENCE: 180

Arg Ser Gly Ser Gly Lys Ser Thr Leu
1               5

<210> SEQ ID NO 181
<211> LENGTH: 11
<212> TYPE: PRT
<213> ORGANISM: Neisseria meningitidis

<400> SEQUENCE: 181

Glu Gln Gly Arg Val Leu Val Asp Gly Asn Asp
1               5                   10

<210> SEQ ID NO 182
<211> LENGTH: 8
<212> TYPE: PRT
<213> ORGANISM: Neisseria meningitidis

<400> SEQUENCE: 182

Arg Ser Ile Arg Asp Asn Ile Ala
1               5

<210> SEQ ID NO 183

<400> SEQUENCE: 183

000

<210> SEQ ID NO 184
<211> LENGTH: 4
<212> TYPE: PRT
<213> ORGANISM: Neisseria meningitidis
```

```
<400> SEQUENCE: 184

Arg Ile Ile Glu
1

<210> SEQ ID NO 185

<400> SEQUENCE: 185

000

<210> SEQ ID NO 186

<400> SEQUENCE: 186

000

<210> SEQ ID NO 187
<211> LENGTH: 9
<212> TYPE: PRT
<213> ORGANISM: Neisseria meningitidis

<400> SEQUENCE: 187

Gly Gly Gln Arg Gln Arg Ile Ala Ile
1               5

<210> SEQ ID NO 188
<211> LENGTH: 4
<212> TYPE: PRT
<213> ORGANISM: Neisseria meningitidis

<400> SEQUENCE: 188

Glu Ala Thr Ser
1

<210> SEQ ID NO 189
<211> LENGTH: 9
<212> TYPE: PRT
<213> ORGANISM: Neisseria meningitidis

<400> SEQUENCE: 189

Leu Asp Tyr Glu Ser Glu Arg Ala Ile
1               5

<210> SEQ ID NO 190

<400> SEQUENCE: 190

000

<210> SEQ ID NO 191
<211> LENGTH: 10
<212> TYPE: PRT
<213> ORGANISM: Neisseria meningitidis

<400> SEQUENCE: 191

Ile Ala Met Asp Lys Gly Arg Ile Val Glu
1               5                   10

<210> SEQ ID NO 192

<400> SEQUENCE: 192

000
```

<210> SEQ ID NO 193

<400> SEQUENCE: 193

000

<210> SEQ ID NO 194
<211> LENGTH: 8
<212> TYPE: PRT
<213> ORGANISM: Neisseria meningitidis

<400> SEQUENCE: 194

Ala Pro Leu Pro Ala Leu Ser Ala
1               5

<210> SEQ ID NO 195
<211> LENGTH: 4
<212> TYPE: PRT
<213> ORGANISM: Neisseria meningitidis

<400> SEQUENCE: 195

His Gly Ile Ala
1

<210> SEQ ID NO 196
<211> LENGTH: 4
<212> TYPE: PRT
<213> ORGANISM: Neisseria meningitidis

<400> SEQUENCE: 196

Ser Ala Gln Ser
1

<210> SEQ ID NO 197
<211> LENGTH: 16
<212> TYPE: PRT
<213> ORGANISM: Neisseria meningitidis

<400> SEQUENCE: 197

Val Val Arg Gln Pro Ile Lys Arg Leu Ala Met Ala Thr Leu Pro Ala
1               5                   10                  15

<210> SEQ ID NO 198
<211> LENGTH: 5
<212> TYPE: PRT
<213> ORGANISM: Neisseria meningitidis

<400> SEQUENCE: 198

Ser Asn Arg Tyr Ser
1               5

<210> SEQ ID NO 199
<211> LENGTH: 6
<212> TYPE: PRT
<213> ORGANISM: Neisseria meningitidis

<400> SEQUENCE: 199

Val Leu Gly Ser Leu Ala
1               5

<210> SEQ ID NO 200
<211> LENGTH: 19
<212> TYPE: PRT
<213> ORGANISM: Neisseria meningitidis

```
<400> SEQUENCE: 200

Val Val Leu Gln Leu Phe Ala Leu Ile Thr Pro Leu Phe Phe Gln Val
1               5                   10                  15

Val Met Asp

<210> SEQ ID NO 201
<211> LENGTH: 4
<212> TYPE: PRT
<213> ORGANISM: Neisseria meningitidis

<400> SEQUENCE: 201

Ser Thr Leu Asp
1

<210> SEQ ID NO 202
<211> LENGTH: 9
<212> TYPE: PRT
<213> ORGANISM: Neisseria meningitidis

<400> SEQUENCE: 202

Arg Leu Phe Arg His Leu Leu Ser Leu
1               5

<210> SEQ ID NO 203
<211> LENGTH: 21
<212> TYPE: PRT
<213> ORGANISM: Neisseria meningitidis

<400> SEQUENCE: 203

Glu His Arg Arg Val Gly Asp Thr Val Ala Arg Val Arg Glu Leu Glu
1               5                   10                  15

Gln Ile Arg Asn Phe
            20

<210> SEQ ID NO 204

<400> SEQUENCE: 204

000

<210> SEQ ID NO 205
<211> LENGTH: 10
<212> TYPE: PRT
<213> ORGANISM: Neisseria meningitidis

<400> SEQUENCE: 205

Val Val Leu Ala Ser Leu Pro Ala Tyr Ala
1               5                   10

<210> SEQ ID NO 206
<211> LENGTH: 10
<212> TYPE: PRT
<213> ORGANISM: Neisseria meningitidis

<400> SEQUENCE: 206

Trp Ser Ala Phe Ile Ser Pro Ile Leu Arg
1               5                   10

<210> SEQ ID NO 207
<211> LENGTH: 9
<212> TYPE: PRT
<213> ORGANISM: Neisseria meningitidis
```

```
<400> SEQUENCE: 207

Leu Asn Asp Lys Phe Ala Arg Asn Ala
 1               5

<210> SEQ ID NO 208
<211> LENGTH: 10
<212> TYPE: PRT
<213> ORGANISM: Neisseria meningitidis

<400> SEQUENCE: 208

Glu Ser Ile Thr Ala Val Gly Thr Val Lys
 1               5                  10

<210> SEQ ID NO 209
<211> LENGTH: 7
<212> TYPE: PRT
<213> ORGANISM: Neisseria meningitidis

<400> SEQUENCE: 209

Arg Trp Asp Asn Gln Leu Ala
 1               5

<210> SEQ ID NO 210

<400> SEQUENCE: 210

000

<210> SEQ ID NO 211

<400> SEQUENCE: 211

000

<210> SEQ ID NO 212
<211> LENGTH: 8
<212> TYPE: PRT
<213> ORGANISM: Neisseria meningitidis

<400> SEQUENCE: 212

Gln Leu Ile Gln Lys Leu Val Thr
 1               5

<210> SEQ ID NO 213
<211> LENGTH: 4
<212> TYPE: PRT
<213> ORGANISM: Neisseria meningitidis

<400> SEQUENCE: 213

Leu Ile Ala Phe
 1

<210> SEQ ID NO 214
<211> LENGTH: 4
<212> TYPE: PRT
<213> ORGANISM: Neisseria meningitidis

<400> SEQUENCE: 214

Gly Gln Val Ala
 1

<210> SEQ ID NO 215
<211> LENGTH: 10
<212> TYPE: PRT
<213> ORGANISM: Neisseria meningitidis
```

```
<400> SEQUENCE: 215

Arg Leu Ala Gln Leu Trp Gln Asp Phe Gln
1               5                   10

<210> SEQ ID NO 216
<211> LENGTH: 10
<212> TYPE: PRT
<213> ORGANISM: Neisseria meningitidis

<400> SEQUENCE: 216

Ala Arg Leu Gly Asp Ile Leu Asn Ala Pro
1               5                   10

<210> SEQ ID NO 217

<400> SEQUENCE: 217

000

<210> SEQ ID NO 218

<400> SEQUENCE: 218

000

<210> SEQ ID NO 219
<211> LENGTH: 9
<212> TYPE: PRT
<213> ORGANISM: Neisseria meningitidis

<400> SEQUENCE: 219

Ser Thr Leu Thr Lys Leu Val Gln Arg
1               5

<210> SEQ ID NO 220
<211> LENGTH: 12
<212> TYPE: PRT
<213> ORGANISM: Neisseria meningitidis

<400> SEQUENCE: 220

Glu Arg Ile Ile Glu Ala Ala Lys Leu Ala Gly Ala
1               5                   10

<210> SEQ ID NO 221
<211> LENGTH: 12
<212> TYPE: PRT
<213> ORGANISM: Neisseria meningitidis

<400> SEQUENCE: 221

Glu Phe Ile Met Glu Leu Pro Glu Gly Tyr Gly Thr
1               5                   10

<210> SEQ ID NO 222

<400> SEQUENCE: 222

000

<210> SEQ ID NO 223
<211> LENGTH: 5
<212> TYPE: PRT
<213> ORGANISM: Neisseria meningitidis
```

<400> SEQUENCE: 223

Val Lys Thr Ala His
1               5

<210> SEQ ID NO 224
<211> LENGTH: 7
<212> TYPE: PRT
<213> ORGANISM: Neisseria meningitidis

<400> SEQUENCE: 224

Asn Pro Ala Asp Ile Gln His
1               5

<210> SEQ ID NO 225
<211> LENGTH: 11
<212> TYPE: PRT
<213> ORGANISM: Neisseria meningitidis

<400> SEQUENCE: 225

Cys Thr Ser Ala Gln Ser Asp Leu Asn Glu Thr
1               5                   10

<210> SEQ ID NO 226
<211> LENGTH: 16
<212> TYPE: PRT
<213> ORGANISM: Neisseria meningitidis

<400> SEQUENCE: 226

Leu Gly Leu Lys Ala Lys Val Val Arg Gln Pro Ile Lys Arg Leu Ala
1               5                   10                  15

<210> SEQ ID NO 227
<211> LENGTH: 6
<212> TYPE: PRT
<213> ORGANISM: Neisseria meningitidis

<400> SEQUENCE: 227

Cys Asp Asp Gly Asn His
1               5

<210> SEQ ID NO 228
<211> LENGTH: 8
<212> TYPE: PRT
<213> ORGANISM: Neisseria meningitidis

<400> SEQUENCE: 228

Lys Thr Asp Gly Gly Gly Glu His
1               5

<210> SEQ ID NO 229
<211> LENGTH: 8
<212> TYPE: PRT
<213> ORGANISM: Neisseria meningitidis

<400> SEQUENCE: 229

Asp Leu Thr Thr Asn Lys Ser Ala
1               5

<210> SEQ ID NO 230
<211> LENGTH: 8
<212> TYPE: PRT
<213> ORGANISM: Neisseria meningitidis

```
<400> SEQUENCE: 230

Phe Ser Asn Arg Tyr Ser Gly Lys
1               5

<210> SEQ ID NO 231

<400> SEQUENCE: 231

000

<210> SEQ ID NO 232

<400> SEQUENCE: 232

000

<210> SEQ ID NO 233
<211> LENGTH: 10
<212> TYPE: PRT
<213> ORGANISM: Neisseria meningitidis

<400> SEQUENCE: 233

Thr Thr Ser Arg Ile Asp Val Glu Leu Gly
1               5                   10

<210> SEQ ID NO 234
<211> LENGTH: 20
<212> TYPE: PRT
<213> ORGANISM: Neisseria meningitidis

<400> SEQUENCE: 234

Phe Glu His Arg Arg Val Gly Asp Thr Val Ala Arg Val Arg Glu Leu
1               5                   10                  15

Glu Gln Ile Arg
            20

<210> SEQ ID NO 235
<211> LENGTH: 4
<212> TYPE: PRT
<213> ORGANISM: Neisseria meningitidis

<400> SEQUENCE: 235

Tyr Ser Ser Thr
1

<210> SEQ ID NO 236
<211> LENGTH: 18
<212> TYPE: PRT
<213> ORGANISM: Neisseria meningitidis

<400> SEQUENCE: 236

Leu Arg Thr Arg Leu Asn Asp Lys Phe Ala Arg Asn Ala Asp Asn Gln
1               5                   10                  15

Ser Phe

<210> SEQ ID NO 237
<211> LENGTH: 10
<212> TYPE: PRT
<213> ORGANISM: Neisseria meningitidis

<400> SEQUENCE: 237

Pro Gln Met Thr Gln Arg Trp Asp Asn Gln
1               5                   10
```

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242
<211> LENGTH: 4
<212> TYPE: PRT
<213> ORGANISM: Neisseria meningitidis

<400> SEQUENCE: 242

Arg Leu Gly Asp
1

<210> SEQ ID NO 243
<211> LENGTH: 8
<212> TYPE: PRT
<213> ORGANISM: Neisseria meningitidis

<400> SEQUENCE: 243

Ala Pro Thr Glu Asn Ala Ser Ser
1               5

<210> SEQ ID NO 244
<211> LENGTH: 5
<212> TYPE: PRT
<213> ORGANISM: Neisseria meningitidis

<400> SEQUENCE: 244

Pro Asp Ile Arg Gly
1               5

<210> SEQ ID NO 245
<211> LENGTH: 12
<212> TYPE: PRT
<213> ORGANISM: Neisseria meningitidis

<400> SEQUENCE: 245

Val Asp Phe Arg Tyr Lys Ala Asp Gly Arg Leu Ile
1               5                   10

<210> SEQ ID NO 246
<211> LENGTH: 9
<212> TYPE: PRT
<213> ORGANISM: Neisseria meningitidis

<400> SEQUENCE: 246

Leu Asn Leu Arg Ile Arg Ala Gly Glu
1               5

<210> SEQ ID NO 247
<211> LENGTH: 10
<212> TYPE: PRT
<213> ORGANISM: Neisseria meningitidis

<400> SEQUENCE: 247

Gly Arg Ser Gly Ser Gly Lys Ser Thr Leu
1               5                   10

<210> SEQ ID NO 248
<211> LENGTH: 7
<212> TYPE: PRT
<213> ORGANISM: Neisseria meningitidis

<400> SEQUENCE: 248

Val Leu Val Asp Gly Asn Asp
1               5

<210> SEQ ID NO 249
<211> LENGTH: 11
<212> TYPE: PRT
<213> ORGANISM: Neisseria meningitidis

<400> SEQUENCE: 249

Leu Leu Asn Arg Ser Ile Arg Asp Asn Ile Ala
1               5                   10

<210> SEQ ID NO 250
<211> LENGTH: 7
<212> TYPE: PRT
<213> ORGANISM: Neisseria meningitidis

<400> SEQUENCE: 250

Thr Asp Thr Gly Met Pro Leu
1               5

<210> SEQ ID NO 251
<211> LENGTH: 4
<212> TYPE: PRT
<213> ORGANISM: Neisseria meningitidis

<400> SEQUENCE: 251

Arg Ile Ile Glu
1

<210> SEQ ID NO 252
<211> LENGTH: 7
<212> TYPE: PRT
<213> ORGANISM: Neisseria meningitidis

<400> SEQUENCE: 252

Glu Leu Pro Glu Gly Tyr Gly
1               5

<210> SEQ ID NO 253
<211> LENGTH: 17
<212> TYPE: PRT
<213> ORGANISM: Neisseria meningitidis

```
<400> SEQUENCE: 253

Gly Glu Gln Gly Ala Gly Leu Ser Gly Gly Gln Arg Gln Arg Ile Ala
1               5                   10                  15

Ile

<210> SEQ ID NO 254

<400> SEQUENCE: 254

000

<210> SEQ ID NO 255
<211> LENGTH: 4
<212> TYPE: PRT
<213> ORGANISM: Neisseria meningitidis

<400> SEQUENCE: 255

Glu Ala Thr Ser
1

<210> SEQ ID NO 256
<211> LENGTH: 9
<212> TYPE: PRT
<213> ORGANISM: Neisseria meningitidis

<400> SEQUENCE: 256

Leu Asp Tyr Glu Ser Glu Arg Ala Ile
1               5

<210> SEQ ID NO 257
<211> LENGTH: 4
<212> TYPE: PRT
<213> ORGANISM: Neisseria meningitidis

<400> SEQUENCE: 257

Cys Ala Asn Arg
1

<210> SEQ ID NO 258

<400> SEQUENCE: 258

000

<210> SEQ ID NO 259
<211> LENGTH: 10
<212> TYPE: PRT
<213> ORGANISM: Neisseria meningitidis

<400> SEQUENCE: 259

Ile Ala Met Asp Lys Gly Arg Ile Val Glu
1               5                   10

<210> SEQ ID NO 260
<211> LENGTH: 4
<212> TYPE: PRT
<213> ORGANISM: Neisseria meningitidis

<400> SEQUENCE: 260

Gly Thr Gln Gln
1
```

```
<210> SEQ ID NO 261
<211> LENGTH: 7
<212> TYPE: PRT
<213> ORGANISM: Neisseria meningitidis

<400> SEQUENCE: 261

Leu Leu Ala Lys Pro Asn Gly
1               5

<210> SEQ ID NO 262
<211> LENGTH: 4
<212> TYPE: PRT
<213> ORGANISM: Neisseria meningitidis

<400> SEQUENCE: 262

Leu Gln Asn Gly
1

<210> SEQ ID NO 263
<211> LENGTH: 5
<212> TYPE: PRT
<213> ORGANISM: Neisseria meningitidis

<400> SEQUENCE: 263

Ala Asp Ile Gln His
1               5

<210> SEQ ID NO 264
<211> LENGTH: 7
<212> TYPE: PRT
<213> ORGANISM: Neisseria meningitidis

<400> SEQUENCE: 264

Ala Gln Ser Asp Leu Asn Glu
1               5

<210> SEQ ID NO 265
<211> LENGTH: 16
<212> TYPE: PRT
<213> ORGANISM: Neisseria meningitidis

<400> SEQUENCE: 265

Leu Gly Leu Lys Ala Lys Val Val Arg Gln Pro Ile Lys Arg Leu Ala
1               5                   10                  15

<210> SEQ ID NO 266
<211> LENGTH: 4
<212> TYPE: PRT
<213> ORGANISM: Neisseria meningitidis

<400> SEQUENCE: 266

Asp Asp Gly Asn
1

<210> SEQ ID NO 267
<211> LENGTH: 7
<212> TYPE: PRT
<213> ORGANISM: Neisseria meningitidis

<400> SEQUENCE: 267

Lys Thr Asp Gly Gly Gly Glu
1               5
```

```
<210> SEQ ID NO 268
<211> LENGTH: 4
<212> TYPE: PRT
<213> ORGANISM: Neisseria meningitidis

<400> SEQUENCE: 268

Thr Thr Asn Lys
1

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272
<211> LENGTH: 8
<212> TYPE: PRT
<213> ORGANISM: Neisseria meningitidis

<400> SEQUENCE: 272

Ser Arg Ile Asp Val Glu Leu Gly
1               5

<210> SEQ ID NO 273
<211> LENGTH: 19
<212> TYPE: PRT
<213> ORGANISM: Neisseria meningitidis

<400> SEQUENCE: 273

Glu His Arg Arg Val Gly Asp Thr Val Ala Arg Val Arg Glu Leu Glu
1               5                   10                  15

Gln Ile Arg

<210> SEQ ID NO 274
<211> LENGTH: 15
<212> TYPE: PRT
<213> ORGANISM: Neisseria meningitidis

<400> SEQUENCE: 274

Leu Arg Thr Arg Leu Asn Asp Lys Phe Ala Arg Asn Ala Asp Asn
1               5                   10                  15

<210> SEQ ID NO 275
<211> LENGTH: 5
<212> TYPE: PRT
<213> ORGANISM: Neisseria meningitidis

<400> SEQUENCE: 275

Gln Arg Trp Asp Asn
1               5
```

```
<210> SEQ ID NO 276

<400> SEQUENCE: 276

000

<210> SEQ ID NO 277

<400> SEQUENCE: 277

000

<210> SEQ ID NO 278
<211> LENGTH: 4
<212> TYPE: PRT
<213> ORGANISM: Neisseria meningitidis

<400> SEQUENCE: 278

Arg Leu Gly Asp
1

<210> SEQ ID NO 279
<211> LENGTH: 6
<212> TYPE: PRT
<213> ORGANISM: Neisseria meningitidis

<400> SEQUENCE: 279

Pro Thr Glu Asn Ala Ser
1               5

<210> SEQ ID NO 280
<211> LENGTH: 5
<212> TYPE: PRT
<213> ORGANISM: Neisseria meningitidis

<400> SEQUENCE: 280

Pro Asp Ile Arg Gly
1               5

<210> SEQ ID NO 281
<211> LENGTH: 12
<212> TYPE: PRT
<213> ORGANISM: Neisseria meningitidis

<400> SEQUENCE: 281

Val Asp Phe Arg Tyr Lys Ala Asp Gly Arg Leu Ile
1               5                   10

<210> SEQ ID NO 282
<211> LENGTH: 9
<212> TYPE: PRT
<213> ORGANISM: Neisseria meningitidis

<400> SEQUENCE: 282

Leu Asn Leu Arg Ile Arg Ala Gly Glu
1               5

<210> SEQ ID NO 283
<211> LENGTH: 9
<212> TYPE: PRT
<213> ORGANISM: Neisseria meningitidis

<400> SEQUENCE: 283

Arg Ser Gly Ser Gly Lys Ser Thr Leu
1               5
```

```
<210> SEQ ID NO 284
<211> LENGTH: 7
<212> TYPE: PRT
<213> ORGANISM: Neisseria meningitidis

<400> SEQUENCE: 284

Val Leu Val Asp Gly Asn Asp
1               5

<210> SEQ ID NO 285
<211> LENGTH: 8
<212> TYPE: PRT
<213> ORGANISM: Neisseria meningitidis

<400> SEQUENCE: 285

Arg Ser Ile Arg Asp Asn Ile Ala
1               5

<210> SEQ ID NO 286

<400> SEQUENCE: 286

000

<210> SEQ ID NO 287
<211> LENGTH: 4
<212> TYPE: PRT
<213> ORGANISM: Neisseria meningitidis

<400> SEQUENCE: 287

Arg Ile Ile Glu
1

<210> SEQ ID NO 288

<400> SEQUENCE: 288

000

<210> SEQ ID NO 289

<400> SEQUENCE: 289

000

<210> SEQ ID NO 290
<211> LENGTH: 9
<212> TYPE: PRT
<213> ORGANISM: Neisseria meningitidis

<400> SEQUENCE: 290

Gly Gly Gln Arg Gln Arg Ile Ala Ile
1               5

<210> SEQ ID NO 291
<211> LENGTH: 4
<212> TYPE: PRT
<213> ORGANISM: Neisseria meningitidis

<400> SEQUENCE: 291

Glu Ala Thr Ser
1
```

```
<210> SEQ ID NO 292
<211> LENGTH: 9
<212> TYPE: PRT
<213> ORGANISM: Neisseria meningitidis

<400> SEQUENCE: 292

Leu Asp Tyr Glu Ser Glu Arg Ala Ile
1               5

<210> SEQ ID NO 293

<400> SEQUENCE: 293

000

<210> SEQ ID NO 294
<211> LENGTH: 10
<212> TYPE: PRT
<213> ORGANISM: Neisseria meningitidis

<400> SEQUENCE: 294

Ile Ala Met Asp Lys Gly Arg Ile Val Glu
1               5                   10

<210> SEQ ID NO 295

<400> SEQUENCE: 295

000

<210> SEQ ID NO 296

<400> SEQUENCE: 296

000

<210> SEQ ID NO 297
<211> LENGTH: 9
<212> TYPE: PRT
<213> ORGANISM: Neisseria meningitidis

<400> SEQUENCE: 297

Arg Ile Ile Trp Asn Ser Ala Leu Asn
1               5

<210> SEQ ID NO 298
<211> LENGTH: 4
<212> TYPE: PRT
<213> ORGANISM: Neisseria meningitidis

<400> SEQUENCE: 298

Trp Val Val Val
1

<210> SEQ ID NO 299
<211> LENGTH: 6
<212> TYPE: PRT
<213> ORGANISM: Neisseria meningitidis

<400> SEQUENCE: 299

Leu Thr Arg Asn His Thr
1               5
```

<210> SEQ ID NO 300
<211> LENGTH: 4
<212> TYPE: PRT
<213> ORGANISM: Neisseria meningitidis

<400> SEQUENCE: 300

Ala Ser Ala Thr
1

<210> SEQ ID NO 301
<211> LENGTH: 4
<212> TYPE: PRT
<213> ORGANISM: Neisseria meningitidis

<400> SEQUENCE: 301

Thr Leu Leu Phe
1

<210> SEQ ID NO 302
<211> LENGTH: 7
<212> TYPE: PRT
<213> ORGANISM: Neisseria meningitidis

<400> SEQUENCE: 302

Leu Asp Pro Val Gln Arg Thr
1               5

<210> SEQ ID NO 303
<211> LENGTH: 11
<212> TYPE: PRT
<213> ORGANISM: Neisseria meningitidis

<400> SEQUENCE: 303

Leu Lys Lys Asp Leu Thr Asp Leu Thr Ser Val
1               5                   10

<210> SEQ ID NO 304
<211> LENGTH: 5
<212> TYPE: PRT
<213> ORGANISM: Neisseria meningitidis

<400> SEQUENCE: 304

Gly Leu Asn Phe Ala
1               5

<210> SEQ ID NO 305
<211> LENGTH: 11
<212> TYPE: PRT
<213> ORGANISM: Neisseria meningitidis

<400> SEQUENCE: 305

Gly Ile Gly Ser Thr Leu Thr Asp Thr Leu Leu
1               5                   10

<210> SEQ ID NO 306
<211> LENGTH: 4
<212> TYPE: PRT
<213> ORGANISM: Neisseria meningitidis

<400> SEQUENCE: 306

Val Thr Asn Asp
1

```
<210> SEQ ID NO 307
<211> LENGTH: 6
<212> TYPE: PRT
<213> ORGANISM: Neisseria meningitidis

<400> SEQUENCE: 307

Val Lys Asp Val Leu Asn
1               5

<210> SEQ ID NO 308
<211> LENGTH: 13
<212> TYPE: PRT
<213> ORGANISM: Neisseria meningitidis

<400> SEQUENCE: 308

Asn Val Asp Phe Val Arg Thr Tyr Asp Thr Val Glu Phe
1               5                   10

<210> SEQ ID NO 309
<211> LENGTH: 5
<212> TYPE: PRT
<213> ORGANISM: Neisseria meningitidis

<400> SEQUENCE: 309

Gly Ser Ser Thr Asp
1               5

<210> SEQ ID NO 310
<211> LENGTH: 6
<212> TYPE: PRT
<213> ORGANISM: Neisseria meningitidis

<400> SEQUENCE: 310

Val Ile Asp Ala Val Asn
1               5

<210> SEQ ID NO 311
<211> LENGTH: 8
<212> TYPE: PRT
<213> ORGANISM: Neisseria meningitidis

<400> SEQUENCE: 311

Gln Ala Asp Lys Phe Glu Thr Val
1               5

<210> SEQ ID NO 312
<211> LENGTH: 8
<212> TYPE: PRT
<213> ORGANISM: Neisseria meningitidis

<400> SEQUENCE: 312

Val Gly Asp Ala Leu Asn Val Asn
1               5

<210> SEQ ID NO 313
<211> LENGTH: 4
<212> TYPE: PRT
<213> ORGANISM: Neisseria meningitidis

<400> SEQUENCE: 313

Gly Ser Ser Gly
1
```

```
<210> SEQ ID NO 314

<400> SEQUENCE: 314

000

<210> SEQ ID NO 315
<211> LENGTH: 4
<212> TYPE: PRT
<213> ORGANISM: Neisseria meningitidis

<400> SEQUENCE: 315

Ile Thr Arg Asn
1

<210> SEQ ID NO 316

<400> SEQUENCE: 316

000

<210> SEQ ID NO 317
<211> LENGTH: 4
<212> TYPE: PRT
<213> ORGANISM: Neisseria meningitidis

<400> SEQUENCE: 317

Val Arg Ile Thr
1

<210> SEQ ID NO 318
<211> LENGTH: 21
<212> TYPE: PRT
<213> ORGANISM: Neisseria meningitidis

<400> SEQUENCE: 318

Gly Asp Val Thr Asn Val Ala Gln Leu Lys Gly Val Ala Gln Asn Leu
1               5                   10                  15

Asn Asn Arg Ile Asp
            20

<210> SEQ ID NO 319

<400> SEQUENCE: 319

000

<210> SEQ ID NO 320
<211> LENGTH: 4
<212> TYPE: PRT
<213> ORGANISM: Neisseria meningitidis

<400> SEQUENCE: 320

Ser Ile Ser Asp
1

<210> SEQ ID NO 321
<211> LENGTH: 12
<212> TYPE: PRT
<213> ORGANISM: Neisseria meningitidis

<400> SEQUENCE: 321

Glu Leu Thr Arg Asn His Thr Lys Arg Ala Ser Ala
1               5                   10
```

```
<210> SEQ ID NO 322
<211> LENGTH: 13
<212> TYPE: PRT
<213> ORGANISM: Neisseria meningitidis

<400> SEQUENCE: 322

Ala Ser Ala Asn Asn Glu Glu Gln Glu Glu Asp Leu Tyr
1               5                   10

<210> SEQ ID NO 323

<400> SEQUENCE: 323

000

<210> SEQ ID NO 324
<211> LENGTH: 19
<212> TYPE: PRT
<213> ORGANISM: Neisseria meningitidis

<400> SEQUENCE: 324

Val Asn Ser Asp Lys Glu Gly Thr Gly Glu Lys Glu Lys Val Glu Glu
1               5                   10                  15

Asn Ser Asp

<210> SEQ ID NO 325
<211> LENGTH: 26
<212> TYPE: PRT
<213> ORGANISM: Neisseria meningitidis

<400> SEQUENCE: 325

Asn Glu Lys Gly Val Leu Thr Ala Arg Glu Ile Thr Leu Lys Ala Gly
1               5                   10                  15

Asp Asn Leu Lys Ile Lys Gln Asn Gly Thr
            20                  25

<210> SEQ ID NO 326
<211> LENGTH: 7
<212> TYPE: PRT
<213> ORGANISM: Neisseria meningitidis

<400> SEQUENCE: 326

Leu Lys Lys Asp Leu Thr Asp
1               5

<210> SEQ ID NO 327
<211> LENGTH: 39
<212> TYPE: PRT
<213> ORGANISM: Neisseria meningitidis

<400> SEQUENCE: 327

Ser Val Gly Thr Glu Lys Leu Ser Phe Ser Ala Asn Gly Asn Lys Val
1               5                   10                  15

Asn Ile Thr Ser Asp Thr Lys Gly Leu Asn Phe Ala Lys Glu Thr Ala
            20                  25                  30

Gly Thr Asn Gly Asp Thr Thr
        35

<210> SEQ ID NO 328

<400> SEQUENCE: 328

000
```

```
<210> SEQ ID NO 329
<211> LENGTH: 21
<212> TYPE: PRT
<213> ORGANISM: Neisseria meningitidis

<400> SEQUENCE: 329

Val Thr Asn Asp Asn Val Thr Asp Asp Glu Lys Lys Arg Ala Ala Ser
1               5                   10                  15

Val Lys Asp Val Leu
            20

<210> SEQ ID NO 330
<211> LENGTH: 15
<212> TYPE: PRT
<213> ORGANISM: Neisseria meningitidis

<400> SEQUENCE: 330

Lys Gly Val Lys Pro Gly Thr Thr Ala Ser Asp Asn Val Asp Phe
1               5                   10                  15

<210> SEQ ID NO 331
<211> LENGTH: 4
<212> TYPE: PRT
<213> ORGANISM: Neisseria meningitidis

<400> SEQUENCE: 331

Arg Thr Tyr Asp
1

<210> SEQ ID NO 332
<211> LENGTH: 7
<212> TYPE: PRT
<213> ORGANISM: Neisseria meningitidis

<400> SEQUENCE: 332

Ser Ala Asp Thr Lys Thr Thr
1               5

<210> SEQ ID NO 333
<211> LENGTH: 16
<212> TYPE: PRT
<213> ORGANISM: Neisseria meningitidis

<400> SEQUENCE: 333

Val Glu Ser Lys Asp Asn Gly Lys Lys Thr Glu Val Lys Ile Gly Ala
1               5                   10                  15

<210> SEQ ID NO 334
<211> LENGTH: 28
<212> TYPE: PRT
<213> ORGANISM: Neisseria meningitidis

<400> SEQUENCE: 334

Ser Val Ile Lys Glu Lys Asp Gly Lys Leu Val Thr Gly Lys Asp Lys
1               5                   10                  15

Gly Glu Asn Gly Ser Ser Thr Asp Glu Gly Glu Gly
            20                  25

<210> SEQ ID NO 335
<211> LENGTH: 39
<212> TYPE: PRT
<213> ORGANISM: Neisseria meningitidis
```

```
<400> SEQUENCE: 335

Val Thr Ala Lys Glu Val Ile Asp Ala Val Asn Lys Ala Gly Trp Arg
1               5                   10                  15

Met Lys Thr Thr Thr Ala Asn Gly Gln Thr Gly Gln Ala Asp Lys Phe
            20                  25                  30

Glu Thr Val Thr Ser Gly Thr
            35

<210> SEQ ID NO 336
<211> LENGTH: 16
<212> TYPE: PRT
<213> ORGANISM: Neisseria meningitidis

<400> SEQUENCE: 336

Ser Gly Lys Gly Thr Thr Ala Thr Val Ser Lys Asp Asp Gln Gly Asn
1               5                   10                  15

<210> SEQ ID NO 337
<211> LENGTH: 4
<212> TYPE: PRT
<213> ORGANISM: Neisseria meningitidis

<400> SEQUENCE: 337

Asn Val Gly Asp
1

<210> SEQ ID NO 338
<211> LENGTH: 23
<212> TYPE: PRT
<213> ORGANISM: Neisseria meningitidis

<400> SEQUENCE: 338

Gln Leu Gln Asn Ser Gly Trp Asn Leu Asp Ser Lys Ala Val Ala Gly
1               5                   10                  15

Ser Ser Gly Lys Val Ile Ser
            20

<210> SEQ ID NO 339
<211> LENGTH: 13
<212> TYPE: PRT
<213> ORGANISM: Neisseria meningitidis

<400> SEQUENCE: 339

Asn Val Ser Pro Ser Lys Gly Lys Met Asp Glu Thr Val
1               5                   10

<210> SEQ ID NO 340
<211> LENGTH: 4
<212> TYPE: PRT
<213> ORGANISM: Neisseria meningitidis

<400> SEQUENCE: 340

Asn Ala Gly Asn
1

<210> SEQ ID NO 341
<211> LENGTH: 11
<212> TYPE: PRT
<213> ORGANISM: Neisseria meningitidis

<400> SEQUENCE: 341

Ile Glu Ile Thr Arg Asn Gly Lys Asn Ile Asp
1               5                   10
```

```
<210> SEQ ID NO 342
<211> LENGTH: 7
<212> TYPE: PRT
<213> ORGANISM: Neisseria meningitidis

<400> SEQUENCE: 342

Gly Ala Gly Ala Asp Ala Pro
1               5

<210> SEQ ID NO 343
<211> LENGTH: 20
<212> TYPE: PRT
<213> ORGANISM: Neisseria meningitidis

<400> SEQUENCE: 343

Ser Val Asp Gly Asp Ala Leu Asn Val Gly Ser Lys Lys Asp Asn Lys
1               5                   10                  15

Pro Val Arg Ile
            20

<210> SEQ ID NO 344
<211> LENGTH: 10
<212> TYPE: PRT
<213> ORGANISM: Neisseria meningitidis

<400> SEQUENCE: 344

Ala Pro Gly Val Lys Glu Gly Asp Val Thr
1               5                   10

<210> SEQ ID NO 345
<211> LENGTH: 13
<212> TYPE: PRT
<213> ORGANISM: Neisseria meningitidis

<400> SEQUENCE: 345

Leu Asn Asn Arg Ile Asp Asn Val Asp Gly Asn Ala Arg
1               5                   10

<210> SEQ ID NO 346
<211> LENGTH: 5
<212> TYPE: PRT
<213> ORGANISM: Neisseria meningitidis

<400> SEQUENCE: 346

Leu Pro Gly Lys Ser
1               5

<210> SEQ ID NO 347
<211> LENGTH: 9
<212> TYPE: PRT
<213> ORGANISM: Neisseria meningitidis

<400> SEQUENCE: 347

Gly Gly Gly Thr Tyr Arg Gly Glu Ala
1               5

<210> SEQ ID NO 348
<211> LENGTH: 8
<212> TYPE: PRT
<213> ORGANISM: Neisseria meningitidis

<400> SEQUENCE: 348

Ser Ser Ile Ser Asp Gly Gly Asn
1               5
```

<210> SEQ ID NO 349
<211> LENGTH: 12
<212> TYPE: PRT
<213> ORGANISM: Neisseria meningitidis

<400> SEQUENCE: 349

Gly Thr Ala Ser Gly Asn Ser Arg Gly His Phe Gly
1               5                   10

<210> SEQ ID NO 350
<211> LENGTH: 12
<212> TYPE: PRT
<213> ORGANISM: Neisseria meningitidis

<400> SEQUENCE: 350

Glu Leu Thr Arg Asn His Thr Lys Arg Ala Ser Ala
1               5                   10

<210> SEQ ID NO 351
<211> LENGTH: 11
<212> TYPE: PRT
<213> ORGANISM: Neisseria meningitidis

<400> SEQUENCE: 351

Ala Asn Asn Glu Glu Gln Glu Glu Asp Leu Tyr
1               5                   10

<210> SEQ ID NO 352

<400> SEQUENCE: 352

000

<210> SEQ ID NO 353
<211> LENGTH: 18
<212> TYPE: PRT
<213> ORGANISM: Neisseria meningitidis

<400> SEQUENCE: 353

Asn Ser Asp Lys Glu Gly Thr Gly Glu Lys Glu Lys Val Glu Glu Asn
1               5                   10                  15

Ser Asp

<210> SEQ ID NO 354
<211> LENGTH: 23
<212> TYPE: PRT
<213> ORGANISM: Neisseria meningitidis

<400> SEQUENCE: 354

Lys Gly Val Leu Thr Ala Arg Glu Ile Thr Leu Lys Ala Gly Asp Asn
1               5                   10                  15

Leu Lys Ile Lys Gln Asn Gly
            20

<210> SEQ ID NO 355
<211> LENGTH: 7
<212> TYPE: PRT
<213> ORGANISM: Neisseria meningitidis

<400> SEQUENCE: 355

Leu Lys Lys Asp Leu Thr Asp
1               5

```
<210> SEQ ID NO 356
<211> LENGTH: 6
<212> TYPE: PRT
<213> ORGANISM: Neisseria meningitidis

<400> SEQUENCE: 356

Gly Thr Glu Lys Leu Ser
1               5

<210> SEQ ID NO 357
<211> LENGTH: 4
<212> TYPE: PRT
<213> ORGANISM: Neisseria meningitidis

<400> SEQUENCE: 357

Asn Gly Asn Lys
1

<210> SEQ ID NO 358
<211> LENGTH: 5
<212> TYPE: PRT
<213> ORGANISM: Neisseria meningitidis

<400> SEQUENCE: 358

Ser Asp Thr Lys Gly
1               5

<210> SEQ ID NO 359
<211> LENGTH: 13
<212> TYPE: PRT
<213> ORGANISM: Neisseria meningitidis

<400> SEQUENCE: 359

Asn Phe Ala Lys Glu Thr Ala Gly Thr Asn Gly Asp Thr
1               5                   10

<210> SEQ ID NO 360

<400> SEQUENCE: 360

000

<210> SEQ ID NO 361
<211> LENGTH: 17
<212> TYPE: PRT
<213> ORGANISM: Neisseria meningitidis

<400> SEQUENCE: 361

Asn Val Thr Asp Asp Glu Lys Lys Arg Ala Ala Ser Val Lys Asp Val
1               5                   10                  15

Leu

<210> SEQ ID NO 362
<211> LENGTH: 14
<212> TYPE: PRT
<213> ORGANISM: Neisseria meningitidis

<400> SEQUENCE: 362

Gly Val Lys Pro Gly Thr Thr Ala Ser Asp Asn Val Asp Phe
1               5                   10

<210> SEQ ID NO 363
<211> LENGTH: 7
<212> TYPE: PRT
<213> ORGANISM: Neisseria meningitidis
```

-continued

```
<400> SEQUENCE: 363

Ser Ala Asp Thr Lys Thr Thr
1               5

<210> SEQ ID NO 364
<211> LENGTH: 16
<212> TYPE: PRT
<213> ORGANISM: Neisseria meningitidis

<400> SEQUENCE: 364

Val Glu Ser Lys Asp Asn Gly Lys Lys Thr Glu Val Lys Ile Gly Ala
1               5                   10                  15

<210> SEQ ID NO 365
<211> LENGTH: 28
<212> TYPE: PRT
<213> ORGANISM: Neisseria meningitidis

<400> SEQUENCE: 365

Ser Val Ile Lys Glu Lys Asp Gly Lys Leu Val Thr Gly Lys Asp Lys
1               5                   10                  15

Gly Glu Asn Gly Ser Ser Thr Asp Glu Gly Glu Gly
            20                  25

<210> SEQ ID NO 366
<211> LENGTH: 11
<212> TYPE: PRT
<213> ORGANISM: Neisseria meningitidis

<400> SEQUENCE: 366

Val Thr Ala Lys Glu Val Ile Asp Ala Val Asn
1               5                   10

<210> SEQ ID NO 367
<211> LENGTH: 9
<212> TYPE: PRT
<213> ORGANISM: Neisseria meningitidis

<400> SEQUENCE: 367

Ala Gly Trp Arg Met Lys Thr Thr Thr
1               5

<210> SEQ ID NO 368
<211> LENGTH: 8
<212> TYPE: PRT
<213> ORGANISM: Neisseria meningitidis

<400> SEQUENCE: 368

Gly Gln Ala Asp Lys Phe Glu Thr
1               5

<210> SEQ ID NO 369

<400> SEQUENCE: 369

000

<210> SEQ ID NO 370
<211> LENGTH: 8
<212> TYPE: PRT
<213> ORGANISM: Neisseria meningitidis
```

```
<400> SEQUENCE: 370

Thr Val Ser Lys Asp Asp Gln Gly
1               5

<210> SEQ ID NO 371
<211> LENGTH: 7
<212> TYPE: PRT
<213> ORGANISM: Neisseria meningitidis

<400> SEQUENCE: 371

Leu Asp Ser Lys Ala Val Ala
1               5

<210> SEQ ID NO 372
<211> LENGTH: 6
<212> TYPE: PRT
<213> ORGANISM: Neisseria meningitidis

<400> SEQUENCE: 372

Ser Ser Gly Lys Val Ile
1               5

<210> SEQ ID NO 373
<211> LENGTH: 11
<212> TYPE: PRT
<213> ORGANISM: Neisseria meningitidis

<400> SEQUENCE: 373

Ser Pro Ser Lys Gly Lys Met Asp Glu Thr Val
1               5                   10

<210> SEQ ID NO 374
<211> LENGTH: 10
<212> TYPE: PRT
<213> ORGANISM: Neisseria meningitidis

<400> SEQUENCE: 374

Glu Ile Thr Arg Asn Gly Lys Asn Ile Asp
1               5                   10

<210> SEQ ID NO 375
<211> LENGTH: 5
<212> TYPE: PRT
<213> ORGANISM: Neisseria meningitidis

<400> SEQUENCE: 375

Val Asp Gly Asp Ala
1               5

<210> SEQ ID NO 376
<211> LENGTH: 10
<212> TYPE: PRT
<213> ORGANISM: Neisseria meningitidis

<400> SEQUENCE: 376

Gly Ser Lys Lys Asp Asn Lys Pro Val Arg
1               5                   10

<210> SEQ ID NO 377
<211> LENGTH: 7
<212> TYPE: PRT
<213> ORGANISM: Neisseria meningitidis
```

```
<400> SEQUENCE: 377

Gly Val Lys Glu Gly Asp Val
1               5

<210> SEQ ID NO 378
<211> LENGTH: 13
<212> TYPE: PRT
<213> ORGANISM: Neisseria meningitidis

<400> SEQUENCE: 378

Leu Asn Asn Arg Ile Asp Asn Val Asp Gly Asn Ala Arg
1               5                   10

<210> SEQ ID NO 379
<211> LENGTH: 6
<212> TYPE: PRT
<213> ORGANISM: Neisseria meningitidis

<400> SEQUENCE: 379

Thr Tyr Arg Gly Glu Ala
1               5

<210> SEQ ID NO 380
<211> LENGTH: 5
<212> TYPE: PRT
<213> ORGANISM: Neisseria meningitidis

<400> SEQUENCE: 380

Gly Asn Ser Arg Gly
1               5

<210> SEQ ID NO 381
<211> LENGTH: 5
<212> TYPE: PRT
<213> ORGANISM: Neisseria meningitidis

<400> SEQUENCE: 381

Arg Ile Ile Trp Asn
1               5

<210> SEQ ID NO 382
<211> LENGTH: 9
<212> TYPE: PRT
<213> ORGANISM: Neisseria meningitidis

<400> SEQUENCE: 382

Val Ser Glu Leu Thr Arg Asn His Thr
1               5

<210> SEQ ID NO 383
<211> LENGTH: 4
<212> TYPE: PRT
<213> ORGANISM: Neisseria meningitidis

<400> SEQUENCE: 383

Ala Ser Ala Thr
1

<210> SEQ ID NO 384
<211> LENGTH: 4
<212> TYPE: PRT
<213> ORGANISM: Neisseria meningitidis
```

```
<400> SEQUENCE: 384

Thr Leu Leu Phe
1

<210> SEQ ID NO 385
<211> LENGTH: 12
<212> TYPE: PRT
<213> ORGANISM: Neisseria meningitidis

<400> SEQUENCE: 385

Glu Ser Val Gln Arg Ser Val Val Gly Ser Ile Gln
1               5                   10

<210> SEQ ID NO 386
<211> LENGTH: 4
<212> TYPE: PRT
<213> ORGANISM: Neisseria meningitidis

<400> SEQUENCE: 386

Ser Gly Glu Leu
1

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390
<211> LENGTH: 5
<212> TYPE: PRT
<213> ORGANISM: Neisseria meningitidis

<400> SEQUENCE: 390

Gly Leu Asn Phe Ala
1               5

<210> SEQ ID NO 391
<211> LENGTH: 13
<212> TYPE: PRT
<213> ORGANISM: Neisseria meningitidis

<400> SEQUENCE: 391

Gly Ile Gly Ser Thr Leu Thr Asp Thr Leu Ala Gly Ser
1               5                   10

<210> SEQ ID NO 392

<400> SEQUENCE: 392

000
```

```
<210> SEQ ID NO 393
<211> LENGTH: 8
<212> TYPE: PRT
<213> ORGANISM: Neisseria meningitidis

<400> SEQUENCE: 393

Ser Thr His Tyr Thr Arg Ala Ala
1               5

<210> SEQ ID NO 394
<211> LENGTH: 6
<212> TYPE: PRT
<213> ORGANISM: Neisseria meningitidis

<400> SEQUENCE: 394

Ile Lys Asp Val Leu Asn
1               5

<210> SEQ ID NO 395

<400> SEQUENCE: 395

000

<210> SEQ ID NO 396
<211> LENGTH: 13
<212> TYPE: PRT
<213> ORGANISM: Neisseria meningitidis

<400> SEQUENCE: 396

Asn Val Asp Phe Val Arg Thr Tyr Asp Thr Val Glu Phe
1               5                   10

<210> SEQ ID NO 397
<211> LENGTH: 5
<212> TYPE: PRT
<213> ORGANISM: Neisseria meningitidis

<400> SEQUENCE: 397

Gly Ser Ser Thr Asp
1               5

<210> SEQ ID NO 398
<211> LENGTH: 6
<212> TYPE: PRT
<213> ORGANISM: Neisseria meningitidis

<400> SEQUENCE: 398

Val Ile Asp Ala Val Asn
1               5

<210> SEQ ID NO 399
<211> LENGTH: 8
<212> TYPE: PRT
<213> ORGANISM: Neisseria meningitidis

<400> SEQUENCE: 399

Gln Ala Asp Lys Phe Glu Thr Val
1               5

<210> SEQ ID NO 400
<211> LENGTH: 8
<212> TYPE: PRT
<213> ORGANISM: Neisseria meningitidis
```

```
<400> SEQUENCE: 400

Val Gly Asp Ala Leu Asn Val Asn
1               5

<210> SEQ ID NO 401
<211> LENGTH: 4
<212> TYPE: PRT
<213> ORGANISM: Neisseria meningitidis

<400> SEQUENCE: 401

Gly Ser Ser Gly
1

<210> SEQ ID NO 402

<400> SEQUENCE: 402

000

<210> SEQ ID NO 403

<400> SEQUENCE: 403

000

<210> SEQ ID NO 404
<211> LENGTH: 9
<212> TYPE: PRT
<213> ORGANISM: Neisseria meningitidis

<400> SEQUENCE: 404

Asp Ala Asn Lys Pro Val Arg Ile Thr
1               5

<210> SEQ ID NO 405
<211> LENGTH: 21
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 405

Gly Asp Val Thr Asn Val Xaa Gln Leu Lys Gly Val Ala Gln Asn Leu
1               5                   10                  15

Asn Asn Arg Ile Asp
            20

<210> SEQ ID NO 406

<400> SEQUENCE: 406

000

<210> SEQ ID NO 407
<211> LENGTH: 4
<212> TYPE: PRT
<213> ORGANISM: Neisseria meningitidis

<400> SEQUENCE: 407

Ser Ile Ser Asp
1
```

```
<210> SEQ ID NO 408
<211> LENGTH: 14
<212> TYPE: PRT
<213> ORGANISM: Neisseria meningitidis

<400> SEQUENCE: 408

Glu Leu Thr Arg Asn His Thr Lys Arg Ala Ser Ala Thr Val
1               5                   10

<210> SEQ ID NO 409
<211> LENGTH: 15
<212> TYPE: PRT
<213> ORGANISM: Neisseria meningitidis

<400> SEQUENCE: 409

Asn Ala Thr Asp Glu Asp Glu Glu Glu Leu Glu Ser Val Gln
1               5                   10              15

<210> SEQ ID NO 410
<211> LENGTH: 9
<212> TYPE: PRT
<213> ORGANISM: Neisseria meningitidis

<400> SEQUENCE: 410

Met Glu Gly Ser Gly Glu Leu Glu Thr
1               5

<210> SEQ ID NO 411
<211> LENGTH: 10
<212> TYPE: PRT
<213> ORGANISM: Neisseria meningitidis

<400> SEQUENCE: 411

Met Thr Asn Asp Ser Lys Glu Phe Val Asp
1               5                   10

<210> SEQ ID NO 412
<211> LENGTH: 18
<212> TYPE: PRT
<213> ORGANISM: Neisseria meningitidis

<400> SEQUENCE: 412

Lys Ala Gly Asp Asn Leu Lys Ile Lys Gln Asn Thr Asn Glu Asn Thr
1               5                   10                  15

Asn Ala

<210> SEQ ID NO 413
<211> LENGTH: 6
<212> TYPE: PRT
<213> ORGANISM: Neisseria meningitidis

<400> SEQUENCE: 413

Leu Lys Lys Asp Leu Thr
1               5

<210> SEQ ID NO 414
<211> LENGTH: 37
<212> TYPE: PRT
<213> ORGANISM: Neisseria meningitidis
<220> FEATURE:
<221> NAME/KEY: Variant
<222> LOCATION: 1
<223> OTHER INFORMATION: Xaa is any amino acid
```

-continued

```
<400> SEQUENCE: 414

Xaa Thr Glu Lys Leu Ser Phe Gly Ala Asn Gly Lys Lys Val Asn Ile
1               5                   10                  15

Ile Ser Asp Thr Lys Gly Leu Asn Phe Ala Lys Glu Thr Ala Gly Thr
            20                  25                  30

Asn Gly Asp Thr Thr
        35

<210> SEQ ID NO 415
<211> LENGTH: 18
<212> TYPE: PRT
<213> ORGANISM: Neisseria meningitidis
<220> FEATURE:
<221> NAME/KEY: Variant
<222> LOCATION: 14
<223> OTHER INFORMATION: Xaa is any amino acid

<400> SEQUENCE: 415

Leu Ala Gly Ser Ser Ala Ser His Val Asp Ala Gly Asn Xaa Ser Thr
1               5                   10                  15

His Tyr

<210> SEQ ID NO 416
<211> LENGTH: 7
<212> TYPE: PRT
<213> ORGANISM: Neisseria meningitidis

<400> SEQUENCE: 416

Ala Ser Ile Lys Asp Val Leu
1               5

<210> SEQ ID NO 417
<211> LENGTH: 17
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid

<400> SEQUENCE: 417

Lys Gly Val Lys Xaa Gly Ser Thr Thr Gly Gln Ser Glu Asn Val Asp
1               5                   10                  15

Phe

<210> SEQ ID NO 418
<211> LENGTH: 4
<212> TYPE: PRT
<213> ORGANISM: Neisseria meningitidis

<400> SEQUENCE: 418

Arg Thr Tyr Asp
1

<210> SEQ ID NO 419
<211> LENGTH: 6
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid
```

<400> SEQUENCE: 419

Leu Ser Ala Asp Thr Xaa
1               5

<210> SEQ ID NO 420
<211> LENGTH: 17
<212> TYPE: PRT
<213> ORGANISM: Neisseria meningitidis

<400> SEQUENCE: 420

Asn Val Glu Ser Lys Asp Asn Gly Lys Arg Thr Glu Val Lys Ile Gly
1               5                   10                  15

Ala

<210> SEQ ID NO 421
<211> LENGTH: 28
<212> TYPE: PRT
<213> ORGANISM: Neisseria meningitidis

<400> SEQUENCE: 421

Ser Val Ile Lys Glu Lys Asp Gly Lys Leu Val Thr Gly Lys Gly Lys
1               5                   10                  15

Gly Glu Asn Gly Ser Ser Thr Asp Glu Gly Glu Gly
            20                  25

<210> SEQ ID NO 422
<211> LENGTH: 39
<212> TYPE: PRT
<213> ORGANISM: Neisseria meningitidis

<400> SEQUENCE: 422

Val Thr Ala Lys Glu Val Ile Asp Ala Val Asn Lys Ala Gly Trp Arg
1               5                   10                  15

Met Lys Thr Thr Thr Ala Asn Gly Gln Thr Gly Gln Ala Asp Lys Phe
            20                  25                  30

Glu Thr Val Thr Ser Gly Thr
        35

<210> SEQ ID NO 423
<211> LENGTH: 16
<212> TYPE: PRT
<213> ORGANISM: Neisseria meningitidis

<400> SEQUENCE: 423

Ser Gly Lys Gly Thr Thr Ala Thr Val Ser Lys Asp Asp Gln Gly Asn
1               5                   10                  15

<210> SEQ ID NO 424
<211> LENGTH: 4
<212> TYPE: PRT
<213> ORGANISM: Neisseria meningitidis

<400> SEQUENCE: 424

Asn Val Gly Asp
1

<210> SEQ ID NO 425
<211> LENGTH: 23
<212> TYPE: PRT
<213> ORGANISM: Neisseria meningitidis

```
<400> SEQUENCE: 425

Gln Leu Gln Asn Ser Gly Trp Asn Leu Asp Ser Lys Ala Val Ala Gly
1               5                   10                  15

Ser Ser Gly Lys Val Ile Ser
            20

<210> SEQ ID NO 426
<211> LENGTH: 13
<212> TYPE: PRT
<213> ORGANISM: Neisseria meningitidis

<400> SEQUENCE: 426

Asn Val Ser Pro Ser Lys Gly Lys Met Asp Glu Thr Val
1               5                   10

<210> SEQ ID NO 427
<211> LENGTH: 16
<212> TYPE: PRT
<213> ORGANISM: Neisseria meningitidis

<400> SEQUENCE: 427

Asn Ala Gly Asn Asn Ile Glu Ile Ser Arg Asn Gly Lys Asn Ile Asp
1               5                   10                  15

<210> SEQ ID NO 428
<211> LENGTH: 16
<212> TYPE: PRT
<213> ORGANISM: Neisseria meningitidis

<400> SEQUENCE: 428

Gly Ala Gly Ala Asp Ala Pro Thr Leu Ser Val Asp Asp Glu Gly Ala
1               5                   10                  15

<210> SEQ ID NO 429
<211> LENGTH: 11
<212> TYPE: PRT
<213> ORGANISM: Neisseria meningitidis

<400> SEQUENCE: 429

Val Gly Ser Lys Asp Ala Asn Lys Pro Val Arg
1               5                   10

<210> SEQ ID NO 430
<211> LENGTH: 7
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid

<400> SEQUENCE: 430

Pro Gly Val Lys Xaa Gly Asp
1               5

<210> SEQ ID NO 431
<211> LENGTH: 13
<212> TYPE: PRT
<213> ORGANISM: Neisseria meningitidis

<400> SEQUENCE: 431

Leu Asn Asn Arg Ile Asp Asn Val Asp Gly Asn Ala Arg
1               5                   10
```

```
<210> SEQ ID NO 432
<211> LENGTH: 5
<212> TYPE: PRT
<213> ORGANISM: Neisseria meningitidis

<400> SEQUENCE: 432

Leu Pro Gly Lys Ser
1               5

<210> SEQ ID NO 433
<211> LENGTH: 9
<212> TYPE: PRT
<213> ORGANISM: Neisseria meningitidis

<400> SEQUENCE: 433

Gly Gly Gly Thr Tyr Arg Gly Glu Ala
1               5

<210> SEQ ID NO 434
<211> LENGTH: 8
<212> TYPE: PRT
<213> ORGANISM: Neisseria meningitidis

<400> SEQUENCE: 434

Ser Ser Ile Ser Asp Gly Gly Asn
1               5

<210> SEQ ID NO 435
<211> LENGTH: 12
<212> TYPE: PRT
<213> ORGANISM: Neisseria meningitidis

<400> SEQUENCE: 435

Gly Thr Ala Ser Gly Asn Ser Arg Gly His Phe Gly
1               5                   10

<210> SEQ ID NO 436
<211> LENGTH: 14
<212> TYPE: PRT
<213> ORGANISM: Neisseria meningitidis

<400> SEQUENCE: 436

Glu Leu Thr Arg Asn His Thr Lys Arg Ala Ser Ala Thr Val
1               5                   10

<210> SEQ ID NO 437
<211> LENGTH: 15
<212> TYPE: PRT
<213> ORGANISM: Neisseria meningitidis

<400> SEQUENCE: 437

Asn Ala Thr Asp Glu Asp Glu Glu Glu Leu Glu Ser Val Gln
1               5                   10                  15

<210> SEQ ID NO 438
<211> LENGTH: 9
<212> TYPE: PRT
<213> ORGANISM: Neisseria meningitidis

<400> SEQUENCE: 438

Met Glu Gly Ser Gly Glu Leu Glu Thr
1               5
```

```
<210> SEQ ID NO 439
<211> LENGTH: 9
<212> TYPE: PRT
<213> ORGANISM: Neisseria meningitidis

<400> SEQUENCE: 439

Met Thr Asn Asp Ser Lys Glu Phe Val
1               5

<210> SEQ ID NO 440
<211> LENGTH: 17
<212> TYPE: PRT
<213> ORGANISM: Neisseria meningitidis

<400> SEQUENCE: 440

Lys Ala Gly Asp Asn Leu Lys Ile Lys Gln Asn Thr Asn Glu Asn Thr
1               5                   10                  15

Asn

<210> SEQ ID NO 441
<211> LENGTH: 6
<212> TYPE: PRT
<213> ORGANISM: Neisseria meningitidis

<400> SEQUENCE: 441

Leu Lys Lys Asp Leu Thr
1               5

<210> SEQ ID NO 442
<211> LENGTH: 6
<212> TYPE: PRT
<213> ORGANISM: Neisseria meningitidis
<220> FEATURE:
<221> NAME/KEY: Variant
<222> LOCATION: 1
<223> OTHER INFORMATION: Xaa is any amino acid

<400> SEQUENCE: 442

Xaa Thr Glu Lys Leu Ser
1               5

<210> SEQ ID NO 443
<211> LENGTH: 8
<212> TYPE: PRT
<213> ORGANISM: Neisseria meningitidis

<400> SEQUENCE: 443

Ala Asn Gly Lys Lys Val Asn Ile
1               5

<210> SEQ ID NO 444
<211> LENGTH: 5
<212> TYPE: PRT
<213> ORGANISM: Neisseria meningitidis

<400> SEQUENCE: 444

Ser Asp Thr Lys Gly
1               5

<210> SEQ ID NO 445
<211> LENGTH: 13
<212> TYPE: PRT
<213> ORGANISM: Neisseria meningitidis
```

```
<400> SEQUENCE: 445

Asn Phe Ala Lys Glu Thr Ala Gly Thr Asn Gly Asp Thr
1               5                   10

<210> SEQ ID NO 446
<211> LENGTH: 7
<212> TYPE: PRT
<213> ORGANISM: Neisseria meningitidis

<400> SEQUENCE: 446

Ser His Val Asp Ala Gly Asn
1               5

<210> SEQ ID NO 447
<211> LENGTH: 7
<212> TYPE: PRT
<213> ORGANISM: Neisseria meningitidis

<400> SEQUENCE: 447

Ala Ser Ile Lys Asp Val Leu
1               5

<210> SEQ ID NO 448
<211> LENGTH: 6
<212> TYPE: PRT
<213> ORGANISM: Neisseria meningitidis
<220> FEATURE:
<221> NAME/KEY: Variant
<222> LOCATION: 4
<223> OTHER INFORMATION: Xaa is any amino acid

<400> SEQUENCE: 448

Gly Val Lys Xaa Gly Ser
1               5

<210> SEQ ID NO 449
<211> LENGTH: 9
<212> TYPE: PRT
<213> ORGANISM: Neisseria meningitidis

<400> SEQUENCE: 449

Thr Gly Gln Ser Glu Asn Val Asp Phe
1               5

<210> SEQ ID NO 450

<400> SEQUENCE: 450

000

<210> SEQ ID NO 451
<211> LENGTH: 16
<212> TYPE: PRT
<213> ORGANISM: Neisseria meningitidis

<400> SEQUENCE: 451

Val Glu Ser Lys Asp Asn Gly Lys Arg Thr Glu Val Lys Ile Gly Ala
1               5                   10                  15

<210> SEQ ID NO 452
<211> LENGTH: 28
<212> TYPE: PRT
<213> ORGANISM: Neisseria meningitidis
```

```
<400> SEQUENCE: 452

Ser Val Ile Lys Glu Lys Asp Gly Lys Leu Val Thr Gly Lys Gly Lys
1               5                   10                  15

Gly Glu Asn Gly Ser Ser Thr Asp Glu Gly Glu Gly
            20                  25

<210> SEQ ID NO 453
<211> LENGTH: 11
<212> TYPE: PRT
<213> ORGANISM: Neisseria meningitidis

<400> SEQUENCE: 453

Val Thr Ala Lys Glu Val Ile Asp Ala Val Asn
1               5                   10

<210> SEQ ID NO 454
<211> LENGTH: 9
<212> TYPE: PRT
<213> ORGANISM: Neisseria meningitidis

<400> SEQUENCE: 454

Ala Gly Trp Arg Met Lys Thr Thr Thr
1               5

<210> SEQ ID NO 455
<211> LENGTH: 8
<212> TYPE: PRT
<213> ORGANISM: Neisseria meningitidis

<400> SEQUENCE: 455

Gly Gln Ala Asp Lys Phe Glu Thr
1               5

<210> SEQ ID NO 456

<400> SEQUENCE: 456

000

<210> SEQ ID NO 457
<211> LENGTH: 8
<212> TYPE: PRT
<213> ORGANISM: Neisseria meningitidis

<400> SEQUENCE: 457

Thr Val Ser Lys Asp Asp Gln Gly
1               5

<210> SEQ ID NO 458
<211> LENGTH: 7
<212> TYPE: PRT
<213> ORGANISM: Neisseria meningitidis

<400> SEQUENCE: 458

Leu Asp Ser Lys Ala Val Ala
1               5

<210> SEQ ID NO 459
<211> LENGTH: 6
<212> TYPE: PRT
<213> ORGANISM: Neisseria meningitidis
```

```
<400> SEQUENCE: 459

Ser Ser Gly Lys Val Ile
1               5

<210> SEQ ID NO 460
<211> LENGTH: 11
<212> TYPE: PRT
<213> ORGANISM: Neisseria meningitidis

<400> SEQUENCE: 460

Ser Pro Ser Lys Gly Lys Met Asp Glu Thr Val
1               5                   10

<210> SEQ ID NO 461
<211> LENGTH: 11
<212> TYPE: PRT
<213> ORGANISM: Neisseria meningitidis

<400> SEQUENCE: 461

Ile Glu Ile Ser Arg Asn Gly Lys Asn Ile Asp
1               5                   10

<210> SEQ ID NO 462
<211> LENGTH: 7
<212> TYPE: PRT
<213> ORGANISM: Neisseria meningitidis

<400> SEQUENCE: 462

Ser Val Asp Asp Glu Gly Ala
1               5

<210> SEQ ID NO 463
<211> LENGTH: 10
<212> TYPE: PRT
<213> ORGANISM: Neisseria meningitidis

<400> SEQUENCE: 463

Gly Ser Lys Asp Ala Asn Lys Pro Val Arg
1               5                   10

<210> SEQ ID NO 464
<211> LENGTH: 5
<212> TYPE: PRT
<213> ORGANISM: Neisseria meningitidis
<220> FEATURE:
<221> NAME/KEY: Variant
<222> LOCATION: 3
<223> OTHER INFORMATION: Xaa is any amino acid

<400> SEQUENCE: 464

Val Lys Xaa Gly Asp
1               5

<210> SEQ ID NO 465
<211> LENGTH: 13
<212> TYPE: PRT
<213> ORGANISM: Neisseria meningitidis

<400> SEQUENCE: 465

Leu Asn Asn Arg Ile Asp Asn Val Asp Gly Asn Ala Arg
1               5                   10
```

```
<210> SEQ ID NO 466
<211> LENGTH: 6
<212> TYPE: PRT
<213> ORGANISM: Neisseria meningitidis

<400> SEQUENCE: 466

Thr Tyr Arg Gly Glu Ala
1               5

<210> SEQ ID NO 467
<211> LENGTH: 5
<212> TYPE: PRT
<213> ORGANISM: Neisseria meningitidis

<400> SEQUENCE: 467

Gly Asn Ser Arg Gly
1               5

<210> SEQ ID NO 468
<211> LENGTH: 7
<212> TYPE: PRT
<213> ORGANISM: Neisseria meningitidis

<400> SEQUENCE: 468

Gln Val Thr Lys Asp Val Asn
1               5

<210> SEQ ID NO 469
<211> LENGTH: 6
<212> TYPE: PRT
<213> ORGANISM: Neisseria meningitidis

<400> SEQUENCE: 469

Phe Ala Ser Leu Ala Ser
1               5

<210> SEQ ID NO 470
<211> LENGTH: 12
<212> TYPE: PRT
<213> ORGANISM: Neisseria meningitidis

<400> SEQUENCE: 470

Ile Gly Asn Thr Leu Lys Glu Leu Gly Arg Ser Ser
1               5                   10

<210> SEQ ID NO 471
<211> LENGTH: 4
<212> TYPE: PRT
<213> ORGANISM: Neisseria meningitidis

<400> SEQUENCE: 471

Asn Leu Met Val
1

<210> SEQ ID NO 472
<211> LENGTH: 8
<212> TYPE: PRT
<213> ORGANISM: Neisseria meningitidis

<400> SEQUENCE: 472

Val Ala Asp Lys Ile Gly Ala Ser
1               5
```

```
<210> SEQ ID NO 473
<211> LENGTH: 6
<212> TYPE: PRT
<213> ORGANISM: Neisseria meningitidis

<400> SEQUENCE: 473

Leu Asn Asn Val Ser Asp
1               5

<210> SEQ ID NO 474

<400> SEQUENCE: 474

000

<210> SEQ ID NO 475
<211> LENGTH: 10
<212> TYPE: PRT
<213> ORGANISM: Neisseria meningitidis

<400> SEQUENCE: 475

Asn Ile Leu Ala Ala Leu Val Asn Thr Ala
1               5                   10

<210> SEQ ID NO 476
<211> LENGTH: 8
<212> TYPE: PRT
<213> ORGANISM: Neisseria meningitidis

<400> SEQUENCE: 476

Ser Lys Ile Lys Gln Leu Asp Gln
1               5

<210> SEQ ID NO 477
<211> LENGTH: 11
<212> TYPE: PRT
<213> ORGANISM: Neisseria meningitidis

<400> SEQUENCE: 477

His Lys Ile Ala His Ala Ile Ala Gly Cys Ala
1               5                   10

<210> SEQ ID NO 478
<211> LENGTH: 12
<212> TYPE: PRT
<213> ORGANISM: Neisseria meningitidis

<400> SEQUENCE: 478

Ala Ile Gly Ala Ala Val Gly Glu Ile Val Gly Glu
1               5                   10

<210> SEQ ID NO 479
<211> LENGTH: 6
<212> TYPE: PRT
<213> ORGANISM: Neisseria meningitidis

<400> SEQUENCE: 479

Thr Asn Gly Lys Asn Pro
1               5

<210> SEQ ID NO 480
<211> LENGTH: 10
<212> TYPE: PRT
<213> ORGANISM: Neisseria meningitidis
```

-continued

```
<400> SEQUENCE: 480

Val Ala Gly Thr Val Ser Gly Val Val Gly
1               5                   10

<210> SEQ ID NO 481
<211> LENGTH: 7
<212> TYPE: PRT
<213> ORGANISM: Neisseria meningitidis

<400> SEQUENCE: 481

Asp Lys Glu Gly Arg Glu Phe
1               5

<210> SEQ ID NO 482
<211> LENGTH: 4
<212> TYPE: PRT
<213> ORGANISM: Neisseria meningitidis

<400> SEQUENCE: 482

Asn Glu Met Thr
1

<210> SEQ ID NO 483
<211> LENGTH: 10
<212> TYPE: PRT
<213> ORGANISM: Neisseria meningitidis

<400> SEQUENCE: 483

Thr Val Lys Lys Tyr Gln Asn Val Ala Asp
1               5                   10

<210> SEQ ID NO 484
<211> LENGTH: 19
<212> TYPE: PRT
<213> ORGANISM: Neisseria meningitidis

<400> SEQUENCE: 484

Ser Ile Ala Ile Cys Thr Asp Ile Ser Arg Ser Thr Glu Cys Arg Thr
1               5                   10                  15

Ile Arg Lys

<210> SEQ ID NO 485
<211> LENGTH: 6
<212> TYPE: PRT
<213> ORGANISM: Neisseria meningitidis

<400> SEQUENCE: 485

His Ser Ser Trp Glu Ala
1               5

<210> SEQ ID NO 486
<211> LENGTH: 8
<212> TYPE: PRT
<213> ORGANISM: Neisseria meningitidis

<400> SEQUENCE: 486

Glu Trp Tyr Lys Leu Phe Ser Lys
1               5

<210> SEQ ID NO 487
<211> LENGTH: 4
<212> TYPE: PRT
<213> ORGANISM: Neisseria meningitidis
```

-continued

```
<400> SEQUENCE: 487

Ala Ala Lys Ser
1

<210> SEQ ID NO 488
<211> LENGTH: 8
<212> TYPE: PRT
<213> ORGANISM: Neisseria meningitidis

<400> SEQUENCE: 488

Thr Lys Pro Leu Ser Glu Trp Met
1               5

<210> SEQ ID NO 489
<211> LENGTH: 6
<212> TYPE: PRT
<213> ORGANISM: Neisseria meningitidis

<400> SEQUENCE: 489

Val Lys Tyr Pro Glu Gly
1               5

<210> SEQ ID NO 490
<211> LENGTH: 5
<212> TYPE: PRT
<213> ORGANISM: Neisseria meningitidis

<400> SEQUENCE: 490

Leu Lys Arg His Leu
1               5

<210> SEQ ID NO 491
<211> LENGTH: 4
<212> TYPE: PRT
<213> ORGANISM: Neisseria meningitidis

<400> SEQUENCE: 491

Ile Lys Gly Ala
1

<210> SEQ ID NO 492
<211> LENGTH: 7
<212> TYPE: PRT
<213> ORGANISM: Neisseria meningitidis

<400> SEQUENCE: 492

Thr Asp Ile Glu Gly Ile Thr
1               5

<210> SEQ ID NO 493
<211> LENGTH: 25
<212> TYPE: PRT
<213> ORGANISM: Neisseria meningitidis

<400> SEQUENCE: 493

Leu Asp Arg Thr Gly Lys Pro Asp Gly Gly Phe Lys Glu Ile Ser Ser
1               5                   10                  15

Ile Lys Thr Val Tyr Asn Pro Lys Lys
            20                  25

<210> SEQ ID NO 494
<211> LENGTH: 16
<212> TYPE: PRT
<213> ORGANISM: Neisseria meningitidis
```

```
<400> SEQUENCE: 494

Ala Ala Ser Gln Gly Tyr Ser Lys Ala Ser Lys Ile Ala Gln Asn Glu
1               5                   10                  15

<210> SEQ ID NO 495
<211> LENGTH: 5
<212> TYPE: PRT
<213> ORGANISM: Neisseria meningitidis

<400> SEQUENCE: 495

Phe Ser Glu Thr Phe
1               5

<210> SEQ ID NO 496
<211> LENGTH: 10
<212> TYPE: PRT
<213> ORGANISM: Neisseria meningitidis

<400> SEQUENCE: 496

Arg Cys Val Arg Ala Glu Asp Thr Pro Tyr
1               5                   10

<210> SEQ ID NO 497
<211> LENGTH: 9
<212> TYPE: PRT
<213> ORGANISM: Neisseria meningitidis

<400> SEQUENCE: 497

Gln Val Thr Lys Asp Val Asn Trp Asn
1               5

<210> SEQ ID NO 498
<211> LENGTH: 13
<212> TYPE: PRT
<213> ORGANISM: Neisseria meningitidis

<400> SEQUENCE: 498

Ala Tyr Asp Lys Trp Asp Tyr Lys Gln Glu Gly Leu Thr
1               5                   10

<210> SEQ ID NO 499

<400> SEQUENCE: 499

000

<210> SEQ ID NO 500

<400> SEQUENCE: 500

000

<210> SEQ ID NO 501
<211> LENGTH: 8
<212> TYPE: PRT
<213> ORGANISM: Neisseria meningitidis

<400> SEQUENCE: 501

Ile Asn Asn Lys Gly Asn Ile Gly
1               5

<210> SEQ ID NO 502
<211> LENGTH: 11
<212> TYPE: PRT
<213> ORGANISM: Neisseria meningitidis
```

```
<400> SEQUENCE: 502

Thr Leu Lys Glu Leu Gly Arg Ser Ser Thr Val
1               5                   10

<210> SEQ ID NO 503
<211> LENGTH: 6
<212> TYPE: PRT
<213> ORGANISM: Neisseria meningitidis

<400> SEQUENCE: 503

Val Ala Asp Lys Ile Gly
1               5

<210> SEQ ID NO 504
<211> LENGTH: 7
<212> TYPE: PRT
<213> ORGANISM: Neisseria meningitidis

<400> SEQUENCE: 504

Asn Val Ser Asp Lys Gln Trp
1               5

<210> SEQ ID NO 505
<211> LENGTH: 4
<212> TYPE: PRT
<213> ORGANISM: Neisseria meningitidis

<400> SEQUENCE: 505

Asn Ala Gly Ser
1

<210> SEQ ID NO 506
<211> LENGTH: 11
<212> TYPE: PRT
<213> ORGANISM: Neisseria meningitidis

<400> SEQUENCE: 506

Val Asn Gly Gly Ser Leu Lys Asp Asn Leu Glu
1               5                   10

<210> SEQ ID NO 507
<211> LENGTH: 13
<212> TYPE: PRT
<213> ORGANISM: Neisseria meningitidis

<400> SEQUENCE: 507

Ala His Gly Glu Ala Ala Ser Lys Ile Lys Gln Leu Asp
1               5                   10

<210> SEQ ID NO 508
<211> LENGTH: 11
<212> TYPE: PRT
<213> ORGANISM: Neisseria meningitidis

<400> SEQUENCE: 508

Ala Ala Asn Lys Gly Lys Cys Gln Asp Gly Ala
1               5                   10

<210> SEQ ID NO 509

<400> SEQUENCE: 509

000
```

<210> SEQ ID NO 510
<211> LENGTH: 17
<212> TYPE: PRT
<213> ORGANISM: Neisseria meningitidis

<400> SEQUENCE: 510

Leu Thr Asn Gly Lys Asn Pro Asp Thr Leu Thr Ala Lys Glu Arg Glu
1               5                   10                  15

Gln

<210> SEQ ID NO 511
<211> LENGTH: 7
<212> TYPE: PRT
<213> ORGANISM: Neisseria meningitidis

<400> SEQUENCE: 511

Val Gly Gly Asp Val Asn Ala
1               5

<210> SEQ ID NO 512
<211> LENGTH: 20
<212> TYPE: PRT
<213> ORGANISM: Neisseria meningitidis

<400> SEQUENCE: 512

Val Ala Val Lys Asn Asn Gln Leu Ser Asp Lys Glu Gly Arg Glu Phe
1               5                   10                  15

Asp Asn Glu Met
            20

<210> SEQ ID NO 513
<211> LENGTH: 26
<212> TYPE: PRT
<213> ORGANISM: Neisseria meningitidis

<400> SEQUENCE: 513

Ala Lys Gln Asn Asn Pro Gln Leu Cys Arg Lys Asn Thr Val Lys Lys
1               5                   10                  15

Tyr Gln Asn Val Ala Asp Lys Arg Leu Ala
            20                  25

<210> SEQ ID NO 514
<211> LENGTH: 26
<212> TYPE: PRT
<213> ORGANISM: Neisseria meningitidis

<400> SEQUENCE: 514

Asp Ile Ser Arg Ser Thr Glu Cys Arg Thr Ile Arg Lys Gln His Leu
1               5                   10                  15

Ile Asp Ser Arg Ser Leu His Ser Ser Trp
            20                  25

<210> SEQ ID NO 515
<211> LENGTH: 8
<212> TYPE: PRT
<213> ORGANISM: Neisseria meningitidis

<400> SEQUENCE: 515

Leu Ile Gly Lys Asp Asp Glu Trp
1               5

```
<210> SEQ ID NO 516
<211> LENGTH: 7
<212> TYPE: PRT
<213> ORGANISM: Neisseria meningitidis

<400> SEQUENCE: 516

Phe Ser Lys Ser Tyr Thr Gln
1               5

<210> SEQ ID NO 517
<211> LENGTH: 10
<212> TYPE: PRT
<213> ORGANISM: Neisseria meningitidis

<400> SEQUENCE: 517

Trp Leu Gln Ser Gly Asn Thr Lys Pro Leu
1               5                   10

<210> SEQ ID NO 518
<211> LENGTH: 6
<212> TYPE: PRT
<213> ORGANISM: Neisseria meningitidis

<400> SEQUENCE: 518

Trp Met Ser Asp Gln Gly
1               5

<210> SEQ ID NO 519
<211> LENGTH: 5
<212> TYPE: PRT
<213> ORGANISM: Neisseria meningitidis

<400> SEQUENCE: 519

Gly Val Asn Pro Arg
1               5

<210> SEQ ID NO 520
<211> LENGTH: 20
<212> TYPE: PRT
<213> ORGANISM: Neisseria meningitidis

<400> SEQUENCE: 520

Arg Gly Phe Val Lys Gln Asn Thr Pro Ile Thr Asn Val Lys Tyr Pro
1               5                   10                  15

Glu Gly Ile Ser
            20

<210> SEQ ID NO 521
<211> LENGTH: 28
<212> TYPE: PRT
<213> ORGANISM: Neisseria meningitidis

<400> SEQUENCE: 521

Thr Asn Leu Lys Arg His Leu Ala Asn Ala Asp Gly Phe Ser Gln Lys
1               5                   10                  15

Gln Gly Ile Lys Gly Ala His Asn Arg Thr Asn Phe
            20                  25

<210> SEQ ID NO 522
<211> LENGTH: 21
<212> TYPE: PRT
<213> ORGANISM: Neisseria meningitidis
```

```
<400> SEQUENCE: 522

Glu Leu Asn Ser Arg Gly Gly Arg Val Lys Ser Glu Thr Gln Thr Asp
1               5                   10                  15

Ile Glu Gly Ile Thr
            20

<210> SEQ ID NO 523

<400> SEQUENCE: 523

000

<210> SEQ ID NO 524
<211> LENGTH: 18
<212> TYPE: PRT
<213> ORGANISM: Neisseria meningitidis

<400> SEQUENCE: 524

Pro Thr Leu Asp Arg Thr Gly Lys Pro Asp Gly Gly Phe Lys Glu Ile
1               5                   10                  15

Ser Ser

<210> SEQ ID NO 525
<211> LENGTH: 12
<212> TYPE: PRT
<213> ORGANISM: Neisseria meningitidis

<400> SEQUENCE: 525

Tyr Asn Pro Lys Lys Phe Ser Asp Asp Lys Ile Leu
1               5                   10

<210> SEQ ID NO 526
<211> LENGTH: 26
<212> TYPE: PRT
<213> ORGANISM: Neisseria meningitidis

<400> SEQUENCE: 526

Ala Ser Gln Gly Tyr Ser Lys Ala Ser Lys Ile Ala Gln Asn Glu Arg
1               5                   10                  15

Thr Lys Ser Ile Ser Glu Arg Lys Asn Val
            20                  25

<210> SEQ ID NO 527
<211> LENGTH: 8
<212> TYPE: PRT
<213> ORGANISM: Neisseria meningitidis

<400> SEQUENCE: 527

Glu Thr Phe Asp Gly Ile Lys Phe
1               5

<210> SEQ ID NO 528
<211> LENGTH: 12
<212> TYPE: PRT
<213> ORGANISM: Neisseria meningitidis

<400> SEQUENCE: 528

Val Asn Thr Gly Arg Ile Thr Asn Ile His Pro Glu
1               5                   10
```

```
<210> SEQ ID NO 529
<211> LENGTH: 8
<212> TYPE: PRT
<213> ORGANISM: Neisseria meningitidis

<400> SEQUENCE: 529

Cys Val Arg Ala Glu Asp Thr Pro
1               5

<210> SEQ ID NO 530
<211> LENGTH: 4
<212> TYPE: PRT
<213> ORGANISM: Neisseria meningitidis

<400> SEQUENCE: 530

Gln Val Thr Lys
1

<210> SEQ ID NO 531
<211> LENGTH: 11
<212> TYPE: PRT
<213> ORGANISM: Neisseria meningitidis

<400> SEQUENCE: 531

Asp Lys Trp Asp Tyr Lys Gln Glu Gly Leu Thr
1               5                   10

<210> SEQ ID NO 532

<400> SEQUENCE: 532

000

<210> SEQ ID NO 533
<211> LENGTH: 6
<212> TYPE: PRT
<213> ORGANISM: Neisseria meningitidis

<400> SEQUENCE: 533

Asn Asn Lys Gly Asn Ile
1               5

<210> SEQ ID NO 534
<211> LENGTH: 7
<212> TYPE: PRT
<213> ORGANISM: Neisseria meningitidis

<400> SEQUENCE: 534

Thr Leu Lys Glu Leu Gly Arg
1               5

<210> SEQ ID NO 535

<400> SEQUENCE: 535

000

<210> SEQ ID NO 536
<211> LENGTH: 6
<212> TYPE: PRT
<213> ORGANISM: Neisseria meningitidis

<400> SEQUENCE: 536

Val Ala Asp Lys Ile Gly
1               5
```

<210> SEQ ID NO 537

<400> SEQUENCE: 537

000

<210> SEQ ID NO 538
<211> LENGTH: 8
<212> TYPE: PRT
<213> ORGANISM: Neisseria meningitidis

<400> SEQUENCE: 538

Gly Ser Leu Lys Asp Asn Leu Glu
1               5

<210> SEQ ID NO 539
<211> LENGTH: 13
<212> TYPE: PRT
<213> ORGANISM: Neisseria meningitidis

<400> SEQUENCE: 539

Ala His Gly Glu Ala Ala Ser Lys Ile Lys Gln Leu Asp
1               5                   10

<210> SEQ ID NO 540
<211> LENGTH: 9
<212> TYPE: PRT
<213> ORGANISM: Neisseria meningitidis

<400> SEQUENCE: 540

Ala Ala Asn Lys Gly Lys Cys Gln Asp
1               5

<210> SEQ ID NO 541
<211> LENGTH: 17
<212> TYPE: PRT
<213> ORGANISM: Neisseria meningitidis

<400> SEQUENCE: 541

Leu Thr Asn Gly Lys Asn Pro Asp Thr Leu Thr Ala Lys Glu Arg Glu
1               5                   10                  15

Gln

<210> SEQ ID NO 542

<400> SEQUENCE: 542

000

<210> SEQ ID NO 543
<211> LENGTH: 4
<212> TYPE: PRT
<213> ORGANISM: Neisseria meningitidis

<400> SEQUENCE: 543

Val Ala Val Lys
1

<210> SEQ ID NO 544
<211> LENGTH: 15
<212> TYPE: PRT
<213> ORGANISM: Neisseria meningitidis

```
<400> SEQUENCE: 544

Asn Gln Leu Ser Asp Lys Glu Gly Arg Glu Phe Asp Asn Glu Met
1               5                   10                  15

<210> SEQ ID NO 545
<211> LENGTH: 5
<212> TYPE: PRT
<213> ORGANISM: Neisseria meningitidis

<400> SEQUENCE: 545

Ala Lys Gln Asn Asn
1               5

<210> SEQ ID NO 546
<211> LENGTH: 20
<212> TYPE: PRT
<213> ORGANISM: Neisseria meningitidis

<400> SEQUENCE: 546

Gln Leu Cys Arg Lys Asn Thr Val Lys Lys Tyr Gln Asn Val Ala Asp
1               5                   10                  15

Lys Arg Leu Ala
            20

<210> SEQ ID NO 547
<211> LENGTH: 22
<212> TYPE: PRT
<213> ORGANISM: Neisseria meningitidis

<400> SEQUENCE: 547

Asp Ile Ser Arg Ser Thr Glu Cys Arg Thr Ile Arg Lys Gln His Leu
1               5                   10                  15

Ile Asp Ser Arg Ser Leu
            20

<210> SEQ ID NO 548
<211> LENGTH: 8
<212> TYPE: PRT
<213> ORGANISM: Neisseria meningitidis

<400> SEQUENCE: 548

Leu Ile Gly Lys Asp Asp Glu Trp
1               5

<210> SEQ ID NO 549
<211> LENGTH: 6
<212> TYPE: PRT
<213> ORGANISM: Neisseria meningitidis

<400> SEQUENCE: 549

Gly Asn Thr Lys Pro Leu
1               5

<210> SEQ ID NO 550

<400> SEQUENCE: 550

000

<210> SEQ ID NO 551

<400> SEQUENCE: 551

000
```

```
<210> SEQ ID NO 552
<211> LENGTH: 4
<212> TYPE: PRT
<213> ORGANISM: Neisseria meningitidis

<400> SEQUENCE: 552

Lys Tyr Pro Glu
1

<210> SEQ ID NO 553
<211> LENGTH: 8
<212> TYPE: PRT
<213> ORGANISM: Neisseria meningitidis

<400> SEQUENCE: 553

Thr Asn Leu Lys Arg His Leu Ala
1               5

<210> SEQ ID NO 554
<211> LENGTH: 4
<212> TYPE: PRT
<213> ORGANISM: Neisseria meningitidis

<400> SEQUENCE: 554

Gly Phe Ser Gln
1

<210> SEQ ID NO 555
<211> LENGTH: 8
<212> TYPE: PRT
<213> ORGANISM: Neisseria meningitidis

<400> SEQUENCE: 555

Gln Gly Ile Lys Gly Ala His Asn
1               5

<210> SEQ ID NO 556
<211> LENGTH: 20
<212> TYPE: PRT
<213> ORGANISM: Neisseria meningitidis

<400> SEQUENCE: 556

Leu Asn Ser Arg Gly Gly Arg Val Lys Ser Glu Thr Gln Thr Asp Ile
1               5                   10                  15

Glu Gly Ile Thr
            20

<210> SEQ ID NO 557

<400> SEQUENCE: 557

000

<210> SEQ ID NO 558
<211> LENGTH: 17
<212> TYPE: PRT
<213> ORGANISM: Neisseria meningitidis

<400> SEQUENCE: 558

Thr Leu Asp Arg Thr Gly Lys Pro Asp Gly Gly Phe Lys Glu Ile Ser
1               5                   10                  15

Ser
```

<210> SEQ ID NO 559
<211> LENGTH: 9
<212> TYPE: PRT
<213> ORGANISM: Neisseria meningitidis

<400> SEQUENCE: 559

Lys Lys Phe Ser Asp Asp Lys Ile Leu
1               5

<210> SEQ ID NO 560
<211> LENGTH: 23
<212> TYPE: PRT
<213> ORGANISM: Neisseria meningitidis

<400> SEQUENCE: 560

Gly Tyr Ser Lys Ala Ser Lys Ile Ala Gln Asn Glu Arg Thr Lys Ser
1               5                   10                  15

Ile Ser Glu Arg Lys Asn Val
            20

<210> SEQ ID NO 561
<211> LENGTH: 4
<212> TYPE: PRT
<213> ORGANISM: Neisseria meningitidis

<400> SEQUENCE: 561

Glu Thr Phe Asp
1

<210> SEQ ID NO 562

<400> SEQUENCE: 562

000

<210> SEQ ID NO 563
<211> LENGTH: 7
<212> TYPE: PRT
<213> ORGANISM: Neisseria meningitidis

<400> SEQUENCE: 563

Gln Val Ala Lys Asn Ile Asn
1               5

<210> SEQ ID NO 564

<400> SEQUENCE: 564

000

<210> SEQ ID NO 565
<211> LENGTH: 6
<212> TYPE: PRT
<213> ORGANISM: Neisseria meningitidis

<400> SEQUENCE: 565

Phe Ala Ser Leu Ala Ser
1               5

<210> SEQ ID NO 566
<211> LENGTH: 13
<212> TYPE: PRT
<213> ORGANISM: Neisseria meningitidis

```
<400> SEQUENCE: 566

Asp Val Gly Lys Thr Leu Lys Glu Leu Gly Arg Ser Ser
1               5                   10

<210> SEQ ID NO 567
<211> LENGTH: 9
<212> TYPE: PRT
<213> ORGANISM: Neisseria meningitidis

<400> SEQUENCE: 567

Gly Val Ala Asp Lys Ile Gly Ala Ser
1               5

<210> SEQ ID NO 568
<211> LENGTH: 6
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 568

Leu Xaa Asn Val Ser Asp
1               5

<210> SEQ ID NO 569

<400> SEQUENCE: 569

000

<210> SEQ ID NO 570
<211> LENGTH: 6
<212> TYPE: PRT
<213> ORGANISM: Neisseria meningitidis
<220> FEATURE:
<221> NAME/KEY: Variant
<222> LOCATION: 4
<223> OTHER INFORMATION: Xaa is any amino acid

<400> SEQUENCE: 570

Leu Lys Asp Xaa Leu Glu
1               5

<210> SEQ ID NO 571
<211> LENGTH: 10
<212> TYPE: PRT
<213> ORGANISM: Neisseria meningitidis

<400> SEQUENCE: 571

Asn Ile Leu Ala Ala Leu Val Asn Thr Ala
1               5                   10

<210> SEQ ID NO 572
<211> LENGTH: 8
<212> TYPE: PRT
<213> ORGANISM: Neisseria meningitidis

<400> SEQUENCE: 572

Ser Lys Ile Lys Gln Leu Asp Gln
1               5
```

```
<210> SEQ ID NO 573
<211> LENGTH: 11
<212> TYPE: PRT
<213> ORGANISM: Neisseria meningitidis

<400> SEQUENCE: 573

His Lys Ile Ala His Ala Ile Ala Gly Cys Ala
1               5                   10

<210> SEQ ID NO 574
<211> LENGTH: 12
<212> TYPE: PRT
<213> ORGANISM: Neisseria meningitidis

<400> SEQUENCE: 574

Ala Ile Gly Ala Ala Val Gly Glu Ile Val Gly Glu
1               5                   10

<210> SEQ ID NO 575
<211> LENGTH: 6
<212> TYPE: PRT
<213> ORGANISM: Neisseria meningitidis

<400> SEQUENCE: 575

Thr Asn Gly Lys Asn Pro
1               5

<210> SEQ ID NO 576
<211> LENGTH: 10
<212> TYPE: PRT
<213> ORGANISM: Neisseria meningitidis

<400> SEQUENCE: 576

Val Ala Gly Thr Val Ser Gly Val Val Gly
1               5                   10

<210> SEQ ID NO 577
<211> LENGTH: 4
<212> TYPE: PRT
<213> ORGANISM: Neisseria meningitidis

<400> SEQUENCE: 577

Asn Glu Met Thr
1

<210> SEQ ID NO 578
<211> LENGTH: 10
<212> TYPE: PRT
<213> ORGANISM: Neisseria meningitidis

<400> SEQUENCE: 578

Thr Val Lys Lys Tyr Gln Asn Val Ala Asp
1               5                   10

<210> SEQ ID NO 579
<211> LENGTH: 19
<212> TYPE: PRT
<213> ORGANISM: Neisseria meningitidis

<400> SEQUENCE: 579

Ser Ile Ala Ile Cys Thr Asp Ile Ser Arg Ser Thr Glu Cys Arg Thr
1               5                   10                  15

Ile Arg Lys
```

```
<210> SEQ ID NO 580
<211> LENGTH: 6
<212> TYPE: PRT
<213> ORGANISM: Neisseria meningitidis

<400> SEQUENCE: 580

His Ser Ser Trp Glu Ala
1               5

<210> SEQ ID NO 581
<211> LENGTH: 8
<212> TYPE: PRT
<213> ORGANISM: Neisseria meningitidis

<400> SEQUENCE: 581

Glu Trp Tyr Lys Leu Phe Ser Lys
1               5

<210> SEQ ID NO 582
<211> LENGTH: 4
<212> TYPE: PRT
<213> ORGANISM: Neisseria meningitidis

<400> SEQUENCE: 582

Ala Ala Lys Ser
1

<210> SEQ ID NO 583
<211> LENGTH: 8
<212> TYPE: PRT
<213> ORGANISM: Neisseria meningitidis

<400> SEQUENCE: 583

Thr Lys Pro Leu Ser Glu Trp Met
1               5

<210> SEQ ID NO 584
<211> LENGTH: 6
<212> TYPE: PRT
<213> ORGANISM: Neisseria meningitidis

<400> SEQUENCE: 584

Val Lys Tyr Pro Glu Gly
1               5

<210> SEQ ID NO 585
<211> LENGTH: 5
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 585

Leu Xaa Arg His Leu
1               5

<210> SEQ ID NO 586
<211> LENGTH: 6
<212> TYPE: PRT
<213> ORGANISM: Neisseria meningitidis

<400> SEQUENCE: 586

Ile Lys Gly Ala His Asn
1               5
```

```
<210> SEQ ID NO 587
<211> LENGTH: 6
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 587

Asn Xaa Met Ala Glu Leu
1               5

<210> SEQ ID NO 588
<211> LENGTH: 7
<212> TYPE: PRT
<213> ORGANISM: Neisseria meningitidis

<400> SEQUENCE: 588

Thr Asp Ile Glu Gly Ile Thr
1               5

<210> SEQ ID NO 589
<211> LENGTH: 23
<212> TYPE: PRT
<213> ORGANISM: Neisseria meningitidis

<400> SEQUENCE: 589

Leu Asp Arg Thr Gly Lys Pro Asp Gly Gly Phe Lys Glu Ile Ser Ser
1               5                   10                  15

Ile Lys Thr Val Tyr Asn Pro
            20

<210> SEQ ID NO 590
<211> LENGTH: 16
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 590

Ala Xaa Ser Gln Gly Tyr Ser Lys Ala Ser Lys Ile Ala Gln Asn Glu
1               5                   10                  15

<210> SEQ ID NO 591
<211> LENGTH: 5
<212> TYPE: PRT
<213> ORGANISM: Neisseria meningitidis

<400> SEQUENCE: 591

Phe Ser Glu Thr Phe
1               5

<210> SEQ ID NO 592
<211> LENGTH: 17
<212> TYPE: PRT
<213> ORGANISM: Neisseria meningitidis
<220> FEATURE:
<221> NAME/KEY: Variant
<222> LOCATION: 3 & 5
<223> OTHER INFORMATION: Xaa is any amino acid
```

```
<400> SEQUENCE: 592

Phe Arg Xaa Tyr Xaa Asp Val Asn Thr Gly Arg Ile Thr Asn Ile His
1               5                   10                  15
Pro

<210> SEQ ID NO 593
<211> LENGTH: 4
<212> TYPE: PRT
<213> ORGANISM: Neisseria meningitidis

<400> SEQUENCE: 593

Asn Ile Asn Trp
1

<210> SEQ ID NO 594
<211> LENGTH: 13
<212> TYPE: PRT
<213> ORGANISM: Neisseria meningitidis

<400> SEQUENCE: 594

Ala Tyr Asp Arg Trp Asp Tyr Lys Gln Glu Gly Leu Thr
1               5                   10

<210> SEQ ID NO 595

<400> SEQUENCE: 595

000

<210> SEQ ID NO 596

<400> SEQUENCE: 596

000

<210> SEQ ID NO 597
<211> LENGTH: 20
<212> TYPE: PRT
<213> ORGANISM: Neisseria meningitidis

<400> SEQUENCE: 597

Asn Asn Lys Gly Asp Val Gly Lys Thr Leu Lys Glu Leu Gly Arg Ser
1               5                   10                  15

Ser Thr Val Lys
            20

<210> SEQ ID NO 598
<211> LENGTH: 6
<212> TYPE: PRT
<213> ORGANISM: Neisseria meningitidis

<400> SEQUENCE: 598

Val Ala Asp Lys Ile Gly
1               5

<210> SEQ ID NO 599
<211> LENGTH: 7
<212> TYPE: PRT
<213> ORGANISM: Neisseria meningitidis

<400> SEQUENCE: 599

Asn Val Ser Asp Lys Gln Trp
1               5
```

```
<210> SEQ ID NO 600
<211> LENGTH: 4
<212> TYPE: PRT
<213> ORGANISM: Neisseria meningitidis

<400> SEQUENCE: 600

Asn Ala Gly Ser
1

<210> SEQ ID NO 601
<211> LENGTH: 11
<212> TYPE: PRT
<213> ORGANISM: Neisseria meningitidis
<220> FEATURE:
<221> NAME/KEY: Variant
<222> LOCATION: 9
<223> OTHER INFORMATION: Xaa is any amino acid

<400> SEQUENCE: 601

Val Asn Gly Gly Ser Leu Lys Asp Xaa Leu Glu
1               5                   10

<210> SEQ ID NO 602
<211> LENGTH: 13
<212> TYPE: PRT
<213> ORGANISM: Neisseria meningitidis

<400> SEQUENCE: 602

Ala His Gly Glu Ala Ala Ser Lys Ile Lys Gln Leu Asp
1               5                   10

<210> SEQ ID NO 603
<211> LENGTH: 11
<212> TYPE: PRT
<213> ORGANISM: Neisseria meningitidis

<400> SEQUENCE: 603

Ala Ala Asn Lys Gly Lys Cys Gln Asp Gly Ala
1               5                   10

<210> SEQ ID NO 604

<400> SEQUENCE: 604

000

<210> SEQ ID NO 605
<211> LENGTH: 17
<212> TYPE: PRT
<213> ORGANISM: Neisseria meningitidis

<400> SEQUENCE: 605

Leu Thr Asn Gly Lys Asn Pro Asp Thr Leu Thr Ala Lys Glu Arg Glu
1               5                   10                  15

Gln

<210> SEQ ID NO 606
<211> LENGTH: 7
<212> TYPE: PRT
<213> ORGANISM: Neisseria meningitidis

<400> SEQUENCE: 606

Val Gly Gly Asp Val Asn Ala
1               5
```

```
<210> SEQ ID NO 607
<211> LENGTH: 20
<212> TYPE: PRT
<213> ORGANISM: Neisseria meningitidis
<220> FEATURE:
<221> NAME/KEY: Variant
<222> LOCATION: 11
<223> OTHER INFORMATION: Xaa is any amino acid

<400> SEQUENCE: 607

Val Ala Val Lys Asn Asn Gln Leu Ser Asp Xaa Glu Gly Arg Glu Phe
1               5                   10                  15

Asp Asn Glu Met
            20

<210> SEQ ID NO 608
<211> LENGTH: 26
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid

<400> SEQUENCE: 608

Ala Lys Gln Asn Xaa Pro Gln Leu Cys Arg Lys Asn Thr Val Lys Lys
1               5                   10                  15

Tyr Gln Asn Val Ala Asp Lys Arg Leu Ala
            20                  25

<210> SEQ ID NO 609
<211> LENGTH: 26
<212> TYPE: PRT
<213> ORGANISM: Neisseria meningitidis

<400> SEQUENCE: 609

Asp Ile Ser Arg Ser Thr Glu Cys Arg Thr Ile Arg Lys Gln His Leu
1               5                   10                  15

Ile Asp Ser Arg Ser Leu His Ser Ser Trp
            20                  25

<210> SEQ ID NO 610
<211> LENGTH: 8
<212> TYPE: PRT
<213> ORGANISM: Neisseria meningitidis

<400> SEQUENCE: 610

Leu Ile Gly Lys Asp Asp Glu Trp
1               5

<210> SEQ ID NO 611
<211> LENGTH: 7
<212> TYPE: PRT
<213> ORGANISM: Neisseria meningitidis

<400> SEQUENCE: 611

Phe Ser Lys Ser Tyr Thr Gln
1               5

<210> SEQ ID NO 612
<211> LENGTH: 10
<212> TYPE: PRT
<213> ORGANISM: Neisseria meningitidis
```

```
<400> SEQUENCE: 612

Trp Leu Gln Ser Gly Asn Thr Lys Pro Leu
1               5                   10

<210> SEQ ID NO 613
<211> LENGTH: 6
<212> TYPE: PRT
<213> ORGANISM: Neisseria meningitidis

<400> SEQUENCE: 613

Trp Met Ser Asp Gln Gly
1               5

<210> SEQ ID NO 614
<211> LENGTH: 5
<212> TYPE: PRT
<213> ORGANISM: Neisseria meningitidis

<400> SEQUENCE: 614

Gly Val Asn Pro Arg
1               5

<210> SEQ ID NO 615
<211> LENGTH: 20
<212> TYPE: PRT
<213> ORGANISM: Neisseria meningitidis

<400> SEQUENCE: 615

Arg Gly Phe Val Lys Gln Asn Thr Pro Ile Thr Asn Val Lys Tyr Pro
1               5                   10                  15

Glu Gly Ile Ser
            20

<210> SEQ ID NO 616

<400> SEQUENCE: 616

000

<210> SEQ ID NO 617
<211> LENGTH: 21
<212> TYPE: PRT
<213> ORGANISM: Neisseria meningitidis
<220> FEATURE:
<221> NAME/KEY: Variant
<222> LOCATION: 21
<223> OTHER INFORMATION: Xaa is any amino acid

<400> SEQUENCE: 617

Ala Asn Ala Asp Gly Phe Ser Gln Glu Gln Gly Ile Lys Gly Ala His
1               5                   10                  15

Asn Arg Thr Asn Xaa
            20

<210> SEQ ID NO 618
<211> LENGTH: 20
<212> TYPE: PRT
<213> ORGANISM: Neisseria meningitidis
<220> FEATURE:
<221> NAME/KEY: Variant
<222> LOCATION: 7 & 13
<223> OTHER INFORMATION: Xaa is any amino acid
```

-continued

```
<400> SEQUENCE: 618

Leu Asn Ser Arg Gly Gly Xaa Val Lys Ser Glu Thr Xaa Thr Asp Ile
1               5                   10                  15

Glu Gly Ile Thr
            20

<210> SEQ ID NO 619

<400> SEQUENCE: 619

000

<210> SEQ ID NO 620
<211> LENGTH: 18
<212> TYPE: PRT
<213> ORGANISM: Neisseria meningitidis

<400> SEQUENCE: 620

Pro Thr Leu Asp Arg Thr Gly Lys Pro Asp Gly Gly Phe Lys Glu Ile
1               5                   10                  15

Ser Ser

<210> SEQ ID NO 621
<211> LENGTH: 12
<212> TYPE: PRT
<213> ORGANISM: Neisseria meningitidis
<220> FEATURE:
<221> NAME/KEY: Variant
<222> LOCATION: 5 & 7
<223> OTHER INFORMATION: Xaa is any amino acid

<400> SEQUENCE: 621

Tyr Asn Pro Lys Xaa Phe Xaa Asp Asp Lys Ile Leu
1               5                   10

<210> SEQ ID NO 622
<211> LENGTH: 27
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 622

Ala Xaa Ser Gln Gly Tyr Ser Lys Ala Ser Lys Ile Ala Gln Asn Glu
1               5                   10                  15

Arg Thr Lys Ser Ile Ser Glu Arg Lys Asn Val
            20                  25

<210> SEQ ID NO 623
<211> LENGTH: 8
<212> TYPE: PRT
<213> ORGANISM: Neisseria meningitidis

<400> SEQUENCE: 623

Glu Thr Phe Asp Gly Ile Lys Phe
1               5

<210> SEQ ID NO 624
<211> LENGTH: 14
<212> TYPE: PRT
<213> ORGANISM: Neisseria meningitidis
```

```
<220> FEATURE:
<221> NAME/KEY: Variant
<222> LOCATION: 1
<223> OTHER INFORMATION: Xaa is any amino acid

<400> SEQUENCE: 624

Xaa Asp Val Asn Thr Gly Arg Ile Thr Asn Ile His Pro Glu
1               5                   10

<210> SEQ ID NO 625
<211> LENGTH: 11
<212> TYPE: PRT
<213> ORGANISM: Neisseria meningitidis

<400> SEQUENCE: 625

Asp Arg Trp Asp Tyr Lys Gln Glu Gly Leu Thr
1               5                   10

<210> SEQ ID NO 626

<400> SEQUENCE: 626

000

<210> SEQ ID NO 627
<211> LENGTH: 14
<212> TYPE: PRT
<213> ORGANISM: Neisseria meningitidis

<400> SEQUENCE: 627

Asn Lys Gly Asp Val Gly Lys Thr Leu Lys Glu Leu Gly Arg
1               5                   10

<210> SEQ ID NO 628

<400> SEQUENCE: 628

000

<210> SEQ ID NO 629
<211> LENGTH: 6
<212> TYPE: PRT
<213> ORGANISM: Neisseria meningitidis

<400> SEQUENCE: 629

Val Ala Asp Lys Ile Gly
1               5

<210> SEQ ID NO 630

<400> SEQUENCE: 630

000

<210> SEQ ID NO 631
<211> LENGTH: 8
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid

<400> SEQUENCE: 631

Gly Ser Leu Lys Asp Xaa Leu Glu
1               5
```

```
<210> SEQ ID NO 632
<211> LENGTH: 13
<212> TYPE: PRT
<213> ORGANISM: Neisseria meningitidis

<400> SEQUENCE: 632

Ala His Gly Glu Ala Ala Ser Lys Ile Lys Gln Leu Asp
1               5                   10

<210> SEQ ID NO 633
<211> LENGTH: 9
<212> TYPE: PRT
<213> ORGANISM: Neisseria meningitidis

<400> SEQUENCE: 633

Ala Ala Asn Lys Gly Lys Cys Gln Asp
1               5

<210> SEQ ID NO 634

<400> SEQUENCE: 634

000

<210> SEQ ID NO 635
<211> LENGTH: 17
<212> TYPE: PRT
<213> ORGANISM: Neisseria meningitidis

<400> SEQUENCE: 635

Leu Thr Asn Gly Lys Asn Pro Asp Thr Leu Thr Ala Lys Glu Arg Glu
1               5                   10                  15

Gln

<210> SEQ ID NO 636

<400> SEQUENCE: 636

000

<210> SEQ ID NO 637
<211> LENGTH: 4
<212> TYPE: PRT
<213> ORGANISM: Neisseria meningitidis

<400> SEQUENCE: 637

Val Ala Val Lys
1

<210> SEQ ID NO 638
<211> LENGTH: 15
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid

<400> SEQUENCE: 638

Asn Gln Leu Ser Asp Xaa Glu Gly Arg Glu Phe Asp Asn Glu Met
1               5                   10                  15

<210> SEQ ID NO 639
<211> LENGTH: 5
<212> TYPE: PRT
<213> ORGANISM: Neisseria meningitidis
```

```
<220> FEATURE:
<221> NAME/KEY: Variant
<222> LOCATION: 5
<223> OTHER INFORMATION: Xaa is any amino acid

<400> SEQUENCE: 639

Ala Lys Gln Asn Xaa
1               5

<210> SEQ ID NO 640
<211> LENGTH: 20
<212> TYPE: PRT
<213> ORGANISM: Neisseria meningitidis

<400> SEQUENCE: 640

Gln Leu Cys Arg Lys Asn Thr Val Lys Lys Tyr Gln Asn Val Ala Asp
1               5                   10                  15

Lys Arg Leu Ala
            20

<210> SEQ ID NO 641
<211> LENGTH: 22
<212> TYPE: PRT
<213> ORGANISM: Neisseria meningitidis

<400> SEQUENCE: 641

Asp Ile Ser Arg Ser Thr Glu Cys Arg Thr Ile Arg Lys Gln His Leu
1               5                   10                  15

Ile Asp Ser Arg Ser Leu
            20

<210> SEQ ID NO 642
<211> LENGTH: 8
<212> TYPE: PRT
<213> ORGANISM: Neisseria meningitidis

<400> SEQUENCE: 642

Leu Ile Gly Lys Asp Asp Glu Trp
1               5

<210> SEQ ID NO 643
<211> LENGTH: 6
<212> TYPE: PRT
<213> ORGANISM: Neisseria meningitidis

<400> SEQUENCE: 643

Gly Asn Thr Lys Pro Leu
1               5

<210> SEQ ID NO 644

<400> SEQUENCE: 644

000

<210> SEQ ID NO 645

<400> SEQUENCE: 645

000

<210> SEQ ID NO 646
<211> LENGTH: 4
<212> TYPE: PRT
<213> ORGANISM: Neisseria meningitidis
```

```
<400> SEQUENCE: 646

Lys Tyr Pro Glu
1

<210> SEQ ID NO 647
<211> LENGTH: 5
<212> TYPE: PRT
<213> ORGANISM: Neisseria meningitidis

<400> SEQUENCE: 647

Asp Gly Phe Ser Gln
1               5

<210> SEQ ID NO 648
<211> LENGTH: 12
<212> TYPE: PRT
<213> ORGANISM: Neisseria meningitidis
<220> FEATURE:
<221> NAME/KEY: Variant
<222> LOCATION: 12
<223> OTHER INFORMATION: Xaa is any amino acid

<400> SEQUENCE: 648

Gln Gly Ile Lys Gly Ala His Asn Arg Thr Asn Xaa
1               5                   10

<210> SEQ ID NO 649
<211> LENGTH: 20
<212> TYPE: PRT
<213> ORGANISM: Neisseria meningitidis
<220> FEATURE:
<221> NAME/KEY: Variant
<222> LOCATION: 7 & 13
<223> OTHER INFORMATION: Xaa is any amino acid

<400> SEQUENCE: 649

Leu Asn Ser Arg Gly Gly Xaa Val Lys Ser Glu Thr Xaa Thr Asp Ile
1               5                   10                  15

Glu Gly Ile Thr
            20

<210> SEQ ID NO 650

<400> SEQUENCE: 650

000

<210> SEQ ID NO 651
<211> LENGTH: 17
<212> TYPE: PRT
<213> ORGANISM: Neisseria meningitidis

<400> SEQUENCE: 651

Thr Leu Asp Arg Thr Gly Lys Pro Asp Gly Gly Phe Lys Glu Ile Ser
1               5                   10                  15

Ser

<210> SEQ ID NO 652
<211> LENGTH: 8
<212> TYPE: PRT
<213> ORGANISM: Neisseria meningitidis
<220> FEATURE:
<221> NAME/KEY: Variant
<222> LOCATION: 1 & 3
<223> OTHER INFORMATION: Xaa is any amino acid
```

```
<400> SEQUENCE: 652

Xaa Phe Xaa Asp Asp Lys Ile Leu
1               5

<210> SEQ ID NO 653
<211> LENGTH: 23
<212> TYPE: PRT
<213> ORGANISM: Neisseria meningitidis

<400> SEQUENCE: 653

Gly Tyr Ser Lys Ala Ser Lys Ile Ala Gln Asn Glu Arg Thr Lys Ser
1               5                   10                  15

Ile Ser Glu Arg Lys Asn Val
            20

<210> SEQ ID NO 654
<211> LENGTH: 4
<212> TYPE: PRT
<213> ORGANISM: Neisseria meningitidis

<400> SEQUENCE: 654

Glu Thr Phe Asp
1

<210> SEQ ID NO 655

<400> SEQUENCE: 655

000

<210> SEQ ID NO 656
<211> LENGTH: 4
<212> TYPE: PRT
<213> ORGANISM: Neisseria meningitidis

<400> SEQUENCE: 656

Thr Tyr Ala Ser
1

<210> SEQ ID NO 657
<211> LENGTH: 4
<212> TYPE: PRT
<213> ORGANISM: Neisseria meningitidis

<400> SEQUENCE: 657

Lys Ser Asp Asn
1

<210> SEQ ID NO 658
<211> LENGTH: 13
<212> TYPE: PRT
<213> ORGANISM: Neisseria meningitidis

<400> SEQUENCE: 658

Ala Gly Thr Asp Asn Pro Thr Val Ala Lys Lys Thr Val
1               5                   10

<210> SEQ ID NO 659
<211> LENGTH: 9
<212> TYPE: PRT
<213> ORGANISM: Neisseria meningitidis
```

<400> SEQUENCE: 659

Cys Gln Gln Gly Lys Lys Val Lys Val
1               5

<210> SEQ ID NO 660
<211> LENGTH: 6
<212> TYPE: PRT
<213> ORGANISM: Neisseria meningitidis

<400> SEQUENCE: 660

Phe Asn Lys Gln Gly Leu
1               5

<210> SEQ ID NO 661
<211> LENGTH: 7
<212> TYPE: PRT
<213> ORGANISM: Neisseria meningitidis

<400> SEQUENCE: 661

Asn Gly Lys Arg Val Gln Met
1               5

<210> SEQ ID NO 662
<211> LENGTH: 9
<212> TYPE: PRT
<213> ORGANISM: Neisseria meningitidis

<400> SEQUENCE: 662

Val Asn Leu Asp Lys Ser Asp Asn Val
1               5

<210> SEQ ID NO 663
<211> LENGTH: 7
<212> TYPE: PRT
<213> ORGANISM: Neisseria meningitidis

<400> SEQUENCE: 663

Phe Tyr Gly Lys Glu Gly Gly
1               5

<210> SEQ ID NO 664
<211> LENGTH: 11
<212> TYPE: PRT
<213> ORGANISM: Neisseria meningitidis

<400> SEQUENCE: 664

Val Met Asp Gly Lys Ser Tyr Arg Lys Gln Pro
1               5                   10

<210> SEQ ID NO 665
<211> LENGTH: 15
<212> TYPE: PRT
<213> ORGANISM: Neisseria meningitidis

<400> SEQUENCE: 665

Thr Ala Pro Asp Asn Gln Ile Val Phe Lys Asp Cys Ser Pro Arg
1               5                   10                  15

<210> SEQ ID NO 666
<211> LENGTH: 13
<212> TYPE: PRT
<213> ORGANISM: Neisseria meningitidis -continued

```
<400> SEQUENCE: 666

Ala Gly Thr Asp Asn Pro Thr Val Ala Lys Lys Thr Val
1               5                   10

<210> SEQ ID NO 667
<211> LENGTH: 7
<212> TYPE: PRT
<213> ORGANISM: Neisseria meningitidis

<400> SEQUENCE: 667

Gln Gly Lys Lys Val Lys Val
1               5

<210> SEQ ID NO 668
<211> LENGTH: 6
<212> TYPE: PRT
<213> ORGANISM: Neisseria meningitidis

<400> SEQUENCE: 668

Asn Gly Lys Arg Val Gln
1               5

<210> SEQ ID NO 669
<211> LENGTH: 8
<212> TYPE: PRT
<213> ORGANISM: Neisseria meningitidis

<400> SEQUENCE: 669

Asn Leu Asp Lys Ser Asp Asn Val
1               5

<210> SEQ ID NO 670
<211> LENGTH: 6
<212> TYPE: PRT
<213> ORGANISM: Neisseria meningitidis

<400> SEQUENCE: 670

Tyr Gly Lys Glu Gly Gly
1               5

<210> SEQ ID NO 671
<211> LENGTH: 10
<212> TYPE: PRT
<213> ORGANISM: Neisseria meningitidis

<400> SEQUENCE: 671

Met Asp Gly Lys Ser Tyr Arg Lys Gln Pro
1               5                   10

<210> SEQ ID NO 672
<211> LENGTH: 5
<212> TYPE: PRT
<213> ORGANISM: Neisseria meningitidis

<400> SEQUENCE: 672

Asp Cys Ser Pro Arg
1               5

<210> SEQ ID NO 673
<211> LENGTH: 4
<212> TYPE: PRT
<213> ORGANISM: Neisseria meningitidis
```

```
<400> SEQUENCE: 673

Thr Tyr Ala Ser
1

<210> SEQ ID NO 674
<211> LENGTH: 4
<212> TYPE: PRT
<213> ORGANISM: Neisseria meningitidis

<400> SEQUENCE: 674

Lys Ser Asp Asn
1

<210> SEQ ID NO 675
<211> LENGTH: 12
<212> TYPE: PRT
<213> ORGANISM: Neisseria meningitidis

<400> SEQUENCE: 675

Gly Thr Asn Asn Pro Thr Val Ala Lys Lys Thr Val
1               5                   10

<210> SEQ ID NO 676
<211> LENGTH: 9
<212> TYPE: PRT
<213> ORGANISM: Neisseria meningitidis

<400> SEQUENCE: 676

Cys Gln Gln Gly Lys Lys Val Lys Val
1               5

<210> SEQ ID NO 677
<211> LENGTH: 6
<212> TYPE: PRT
<213> ORGANISM: Neisseria meningitidis

<400> SEQUENCE: 677

Phe Asn Lys Gln Gly Leu
1               5

<210> SEQ ID NO 678
<211> LENGTH: 7
<212> TYPE: PRT
<213> ORGANISM: Neisseria meningitidis

<400> SEQUENCE: 678

Asn Gly Lys Arg Val Gln Met
1               5

<210> SEQ ID NO 679
<211> LENGTH: 9
<212> TYPE: PRT
<213> ORGANISM: Neisseria meningitidis

<400> SEQUENCE: 679

Val Asn Leu Asp Lys Ser Asp Asn Val
1               5

<210> SEQ ID NO 680
<211> LENGTH: 7
<212> TYPE: PRT
<213> ORGANISM: Neisseria meningitidis
```

```
<400> SEQUENCE: 680

Phe Tyr Gly Lys Glu Gly Gly
1               5

<210> SEQ ID NO 681
<211> LENGTH: 11
<212> TYPE: PRT
<213> ORGANISM: Neisseria meningitidis

<400> SEQUENCE: 681

Val Met Asp Gly Lys Ser Tyr Arg Lys Gln Pro
1               5                   10

<210> SEQ ID NO 682
<211> LENGTH: 15
<212> TYPE: PRT
<213> ORGANISM: Neisseria meningitidis

<400> SEQUENCE: 682

Thr Ala Pro Asp Asn Gln Ile Val Phe Lys Asp Cys Ser Pro Arg
1               5                   10                  15

<210> SEQ ID NO 683
<211> LENGTH: 7
<212> TYPE: PRT
<213> ORGANISM: Neisseria meningitidis

<400> SEQUENCE: 683

Thr Val Ala Lys Lys Thr Val
1               5

<210> SEQ ID NO 684
<211> LENGTH: 7
<212> TYPE: PRT
<213> ORGANISM: Neisseria meningitidis

<400> SEQUENCE: 684

Gln Gly Lys Lys Val Lys Val
1               5

<210> SEQ ID NO 685
<211> LENGTH: 6
<212> TYPE: PRT
<213> ORGANISM: Neisseria meningitidis

<400> SEQUENCE: 685

Asn Gly Lys Arg Val Gln
1               5

<210> SEQ ID NO 686
<211> LENGTH: 8
<212> TYPE: PRT
<213> ORGANISM: Neisseria meningitidis

<400> SEQUENCE: 686

Asn Leu Asp Lys Ser Asp Asn Val
1               5

<210> SEQ ID NO 687
<211> LENGTH: 6
<212> TYPE: PRT
<213> ORGANISM: Neisseria meningitidis
```

<400> SEQUENCE: 687

Tyr Gly Lys Glu Gly Gly
1               5

<210> SEQ ID NO 688
<211> LENGTH: 10
<212> TYPE: PRT
<213> ORGANISM: Neisseria meningitidis

<400> SEQUENCE: 688

Met Asp Gly Lys Ser Tyr Arg Lys Gln Pro
1               5                   10

<210> SEQ ID NO 689
<211> LENGTH: 5
<212> TYPE: PRT
<213> ORGANISM: Neisseria meningitidis

<400> SEQUENCE: 689

Asp Cys Ser Pro Arg
1               5

<210> SEQ ID NO 690
<211> LENGTH: 6
<212> TYPE: PRT
<213> ORGANISM: Neisseria meningitidis

<400> SEQUENCE: 690

Val Gln Lys Ser Thr Arg
1               5

<210> SEQ ID NO 691
<211> LENGTH: 5
<212> TYPE: PRT
<213> ORGANISM: Neisseria meningitidis

<400> SEQUENCE: 691

Val Arg Val Ile Ala
1               5

<210> SEQ ID NO 692
<211> LENGTH: 6
<212> TYPE: PRT
<213> ORGANISM: Neisseria meningitidis

<400> SEQUENCE: 692

Gly Trp Asp Thr Val Leu
1               5

<210> SEQ ID NO 693
<211> LENGTH: 6
<212> TYPE: PRT
<213> ORGANISM: Neisseria meningitidis

<400> SEQUENCE: 693

Lys Gly Ile Val Asn Arg
1               5

<210> SEQ ID NO 694
<211> LENGTH: 10
<212> TYPE: PRT
<213> ORGANISM: Neisseria meningitidis -continued

```
<400> SEQUENCE: 694

Gly Ser Thr Val Glu Thr Leu Lys Leu Pro
1               5                   10

<210> SEQ ID NO 695
<211> LENGTH: 20
<212> TYPE: PRT
<213> ORGANISM: Neisseria meningitidis

<400> SEQUENCE: 695

Glu Gly Pro Ala Leu Pro Lys Leu Thr Ala Pro Gly Gly Tyr Ile Ala
1               5                   10                  15

Asp Ile Pro Lys
            20

<210> SEQ ID NO 696
<211> LENGTH: 23
<212> TYPE: PRT
<213> ORGANISM: Neisseria meningitidis

<400> SEQUENCE: 696

Ile Glu Lys Leu Ala Lys Gln Pro Glu Tyr Ala Tyr Leu Lys Gln Leu
1               5                   10                  15

Gln Thr Val Lys Asp Val Asn
            20

<210> SEQ ID NO 697
<211> LENGTH: 6
<212> TYPE: PRT
<213> ORGANISM: Neisseria meningitidis

<400> SEQUENCE: 697

Phe Ala Ser Leu Ala Ser
1               5

<210> SEQ ID NO 698
<211> LENGTH: 12
<212> TYPE: PRT
<213> ORGANISM: Neisseria meningitidis

<400> SEQUENCE: 698

Ile Gly Asn Thr Leu Lys Glu Leu Gly Arg Ser Ser
1               5                   10

<210> SEQ ID NO 699
<211> LENGTH: 4
<212> TYPE: PRT
<213> ORGANISM: Neisseria meningitidis

<400> SEQUENCE: 699

Asn Leu Met Val
1

<210> SEQ ID NO 700
<211> LENGTH: 8
<212> TYPE: PRT
<213> ORGANISM: Neisseria meningitidis

<400> SEQUENCE: 700

Val Ala Asp Lys Ile Gly Ala Ser
1               5
```

```
<210> SEQ ID NO 701
<211> LENGTH: 6
<212> TYPE: PRT
<213> ORGANISM: Neisseria meningitidis

<400> SEQUENCE: 701

Leu Asn Asn Val Ser Asp
1               5

<210> SEQ ID NO 702

<400> SEQUENCE: 702

000

<210> SEQ ID NO 703
<211> LENGTH: 10
<212> TYPE: PRT
<213> ORGANISM: Neisseria meningitidis

<400> SEQUENCE: 703

Asn Ile Leu Ala Ala Leu Val Asn Thr Ala
1               5                   10

<210> SEQ ID NO 704
<211> LENGTH: 8
<212> TYPE: PRT
<213> ORGANISM: Neisseria meningitidis

<400> SEQUENCE: 704

Ser Lys Ile Lys Gln Leu Asp Gln
1               5

<210> SEQ ID NO 705
<211> LENGTH: 11
<212> TYPE: PRT
<213> ORGANISM: Neisseria meningitidis

<400> SEQUENCE: 705

His Lys Ile Ala His Ala Ile Ala Gly Cys Ala
1               5                   10

<210> SEQ ID NO 706
<211> LENGTH: 12
<212> TYPE: PRT
<213> ORGANISM: Neisseria meningitidis

<400> SEQUENCE: 706

Ala Ile Gly Ala Ala Val Gly Glu Ile Leu Gly Glu
1               5                   10

<210> SEQ ID NO 707

<400> SEQUENCE: 707

000

<210> SEQ ID NO 708
<211> LENGTH: 9
<212> TYPE: PRT
<213> ORGANISM: Neisseria meningitidis

<400> SEQUENCE: 708

Ser Leu Asn Asp Ile Gln Asp Arg Leu
1               5
```

```
<210> SEQ ID NO 709
<211> LENGTH: 18
<212> TYPE: PRT
<213> ORGANISM: Neisseria meningitidis

<400> SEQUENCE: 709

Ala Glu Ser Phe Cys Glu Ser Tyr Arg Pro Leu Gly Leu Pro His Phe
1               5                   10                  15
Val Ser

<210> SEQ ID NO 710
<211> LENGTH: 11
<212> TYPE: PRT
<213> ORGANISM: Neisseria meningitidis

<400> SEQUENCE: 710

Met Lys Leu Pro Asn Lys Phe Gly Asn Arg Met
1               5                   10

<210> SEQ ID NO 711
<211> LENGTH: 8
<212> TYPE: PRT
<213> ORGANISM: Neisseria meningitidis

<400> SEQUENCE: 711

Val Gly Lys Ile Trp Ser Thr Val
1               5

<210> SEQ ID NO 712
<211> LENGTH: 4
<212> TYPE: PRT
<213> ORGANISM: Neisseria meningitidis

<400> SEQUENCE: 712

Ala Ser Met Asn
1

<210> SEQ ID NO 713
<211> LENGTH: 5
<212> TYPE: PRT
<213> ORGANISM: Neisseria meningitidis

<400> SEQUENCE: 713

Phe Arg Asn Ser Asn
1               5

<210> SEQ ID NO 714
<211> LENGTH: 7
<212> TYPE: PRT
<213> ORGANISM: Neisseria meningitidis

<400> SEQUENCE: 714

Tyr Ala Glu Met Ile Ser Gln
1               5

<210> SEQ ID NO 715

<400> SEQUENCE: 715

000
```

<210> SEQ ID NO 716

<400> SEQUENCE: 716

000

<210> SEQ ID NO 717

<400> SEQUENCE: 717

000

<210> SEQ ID NO 718
<211> LENGTH: 5
<212> TYPE: PRT
<213> ORGANISM: Neisseria meningitidis

<400> SEQUENCE: 718

Val Ala Ala Gly Val
1               5

<210> SEQ ID NO 719
<211> LENGTH: 7
<212> TYPE: PRT
<213> ORGANISM: Neisseria meningitidis

<400> SEQUENCE: 719

Asn Val Gln Lys Ser Thr Arg
1               5

<210> SEQ ID NO 720
<211> LENGTH: 18
<212> TYPE: PRT
<213> ORGANISM: Neisseria meningitidis

<400> SEQUENCE: 720

Lys Val Gly Lys Ser Asn Tyr Ser Lys Asn Glu Leu Asn Glu Thr Lys
1               5                   10                  15

Leu Pro

<210> SEQ ID NO 721
<211> LENGTH: 10
<212> TYPE: PRT
<213> ORGANISM: Neisseria meningitidis

<400> SEQUENCE: 721

Thr Ala Lys Thr Arg Ser Gly Trp Asp Thr
1               5                   10

<210> SEQ ID NO 722
<211> LENGTH: 15
<212> TYPE: PRT
<213> ORGANISM: Neisseria meningitidis

<400> SEQUENCE: 722

Leu Glu Gly Thr Glu Phe Lys Thr Thr Leu Ser Gly Ala Asp Ile
1               5                   10                  15

<210> SEQ ID NO 723
<211> LENGTH: 9
<212> TYPE: PRT
<213> ORGANISM: Neisseria meningitidis

```
<400> SEQUENCE: 723

Val Gly Glu Lys Ala Arg Ala Asp Ala
1               5

<210> SEQ ID NO 724
<211> LENGTH: 11
<212> TYPE: PRT
<213> ORGANISM: Neisseria meningitidis

<400> SEQUENCE: 724

Ile Gln Thr Glu Glu Lys Leu Glu Ser Asn Ser
1               5                   10

<210> SEQ ID NO 725
<211> LENGTH: 11
<212> TYPE: PRT
<213> ORGANISM: Neisseria meningitidis

<400> SEQUENCE: 725

Val Trp Gln Lys Gln Ala Gly Ser Gly Ser Thr
1               5                   10

<210> SEQ ID NO 726
<211> LENGTH: 18
<212> TYPE: PRT
<213> ORGANISM: Neisseria meningitidis

<400> SEQUENCE: 726

Glu Thr Leu Lys Leu Pro Ser Phe Glu Gly Pro Ala Leu Pro Lys Leu
1               5                   10                  15

Thr Ala

<210> SEQ ID NO 727
<211> LENGTH: 18
<212> TYPE: PRT
<213> ORGANISM: Neisseria meningitidis

<400> SEQUENCE: 727

Ile Pro Lys Gly Asn Leu Lys Thr Glu Ile Glu Lys Leu Ala Lys Gln
1               5                   10                  15

Pro Glu

<210> SEQ ID NO 728
<211> LENGTH: 9
<212> TYPE: PRT
<213> ORGANISM: Neisseria meningitidis

<400> SEQUENCE: 728

Leu Gln Thr Val Lys Asp Val Asn Trp
1               5

<210> SEQ ID NO 729
<211> LENGTH: 13
<212> TYPE: PRT
<213> ORGANISM: Neisseria meningitidis

<400> SEQUENCE: 729

Ala Tyr Asp Lys Trp Asp Tyr Lys Gln Glu Gly Leu Thr
1               5                   10
```

<210> SEQ ID NO 730

<400> SEQUENCE: 730

000

<210> SEQ ID NO 731

<400> SEQUENCE: 731

000

<210> SEQ ID NO 732
<211> LENGTH: 19
<212> TYPE: PRT
<213> ORGANISM: Neisseria meningitidis

<400> SEQUENCE: 732

Asn Asn Lys Gly Asn Ile Gly Asn Thr Leu Lys Glu Leu Gly Arg Ser
1               5                   10                  15

Ser Thr Val

<210> SEQ ID NO 733
<211> LENGTH: 6
<212> TYPE: PRT
<213> ORGANISM: Neisseria meningitidis

<400> SEQUENCE: 733

Val Ala Asp Lys Ile Gly
1               5

<210> SEQ ID NO 734
<211> LENGTH: 7
<212> TYPE: PRT
<213> ORGANISM: Neisseria meningitidis

<400> SEQUENCE: 734

Asn Val Ser Asp Lys Gln Trp
1               5

<210> SEQ ID NO 735
<211> LENGTH: 11
<212> TYPE: PRT
<213> ORGANISM: Neisseria meningitidis

<400> SEQUENCE: 735

Val Asn Gly Gly Ser Leu Lys Asp Asn Leu Glu
1               5                   10

<210> SEQ ID NO 736
<211> LENGTH: 13
<212> TYPE: PRT
<213> ORGANISM: Neisseria meningitidis

<400> SEQUENCE: 736

Ala His Gly Glu Ala Ala Ser Lys Ile Lys Gln Leu Asp
1               5                   10

<210> SEQ ID NO 737
<211> LENGTH: 11
<212> TYPE: PRT
<213> ORGANISM: Neisseria meningitidis

```
<400> SEQUENCE: 737

Ala Ala Asn Lys Gly Lys Cys Gln Asp Gly Ala
1               5                   10

<210> SEQ ID NO 738

<400> SEQUENCE: 738

000

<210> SEQ ID NO 739
<211> LENGTH: 21
<212> TYPE: PRT
<213> ORGANISM: Neisseria meningitidis

<400> SEQUENCE: 739

Thr Leu Leu Asp Gly Arg Asp Pro Gly Ser Leu Asn Val Lys Asp Arg
1               5                   10                  15

Ala Lys Ile Ile Ala
            20

<210> SEQ ID NO 740

<400> SEQUENCE: 740

000

<210> SEQ ID NO 741
<211> LENGTH: 7
<212> TYPE: PRT
<213> ORGANISM: Neisseria meningitidis

<400> SEQUENCE: 741

Ser Lys Gly Asp Val Ser Thr
1               5

<210> SEQ ID NO 742
<211> LENGTH: 17
<212> TYPE: PRT
<213> ORGANISM: Neisseria meningitidis

<400> SEQUENCE: 742

Val Glu Asn Asn Ser Leu Asn Asp Ile Gln Asp Arg Leu Leu Ser Gly
1               5                   10                  15

Asn

<210> SEQ ID NO 743
<211> LENGTH: 14
<212> TYPE: PRT
<213> ORGANISM: Neisseria meningitidis

<400> SEQUENCE: 743

Gly Gly Ala Glu Ser Phe Cys Glu Ser Tyr Arg Pro Leu Gly
1               5                   10

<210> SEQ ID NO 744
<211> LENGTH: 19
<212> TYPE: PRT
<213> ORGANISM: Neisseria meningitidis
```

```
<400> SEQUENCE: 744

Val Ser Gly Glu Met Lys Leu Pro Asn Lys Phe Gly Asn Arg Met Val
1               5                   10                  15

Asn Gly Lys

<210> SEQ ID NO 745
<211> LENGTH: 7
<212> TYPE: PRT
<213> ORGANISM: Neisseria meningitidis

<400> SEQUENCE: 745

Ile Asn Thr Arg Asn Gly Asn
1               5

<210> SEQ ID NO 746
<211> LENGTH: 8
<212> TYPE: PRT
<213> ORGANISM: Neisseria meningitidis

<400> SEQUENCE: 746

Val Lys Ser Thr Lys Ser Asn Ile
1               5

<210> SEQ ID NO 747
<211> LENGTH: 23
<212> TYPE: PRT
<213> ORGANISM: Neisseria meningitidis

<400> SEQUENCE: 747

Ser Pro Asn Asp Tyr Leu Lys Glu Ala Ser Met Asn Asp Phe Arg Asn
1               5                   10                  15

Ser Asn Gln Asn Lys Ala Tyr
            20

<210> SEQ ID NO 748
<211> LENGTH: 8
<212> TYPE: PRT
<213> ORGANISM: Neisseria meningitidis

<400> SEQUENCE: 748

Gly Glu Ser Val Gly Gly Ser Leu
1               5

<210> SEQ ID NO 749
<211> LENGTH: 17
<212> TYPE: PRT
<213> ORGANISM: Neisseria meningitidis

<400> SEQUENCE: 749

Ser Thr Ile Ser Lys Ser Lys Ser Pro Phe Lys Asp Ser Lys Ile Ile
1               5                   10                  15

Gly

<210> SEQ ID NO 750

<400> SEQUENCE: 750

000
```

<210> SEQ ID NO 751

<400> SEQUENCE: 751

000

<210> SEQ ID NO 752
<211> LENGTH: 9
<212> TYPE: PRT
<213> ORGANISM: Neisseria meningitidis

<400> SEQUENCE: 752

Asn Ile Lys Asp Ile Asp Lys Phe Ile
1               5

<210> SEQ ID NO 753
<211> LENGTH: 4
<212> TYPE: PRT
<213> ORGANISM: Neisseria meningitidis

<400> SEQUENCE: 753

Asn Ile Lys Lys
1

<210> SEQ ID NO 754
<211> LENGTH: 4
<212> TYPE: PRT
<213> ORGANISM: Neisseria meningitidis

<400> SEQUENCE: 754

Lys Ser Thr Arg
1

<210> SEQ ID NO 755
<211> LENGTH: 4
<212> TYPE: PRT
<213> ORGANISM: Neisseria meningitidis

<400> SEQUENCE: 755

Lys Val Gly Lys
1

<210> SEQ ID NO 756
<211> LENGTH: 13
<212> TYPE: PRT
<213> ORGANISM: Neisseria meningitidis

<400> SEQUENCE: 756

Asn Tyr Ser Lys Asn Glu Leu Asn Glu Thr Lys Leu Pro
1               5                   10

<210> SEQ ID NO 757
<211> LENGTH: 7
<212> TYPE: PRT
<213> ORGANISM: Neisseria meningitidis

<400> SEQUENCE: 757

Ala Lys Thr Arg Ser Gly Trp
1               5

<210> SEQ ID NO 758
<211> LENGTH: 5
<212> TYPE: PRT
<213> ORGANISM: Neisseria meningitidis -continued

```
<400> SEQUENCE: 758

Thr Glu Phe Lys Thr
1               5

<210> SEQ ID NO 759
<211> LENGTH: 9
<212> TYPE: PRT
<213> ORGANISM: Neisseria meningitidis

<400> SEQUENCE: 759

Val Gly Glu Lys Ala Arg Ala Asp Ala
1               5

<210> SEQ ID NO 760
<211> LENGTH: 10
<212> TYPE: PRT
<213> ORGANISM: Neisseria meningitidis

<400> SEQUENCE: 760

Ile Gln Thr Glu Glu Lys Leu Glu Ser Asn
1               5                   10

<210> SEQ ID NO 761
<211> LENGTH: 4
<212> TYPE: PRT
<213> ORGANISM: Neisseria meningitidis

<400> SEQUENCE: 761

Glu Thr Leu Lys
1

<210> SEQ ID NO 762
<211> LENGTH: 18
<212> TYPE: PRT
<213> ORGANISM: Neisseria meningitidis

<400> SEQUENCE: 762

Ile Pro Lys Gly Asn Leu Lys Thr Glu Ile Glu Lys Leu Ala Lys Gln
1               5                   10                  15

Pro Glu

<210> SEQ ID NO 763
<211> LENGTH: 4
<212> TYPE: PRT
<213> ORGANISM: Neisseria meningitidis

<400> SEQUENCE: 763

Gln Thr Val Lys
1

<210> SEQ ID NO 764
<211> LENGTH: 11
<212> TYPE: PRT
<213> ORGANISM: Neisseria meningitidis

<400> SEQUENCE: 764

Asp Lys Trp Asp Tyr Lys Gln Glu Gly Leu Thr
1               5                   10

<210> SEQ ID NO 765

<400> SEQUENCE: 765

000
```

```
<210> SEQ ID NO 766
<211> LENGTH: 7
<212> TYPE: PRT
<213> ORGANISM: Neisseria meningitidis

<400> SEQUENCE: 766

Thr Leu Lys Glu Leu Gly Arg
1               5

<210> SEQ ID NO 767

<400> SEQUENCE: 767

000

<210> SEQ ID NO 768
<211> LENGTH: 6
<212> TYPE: PRT
<213> ORGANISM: Neisseria meningitidis

<400> SEQUENCE: 768

Val Ala Asp Lys Ile Gly
1               5

<210> SEQ ID NO 769

<400> SEQUENCE: 769

000

<210> SEQ ID NO 770
<211> LENGTH: 8
<212> TYPE: PRT
<213> ORGANISM: Neisseria meningitidis

<400> SEQUENCE: 770

Gly Ser Leu Lys Asp Asn Leu Glu
1               5

<210> SEQ ID NO 771
<211> LENGTH: 13
<212> TYPE: PRT
<213> ORGANISM: Neisseria meningitidis

<400> SEQUENCE: 771

Ala His Gly Glu Ala Ala Ser Lys Ile Lys Gln Leu Asp
1               5                   10

<210> SEQ ID NO 772
<211> LENGTH: 9
<212> TYPE: PRT
<213> ORGANISM: Neisseria meningitidis

<400> SEQUENCE: 772

Ala Ala Asn Lys Gly Lys Cys Gln Asp
1               5

<210> SEQ ID NO 773

<400> SEQUENCE: 773

000
```

<210> SEQ ID NO 774
<211> LENGTH: 21
<212> TYPE: PRT
<213> ORGANISM: Neisseria meningitidis

<400> SEQUENCE: 774

Thr Leu Leu Asp Gly Arg Asp Pro Gly Ser Leu Asn Val Lys Asp Arg
1               5                   10                  15

Ala Lys Ile Ile Ala
            20

<210> SEQ ID NO 775

<400> SEQUENCE: 775

000

<210> SEQ ID NO 776
<211> LENGTH: 7
<212> TYPE: PRT
<213> ORGANISM: Neisseria meningitidis

<400> SEQUENCE: 776

Ser Lys Gly Asp Val Ser Thr
1               5

<210> SEQ ID NO 777
<211> LENGTH: 11
<212> TYPE: PRT
<213> ORGANISM: Neisseria meningitidis

<400> SEQUENCE: 777

Asn Ser Leu Asn Asp Ile Gln Asp Arg Leu Leu
1               5                   10

<210> SEQ ID NO 778
<211> LENGTH: 7
<212> TYPE: PRT
<213> ORGANISM: Neisseria meningitidis

<400> SEQUENCE: 778

Ser Phe Cys Glu Ser Tyr Arg
1               5

<210> SEQ ID NO 779
<211> LENGTH: 7
<212> TYPE: PRT
<213> ORGANISM: Neisseria meningitidis

<400> SEQUENCE: 779

Gly Glu Met Lys Leu Pro Asn
1               5

<210> SEQ ID NO 780

<400> SEQUENCE: 780

000

<210> SEQ ID NO 781

<400> SEQUENCE: 781

000

```
<210> SEQ ID NO 782
<211> LENGTH: 7
<212> TYPE: PRT
<213> ORGANISM: Neisseria meningitidis

<400> SEQUENCE: 782

Lys Ser Thr Lys Ser Asn Ile
1               5

<210> SEQ ID NO 783
<211> LENGTH: 20
<212> TYPE: PRT
<213> ORGANISM: Neisseria meningitidis

<400> SEQUENCE: 783

Asp Tyr Leu Lys Glu Ala Ser Met Asn Asp Phe Arg Asn Ser Asn Gln
1               5                   10                  15

Asn Lys Ala Tyr
            20

<210> SEQ ID NO 784
<211> LENGTH: 16
<212> TYPE: PRT
<213> ORGANISM: Neisseria meningitidis

<400> SEQUENCE: 784

Thr Ile Ser Lys Ser Lys Ser Pro Phe Lys Asp Ser Lys Ile Ile Gly
1               5                   10                  15

<210> SEQ ID NO 785

<400> SEQUENCE: 785

000

<210> SEQ ID NO 786
<211> LENGTH: 7
<212> TYPE: PRT
<213> ORGANISM: Neisseria meningitidis

<400> SEQUENCE: 786

Asn Ile Lys Asp Ile Asp Lys
1               5

<210> SEQ ID NO 787
<211> LENGTH: 4
<212> TYPE: PRT
<213> ORGANISM: Neisseria meningitidis

<400> SEQUENCE: 787

Asn Ile Lys Lys
1

<210> SEQ ID NO 788
<211> LENGTH: 7
<212> TYPE: PRT
<213> ORGANISM: Neisseria meningitidis

<400> SEQUENCE: 788

Ser Gly Trp Asp Thr Val Leu
1               5
```

```
<210> SEQ ID NO 789
<211> LENGTH: 6
<212> TYPE: PRT
<213> ORGANISM: Neisseria meningitidis

<400> SEQUENCE: 789

Lys Gly Ile Val Asn Arg
1               5

<210> SEQ ID NO 790
<211> LENGTH: 10
<212> TYPE: PRT
<213> ORGANISM: Neisseria meningitidis

<400> SEQUENCE: 790

Gly Ser Thr Ile Glu Thr Leu Lys Leu Pro
1               5                   10

<210> SEQ ID NO 791
<211> LENGTH: 7
<212> TYPE: PRT
<213> ORGANISM: Neisseria meningitidis

<400> SEQUENCE: 791

Phe Glu Ser Pro Thr Pro Pro
1               5

<210> SEQ ID NO 792
<211> LENGTH: 9
<212> TYPE: PRT
<213> ORGANISM: Neisseria meningitidis

<400> SEQUENCE: 792

Leu Ser Ala Pro Gly Gly Tyr Ile Val
1               5

<210> SEQ ID NO 793
<211> LENGTH: 23
<212> TYPE: PRT
<213> ORGANISM: Neisseria meningitidis

<400> SEQUENCE: 793

Ile Glu Lys Leu Ser Lys Gln Pro Glu Tyr Ala Tyr Leu Lys Gln Leu
1               5                   10                  15

Gln Val Ala Lys Asn Ile Asn
            20

<210> SEQ ID NO 794

<400> SEQUENCE: 794

000

<210> SEQ ID NO 795
<211> LENGTH: 6
<212> TYPE: PRT
<213> ORGANISM: Neisseria meningitidis

<400> SEQUENCE: 795

Phe Ala Ser Leu Ala Ser
1               5
```

```
<210> SEQ ID NO 796
<211> LENGTH: 13
<212> TYPE: PRT
<213> ORGANISM: Neisseria meningitidis

<400> SEQUENCE: 796

Asp Val Gly Lys Thr Leu Lys Glu Leu Gly Arg Ser Ser
1               5                   10

<210> SEQ ID NO 797
<211> LENGTH: 9
<212> TYPE: PRT
<213> ORGANISM: Neisseria meningitidis

<400> SEQUENCE: 797

Gly Val Ala Asp Lys Ile Gly Ala Ser
1               5

<210> SEQ ID NO 798
<211> LENGTH: 6
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 798

Leu Xaa Asn Val Ser Asp
1               5

<210> SEQ ID NO 799

<400> SEQUENCE: 799

000

<210> SEQ ID NO 800
<211> LENGTH: 6
<212> TYPE: PRT
<213> ORGANISM: Neisseria meningitidis
<220> FEATURE:
<221> NAME/KEY: Variant
<222> LOCATION: 4
<223> OTHER INFORMATION: Xaa is any amino acid

<400> SEQUENCE: 800

Leu Lys Asp Xaa Leu Glu
1               5

<210> SEQ ID NO 801
<211> LENGTH: 10
<212> TYPE: PRT
<213> ORGANISM: Neisseria meningitidis

<400> SEQUENCE: 801

Asn Ile Leu Ala Ala Leu Val Asn Thr Ala
1               5                   10

<210> SEQ ID NO 802
<211> LENGTH: 8
<212> TYPE: PRT
<213> ORGANISM: Neisseria meningitidis

<400> SEQUENCE: 802

Ser Lys Ile Lys Gln Leu Asp Gln
1               5
```

```
<210> SEQ ID NO 803
<211> LENGTH: 11
<212> TYPE: PRT
<213> ORGANISM: Neisseria meningitidis

<400> SEQUENCE: 803

His Lys Ile Ala His Ala Ile Ala Gly Cys Ala
1               5                   10

<210> SEQ ID NO 804
<211> LENGTH: 12
<212> TYPE: PRT
<213> ORGANISM: Neisseria meningitidis

<400> SEQUENCE: 804

Ala Ile Gly Ala Ala Val Gly Glu Ile Val Gly Glu
1               5                   10

<210> SEQ ID NO 805
<211> LENGTH: 6
<212> TYPE: PRT
<213> ORGANISM: Neisseria meningitidis

<400> SEQUENCE: 805

Thr Asn Gly Lys Asn Pro
1               5

<210> SEQ ID NO 806
<211> LENGTH: 10
<212> TYPE: PRT
<213> ORGANISM: Neisseria meningitidis

<400> SEQUENCE: 806

Val Ala Gly Thr Val Ser Gly Val Val Gly
1               5                   10

<210> SEQ ID NO 807
<211> LENGTH: 4
<212> TYPE: PRT
<213> ORGANISM: Neisseria meningitidis

<400> SEQUENCE: 807

Asn Glu Met Thr
1

<210> SEQ ID NO 808
<211> LENGTH: 10
<212> TYPE: PRT
<213> ORGANISM: Neisseria meningitidis

<400> SEQUENCE: 808

Thr Val Lys Lys Tyr Gln Asn Val Ala Asp
1               5                   10

<210> SEQ ID NO 809
<211> LENGTH: 19
<212> TYPE: PRT
<213> ORGANISM: Neisseria meningitidis

<400> SEQUENCE: 809

Ser Ile Ala Ile Cys Thr Asp Ile Ser Arg Ser Thr Glu Cys Arg Thr
1               5                   10                  15

Ile Arg Lys
```

```
<210> SEQ ID NO 810
<211> LENGTH: 6
<212> TYPE: PRT
<213> ORGANISM: Neisseria meningitidis

<400> SEQUENCE: 810

His Ser Ser Trp Glu Ala
1               5

<210> SEQ ID NO 811
<211> LENGTH: 8
<212> TYPE: PRT
<213> ORGANISM: Neisseria meningitidis

<400> SEQUENCE: 811

Glu Trp Tyr Lys Leu Phe Ser Lys
1               5

<210> SEQ ID NO 812
<211> LENGTH: 4
<212> TYPE: PRT
<213> ORGANISM: Neisseria meningitidis

<400> SEQUENCE: 812

Ala Ala Lys Ser
1

<210> SEQ ID NO 813
<211> LENGTH: 8
<212> TYPE: PRT
<213> ORGANISM: Neisseria meningitidis

<400> SEQUENCE: 813

Thr Lys Pro Leu Ser Glu Trp Met
1               5

<210> SEQ ID NO 814
<211> LENGTH: 6
<212> TYPE: PRT
<213> ORGANISM: Neisseria meningitidis

<400> SEQUENCE: 814

Val Lys Tyr Pro Glu Gly
1               5

<210> SEQ ID NO 815
<211> LENGTH: 5
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 815

Leu Xaa Arg His Leu
1               5

<210> SEQ ID NO 816
<211> LENGTH: 6
<212> TYPE: PRT
<213> ORGANISM: Neisseria meningitidis

<400> SEQUENCE: 816

Ile Lys Gly Ala His Asn
1               5
```

```
<210> SEQ ID NO 817
<211> LENGTH: 6
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 817

Asn Xaa Met Ala Glu Leu
1               5

<210> SEQ ID NO 818
<211> LENGTH: 7
<212> TYPE: PRT
<213> ORGANISM: Neisseria meningitidis

<400> SEQUENCE: 818

Thr Asp Ile Glu Gly Ile Thr
1               5

<210> SEQ ID NO 819
<211> LENGTH: 23
<212> TYPE: PRT
<213> ORGANISM: Neisseria meningitidis

<400> SEQUENCE: 819

Leu Asp Arg Thr Gly Lys Pro Asp Gly Gly Phe Lys Glu Ile Ser Ser
1               5                   10                  15

Ile Lys Thr Val Tyr Asn Pro
            20

<210> SEQ ID NO 820
<211> LENGTH: 16
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 820

Ala Xaa Ser Gln Gly Tyr Ser Lys Ala Ser Lys Ile Ala Gln Asn Glu
1               5                   10                  15

<210> SEQ ID NO 821
<211> LENGTH: 5
<212> TYPE: PRT
<213> ORGANISM: Neisseria meningitidis

<400> SEQUENCE: 821

Phe Ser Glu Thr Phe
1               5

<210> SEQ ID NO 822
<211> LENGTH: 17
<212> TYPE: PRT
<213> ORGANISM: Neisseria meningitidis
<220> FEATURE:
<221> NAME/KEY: Variant
<222> LOCATION: 3 & 5
<223> OTHER INFORMATION: Xaa is any amino acid
```

-continued

```
<400> SEQUENCE: 822

Phe Arg Xaa Tyr Xaa Asp Val Asn Thr Gly Arg Ile Thr Asn Ile His
1               5                   10                  15

Pro

<210> SEQ ID NO 823
<211> LENGTH: 20
<212> TYPE: PRT
<213> ORGANISM: Neisseria meningitidis

<400> SEQUENCE: 823

Leu Ala Glu Glu Gly Ile His Lys His Glu Leu Asp Val Gln Lys Ser
1               5                   10                  15

Arg Arg Phe Ile
            20

<210> SEQ ID NO 824
<211> LENGTH: 17
<212> TYPE: PRT
<213> ORGANISM: Neisseria meningitidis
<220> FEATURE:
<221> NAME/KEY: Variant
<222> LOCATION: 3
<223> OTHER INFORMATION: Xaa is any amino acid

<400> SEQUENCE: 824

Val Gly Xaa Ser Asn Tyr Ser Lys Asn Glu Leu Asn Glu Thr Lys Leu
1               5                   10                  15

Pro

<210> SEQ ID NO 825
<211> LENGTH: 12
<212> TYPE: PRT
<213> ORGANISM: Neisseria meningitidis

<400> SEQUENCE: 825

Ala Ala Thr Arg Ser Gly Trp Asp Thr Val Leu Glu
1               5                   10

<210> SEQ ID NO 826
<211> LENGTH: 5
<212> TYPE: PRT
<213> ORGANISM: Neisseria meningitidis

<400> SEQUENCE: 826

Thr Glu Phe Lys Thr
1               5

<210> SEQ ID NO 827
<211> LENGTH: 4
<212> TYPE: PRT
<213> ORGANISM: Neisseria meningitidis

<400> SEQUENCE: 827

Gly Ala Asp Ile
1

<210> SEQ ID NO 828
<211> LENGTH: 9
<212> TYPE: PRT
<213> ORGANISM: Neisseria meningitidis
```

```
<220> FEATURE:
<221> NAME/KEY: Variant
<222> LOCATION: 2
<223> OTHER INFORMATION: Xaa is any amino acid

<400> SEQUENCE: 828

Val Xaa Glu Lys Ala Arg Val Asp Ala
1               5

<210> SEQ ID NO 829
<211> LENGTH: 11
<212> TYPE: PRT
<213> ORGANISM: Neisseria meningitidis

<400> SEQUENCE: 829

Ile Gln Ser Glu Glu Lys Leu Glu Thr Asn Ser
1               5                   10

<210> SEQ ID NO 830
<211> LENGTH: 11
<212> TYPE: PRT
<213> ORGANISM: Neisseria meningitidis

<400> SEQUENCE: 830

Val Trp Gln Lys Gln Ala Gly Arg Gly Ser Thr
1               5                   10

<210> SEQ ID NO 831
<211> LENGTH: 16
<212> TYPE: PRT
<213> ORGANISM: Neisseria meningitidis

<400> SEQUENCE: 831

Leu Lys Leu Pro Ser Phe Glu Ser Pro Thr Pro Pro Lys Leu Ser Ala
1               5                   10                  15

<210> SEQ ID NO 832
<211> LENGTH: 18
<212> TYPE: PRT
<213> ORGANISM: Neisseria meningitidis

<400> SEQUENCE: 832

Ile Pro Lys Gly Asn Leu Lys Thr Glu Ile Glu Lys Leu Ser Lys Gln
1               5                   10                  15

Pro Glu

<210> SEQ ID NO 833
<211> LENGTH: 4
<212> TYPE: PRT
<213> ORGANISM: Neisseria meningitidis

<400> SEQUENCE: 833

Asn Ile Asn Trp
1

<210> SEQ ID NO 834
<211> LENGTH: 13
<212> TYPE: PRT
<213> ORGANISM: Neisseria meningitidis

<400> SEQUENCE: 834

Ala Tyr Asp Arg Trp Asp Tyr Lys Gln Glu Gly Leu Thr
1               5                   10
```

```
<210> SEQ ID NO 835

<400> SEQUENCE: 835

000

<210> SEQ ID NO 836

<400> SEQUENCE: 836

000

<210> SEQ ID NO 837
<211> LENGTH: 20
<212> TYPE: PRT
<213> ORGANISM: Neisseria meningitidis

<400> SEQUENCE: 837

Asn Asn Lys Gly Asp Val Gly Lys Thr Leu Lys Glu Leu Gly Arg Ser
1               5                   10                  15

Ser Thr Val Lys
            20

<210> SEQ ID NO 838
<211> LENGTH: 6
<212> TYPE: PRT
<213> ORGANISM: Neisseria meningitidis

<400> SEQUENCE: 838

Val Ala Asp Lys Ile Gly
1               5

<210> SEQ ID NO 839
<211> LENGTH: 7
<212> TYPE: PRT
<213> ORGANISM: Neisseria meningitidis

<400> SEQUENCE: 839

Asn Val Ser Asp Lys Gln Trp
1               5

<210> SEQ ID NO 840
<211> LENGTH: 4
<212> TYPE: PRT
<213> ORGANISM: Neisseria meningitidis

<400> SEQUENCE: 840

Asn Ala Gly Ser
1

<210> SEQ ID NO 841
<211> LENGTH: 11
<212> TYPE: PRT
<213> ORGANISM: Neisseria meningitidis
<220> FEATURE:
<221> NAME/KEY: Variant
<222> LOCATION: 9
<223> OTHER INFORMATION: Xaa is any amino acid

<400> SEQUENCE: 841

Val Asn Gly Gly Ser Leu Lys Asp Xaa Leu Glu
1               5                   10
```

```
<210> SEQ ID NO 842
<211> LENGTH: 13
<212> TYPE: PRT
<213> ORGANISM: Neisseria meningitidis

<400> SEQUENCE: 842

Ala His Gly Glu Ala Ala Ser Lys Ile Lys Gln Leu Asp
1               5                   10

<210> SEQ ID NO 843
<211> LENGTH: 11
<212> TYPE: PRT
<213> ORGANISM: Neisseria meningitidis

<400> SEQUENCE: 843

Ala Ala Asn Lys Gly Lys Cys Gln Asp Gly Ala
1               5                   10

<210> SEQ ID NO 844

<400> SEQUENCE: 844

000

<210> SEQ ID NO 845
<211> LENGTH: 17
<212> TYPE: PRT
<213> ORGANISM: Neisseria meningitidis

<400> SEQUENCE: 845

Leu Thr Asn Gly Lys Asn Pro Asp Thr Leu Thr Ala Lys Glu Arg Glu
1               5                   10                  15

Gln

<210> SEQ ID NO 846
<211> LENGTH: 7
<212> TYPE: PRT
<213> ORGANISM: Neisseria meningitidis

<400> SEQUENCE: 846

Val Gly Gly Asp Val Asn Ala
1               5

<210> SEQ ID NO 847
<211> LENGTH: 20
<212> TYPE: PRT
<213> ORGANISM: Neisseria meningitidis
<220> FEATURE:
<221> NAME/KEY: Variant
<222> LOCATION: 11
<223> OTHER INFORMATION: Xaa is any amino acid

<400> SEQUENCE: 847

Val Ala Val Lys Asn Asn Gln Leu Ser Asp Xaa Glu Gly Arg Glu Phe
1               5                   10                  15

Asp Asn Glu Met
            20

<210> SEQ ID NO 848
<211> LENGTH: 26
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid
```

-continued

```
<400> SEQUENCE: 848

Ala Lys Gln Asn Xaa Pro Gln Leu Cys Arg Lys Asn Thr Val Lys Lys
1               5                   10                  15

Tyr Gln Asn Val Ala Asp Lys Arg Leu Ala
            20                  25

<210> SEQ ID NO 849
<211> LENGTH: 26
<212> TYPE: PRT
<213> ORGANISM: Neisseria meningitidis

<400> SEQUENCE: 849

Asp Ile Ser Arg Ser Thr Glu Cys Arg Thr Ile Arg Lys Gln His Leu
1               5                   10                  15

Ile Asp Ser Arg Ser Leu His Ser Ser Trp
            20                  25

<210> SEQ ID NO 850
<211> LENGTH: 8
<212> TYPE: PRT
<213> ORGANISM: Neisseria meningitidis

<400> SEQUENCE: 850

Leu Ile Gly Lys Asp Asp Glu Trp
1               5

<210> SEQ ID NO 851
<211> LENGTH: 8
<212> TYPE: PRT
<213> ORGANISM: Neisseria meningitidis

<400> SEQUENCE: 851

Phe Ser Lys Ser Tyr Thr Gln Ala
1               5

<210> SEQ ID NO 852
<211> LENGTH: 10
<212> TYPE: PRT
<213> ORGANISM: Neisseria meningitidis

<400> SEQUENCE: 852

Trp Leu Gln Ser Gly Asn Thr Lys Pro Leu
1               5                   10

<210> SEQ ID NO 853
<211> LENGTH: 6
<212> TYPE: PRT
<213> ORGANISM: Neisseria meningitidis

<400> SEQUENCE: 853

Trp Met Ser Asp Gln Gly
1               5

<210> SEQ ID NO 854
<211> LENGTH: 5
<212> TYPE: PRT
<213> ORGANISM: Neisseria meningitidis

<400> SEQUENCE: 854

Gly Val Asn Pro Arg
1               5
```

```
<210> SEQ ID NO 855
<211> LENGTH: 20
<212> TYPE: PRT
<213> ORGANISM: Neisseria meningitidis

<400> SEQUENCE: 855

Arg Gly Phe Val Lys Gln Asn Thr Pro Ile Thr Asn Val Lys Tyr Pro
1               5                   10                  15

Glu Gly Ile Ser
            20

<210> SEQ ID NO 856

<400> SEQUENCE: 856

000

<210> SEQ ID NO 857
<211> LENGTH: 21
<212> TYPE: PRT
<213> ORGANISM: Neisseria meningitidis
<220> FEATURE:
<221> NAME/KEY: Variant
<222> LOCATION: 21
<223> OTHER INFORMATION: Xaa is any amino acid

<400> SEQUENCE: 857

Ala Asn Ala Asp Gly Phe Ser Gln Glu Gln Gly Ile Lys Gly Ala His
1               5                   10                  15

Asn Arg Thr Asn Xaa
            20

<210> SEQ ID NO 858
<211> LENGTH: 20
<212> TYPE: PRT
<213> ORGANISM: Neisseria meningitidis
<220> FEATURE:
<221> NAME/KEY: Variant
<222> LOCATION: 7 & 13
<223> OTHER INFORMATION: Xaa is any amino acid

<400> SEQUENCE: 858

Leu Asn Ser Arg Gly Gly Xaa Val Lys Ser Glu Thr Xaa Thr Asp Ile
1               5                   10                  15

Glu Gly Ile Thr
            20

<210> SEQ ID NO 859

<400> SEQUENCE: 859

000

<210> SEQ ID NO 860
<211> LENGTH: 18
<212> TYPE: PRT
<213> ORGANISM: Neisseria meningitidis

<400> SEQUENCE: 860

Pro Thr Leu Asp Arg Thr Gly Lys Pro Asp Gly Gly Phe Lys Glu Ile
1               5                   10                  15

Ser Ser
```

```
<210> SEQ ID NO 861
<211> LENGTH: 12
<212> TYPE: PRT
<213> ORGANISM: Neisseria meningitidis
<220> FEATURE:
<221> NAME/KEY: Variant
<222> LOCATION: 5 & 7
<223> OTHER INFORMATION: Xaa is any amino acid

<400> SEQUENCE: 861

Tyr Asn Pro Lys Xaa Phe Xaa Asp Asp Lys Ile Leu
1               5                   10

<210> SEQ ID NO 862
<211> LENGTH: 27
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 862

Ala Xaa Ser Gln Gly Tyr Ser Lys Ala Ser Lys Ile Ala Gln Asn Glu
1               5                   10                  15

Arg Thr Lys Ser Ile Ser Glu Arg Lys Asn Val
            20                  25

<210> SEQ ID NO 863
<211> LENGTH: 8
<212> TYPE: PRT
<213> ORGANISM: Neisseria meningitidis

<400> SEQUENCE: 863

Glu Thr Phe Asp Gly Ile Lys Phe
1               5

<210> SEQ ID NO 864
<211> LENGTH: 14
<212> TYPE: PRT
<213> ORGANISM: Neisseria meningitidis
<220> FEATURE:
<221> NAME/KEY: Variant
<222> LOCATION: 1
<223> OTHER INFORMATION: Xaa is any amino acid

<400> SEQUENCE: 864

Xaa Asp Val Asn Thr Gly Arg Ile Thr Asn Ile His Pro Glu
1               5                   10

<210> SEQ ID NO 865
<211> LENGTH: 20
<212> TYPE: PRT
<213> ORGANISM: Neisseria meningitidis

<400> SEQUENCE: 865

Leu Ala Glu Glu Gly Ile His Lys His Glu Leu Asp Val Gln Lys Ser
1               5                   10                  15

Arg Arg Phe Ile
            20

<210> SEQ ID NO 866
<211> LENGTH: 13
<212> TYPE: PRT
<213> ORGANISM: Neisseria meningitidis
```

-continued

```
<400> SEQUENCE: 866

Asn Tyr Ser Lys Asn Glu Leu Asn Glu Thr Lys Leu Pro
1               5                   10

<210> SEQ ID NO 867

<400> SEQUENCE: 867

000

<210> SEQ ID NO 868

<400> SEQUENCE: 868

000

<210> SEQ ID NO 869
<211> LENGTH: 5
<212> TYPE: PRT
<213> ORGANISM: Neisseria meningitidis

<400> SEQUENCE: 869

Thr Glu Phe Lys Thr
1               5

<210> SEQ ID NO 870
<211> LENGTH: 9
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 870

Val Xaa Glu Lys Ala Arg Val Asp Ala
1               5

<210> SEQ ID NO 871
<211> LENGTH: 9
<212> TYPE: PRT
<213> ORGANISM: Neisseria meningitidis

<400> SEQUENCE: 871

Ile Gln Ser Glu Glu Lys Leu Glu Thr
1               5

<210> SEQ ID NO 872
<211> LENGTH: 7
<212> TYPE: PRT
<213> ORGANISM: Neisseria meningitidis

<400> SEQUENCE: 872

Gln Ala Gly Arg Gly Ser Thr
1               5

<210> SEQ ID NO 873
<211> LENGTH: 10
<212> TYPE: PRT
<213> ORGANISM: Neisseria meningitidis

<400> SEQUENCE: 873

Glu Ser Pro Thr Pro Pro Lys Leu Ser Ala
1               5                   10
```

<210> SEQ ID NO 874
<211> LENGTH: 18
<212> TYPE: PRT
<213> ORGANISM: Neisseria meningitidis

<400> SEQUENCE: 874

Ile Pro Lys Gly Asn Leu Lys Thr Glu Ile Glu Lys Leu Ser Lys Gln
1               5                   10                  15
Pro Glu

<210> SEQ ID NO 875
<211> LENGTH: 11
<212> TYPE: PRT
<213> ORGANISM: Neisseria meningitidis

<400> SEQUENCE: 875

Asp Arg Trp Asp Tyr Lys Gln Glu Gly Leu Thr
1               5                   10

<210> SEQ ID NO 876

<400> SEQUENCE: 876

000

<210> SEQ ID NO 877
<211> LENGTH: 14
<212> TYPE: PRT
<213> ORGANISM: Neisseria meningitidis

<400> SEQUENCE: 877

Asn Lys Gly Asp Val Gly Lys Thr Leu Lys Glu Leu Gly Arg
1               5                   10

<210> SEQ ID NO 878

<400> SEQUENCE: 878

000

<210> SEQ ID NO 879
<211> LENGTH: 6
<212> TYPE: PRT
<213> ORGANISM: Neisseria meningitidis

<400> SEQUENCE: 879

Val Ala Asp Lys Ile Gly
1               5

<210> SEQ ID NO 880

<400> SEQUENCE: 880

000

<210> SEQ ID NO 881
<211> LENGTH: 8
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid -continued

```
<400> SEQUENCE: 881

Gly Ser Leu Lys Asp Xaa Leu Glu
1               5

<210> SEQ ID NO 882
<211> LENGTH: 13
<212> TYPE: PRT
<213> ORGANISM: Neisseria meningitidis

<400> SEQUENCE: 882

Ala His Gly Glu Ala Ala Ser Lys Ile Lys Gln Leu Asp
1               5                   10

<210> SEQ ID NO 883
<211> LENGTH: 9
<212> TYPE: PRT
<213> ORGANISM: Neisseria meningitidis

<400> SEQUENCE: 883

Ala Ala Asn Lys Gly Lys Cys Gln Asp
1               5

<210> SEQ ID NO 884

<400> SEQUENCE: 884

000

<210> SEQ ID NO 885
<211> LENGTH: 17
<212> TYPE: PRT
<213> ORGANISM: Neisseria meningitidis

<400> SEQUENCE: 885

Leu Thr Asn Gly Lys Asn Pro Asp Thr Leu Thr Ala Lys Glu Arg Glu
1               5                   10                  15

Gln

<210> SEQ ID NO 886

<400> SEQUENCE: 886

000

<210> SEQ ID NO 887
<211> LENGTH: 4
<212> TYPE: PRT
<213> ORGANISM: Neisseria meningitidis

<400> SEQUENCE: 887

Val Ala Val Lys
1

<210> SEQ ID NO 888
<211> LENGTH: 15
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid

<400> SEQUENCE: 888

Asn Gln Leu Ser Asp Xaa Glu Gly Arg Glu Phe Asp Asn Glu Met
1               5                   10                  15
```

```
<210> SEQ ID NO 889
<211> LENGTH: 5
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid

<400> SEQUENCE: 889

Ala Lys Gln Asn Xaa
1               5

<210> SEQ ID NO 890
<211> LENGTH: 20
<212> TYPE: PRT
<213> ORGANISM: Neisseria meningitidis

<400> SEQUENCE: 890

Gln Leu Cys Arg Lys Asn Thr Val Lys Lys Tyr Gln Asn Val Ala Asp
1               5                   10                  15

Lys Arg Leu Ala
            20

<210> SEQ ID NO 891
<211> LENGTH: 22
<212> TYPE: PRT
<213> ORGANISM: Neisseria meningitidis

<400> SEQUENCE: 891

Asp Ile Ser Arg Ser Thr Glu Cys Arg Thr Ile Arg Lys Gln His Leu
1               5                   10                  15

Ile Asp Ser Arg Ser Leu
            20

<210> SEQ ID NO 892
<211> LENGTH: 8
<212> TYPE: PRT
<213> ORGANISM: Neisseria meningitidis

<400> SEQUENCE: 892

Leu Ile Gly Lys Asp Asp Glu Trp
1               5

<210> SEQ ID NO 893
<211> LENGTH: 6
<212> TYPE: PRT
<213> ORGANISM: Neisseria meningitidis

<400> SEQUENCE: 893

Gly Asn Thr Lys Pro Leu
1               5

<210> SEQ ID NO 894

<400> SEQUENCE: 894

000

<210> SEQ ID NO 895

<400> SEQUENCE: 895

000
```

```
<210> SEQ ID NO 896
<211> LENGTH: 4
<212> TYPE: PRT
<213> ORGANISM: Neisseria meningitidis

<400> SEQUENCE: 896

Lys Tyr Pro Glu
1

<210> SEQ ID NO 897
<211> LENGTH: 5
<212> TYPE: PRT
<213> ORGANISM: Neisseria meningitidis

<400> SEQUENCE: 897

Asp Gly Phe Ser Gln
1               5

<210> SEQ ID NO 898
<211> LENGTH: 12
<212> TYPE: PRT
<213> ORGANISM: Neisseria meningitidis
<220> FEATURE:
<221> NAME/KEY: Variant
<222> LOCATION: 12
<223> OTHER INFORMATION: Xaa is any amino acid

<400> SEQUENCE: 898

Gln Gly Ile Lys Gly Ala His Asn Arg Thr Asn Xaa
1               5                   10

<210> SEQ ID NO 899
<211> LENGTH: 20
<212> TYPE: PRT
<213> ORGANISM: Neisseria meningitidis
<220> FEATURE:
<221> NAME/KEY: Variant
<222> LOCATION: 7 & 13
<223> OTHER INFORMATION: Xaa is any amino acid

<400> SEQUENCE: 899

Leu Asn Ser Arg Gly Gly Xaa Val Lys Ser Glu Thr Xaa Thr Asp Ile
1               5                   10                  15

Glu Gly Ile Thr
            20

<210> SEQ ID NO 900

<400> SEQUENCE: 900

000

<210> SEQ ID NO 901
<211> LENGTH: 17
<212> TYPE: PRT
<213> ORGANISM: Neisseria meningitidis

<400> SEQUENCE: 901

Thr Leu Asp Arg Thr Gly Lys Pro Asp Gly Gly Phe Lys Glu Ile Ser
1               5                   10                  15

Ser

<210> SEQ ID NO 902
<211> LENGTH: 8
<212> TYPE: PRT
<213> ORGANISM: Neisseria meningitidis
```

```
<220> FEATURE:
<221> NAME/KEY: Variant
<222> LOCATION: 1 & 3
<223> OTHER INFORMATION: Xaa is any amino acid

<400> SEQUENCE: 902

Xaa Phe Xaa Asp Asp Lys Ile Leu
1               5

<210> SEQ ID NO 903
<211> LENGTH: 23
<212> TYPE: PRT
<213> ORGANISM: Neisseria meningitidis

<400> SEQUENCE: 903

Gly Tyr Ser Lys Ala Ser Lys Ile Ala Gln Asn Glu Arg Thr Lys Ser
1               5                   10                  15

Ile Ser Glu Arg Lys Asn Val
            20

<210> SEQ ID NO 904
<211> LENGTH: 4
<212> TYPE: PRT
<213> ORGANISM: Neisseria meningitidis

<400> SEQUENCE: 904

Glu Thr Phe Asp
1

<210> SEQ ID NO 905

<400> SEQUENCE: 905

000

<210> SEQ ID NO 906
<211> LENGTH: 7
<212> TYPE: PRT
<213> ORGANISM: Neisseria meningitidis

<400> SEQUENCE: 906

Ile Leu His Gly Ile Thr Gly
1               5

<210> SEQ ID NO 907
<211> LENGTH: 15
<212> TYPE: PRT
<213> ORGANISM: Neisseria meningitidis

<400> SEQUENCE: 907

Lys Val Val Ala Leu Val Ala Leu Pro Ser Leu Leu Met Ser Leu
1               5                   10                  15

<210> SEQ ID NO 908
<211> LENGTH: 12
<212> TYPE: PRT
<213> ORGANISM: Neisseria meningitidis

<400> SEQUENCE: 908

Thr Tyr Lys Leu Leu Ala Ile Gly Ser Val Val Gly
1               5                   10
```

<210> SEQ ID NO 909

<400> SEQUENCE: 909

000

<210> SEQ ID NO 910
<211> LENGTH: 13
<212> TYPE: PRT
<213> ORGANISM: Neisseria meningitidis

<400> SEQUENCE: 910

Tyr Tyr Ser Val Asn Gly Ile Leu Asn Val Cys Ala Lys
1               5                   10

<210> SEQ ID NO 911
<211> LENGTH: 8
<212> TYPE: PRT
<213> ORGANISM: Neisseria meningitidis

<400> SEQUENCE: 911

Gly Phe Leu Ala Gly Ile Ile Gly
1               5

<210> SEQ ID NO 912
<211> LENGTH: 6
<212> TYPE: PRT
<213> ORGANISM: Neisseria meningitidis

<400> SEQUENCE: 912

Lys Ile Val Gln Ile Tyr
1               5

<210> SEQ ID NO 913
<211> LENGTH: 6
<212> TYPE: PRT
<213> ORGANISM: Neisseria meningitidis

<400> SEQUENCE: 913

Val Leu Ser Val Ile Gly
1               5

<210> SEQ ID NO 914
<211> LENGTH: 8
<212> TYPE: PRT
<213> ORGANISM: Neisseria meningitidis

<400> SEQUENCE: 914

Cys Ser Asn Asn Lys Lys Gly Phe
1               5

<210> SEQ ID NO 915
<211> LENGTH: 5
<212> TYPE: PRT
<213> ORGANISM: Neisseria meningitidis

<400> SEQUENCE: 915

Ala Lys Ala Lys Asn
1               5

<210> SEQ ID NO 916
<211> LENGTH: 6
<212> TYPE: PRT
<213> ORGANISM: Neisseria meningitidis

<400> SEQUENCE: 916

Ala Asn Asn Lys Asn Met
1               5

<210> SEQ ID NO 917
<211> LENGTH: 5
<212> TYPE: PRT
<213> ORGANISM: Neisseria meningitidis

<400> SEQUENCE: 917

Gly Ser Thr Asn Ala
1               5

<210> SEQ ID NO 918
<211> LENGTH: 13
<212> TYPE: PRT
<213> ORGANISM: Neisseria meningitidis

<400> SEQUENCE: 918

Glu Thr Glu Asn Lys Asn Arg Ile Val Lys Ser Ser Asn
1               5                   10

<210> SEQ ID NO 919
<211> LENGTH: 7
<212> TYPE: PRT
<213> ORGANISM: Neisseria meningitidis

<400> SEQUENCE: 919

Leu Asn Lys Ser Glu Tyr Gly
1               5

<210> SEQ ID NO 920
<211> LENGTH: 10
<212> TYPE: PRT
<213> ORGANISM: Neisseria meningitidis

<400> SEQUENCE: 920

Arg Leu Arg Thr Lys Ile Ser Pro Asn Phe
1               5                   10

<210> SEQ ID NO 921
<211> LENGTH: 6
<212> TYPE: PRT
<213> ORGANISM: Neisseria meningitidis

<400> SEQUENCE: 921

Asn Asn Lys Lys Gly Phe
1               5

<210> SEQ ID NO 922
<211> LENGTH: 5
<212> TYPE: PRT
<213> ORGANISM: Neisseria meningitidis

<400> SEQUENCE: 922

Ala Lys Ala Lys Asn
1               5

<210> SEQ ID NO 923
<211> LENGTH: 4
<212> TYPE: PRT
<213> ORGANISM: Neisseria meningitidis

```
<400> SEQUENCE: 923

Ala Asn Asn Lys
1

<210> SEQ ID NO 924
<211> LENGTH: 10
<212> TYPE: PRT
<213> ORGANISM: Neisseria meningitidis

<400> SEQUENCE: 924

Glu Thr Glu Asn Lys Asn Arg Ile Val Lys
1               5                  10

<210> SEQ ID NO 925
<211> LENGTH: 4
<212> TYPE: PRT
<213> ORGANISM: Neisseria meningitidis

<400> SEQUENCE: 925

Lys Ser Glu Tyr
1

<210> SEQ ID NO 926
<211> LENGTH: 6
<212> TYPE: PRT
<213> ORGANISM: Neisseria meningitidis

<400> SEQUENCE: 926

Arg Leu Arg Thr Lys Ile
1               5

<210> SEQ ID NO 927
<211> LENGTH: 7
<212> TYPE: PRT
<213> ORGANISM: Neisseria meningitidis

<400> SEQUENCE: 927

Ile Leu His Gly Ile Thr Gly
1               5

<210> SEQ ID NO 928
<211> LENGTH: 15
<212> TYPE: PRT
<213> ORGANISM: Neisseria meningitidis

<400> SEQUENCE: 928

Lys Val Val Ala Leu Val Ala Leu Pro Ser Leu Leu Met Ser Leu
1               5                  10                  15

<210> SEQ ID NO 929
<211> LENGTH: 12
<212> TYPE: PRT
<213> ORGANISM: Neisseria meningitidis

<400> SEQUENCE: 929

Thr Tyr Lys Leu Leu Ala Ile Gly Ser Val Val Gly
1               5                  10

<210> SEQ ID NO 930

<400> SEQUENCE: 930

000
```

```
<210> SEQ ID NO 931
<211> LENGTH: 13
<212> TYPE: PRT
<213> ORGANISM: Neisseria meningitidis

<400> SEQUENCE: 931

Tyr Tyr Ser Val Asn Gly Ile Leu Asn Val Cys Ala Lys
1               5                   10

<210> SEQ ID NO 932
<211> LENGTH: 8
<212> TYPE: PRT
<213> ORGANISM: Neisseria meningitidis

<400> SEQUENCE: 932

Gly Phe Leu Ala Gly Ile Ile Gly
1               5

<210> SEQ ID NO 933
<211> LENGTH: 6
<212> TYPE: PRT
<213> ORGANISM: Neisseria meningitidis

<400> SEQUENCE: 933

Lys Ile Val Gln Ile Tyr
1               5

<210> SEQ ID NO 934
<211> LENGTH: 6
<212> TYPE: PRT
<213> ORGANISM: Neisseria meningitidis

<400> SEQUENCE: 934

Val Leu Ser Val Ile Gly
1               5

<210> SEQ ID NO 935
<211> LENGTH: 6
<212> TYPE: PRT
<213> ORGANISM: Neisseria meningitidis

<400> SEQUENCE: 935

Asn Asn Lys Lys Gly Phe
1               5

<210> SEQ ID NO 936
<211> LENGTH: 5
<212> TYPE: PRT
<213> ORGANISM: Neisseria meningitidis

<400> SEQUENCE: 936

Ala Lys Ala Lys Asn
1               5

<210> SEQ ID NO 937
<211> LENGTH: 4
<212> TYPE: PRT
<213> ORGANISM: Neisseria meningitidis

<400> SEQUENCE: 937

Ala Asn Asn Lys
1
```

<210> SEQ ID NO 938
<211> LENGTH: 10
<212> TYPE: PRT
<213> ORGANISM: Neisseria meningitidis

<400> SEQUENCE: 938

Glu Thr Glu Asn Lys Asn Arg Ile Ala Lys
1               5                   10

<210> SEQ ID NO 939
<211> LENGTH: 4
<212> TYPE: PRT
<213> ORGANISM: Neisseria meningitidis

<400> SEQUENCE: 939

Lys Ser Glu Tyr
1

<210> SEQ ID NO 940
<211> LENGTH: 6
<212> TYPE: PRT
<213> ORGANISM: Neisseria meningitidis

<400> SEQUENCE: 940

Arg Leu Arg Thr Lys Ile
1               5

<210> SEQ ID NO 941

<400> SEQUENCE: 941

000

<210> SEQ ID NO 942
<211> LENGTH: 10
<212> TYPE: PRT
<213> ORGANISM: Neisseria meningitidis

<400> SEQUENCE: 942

Arg Glu Ala Glu Glu Leu Lys Asp Tyr Arg
1               5                   10

<210> SEQ ID NO 943
<211> LENGTH: 8
<212> TYPE: PRT
<213> ORGANISM: Neisseria meningitidis

<400> SEQUENCE: 943

Ala Cys Gln Pro Gln Ser Glu Ala
1               5

<210> SEQ ID NO 944
<211> LENGTH: 6
<212> TYPE: PRT
<213> ORGANISM: Neisseria meningitidis

<400> SEQUENCE: 944

Val Lys Ala Glu Asn Ser
1               5

<210> SEQ ID NO 945
<211> LENGTH: 11
<212> TYPE: PRT
<213> ORGANISM: Neisseria meningitidis

<400> SEQUENCE: 945

Ala Val Ala Asp Lys Gln Ala Glu Ile Asp Gly
1               5                   10

<210> SEQ ID NO 946
<211> LENGTH: 30
<212> TYPE: PRT
<213> ORGANISM: Neisseria meningitidis

<400> SEQUENCE: 946

Ile Asp Ala Glu Ile Arg Gln Arg Glu Ala Glu Glu Leu Lys Asp Tyr
1               5                   10                  15

Arg Trp Ile His Gly Asp Ala Glu Val Pro Glu Leu Glu Lys
            20                  25                  30

<210> SEQ ID NO 947
<211> LENGTH: 5
<212> TYPE: PRT
<213> ORGANISM: Neisseria meningitidis

<400> SEQUENCE: 947

Pro Gln Ser Glu Ala
1               5

<210> SEQ ID NO 948
<211> LENGTH: 6
<212> TYPE: PRT
<213> ORGANISM: Neisseria meningitidis

<400> SEQUENCE: 948

Val Lys Ala Glu Asn Ser
1               5

<210> SEQ ID NO 949
<211> LENGTH: 11
<212> TYPE: PRT
<213> ORGANISM: Neisseria meningitidis

<400> SEQUENCE: 949

Ala Val Ala Asp Lys Gln Ala Glu Ile Asp Gly
1               5                   10

<210> SEQ ID NO 950
<211> LENGTH: 15
<212> TYPE: PRT
<213> ORGANISM: Neisseria meningitidis

<400> SEQUENCE: 950

Ile Asp Ala Glu Ile Arg Gln Arg Glu Ala Glu Glu Leu Lys Asp
1               5                   10                  15

<210> SEQ ID NO 951
<211> LENGTH: 9
<212> TYPE: PRT
<213> ORGANISM: Neisseria meningitidis

<400> SEQUENCE: 951

Asp Ala Glu Val Pro Glu Leu Glu Lys
1               5

<210> SEQ ID NO 952

<400> SEQUENCE: 952

000

<210> SEQ ID NO 953
<211> LENGTH: 21
<212> TYPE: PRT
<213> ORGANISM: Neisseria meningitidis

<400> SEQUENCE: 953

Asp Trp Gln His Phe Leu Pro Ala Met Gly Thr Val Ser Ala Trp Val
1               5                   10                  15

Ala Val Ile Trp Ala
            20

<210> SEQ ID NO 954
<211> LENGTH: 10
<212> TYPE: PRT
<213> ORGANISM: Neisseria meningitidis

<400> SEQUENCE: 954

Ala Glu Ile Glu Cys Gly Arg Cys Pro Val
1               5                   10

<210> SEQ ID NO 955

<400> SEQUENCE: 955

000

<210> SEQ ID NO 956
<211> LENGTH: 8
<212> TYPE: PRT
<213> ORGANISM: Neisseria meningitidis

<400> SEQUENCE: 956

Glu Ser Glu Lys Asn Gly Arg Tyr
1               5

<210> SEQ ID NO 957
<211> LENGTH: 7
<212> TYPE: PRT
<213> ORGANISM: Neisseria meningitidis

<400> SEQUENCE: 957

Ala Glu Ile Glu Cys Gly Arg
1               5

<210> SEQ ID NO 958
<211> LENGTH: 8
<212> TYPE: PRT
<213> ORGANISM: Neisseria meningitidis

<400> SEQUENCE: 958

Glu Ser Glu Lys Asn Gly Arg Tyr
1               5

<210> SEQ ID NO 959

<400> SEQUENCE: 959

000

```
<210> SEQ ID NO 960
<211> LENGTH: 21
<212> TYPE: PRT
<213> ORGANISM: Neisseria meningitidis

<400> SEQUENCE: 960

Asp Trp Gln His Phe Leu Pro Thr Met Gly Thr Val Ala Ala Trp Val
1               5                   10                  15

Ala Val Ile Trp Ala
            20

<210> SEQ ID NO 961
<211> LENGTH: 10
<212> TYPE: PRT
<213> ORGANISM: Neisseria meningitidis

<400> SEQUENCE: 961

Ala Glu Ile Glu Cys Gly Arg Cys Pro Val
1               5                   10

<210> SEQ ID NO 962
<211> LENGTH: 4
<212> TYPE: PRT
<213> ORGANISM: Neisseria meningitidis

<400> SEQUENCE: 962

Pro Met Thr Asp
1

<210> SEQ ID NO 963
<211> LENGTH: 8
<212> TYPE: PRT
<213> ORGANISM: Neisseria meningitidis

<400> SEQUENCE: 963

Glu Ser Glu Lys Asn Gly Arg Tyr
1               5

<210> SEQ ID NO 964
<211> LENGTH: 7
<212> TYPE: PRT
<213> ORGANISM: Neisseria meningitidis

<400> SEQUENCE: 964

Ala Glu Ile Glu Cys Gly Arg
1               5

<210> SEQ ID NO 965
<211> LENGTH: 8
<212> TYPE: PRT
<213> ORGANISM: Neisseria meningitidis

<400> SEQUENCE: 965

Glu Ser Glu Lys Asn Gly Arg Tyr
1               5

<210> SEQ ID NO 966
<211> LENGTH: 5
<212> TYPE: PRT
<213> ORGANISM: Neisseria meningitidis

<400> SEQUENCE: 966

Leu Ala Val Leu Pro
1               5
```

```
<210> SEQ ID NO 967
<211> LENGTH: 11
<212> TYPE: PRT
<213> ORGANISM: Neisseria meningitidis

<400> SEQUENCE: 967

Val Arg Glu Val Ala Arg Gly Tyr Thr Ala Arg
1               5                   10

<210> SEQ ID NO 968
<211> LENGTH: 8
<212> TYPE: PRT
<213> ORGANISM: Neisseria meningitidis

<400> SEQUENCE: 968

Trp Gly Asp Asn Thr Ala Glu Gln
1               5

<210> SEQ ID NO 969
<211> LENGTH: 7
<212> TYPE: PRT
<213> ORGANISM: Neisseria meningitidis

<400> SEQUENCE: 969

Leu Pro His Ile Asp Leu Val
1               5

<210> SEQ ID NO 970
<211> LENGTH: 4
<212> TYPE: PRT
<213> ORGANISM: Neisseria meningitidis

<400> SEQUENCE: 970

Leu Met Phe Thr
1

<210> SEQ ID NO 971
<211> LENGTH: 7
<212> TYPE: PRT
<213> ORGANISM: Neisseria meningitidis

<400> SEQUENCE: 971

Leu Phe Gly Trp Ala Arg Pro
1               5

<210> SEQ ID NO 972

<400> SEQUENCE: 972

000

<210> SEQ ID NO 973
<211> LENGTH: 5
<212> TYPE: PRT
<213> ORGANISM: Neisseria meningitidis

<400> SEQUENCE: 973

Leu Ala Gln Met Ala
1               5

<210> SEQ ID NO 974
<211> LENGTH: 14
<212> TYPE: PRT
<213> ORGANISM: Neisseria meningitidis
```

-continued

```
<400> SEQUENCE: 974

Leu Ser Ala Lys Tyr Ser Gln Ala Phe Arg Lys Ile Glu Pro
1               5                   10

<210> SEQ ID NO 975
<211> LENGTH: 21
<212> TYPE: PRT
<213> ORGANISM: Neisseria meningitidis

<400> SEQUENCE: 975

Gly Val Leu Gly Ala Phe Ile Ala Pro Ile Val Arg Leu Val Ile Ala
1               5                   10                  15

Phe Val Gln Met Phe
            20

<210> SEQ ID NO 976
<211> LENGTH: 10
<212> TYPE: PRT
<213> ORGANISM: Neisseria meningitidis

<400> SEQUENCE: 976

Thr Val Arg Glu Val Ala Arg Gly Tyr Thr
1               5                   10

<210> SEQ ID NO 977
<211> LENGTH: 11
<212> TYPE: PRT
<213> ORGANISM: Neisseria meningitidis

<400> SEQUENCE: 977

Tyr Trp Gly Asp Asn Thr Ala Glu Gln Tyr Gly
1               5                   10

<210> SEQ ID NO 978
<211> LENGTH: 15
<212> TYPE: PRT
<213> ORGANISM: Neisseria meningitidis

<400> SEQUENCE: 978

Ile Pro Ile Asp Ser Arg Asn Phe Arg Asn Pro Arg Leu Ala Trp
1               5                   10                  15

<210> SEQ ID NO 979
<211> LENGTH: 4
<212> TYPE: PRT
<213> ORGANISM: Neisseria meningitidis

<400> SEQUENCE: 979

Gly Pro Leu Ser
1

<210> SEQ ID NO 980
<211> LENGTH: 4
<212> TYPE: PRT
<213> ORGANISM: Neisseria meningitidis

<400> SEQUENCE: 980

Trp Asp Gly Gly
1

<210> SEQ ID NO 981
<211> LENGTH: 15
<212> TYPE: PRT
<213> ORGANISM: Neisseria meningitidis
```

<400> SEQUENCE: 981

Ala Lys Tyr Ser Gln Ala Phe Arg Lys Ile Glu Pro Tyr Gly Thr
1               5                   10                  15

<210> SEQ ID NO 982
<211> LENGTH: 7
<212> TYPE: PRT
<213> ORGANISM: Neisseria meningitidis

<400> SEQUENCE: 982

Thr Val Arg Glu Val Ala Arg
1               5

<210> SEQ ID NO 983
<211> LENGTH: 7
<212> TYPE: PRT
<213> ORGANISM: Neisseria meningitidis

<400> SEQUENCE: 983

Asn Thr Ala Glu Gln Tyr Gly
1               5

<210> SEQ ID NO 984
<211> LENGTH: 13
<212> TYPE: PRT
<213> ORGANISM: Neisseria meningitidis

<400> SEQUENCE: 984

Ile Pro Ile Asp Ser Arg Asn Phe Arg Asn Pro Arg Leu
1               5                   10

<210> SEQ ID NO 985
<211> LENGTH: 8
<212> TYPE: PRT
<213> ORGANISM: Neisseria meningitidis

<400> SEQUENCE: 985

Gln Ala Phe Arg Lys Ile Glu Pro
1               5

<210> SEQ ID NO 986
<211> LENGTH: 8
<212> TYPE: PRT
<213> ORGANISM: Neisseria meningitidis

<400> SEQUENCE: 986

Trp Gly Asp Asn Thr Ala Glu Gln
1               5

<210> SEQ ID NO 987
<211> LENGTH: 7
<212> TYPE: PRT
<213> ORGANISM: Neisseria meningitidis

<400> SEQUENCE: 987

Leu Pro His Ile Asp Leu Val
1               5

<210> SEQ ID NO 988
<211> LENGTH: 4
<212> TYPE: PRT
<213> ORGANISM: Neisseria meningitidis -continued

```
<400> SEQUENCE: 988

Leu Met Phe Thr
1

<210> SEQ ID NO 989
<211> LENGTH: 7
<212> TYPE: PRT
<213> ORGANISM: Neisseria meningitidis

<400> SEQUENCE: 989

Leu Phe Gly Trp Ala Arg Pro
1               5

<210> SEQ ID NO 990

<400> SEQUENCE: 990

000

<210> SEQ ID NO 991
<211> LENGTH: 5
<212> TYPE: PRT
<213> ORGANISM: Neisseria meningitidis

<400> SEQUENCE: 991

Leu Ala Gln Met Ala
1               5

<210> SEQ ID NO 992
<211> LENGTH: 12
<212> TYPE: PRT
<213> ORGANISM: Neisseria meningitidis
<220> FEATURE:
<221> NAME/KEY: Variant
<222> LOCATION: 5
<223> OTHER INFORMATION: Xaa is any amino acid

<400> SEQUENCE: 992

Asn Ala Ile Leu Xaa Ala Leu Asn Ile Ile Pro Ile
1               5                   10

<210> SEQ ID NO 993
<211> LENGTH: 8
<212> TYPE: PRT
<213> ORGANISM: Neisseria meningitidis

<400> SEQUENCE: 993

Gln Ala Phe Arg Lys Ile Glu Pro
1               5

<210> SEQ ID NO 994

<400> SEQUENCE: 994

000

<210> SEQ ID NO 995
<211> LENGTH: 19
<212> TYPE: PRT
<213> ORGANISM: Neisseria meningitidis
<220> FEATURE:
<221> NAME/KEY: Variant
<222> LOCATION: 4
<223> OTHER INFORMATION: Xaa is any amino acid
```

-continued

```
<400> SEQUENCE: 995

Leu Gly Ala Xaa Ile Ala Pro Ile Val Gln Leu Val Ile Ala Phe Val
1               5                   10                  15

Gln Met Phe

<210> SEQ ID NO 996
<211> LENGTH: 11
<212> TYPE: PRT
<213> ORGANISM: Neisseria meningitidis

<400> SEQUENCE: 996

Tyr Trp Gly Asp Asn Thr Ala Glu Gln Tyr Gly
1               5                   10

<210> SEQ ID NO 997
<211> LENGTH: 15
<212> TYPE: PRT
<213> ORGANISM: Neisseria meningitidis

<400> SEQUENCE: 997

Ile Pro Ile Asp Ser Arg Asn Phe Arg Asn Pro Arg Leu Ala Trp
1               5                   10                  15

<210> SEQ ID NO 998
<211> LENGTH: 4
<212> TYPE: PRT
<213> ORGANISM: Neisseria meningitidis

<400> SEQUENCE: 998

Gly Pro Leu Ser
1

<210> SEQ ID NO 999
<211> LENGTH: 4
<212> TYPE: PRT
<213> ORGANISM: Neisseria meningitidis

<400> SEQUENCE: 999

Trp Asp Gly Gly
1

<210> SEQ ID NO 1000
<211> LENGTH: 15
<212> TYPE: PRT
<213> ORGANISM: Neisseria meningitidis
<220> FEATURE:
<221> NAME/KEY: Variant
<222> LOCATION: 3
<223> OTHER INFORMATION: Xaa is any amino acid

<400> SEQUENCE: 1000

Ala Lys Xaa Ser Gln Ala Phe Arg Lys Ile Glu Pro Tyr Gly Thr
1               5                   10                  15

<210> SEQ ID NO 1001
<211> LENGTH: 7
<212> TYPE: PRT
<213> ORGANISM: Neisseria meningitidis

<400> SEQUENCE: 1001

Asn Thr Ala Glu Gln Tyr Gly
1               5
```

```
<210> SEQ ID NO 1002
<211> LENGTH: 13
<212> TYPE: PRT
<213> ORGANISM: Neisseria meningitidis

<400> SEQUENCE: 1002

Ile Pro Ile Asp Ser Arg Asn Phe Arg Asn Pro Arg Leu
1               5                   10

<210> SEQ ID NO 1003
<211> LENGTH: 11
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1003

Lys Xaa Ser Gln Ala Phe Arg Lys Ile Glu Pro
1               5                   10

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000
```

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

-continued

<210> SEQ ID NO 1022
<400> SEQUENCE: 1022
000

<210> SEQ ID NO 1023
<400> SEQUENCE: 1023
000

<210> SEQ ID NO 1024
<400> SEQUENCE: 1024
000

<210> SEQ ID NO 1025
<400> SEQUENCE: 1025
000

<210> SEQ ID NO 1026
<400> SEQUENCE: 1026
000

<210> SEQ ID NO 1027
<400> SEQUENCE: 1027
000

<210> SEQ ID NO 1028
<400> SEQUENCE: 1028
000

<210> SEQ ID NO 1029
<400> SEQUENCE: 1029
000

<210> SEQ ID NO 1030
<400> SEQUENCE: 1030
000

<210> SEQ ID NO 1031
<400> SEQUENCE: 1031
000

<210> SEQ ID NO 1032
<400> SEQUENCE: 1032
000

-continued

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

-continued

<210> SEQ ID NO 1044
<400> SEQUENCE: 1044
000

<210> SEQ ID NO 1045
<400> SEQUENCE: 1045
000

<210> SEQ ID NO 1046
<400> SEQUENCE: 1046
000

<210> SEQ ID NO 1047
<400> SEQUENCE: 1047
000

<210> SEQ ID NO 1048
<400> SEQUENCE: 1048
000

<210> SEQ ID NO 1049
<400> SEQUENCE: 1049
000

<210> SEQ ID NO 1050
<400> SEQUENCE: 1050
000

<210> SEQ ID NO 1051
<400> SEQUENCE: 1051
000

<210> SEQ ID NO 1052
<400> SEQUENCE: 1052
000

<210> SEQ ID NO 1053
<400> SEQUENCE: 1053
000

<210> SEQ ID NO 1054
<400> SEQUENCE: 1054
000

-continued

<210> SEQ ID NO 1055
<400> SEQUENCE: 1055
000

<210> SEQ ID NO 1056
<400> SEQUENCE: 1056
000

<210> SEQ ID NO 1057
<400> SEQUENCE: 1057
000

<210> SEQ ID NO 1058
<400> SEQUENCE: 1058
000

<210> SEQ ID NO 1059
<400> SEQUENCE: 1059
000

<210> SEQ ID NO 1060
<400> SEQUENCE: 1060
000

<210> SEQ ID NO 1061
<400> SEQUENCE: 1061
000

<210> SEQ ID NO 1062
<400> SEQUENCE: 1062
000

<210> SEQ ID NO 1063
<400> SEQUENCE: 1063
000

<210> SEQ ID NO 1064
<400> SEQUENCE: 1064
000

<210> SEQ ID NO 1065
<400> SEQUENCE: 1065
000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074
<211> LENGTH: 5
<212> TYPE: PRT
<213> ORGANISM: Neisseria meningitidis

<400> SEQUENCE: 1074

Phe Phe Ala Phe Leu
1               5

<210> SEQ ID NO 1075
<211> LENGTH: 17
<212> TYPE: PRT
<213> ORGANISM: Neisseria meningitidis

<400> SEQUENCE: 1075

Gln Asn Ile Ser Ser Ile Thr Gly Val Ile Lys Pro His Asp Ser Tyr
1               5                   10                  15

Asn

<210> SEQ ID NO 1076
<211> LENGTH: 16
<212> TYPE: PRT
<213> ORGANISM: Neisseria meningitidis

<400> SEQUENCE: 1076

Asn Gly Tyr Ala Lys Leu Lys Asp Asn His Arg Tyr Gly Arg Val Ile
1               5                   10                  15

<210> SEQ ID NO 1077

<400> SEQUENCE: 1077

000

<210> SEQ ID NO 1078
<211> LENGTH: 15
<212> TYPE: PRT
<213> ORGANISM: Neisseria meningitidis

<400> SEQUENCE: 1078

Ser Tyr Ala Pro Cys Ala Asn Phe Ile Lys Phe Ala Lys Lys Pro
1               5                   10                  15

<210> SEQ ID NO 1079
<211> LENGTH: 5
<212> TYPE: PRT
<213> ORGANISM: Neisseria meningitidis

<400> SEQUENCE: 1079

Pro Gln Gly Asp Phe
1               5

<210> SEQ ID NO 1080
<211> LENGTH: 7
<212> TYPE: PRT
<213> ORGANISM: Neisseria meningitidis

<400> SEQUENCE: 1080

Arg His Met Lys Asn Lys Asn
1               5

<210> SEQ ID NO 1081
<211> LENGTH: 5
<212> TYPE: PRT
<213> ORGANISM: Neisseria meningitidis

<400> SEQUENCE: 1081

Lys Asn Ile Lys Asn
1               5

<210> SEQ ID NO 1082
<211> LENGTH: 8
<212> TYPE: PRT
<213> ORGANISM: Neisseria meningitidis

<400> SEQUENCE: 1082

His Gln Ile Lys Glu Gln Asn Ile
1               5

<210> SEQ ID NO 1083
<211> LENGTH: 8
<212> TYPE: PRT
<213> ORGANISM: Neisseria meningitidis

```
<400> SEQUENCE: 1083

Ile Lys Pro His Asp Ser Tyr Asn
1               5

<210> SEQ ID NO 1084
<211> LENGTH: 24
<212> TYPE: PRT
<213> ORGANISM: Neisseria meningitidis

<400> SEQUENCE: 1084

Tyr Asp Ser Asn Gly Tyr Ala Lys Leu Lys Asp Asn His Arg Tyr Gly
1               5                   10                  15

Arg Val Ile Arg Glu Thr Pro Tyr
            20

<210> SEQ ID NO 1085
<211> LENGTH: 11
<212> TYPE: PRT
<213> ORGANISM: Neisseria meningitidis

<400> SEQUENCE: 1085

Val Ala Ser Asp Val Lys Asn Lys Ser Ile Arg
1               5                   10

<210> SEQ ID NO 1086
<211> LENGTH: 6
<212> TYPE: PRT
<213> ORGANISM: Neisseria meningitidis

<400> SEQUENCE: 1086

Phe Ala Lys Lys Pro Val
1               5

<210> SEQ ID NO 1087
<211> LENGTH: 9
<212> TYPE: PRT
<213> ORGANISM: Neisseria meningitidis

<400> SEQUENCE: 1087

Tyr Asn Gln Pro Gln Gly Asp Phe Ile
1               5

<210> SEQ ID NO 1088
<211> LENGTH: 8
<212> TYPE: PRT
<213> ORGANISM: Neisseria meningitidis

<400> SEQUENCE: 1088

Glu Ile Asn Asp Gly Lys Lys Ser
1               5

<210> SEQ ID NO 1089
<211> LENGTH: 4
<212> TYPE: PRT
<213> ORGANISM: Neisseria meningitidis

<400> SEQUENCE: 1089

Asp Lys Tyr Lys
1
```

<210> SEQ ID NO 1090

<400> SEQUENCE: 1090

000

<210> SEQ ID NO 1091
<211> LENGTH: 7
<212> TYPE: PRT
<213> ORGANISM: Neisseria meningitidis

<400> SEQUENCE: 1091

Arg His Met Lys Asn Lys Asn
1               5

<210> SEQ ID NO 1092
<211> LENGTH: 5
<212> TYPE: PRT
<213> ORGANISM: Neisseria meningitidis

<400> SEQUENCE: 1092

Lys Asn Ile Lys Asn
1               5

<210> SEQ ID NO 1093
<211> LENGTH: 8
<212> TYPE: PRT
<213> ORGANISM: Neisseria meningitidis

<400> SEQUENCE: 1093

His Gln Ile Lys Glu Gln Asn Ile
1               5

<210> SEQ ID NO 1094
<211> LENGTH: 4
<212> TYPE: PRT
<213> ORGANISM: Neisseria meningitidis

<400> SEQUENCE: 1094

Lys Pro His Asp
1

<210> SEQ ID NO 1095
<211> LENGTH: 9
<212> TYPE: PRT
<213> ORGANISM: Neisseria meningitidis

<400> SEQUENCE: 1095

Ala Lys Leu Lys Asp Asn His Arg Tyr
1               5

<210> SEQ ID NO 1096
<211> LENGTH: 5
<212> TYPE: PRT
<213> ORGANISM: Neisseria meningitidis

<400> SEQUENCE: 1096

Arg Val Ile Arg Glu
1               5

<210> SEQ ID NO 1097
<211> LENGTH: 11
<212> TYPE: PRT
<213> ORGANISM: Neisseria meningitidis

```
<400> SEQUENCE: 1097

Val Ala Ser Asp Val Lys Asn Lys Ser Ile Arg
1               5                   10

<210> SEQ ID NO 1098
<211> LENGTH: 6
<212> TYPE: PRT
<213> ORGANISM: Neisseria meningitidis

<400> SEQUENCE: 1098

Phe Ala Lys Lys Pro Val
1               5

<210> SEQ ID NO 1099

<400> SEQUENCE: 1099

000

<210> SEQ ID NO 1100
<211> LENGTH: 7
<212> TYPE: PRT
<213> ORGANISM: Neisseria meningitidis

<400> SEQUENCE: 1100

Ile Asn Asp Gly Lys Lys Ser
1               5

<210> SEQ ID NO 1101
<211> LENGTH: 4
<212> TYPE: PRT
<213> ORGANISM: Neisseria meningitidis

<400> SEQUENCE: 1101

Asp Lys Tyr Lys
1

<210> SEQ ID NO 1102

<400> SEQUENCE: 1102

000

<210> SEQ ID NO 1103
<211> LENGTH: 23
<212> TYPE: PRT
<213> ORGANISM: Neisseria meningitidis

<400> SEQUENCE: 1103

Met Ala Val Met Ala Val Tyr Ala Leu Leu Ala Phe Leu Ala Leu Tyr
1               5                   10                  15

Ser Phe Phe Glu Ile Leu Tyr
            20

<210> SEQ ID NO 1104
<211> LENGTH: 9
<212> TYPE: PRT
<213> ORGANISM: Neisseria meningitidis

<400> SEQUENCE: 1104

Gly Ile Trp Glu Met Leu Gly Tyr Thr
1               5
```

<210> SEQ ID NO 1105

<400> SEQUENCE: 1105

000

<210> SEQ ID NO 1106
<211> LENGTH: 13
<212> TYPE: PRT
<213> ORGANISM: Neisseria meningitidis

<400> SEQUENCE: 1106

Leu Ile Gly Gly Leu Val Ser Leu Ser Gln Leu Ala Ala
1               5                   10

<210> SEQ ID NO 1107

<400> SEQUENCE: 1107

000

<210> SEQ ID NO 1108

<400> SEQUENCE: 1108

000

<210> SEQ ID NO 1109
<211> LENGTH: 8
<212> TYPE: PRT
<213> ORGANISM: Neisseria meningitidis

<400> SEQUENCE: 1109

Ala Leu Gly Glu Trp Val Ala Pro
1               5

<210> SEQ ID NO 1110
<211> LENGTH: 4
<212> TYPE: PRT
<213> ORGANISM: Neisseria meningitidis

<400> SEQUENCE: 1110

Ala Glu Ala Val
1

<210> SEQ ID NO 1111

<400> SEQUENCE: 1111

000

<210> SEQ ID NO 1112
<211> LENGTH: 11
<212> TYPE: PRT
<213> ORGANISM: Neisseria meningitidis

<400> SEQUENCE: 1112

Leu Thr Thr Tyr Ile Arg His Leu Gln Asn Asn
1               5                   10

<210> SEQ ID NO 1113

<400> SEQUENCE: 1113

000

```
<210> SEQ ID NO 1114
<211> LENGTH: 12
<212> TYPE: PRT
<213> ORGANISM: Neisseria meningitidis
<220> FEATURE:
<221> NAME/KEY: Variant
<222> LOCATION: 8
<223> OTHER INFORMATION: Xaa is any amino acid

<400> SEQUENCE: 1114

Lys Leu Phe Gly Gly Ile Cys Xaa Gly Leu Leu Phe
1               5                   10

<210> SEQ ID NO 1115
<211> LENGTH: 10
<212> TYPE: PRT
<213> ORGANISM: Neisseria meningitidis

<400> SEQUENCE: 1115

Glu Thr Gly Asn Leu Gly Lys Gly Ser Tyr
1               5                   10

<210> SEQ ID NO 1116
<211> LENGTH: 5
<212> TYPE: PRT
<213> ORGANISM: Neisseria meningitidis

<400> SEQUENCE: 1116

Met Pro Ala Arg Ala
1               5

<210> SEQ ID NO 1117
<211> LENGTH: 4
<212> TYPE: PRT
<213> ORGANISM: Neisseria meningitidis

<400> SEQUENCE: 1117

Ala Ala Gly Ser
1

<210> SEQ ID NO 1118
<211> LENGTH: 8
<212> TYPE: PRT
<213> ORGANISM: Neisseria meningitidis

<400> SEQUENCE: 1118

Ala Ser Gly Met Ser Thr Lys Lys
1               5

<210> SEQ ID NO 1119
<211> LENGTH: 9
<212> TYPE: PRT
<213> ORGANISM: Neisseria meningitidis

<400> SEQUENCE: 1119

Leu Ser Gln Lys Ala Glu Asn Ile Lys
1               5

<210> SEQ ID NO 1120
<211> LENGTH: 8
<212> TYPE: PRT
<213> ORGANISM: Neisseria meningitidis

<400> SEQUENCE: 1120

Lys Ile Ser Thr Gly Asn Thr Gly
1               5
```

```
<210> SEQ ID NO 1121
<211> LENGTH: 11
<212> TYPE: PRT
<213> ORGANISM: Neisseria meningitidis
<220> FEATURE:
<221> NAME/KEY: Variant
<222> LOCATION: 8
<223> OTHER INFORMATION: Xaa is any amino acid

<400> SEQUENCE: 1121

Trp Leu Lys Glu Lys Asn Ser Xaa Ile Asn Val
1               5                   10

<210> SEQ ID NO 1122
<211> LENGTH: 5
<212> TYPE: PRT
<213> ORGANISM: Neisseria meningitidis

<400> SEQUENCE: 1122

Glu Met Leu Pro Asp
1               5

<210> SEQ ID NO 1123
<211> LENGTH: 17
<212> TYPE: PRT
<213> ORGANISM: Neisseria meningitidis

<400> SEQUENCE: 1123

Trp Ala Arg Asn Asp Lys Asn Glu Leu Ala Glu Ala Val Glu Ala Asp
1               5                   10                  15

Ser

<210> SEQ ID NO 1124
<211> LENGTH: 9
<212> TYPE: PRT
<213> ORGANISM: Neisseria meningitidis

<400> SEQUENCE: 1124

Val Leu Asn Ser Asp Gly Ser Trp Gln
1               5

<210> SEQ ID NO 1125
<211> LENGTH: 15
<212> TYPE: PRT
<213> ORGANISM: Neisseria meningitidis

<400> SEQUENCE: 1125

Lys Asn Ile Arg Arg Ser Thr Leu Gly Glu Asp Lys Val Glu Val
1               5                   10                  15

<210> SEQ ID NO 1126
<211> LENGTH: 7
<212> TYPE: PRT
<213> ORGANISM: Neisseria meningitidis

<400> SEQUENCE: 1126

Ile Ala Ala Glu Glu Asn Trp
1               5

<210> SEQ ID NO 1127
<211> LENGTH: 5
<212> TYPE: PRT
<213> ORGANISM: Neisseria meningitidis
```

```
<400> SEQUENCE: 1127

Val Lys Arg Asn Leu
1               5

<210> SEQ ID NO 1128
<211> LENGTH: 6
<212> TYPE: PRT
<213> ORGANISM: Neisseria meningitidis

<400> SEQUENCE: 1128

Lys Pro Asp Gln Met Ser
1               5

<210> SEQ ID NO 1129
<211> LENGTH: 9
<212> TYPE: PRT
<213> ORGANISM: Neisseria meningitidis

<400> SEQUENCE: 1129

Leu Gln Asn Asn Ser Gln Asn Thr Arg
1               5

<210> SEQ ID NO 1130
<211> LENGTH: 11
<212> TYPE: PRT
<213> ORGANISM: Neisseria meningitidis

<400> SEQUENCE: 1130

Thr Pro Gln Thr Thr Arg His Gly Asn Met Gly
1               5                   10

<210> SEQ ID NO 1131

<400> SEQUENCE: 1131

000

<210> SEQ ID NO 1132
<211> LENGTH: 5
<212> TYPE: PRT
<213> ORGANISM: Neisseria meningitidis

<400> SEQUENCE: 1132

Met Pro Ala Arg Ala
1               5

<210> SEQ ID NO 1133
<211> LENGTH: 7
<212> TYPE: PRT
<213> ORGANISM: Neisseria meningitidis

<400> SEQUENCE: 1133

Ser Gly Met Ser Thr Lys Lys
1               5

<210> SEQ ID NO 1134
<211> LENGTH: 9
<212> TYPE: PRT
<213> ORGANISM: Neisseria meningitidis

<400> SEQUENCE: 1134

Leu Ser Gln Lys Ala Glu Asn Ile Lys
1               5
```

<210> SEQ ID NO 1135

<400> SEQUENCE: 1135

000

<210> SEQ ID NO 1136
<211> LENGTH: 10
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 1136

Leu Lys Glu Lys Asn Ser Xaa Ile Asn Val
1               5                   10

<210> SEQ ID NO 1137
<211> LENGTH: 4
<212> TYPE: PRT
<213> ORGANISM: Neisseria meningitidis

<400> SEQUENCE: 1137

Glu Met Leu Pro
1

<210> SEQ ID NO 1138
<211> LENGTH: 16
<212> TYPE: PRT
<213> ORGANISM: Neisseria meningitidis

<400> SEQUENCE: 1138

Ala Arg Asn Asp Lys Asn Glu Leu Ala Glu Ala Val Glu Ala Asp Ser
1               5                   10                  15

<210> SEQ ID NO 1139
<211> LENGTH: 14
<212> TYPE: PRT
<213> ORGANISM: Neisseria meningitidis

<400> SEQUENCE: 1139

Asn Ile Arg Arg Ser Thr Leu Gly Glu Asp Lys Val Glu Val
1               5                   10

<210> SEQ ID NO 1140
<211> LENGTH: 7
<212> TYPE: PRT
<213> ORGANISM: Neisseria meningitidis

<400> SEQUENCE: 1140

Ile Ala Ala Glu Glu Asn Trp
1               5

<210> SEQ ID NO 1141
<211> LENGTH: 5
<212> TYPE: PRT
<213> ORGANISM: Neisseria meningitidis

<400> SEQUENCE: 1141

Val Lys Arg Asn Leu
1               5

```
<210> SEQ ID NO 1142
<211> LENGTH: 6
<212> TYPE: PRT
<213> ORGANISM: Neisseria meningitidis

<400> SEQUENCE: 1142

Lys Pro Asp Gln Met Ser
1               5

<210> SEQ ID NO 1143

<400> SEQUENCE: 1143

000

<210> SEQ ID NO 1144
<211> LENGTH: 5
<212> TYPE: PRT
<213> ORGANISM: Neisseria meningitidis

<400> SEQUENCE: 1144

Thr Thr Arg His Gly
1               5

<210> SEQ ID NO 1145

<400> SEQUENCE: 1145

000

<210> SEQ ID NO 1146
<211> LENGTH: 23
<212> TYPE: PRT
<213> ORGANISM: Neisseria meningitidis

<400> SEQUENCE: 1146

Met Ala Val Met Ala Val Tyr Ala Leu Leu Ala Phe Leu Ala Leu Tyr
1               5                   10                  15

Ser Phe Phe Glu Ile Leu Tyr
            20

<210> SEQ ID NO 1147
<211> LENGTH: 8
<212> TYPE: PRT
<213> ORGANISM: Neisseria meningitidis
<220> FEATURE:
<221> NAME/KEY: Variant
<222> LOCATION: 4
<223> OTHER INFORMATION: Xaa is any amino acid

<400> SEQUENCE: 1147

Trp Glu Met Xaa Gly Tyr Thr Ala
1               5

<210> SEQ ID NO 1148

<400> SEQUENCE: 1148

000

<210> SEQ ID NO 1149
<211> LENGTH: 4
<212> TYPE: PRT
<213> ORGANISM: Neisseria meningitidis
```

```
<400> SEQUENCE: 1149

Val Leu Ile Gly
 1

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153
<211> LENGTH: 8
<212> TYPE: PRT
<213> ORGANISM: Neisseria meningitidis

<400> SEQUENCE: 1153

Ala Leu Gly Glu Trp Val Ala Pro
 1               5

<210> SEQ ID NO 1154
<211> LENGTH: 4
<212> TYPE: PRT
<213> ORGANISM: Neisseria meningitidis

<400> SEQUENCE: 1154

Ala Glu Ala Val
 1

<210> SEQ ID NO 1155

<400> SEQUENCE: 1155

000

<210> SEQ ID NO 1156
<211> LENGTH: 11
<212> TYPE: PRT
<213> ORGANISM: Neisseria meningitidis
<220> FEATURE:
<221> NAME/KEY: Variant
<222> LOCATION: 10-11
<223> OTHER INFORMATION: Xaa is any amino acid

<400> SEQUENCE: 1156

Leu Thr Thr Tyr Ile Arg His Leu Gln Xaa Xaa
 1               5                  10

<210> SEQ ID NO 1157

<400> SEQUENCE: 1157

000
```

```
<210> SEQ ID NO 1158
<211> LENGTH: 9
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1158

Lys Xaa Phe Gly Gly Ile Cys Leu Gly
1               5

<210> SEQ ID NO 1159
<211> LENGTH: 16
<212> TYPE: PRT
<213> ORGANISM: Neisseria meningitidis
<220> FEATURE:
<221> NAME/KEY: Variant
<222> LOCATION: 1 & 14
<223> OTHER INFORMATION: Xaa is any amino acid

<400> SEQUENCE: 1159

Xaa Phe Thr Ser Gln Leu Tyr Gly Ile Pro Pro Phe Leu Xaa Gly Ala
1               5                   10                  15

<210> SEQ ID NO 1160
<211> LENGTH: 10
<212> TYPE: PRT
<213> ORGANISM: Neisseria meningitidis

<400> SEQUENCE: 1160

Glu Thr Gly Asn Leu Gly Lys Gly Ser Tyr
1               5                   10

<210> SEQ ID NO 1161
<211> LENGTH: 5
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1161

Met Xaa Ala Arg Ala
1               5

<210> SEQ ID NO 1162
<211> LENGTH: 4
<212> TYPE: PRT
<213> ORGANISM: Neisseria meningitidis

<400> SEQUENCE: 1162

Ala Ala Gly Ser
1

<210> SEQ ID NO 1163
<211> LENGTH: 8
<212> TYPE: PRT
<213> ORGANISM: Neisseria meningitidis

<400> SEQUENCE: 1163

Ala Ser Gly Met Ser Thr Lys Lys
1               5
```

```
<210> SEQ ID NO 1164
<211> LENGTH: 9
<212> TYPE: PRT
<213> ORGANISM: Neisseria meningitidis

<400> SEQUENCE: 1164

Leu Ser Gln Lys Ala Glu Asn Ile Lys
1               5

<210> SEQ ID NO 1165
<211> LENGTH: 8
<212> TYPE: PRT
<213> ORGANISM: Neisseria meningitidis

<400> SEQUENCE: 1165

Lys Ile Ser Thr Gly Asn Thr Gly
1               5

<210> SEQ ID NO 1166
<211> LENGTH: 9
<212> TYPE: PRT
<213> ORGANISM: Neisseria meningitidis

<400> SEQUENCE: 1166

Leu Lys Glu Lys Asn Ser Ile Ile Asn
1               5

<210> SEQ ID NO 1167
<211> LENGTH: 4
<212> TYPE: PRT
<213> ORGANISM: Neisseria meningitidis

<400> SEQUENCE: 1167

Glu Met Leu Pro
1

<210> SEQ ID NO 1168
<211> LENGTH: 17
<212> TYPE: PRT
<213> ORGANISM: Neisseria meningitidis

<400> SEQUENCE: 1168

Trp Ala Arg Asn Asp Lys Asn Glu Leu Ala Glu Ala Val Glu Ala Asp
1               5                   10                  15

Ser

<210> SEQ ID NO 1169
<211> LENGTH: 7
<212> TYPE: PRT
<213> ORGANISM: Neisseria meningitidis

<400> SEQUENCE: 1169

Asn Ser Asp Gly Ser Trp Gln
1               5

<210> SEQ ID NO 1170
<211> LENGTH: 15
<212> TYPE: PRT
<213> ORGANISM: Neisseria meningitidis

<400> SEQUENCE: 1170

Lys Asn Ile Arg Arg Ser Thr Leu Gly Glu Asp Lys Val Glu Val
1               5                   10                  15
```

```
<210> SEQ ID NO 1171

<400> SEQUENCE: 1171

000

<210> SEQ ID NO 1172

<400> SEQUENCE: 1172

000

<210> SEQ ID NO 1173
<211> LENGTH: 5
<212> TYPE: PRT
<213> ORGANISM: Neisseria meningitidis

<400> SEQUENCE: 1173

Val Lys Arg Asn Leu
1               5

<210> SEQ ID NO 1174
<211> LENGTH: 6
<212> TYPE: PRT
<213> ORGANISM: Neisseria meningitidis

<400> SEQUENCE: 1174

Lys Pro Asp Gln Met Ser
1               5

<210> SEQ ID NO 1175
<211> LENGTH: 8
<212> TYPE: PRT
<213> ORGANISM: Neisseria meningitidis
<220> FEATURE:
<221> NAME/KEY: Variant
<222> LOCATION: 2-3
<223> OTHER INFORMATION: Xaa is any amino acid

<400> SEQUENCE: 1175

Gln Xaa Xaa Ser Gln Asn Thr Arg
1               5

<210> SEQ ID NO 1176
<211> LENGTH: 12
<212> TYPE: PRT
<213> ORGANISM: Neisseria meningitidis

<400> SEQUENCE: 1176

Thr Pro Gln Thr Thr Arg His Gly Asn Met Gly Leu
1               5                   10

<210> SEQ ID NO 1177
<211> LENGTH: 6
<212> TYPE: PRT
<213> ORGANISM: Neisseria meningitidis

<400> SEQUENCE: 1177

Arg Lys Gln Glu Lys Arg
1               5

<210> SEQ ID NO 1178

<400> SEQUENCE: 1178

000
```

```
<210> SEQ ID NO 1179
<211> LENGTH: 5
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1179

Met Xaa Ala Arg Ala
1               5

<210> SEQ ID NO 1180
<211> LENGTH: 6
<212> TYPE: PRT
<213> ORGANISM: Neisseria meningitidis

<400> SEQUENCE: 1180

Gly Met Ser Thr Lys Lys
1               5

<210> SEQ ID NO 1181
<211> LENGTH: 9
<212> TYPE: PRT
<213> ORGANISM: Neisseria meningitidis

<400> SEQUENCE: 1181

Leu Ser Gln Lys Ala Glu Asn Ile Lys
1               5

<210> SEQ ID NO 1182

<400> SEQUENCE: 1182

000

<210> SEQ ID NO 1183
<211> LENGTH: 6
<212> TYPE: PRT
<213> ORGANISM: Neisseria meningitidis

<400> SEQUENCE: 1183

Leu Lys Glu Lys Asn Ser
1               5

<210> SEQ ID NO 1184
<211> LENGTH: 4
<212> TYPE: PRT
<213> ORGANISM: Neisseria meningitidis

<400> SEQUENCE: 1184

Glu Met Leu Pro
1

<210> SEQ ID NO 1185
<211> LENGTH: 16
<212> TYPE: PRT
<213> ORGANISM: Neisseria meningitidis

<400> SEQUENCE: 1185

Ala Arg Asn Asp Lys Asn Glu Leu Ala Glu Ala Val Glu Ala Asp Ser
1               5                   10                  15
```

<210> SEQ ID NO 1186
<211> LENGTH: 14
<212> TYPE: PRT
<213> ORGANISM: Neisseria meningitidis

<400> SEQUENCE: 1186

Asn Ile Arg Arg Ser Thr Leu Gly Glu Asp Lys Val Glu Val
1               5                   10

<210> SEQ ID NO 1187

<400> SEQUENCE: 1187

000

<210> SEQ ID NO 1188

<400> SEQUENCE: 1188

000

<210> SEQ ID NO 1189
<211> LENGTH: 5
<212> TYPE: PRT
<213> ORGANISM: Neisseria meningitidis

<400> SEQUENCE: 1189

Val Lys Arg Asn Leu
1               5

<210> SEQ ID NO 1190
<211> LENGTH: 6
<212> TYPE: PRT
<213> ORGANISM: Neisseria meningitidis

<400> SEQUENCE: 1190

Lys Pro Asp Gln Met Ser
1               5

<210> SEQ ID NO 1191

<400> SEQUENCE: 1191

000

<210> SEQ ID NO 1192
<211> LENGTH: 5
<212> TYPE: PRT
<213> ORGANISM: Neisseria meningitidis

<400> SEQUENCE: 1192

Thr Thr Arg His Gly
1               5

<210> SEQ ID NO 1193
<211> LENGTH: 6
<212> TYPE: PRT
<213> ORGANISM: Neisseria meningitidis

<400> SEQUENCE: 1193

Arg Lys Gln Glu Lys Arg
1               5

<210> SEQ ID NO 1194
<211> LENGTH: 10
<212> TYPE: PRT
<213> ORGANISM: Neisseria meningitidis

<400> SEQUENCE: 1194

Gly Asp Leu Cys Gly Lys Leu Lys Thr Thr
1               5                   10

<210> SEQ ID NO 1195
<211> LENGTH: 7
<212> TYPE: PRT
<213> ORGANISM: Neisseria meningitidis

<400> SEQUENCE: 1195

Lys Leu Asn Gly Ile Val Thr
1               5

<210> SEQ ID NO 1196
<211> LENGTH: 9
<212> TYPE: PRT
<213> ORGANISM: Neisseria meningitidis

<400> SEQUENCE: 1196

Gly Phe Lys Asn Val Gly Arg Gly Ile
1               5

<210> SEQ ID NO 1197

<400> SEQUENCE: 1197

000

<210> SEQ ID NO 1198
<211> LENGTH: 5
<212> TYPE: PRT
<213> ORGANISM: Neisseria meningitidis

<400> SEQUENCE: 1198

Tyr Thr Gly Val Leu
1               5

<210> SEQ ID NO 1199

<400> SEQUENCE: 1199

000

<210> SEQ ID NO 1200
<211> LENGTH: 8
<212> TYPE: PRT
<213> ORGANISM: Neisseria meningitidis

<400> SEQUENCE: 1200

Lys Asn Ala Gly Thr Leu Glu Ala
1               5

<210> SEQ ID NO 1201
<211> LENGTH: 12
<212> TYPE: PRT
<213> ORGANISM: Neisseria meningitidis

<400> SEQUENCE: 1201

Arg Ile Glu Asn Ser Gly Arg Ile Ala Thr Thr Ala
1               5                   10

```
<210> SEQ ID NO 1202
<211> LENGTH: 7
<212> TYPE: PRT
<213> ORGANISM: Neisseria meningitidis

<400> SEQUENCE: 1202

Ala Thr Thr Val Leu Asn Ala
1               5

<210> SEQ ID NO 1203
<211> LENGTH: 4
<212> TYPE: PRT
<213> ORGANISM: Neisseria meningitidis

<400> SEQUENCE: 1203

Ala Lys Gly Pro
1

<210> SEQ ID NO 1204

<400> SEQUENCE: 1204

000

<210> SEQ ID NO 1205
<211> LENGTH: 11
<212> TYPE: PRT
<213> ORGANISM: Neisseria meningitidis

<400> SEQUENCE: 1205

Asp Thr Ala His Ile Glu Ala Gly Lys Pro Leu
1               5                   10

<210> SEQ ID NO 1206
<211> LENGTH: 4
<212> TYPE: PRT
<213> ORGANISM: Neisseria meningitidis

<400> SEQUENCE: 1206

Lys Gly Gly Lys
1

<210> SEQ ID NO 1207
<211> LENGTH: 5
<212> TYPE: PRT
<213> ORGANISM: Neisseria meningitidis

<400> SEQUENCE: 1207

Asn Leu Asn Thr Pro
1               5

<210> SEQ ID NO 1208

<400> SEQUENCE: 1208

000

<210> SEQ ID NO 1209
<211> LENGTH: 8
<212> TYPE: PRT
<213> ORGANISM: Neisseria meningitidis

<400> SEQUENCE: 1209

Asn Ala Ala Lys Ala Leu Glu Thr
1               5
```

```
<210> SEQ ID NO 1210
<211> LENGTH: 5
<212> TYPE: PRT
<213> ORGANISM: Neisseria meningitidis

<400> SEQUENCE: 1210

Asp Gly Leu His Ala
1               5

<210> SEQ ID NO 1211
<211> LENGTH: 5
<212> TYPE: PRT
<213> ORGANISM: Neisseria meningitidis

<400> SEQUENCE: 1211

Val Asp Ala Tyr Ala
1               5

<210> SEQ ID NO 1212
<211> LENGTH: 4
<212> TYPE: PRT
<213> ORGANISM: Neisseria meningitidis

<400> SEQUENCE: 1212

Ser Gln Ile Ala
1

<210> SEQ ID NO 1213

<400> SEQUENCE: 1213

000

<210> SEQ ID NO 1214

<400> SEQUENCE: 1214

000

<210> SEQ ID NO 1215
<211> LENGTH: 5
<212> TYPE: PRT
<213> ORGANISM: Neisseria meningitidis

<400> SEQUENCE: 1215

Asn Arg Ile Ser Ala
1               5

<210> SEQ ID NO 1216
<211> LENGTH: 6
<212> TYPE: PRT
<213> ORGANISM: Neisseria meningitidis

<400> SEQUENCE: 1216

Asn Asn Ser Phe Ser Asn
1               5

<210> SEQ ID NO 1217
<211> LENGTH: 6
<212> TYPE: PRT
<213> ORGANISM: Neisseria meningitidis

<400> SEQUENCE: 1217

Gln Gln Ile Ala Gln Leu
1               5
```

<210> SEQ ID NO 1218

<400> SEQUENCE: 1218

000

<210> SEQ ID NO 1219
<211> LENGTH: 4
<212> TYPE: PRT
<213> ORGANISM: Neisseria meningitidis

<400> SEQUENCE: 1219

Ala Ser Lys Lys
1

<210> SEQ ID NO 1220
<211> LENGTH: 9
<212> TYPE: PRT
<213> ORGANISM: Neisseria meningitidis

<400> SEQUENCE: 1220

Ile Asp Gly Ile Thr Asp Gln Tyr Glu
1               5

<210> SEQ ID NO 1221
<211> LENGTH: 5
<212> TYPE: PRT
<213> ORGANISM: Neisseria meningitidis

<400> SEQUENCE: 1221

Thr Tyr Lys Ser His
1               5

<210> SEQ ID NO 1222
<211> LENGTH: 8
<212> TYPE: PRT
<213> ORGANISM: Neisseria meningitidis

<400> SEQUENCE: 1222

Ala Leu Asn Lys Pro Ser Arg Leu
1               5

<210> SEQ ID NO 1223
<211> LENGTH: 5
<212> TYPE: PRT
<213> ORGANISM: Neisseria meningitidis

<400> SEQUENCE: 1223

His Ala Ala Ala Ala
1               5

<210> SEQ ID NO 1224
<211> LENGTH: 5
<212> TYPE: PRT
<213> ORGANISM: Neisseria meningitidis

<400> SEQUENCE: 1224

Gly Lys Ile Ile Arg
1               5

<210> SEQ ID NO 1225
<211> LENGTH: 4
<212> TYPE: PRT
<213> ORGANISM: Neisseria meningitidis

```
<400> SEQUENCE: 1225

Phe Ile Gly Ile
1

<210> SEQ ID NO 1226
<211> LENGTH: 7
<212> TYPE: PRT
<213> ORGANISM: Neisseria meningitidis

<400> SEQUENCE: 1226

Ser Gly Trp Asp Thr Val Leu
1               5

<210> SEQ ID NO 1227
<211> LENGTH: 6
<212> TYPE: PRT
<213> ORGANISM: Neisseria meningitidis

<400> SEQUENCE: 1227

Lys Gly Ile Val Asn Arg
1               5

<210> SEQ ID NO 1228
<211> LENGTH: 10
<212> TYPE: PRT
<213> ORGANISM: Neisseria meningitidis

<400> SEQUENCE: 1228

Gly Ser Thr Ile Glu Thr Leu Lys Leu Pro
1               5                   10

<210> SEQ ID NO 1229
<211> LENGTH: 7
<212> TYPE: PRT
<213> ORGANISM: Neisseria meningitidis

<400> SEQUENCE: 1229

Phe Glu Ser Pro Thr Pro Pro
1               5

<210> SEQ ID NO 1230
<211> LENGTH: 4
<212> TYPE: PRT
<213> ORGANISM: Neisseria meningitidis

<400> SEQUENCE: 1230

Leu Thr Ala Pro
1

<210> SEQ ID NO 1231
<211> LENGTH: 4
<212> TYPE: PRT
<213> ORGANISM: Neisseria meningitidis

<400> SEQUENCE: 1231

Gly Tyr Ile Val
1

<210> SEQ ID NO 1232
<211> LENGTH: 23
<212> TYPE: PRT
<213> ORGANISM: Neisseria meningitidis
```

-continued

```
<400> SEQUENCE: 1232

Ile Glu Lys Leu Ala Lys Gln Pro Glu Tyr Ala Tyr Leu Lys Gln Leu
1               5                   10                  15

Gln Val Ala Lys Asn Val Asn
            20

<210> SEQ ID NO 1233
<211> LENGTH: 4
<212> TYPE: PRT
<213> ORGANISM: Neisseria meningitidis

<400> SEQUENCE: 1233

Arg Ala Gly Ala
1

<210> SEQ ID NO 1234
<211> LENGTH: 5
<212> TYPE: PRT
<213> ORGANISM: Neisseria meningitidis

<400> SEQUENCE: 1234

Thr Ile Ile Val Thr
1               5

<210> SEQ ID NO 1235
<211> LENGTH: 6
<212> TYPE: PRT
<213> ORGANISM: Neisseria meningitidis

<400> SEQUENCE: 1235

Ser Thr Ala Thr Ala Met
1               5

<210> SEQ ID NO 1236
<211> LENGTH: 10
<212> TYPE: PRT
<213> ORGANISM: Neisseria meningitidis

<400> SEQUENCE: 1236

Ala Ala Leu Ala Ser Leu Tyr Ser Gln Ala
1               5                   10

<210> SEQ ID NO 1237
<211> LENGTH: 21
<212> TYPE: PRT
<213> ORGANISM: Neisseria meningitidis

<400> SEQUENCE: 1237

Asp Val Gly Lys Ala Leu Lys Asp Leu Gly Thr Ser Asp Thr Val Lys
1               5                   10                  15

Gln Ile Val Thr Ser
            20

<210> SEQ ID NO 1238
<211> LENGTH: 9
<212> TYPE: PRT
<213> ORGANISM: Neisseria meningitidis

<400> SEQUENCE: 1238

Thr Ala Gly Ala Leu Asn Gln Met Gly
1               5
```

<210> SEQ ID NO 1239
<211> LENGTH: 10
<212> TYPE: PRT
<213> ORGANISM: Neisseria meningitidis

<400> SEQUENCE: 1239

Asn Gln Thr Ile Ala Asn Leu Gly Gly Arg
1               5                   10

<210> SEQ ID NO 1240

<400> SEQUENCE: 1240

000

<210> SEQ ID NO 1241
<211> LENGTH: 4
<212> TYPE: PRT
<213> ORGANISM: Neisseria meningitidis

<400> SEQUENCE: 1241

Asp Asn Leu Gly
1

<210> SEQ ID NO 1242
<211> LENGTH: 13
<212> TYPE: PRT
<213> ORGANISM: Neisseria meningitidis

<400> SEQUENCE: 1242

Ala Ala Leu Gly Ala Leu Val Asn Ser Phe Gln Gly Glu
1               5                   10

<210> SEQ ID NO 1243

<400> SEQUENCE: 1243

000

<210> SEQ ID NO 1244
<211> LENGTH: 12
<212> TYPE: PRT
<213> ORGANISM: Neisseria meningitidis

<400> SEQUENCE: 1244

Lys Gln Phe Ala His Ala Leu Ala Gly Cys Val Ser
1               5                   10

<210> SEQ ID NO 1245
<211> LENGTH: 5
<212> TYPE: PRT
<213> ORGANISM: Neisseria meningitidis

<400> SEQUENCE: 1245

Leu Val Gln Gly Lys
1               5

<210> SEQ ID NO 1246
<211> LENGTH: 7
<212> TYPE: PRT
<213> ORGANISM: Neisseria meningitidis

<400> SEQUENCE: 1246

Ala Ala Val Gly Glu Ile Val
1               5

-continued

<210> SEQ ID NO 1247
<211> LENGTH: 6
<212> TYPE: PRT
<213> ORGANISM: Neisseria meningitidis

<400> SEQUENCE: 1247

Ala Thr Leu Ser Asp Ala
1               5

<210> SEQ ID NO 1248

<400> SEQUENCE: 1248

000

<210> SEQ ID NO 1249

<400> SEQUENCE: 1249

000

<210> SEQ ID NO 1250

<400> SEQUENCE: 1250

000

<210> SEQ ID NO 1251
<211> LENGTH: 4
<212> TYPE: PRT
<213> ORGANISM: Neisseria meningitidis

<400> SEQUENCE: 1251

Ala Glu Val Ala
1

<210> SEQ ID NO 1252
<211> LENGTH: 4
<212> TYPE: PRT
<213> ORGANISM: Neisseria meningitidis

<400> SEQUENCE: 1252

Gln Pro Gln Lys
1

<210> SEQ ID NO 1253
<211> LENGTH: 11
<212> TYPE: PRT
<213> ORGANISM: Neisseria meningitidis

<400> SEQUENCE: 1253

Lys Thr Ala Leu Glu Lys Ile Ile Gln Gly Ile
1               5                   10

<210> SEQ ID NO 1254
<211> LENGTH: 4
<212> TYPE: PRT
<213> ORGANISM: Neisseria meningitidis

<400> SEQUENCE: 1254

Ala Gly Ala Met
1

```
<210> SEQ ID NO 1255
<211> LENGTH: 5
<212> TYPE: PRT
<213> ORGANISM: Neisseria meningitidis

<400> SEQUENCE: 1255

Ile Arg Asn Gly Ile
1               5

<210> SEQ ID NO 1256
<211> LENGTH: 7
<212> TYPE: PRT
<213> ORGANISM: Neisseria meningitidis

<400> SEQUENCE: 1256

Gly Trp Thr Ala Pro Leu Ile
1               5

<210> SEQ ID NO 1257

<400> SEQUENCE: 1257

000

<210> SEQ ID NO 1258
<211> LENGTH: 10
<212> TYPE: PRT
<213> ORGANISM: Neisseria meningitidis

<400> SEQUENCE: 1258

Val Gly Asn Ala Trp Glu Ala Pro Val Gly
1               5                   10

<210> SEQ ID NO 1259
<211> LENGTH: 5
<212> TYPE: PRT
<213> ORGANISM: Neisseria meningitidis

<400> SEQUENCE: 1259

Leu Ser Lys Ala Lys
1               5

<210> SEQ ID NO 1260
<211> LENGTH: 12
<212> TYPE: PRT
<213> ORGANISM: Neisseria meningitidis

<400> SEQUENCE: 1260

Thr Gln Thr Val Lys Glu Leu Asp Gly Leu Leu Gln
1               5                   10

<210> SEQ ID NO 1261

<400> SEQUENCE: 1261

000

<210> SEQ ID NO 1262
<211> LENGTH: 11
<212> TYPE: PRT
<213> ORGANISM: Neisseria meningitidis

<400> SEQUENCE: 1262

Arg Tyr Thr Pro Met Arg Gln Thr Gly Gln Pro
1               5                   10
```

<210> SEQ ID NO 1263
<211> LENGTH: 14
<212> TYPE: PRT
<213> ORGANISM: Neisseria meningitidis

<400> SEQUENCE: 1263

Ser Ala Gly Phe Glu His Val Leu Glu Gly His Phe His Arg
1               5                   10

<210> SEQ ID NO 1264
<211> LENGTH: 6
<212> TYPE: PRT
<213> ORGANISM: Neisseria meningitidis

<400> SEQUENCE: 1264

Val Ser Ser Pro Val Ser
1               5

<210> SEQ ID NO 1265
<211> LENGTH: 13
<212> TYPE: PRT
<213> ORGANISM: Neisseria meningitidis

<400> SEQUENCE: 1265

Tyr Met Arg Thr Val Asp Val Gly Lys Val Ile Gly Thr
1               5                   10

<210> SEQ ID NO 1266
<211> LENGTH: 6
<212> TYPE: PRT
<213> ORGANISM: Neisseria meningitidis

<400> SEQUENCE: 1266

Lys Glu Gly Gly Gln Pro
1               5

<210> SEQ ID NO 1267
<211> LENGTH: 8
<212> TYPE: PRT
<213> ORGANISM: Neisseria meningitidis

<400> SEQUENCE: 1267

Thr Thr Ile Lys Val Phe Thr Asp
1               5

<210> SEQ ID NO 1268
<211> LENGTH: 6
<212> TYPE: PRT
<213> ORGANISM: Neisseria meningitidis

<400> SEQUENCE: 1268

Met Asn Lys Gly Leu His
1               5

<210> SEQ ID NO 1269
<211> LENGTH: 7
<212> TYPE: PRT
<213> ORGANISM: Neisseria meningitidis

<400> SEQUENCE: 1269

Phe Ser Lys Lys His Ser Thr
1               5

<210> SEQ ID NO 1270
<211> LENGTH: 15
<212> TYPE: PRT
<213> ORGANISM: Neisseria meningitidis

<400> SEQUENCE: 1270

Thr Ala Asn Ser Gln Gly Lys Gly Lys Gln Ala Gly Ser Ser Val
1               5                   10                  15

<210> SEQ ID NO 1271
<211> LENGTH: 15
<212> TYPE: PRT
<213> ORGANISM: Neisseria meningitidis

<400> SEQUENCE: 1271

Leu Lys Thr Ser Gly Asp Leu Cys Gly Lys Leu Lys Thr Thr Leu
1               5                   10                  15

<210> SEQ ID NO 1272
<211> LENGTH: 11
<212> TYPE: PRT
<213> ORGANISM: Neisseria meningitidis

<400> SEQUENCE: 1272

Ile Thr Thr Asp Lys Ser Ala Pro Lys Asn Gln
1               5                   10

<210> SEQ ID NO 1273
<211> LENGTH: 7
<212> TYPE: PRT
<213> ORGANISM: Neisseria meningitidis

<400> SEQUENCE: 1273

Lys Thr Asn Thr Gly Ala Pro
1               5

<210> SEQ ID NO 1274
<211> LENGTH: 39
<212> TYPE: PRT
<213> ORGANISM: Neisseria meningitidis

<400> SEQUENCE: 1274

Gln Thr Pro Asn Gly Arg Gly Leu Ser His Asn Arg Tyr Thr Gln Phe
1               5                   10                  15

Asp Val Asp Asn Lys Gly Ala Val Leu Asn Asn Asp Arg Asn Asn Asn
            20                  25                  30

Pro Phe Val Val Lys Gly Ser
        35

<210> SEQ ID NO 1275
<211> LENGTH: 10
<212> TYPE: PRT
<213> ORGANISM: Neisseria meningitidis

<400> SEQUENCE: 1275

Glu Val Arg Gly Thr Ala Ser Lys Leu Asn
1               5                   10

<210> SEQ ID NO 1276
<211> LENGTH: 8
<212> TYPE: PRT
<213> ORGANISM: Neisseria meningitidis -continued

```
<400> SEQUENCE: 1276

Val Gly Gly Gln Lys Ala Asp Val
1               5

<210> SEQ ID NO 1277

<400> SEQUENCE: 1277

000

<210> SEQ ID NO 1278
<211> LENGTH: 9
<212> TYPE: PRT
<213> ORGANISM: Neisseria meningitidis

<400> SEQUENCE: 1278

Gly Gly Phe Lys Asn Val Gly Arg Gly
1               5

<210> SEQ ID NO 1279
<211> LENGTH: 8
<212> TYPE: PRT
<213> ORGANISM: Neisseria meningitidis

<400> SEQUENCE: 1279

Pro Gln Ile Gly Lys Asp Gly Ala
1               5

<210> SEQ ID NO 1280
<211> LENGTH: 6
<212> TYPE: PRT
<213> ORGANISM: Neisseria meningitidis

<400> SEQUENCE: 1280

Asp Val Arg Gln Gly Thr
1               5

<210> SEQ ID NO 1281
<211> LENGTH: 10
<212> TYPE: PRT
<213> ORGANISM: Neisseria meningitidis

<400> SEQUENCE: 1281

Gly Trp Asn Asp Lys Gly Gly Ala Asp Tyr
1               5                   10

<210> SEQ ID NO 1282
<211> LENGTH: 7
<212> TYPE: PRT
<213> ORGANISM: Neisseria meningitidis

<400> SEQUENCE: 1282

Lys Leu Gln Gly Lys Asn Leu
1               5

<210> SEQ ID NO 1283
<211> LENGTH: 16
<212> TYPE: PRT
<213> ORGANISM: Neisseria meningitidis

<400> SEQUENCE: 1283

Ser Thr Gly Pro Gln Lys Val Asp Tyr Ala Ser Gly Glu Ile Ser Ala
1               5                   10                  15
```

<210> SEQ ID NO 1284
<211> LENGTH: 9
<212> TYPE: PRT
<213> ORGANISM: Neisseria meningitidis

<400> SEQUENCE: 1284

Thr Ala Ala Gly Thr Lys Pro Thr Ile
1               5

<210> SEQ ID NO 1285
<211> LENGTH: 13
<212> TYPE: PRT
<213> ORGANISM: Neisseria meningitidis

<400> SEQUENCE: 1285

Ala Asn Glu Lys Gly Val Gly Val Lys Asn Ala Gly Thr
1               5                   10

<210> SEQ ID NO 1286
<211> LENGTH: 4
<212> TYPE: PRT
<213> ORGANISM: Neisseria meningitidis

<400> SEQUENCE: 1286

Glu Ala Ala Lys
1

<210> SEQ ID NO 1287
<211> LENGTH: 23
<212> TYPE: PRT
<213> ORGANISM: Neisseria meningitidis

<400> SEQUENCE: 1287

Ser Ser Gly Arg Ile Glu Asn Ser Gly Arg Ile Ala Thr Thr Ala Asp
1               5                   10                  15

Gly Thr Glu Ala Ser Pro Thr
            20

<210> SEQ ID NO 1288
<211> LENGTH: 7
<212> TYPE: PRT
<213> ORGANISM: Neisseria meningitidis

<400> SEQUENCE: 1288

Glu Thr Thr Glu Lys Gly Ala
1               5

<210> SEQ ID NO 1289
<211> LENGTH: 10
<212> TYPE: PRT
<213> ORGANISM: Neisseria meningitidis

<400> SEQUENCE: 1289

Ser Asn Gly Gly Arg Ile Glu Ser Lys Gly
1               5                   10

<210> SEQ ID NO 1290
<211> LENGTH: 11
<212> TYPE: PRT
<213> ORGANISM: Neisseria meningitidis

<400> SEQUENCE: 1290

Glu Thr Gly Glu Asp Ile Ser Leu Arg Asn Gly
1               5                   10

<210> SEQ ID NO 1291
<211> LENGTH: 8
<212> TYPE: PRT
<213> ORGANISM: Neisseria meningitidis

<400> SEQUENCE: 1291

Gln Asn Asn Gly Ser Arg Pro Ala
1               5

<210> SEQ ID NO 1292
<211> LENGTH: 14
<212> TYPE: PRT
<213> ORGANISM: Neisseria meningitidis

<400> SEQUENCE: 1292

Ile Glu Ser Lys Thr Asn Val Asn Asn Ala Lys Gly Pro Ala
1               5                   10

<210> SEQ ID NO 1293
<211> LENGTH: 14
<212> TYPE: PRT
<213> ORGANISM: Neisseria meningitidis

<400> SEQUENCE: 1293

Leu Ser Ala Asp Gly Arg Thr Val Ile Lys Glu Ala Ser Ile
1               5                   10

<210> SEQ ID NO 1294
<211> LENGTH: 17
<212> TYPE: PRT
<213> ORGANISM: Neisseria meningitidis

<400> SEQUENCE: 1294

Ser Ser Ser Lys Gly Asn Ala Glu Leu Gly Asn Asn Thr Arg Ile Thr
1               5                   10                  15

Gly

<210> SEQ ID NO 1295
<211> LENGTH: 5
<212> TYPE: PRT
<213> ORGANISM: Neisseria meningitidis

<400> SEQUENCE: 1295

Asn Gly Thr Ile Ser
1               5

<210> SEQ ID NO 1296
<211> LENGTH: 8
<212> TYPE: PRT
<213> ORGANISM: Neisseria meningitidis

<400> SEQUENCE: 1296

Ile Asp Ala Lys Asp Thr Ala His
1               5

<210> SEQ ID NO 1297
<211> LENGTH: 7
<212> TYPE: PRT
<213> ORGANISM: Neisseria meningitidis

<400> SEQUENCE: 1297

Glu Ala Gly Lys Pro Leu Ser
1               5

```
<210> SEQ ID NO 1298
<211> LENGTH: 16
<212> TYPE: PRT
<213> ORGANISM: Neisseria meningitidis

<400> SEQUENCE: 1298

Ser Asp Ile Arg Leu Asn Gly Gly Ser Ile Lys Gly Gly Lys Gln Leu
1               5                   10                  15

<210> SEQ ID NO 1299
<211> LENGTH: 16
<212> TYPE: PRT
<213> ORGANISM: Neisseria meningitidis

<400> SEQUENCE: 1299

Ala Asp Asp Asn Ile Thr Ala Lys Thr Thr Asn Leu Asn Thr Pro Gly
1               5                   10                  15

<210> SEQ ID NO 1300
<211> LENGTH: 15
<212> TYPE: PRT
<213> ORGANISM: Neisseria meningitidis

<400> SEQUENCE: 1300

His Thr Gly Lys Asp Leu Asn Leu Asn Val Asp Lys Asp Leu Ser
1               5                   10                  15

<210> SEQ ID NO 1301
<211> LENGTH: 6
<212> TYPE: PRT
<213> ORGANISM: Neisseria meningitidis

<400> SEQUENCE: 1301

Leu Lys Ser Asp Asn Ala
1               5

<210> SEQ ID NO 1302
<211> LENGTH: 19
<212> TYPE: PRT
<213> ORGANISM: Neisseria meningitidis

<400> SEQUENCE: 1302

Thr Gly Thr Ser Lys Thr Leu Thr Ala Ser Lys Asp Met Gly Val Glu
1               5                   10                  15

Ala Gly Ser

<210> SEQ ID NO 1303
<211> LENGTH: 9
<212> TYPE: PRT
<213> ORGANISM: Neisseria meningitidis

<400> SEQUENCE: 1303

Thr Asn Leu Arg Thr Asn Ser Gly Asn
1               5

<210> SEQ ID NO 1304
<211> LENGTH: 14
<212> TYPE: PRT
<213> ORGANISM: Neisseria meningitidis

<400> SEQUENCE: 1304

Ala Lys Gly Asn Ile Gln Leu Arg Asn Thr Lys Leu Asn Ala
1               5                   10
```

<210> SEQ ID NO 1305
<211> LENGTH: 4
<212> TYPE: PRT
<213> ORGANISM: Neisseria meningitidis

<400> SEQUENCE: 1305

Lys Ala Leu Glu
1

<210> SEQ ID NO 1306

<400> SEQUENCE: 1306

000

<210> SEQ ID NO 1307
<211> LENGTH: 5
<212> TYPE: PRT
<213> ORGANISM: Neisseria meningitidis

<400> SEQUENCE: 1307

Ile Val Ser Asp Gly
1               5

<210> SEQ ID NO 1308
<211> LENGTH: 4
<212> TYPE: PRT
<213> ORGANISM: Neisseria meningitidis

<400> SEQUENCE: 1308

Ser Ala Asp Gly
1

<210> SEQ ID NO 1309
<211> LENGTH: 8
<212> TYPE: PRT
<213> ORGANISM: Neisseria meningitidis

<400> SEQUENCE: 1309

Asn Gly Asn Ala Asp Phe Thr Gly
1               5

<210> SEQ ID NO 1310
<211> LENGTH: 7
<212> TYPE: PRT
<213> ORGANISM: Neisseria meningitidis

<400> SEQUENCE: 1310

Ala Lys Ala Asp Val Asn Ala
1               5

<210> SEQ ID NO 1311
<211> LENGTH: 21
<212> TYPE: PRT
<213> ORGANISM: Neisseria meningitidis

<400> SEQUENCE: 1311

Ser Val Gly Lys Gly Arg Leu Lys Ala Asp Asn Thr Asn Ile Thr Ser
1               5                   10                  15

Ser Ser Gly Asp Ile
            20

```
<210> SEQ ID NO 1312
<211> LENGTH: 30
<212> TYPE: PRT
<213> ORGANISM: Neisseria meningitidis

<400> SEQUENCE: 1312

Ile Gln Leu Gly Asp Gly Lys Gln Arg Asn Ser Ile Asn Gly Lys His
1               5                   10                  15

Ile Ser Ile Lys Asn Asn Gly Gly Asn Ala Asp Leu Lys Asn
            20                  25                  30

<210> SEQ ID NO 1313
<211> LENGTH: 4
<212> TYPE: PRT
<213> ORGANISM: Neisseria meningitidis

<400> SEQUENCE: 1313

Ala Lys Ser Gly
1

<210> SEQ ID NO 1314
<211> LENGTH: 18
<212> TYPE: PRT
<213> ORGANISM: Neisseria meningitidis

<400> SEQUENCE: 1314

His Ser Asp Arg Ala Leu Ser Ile Glu Asn Thr Lys Leu Glu Ser Thr
1               5                   10                  15

His Asn

<210> SEQ ID NO 1315
<211> LENGTH: 7
<212> TYPE: PRT
<213> ORGANISM: Neisseria meningitidis

<400> SEQUENCE: 1315

Ala Gln His Glu Arg Val Thr
1               5

<210> SEQ ID NO 1316
<211> LENGTH: 5
<212> TYPE: PRT
<213> ORGANISM: Neisseria meningitidis

<400> SEQUENCE: 1316

Ser Ile Thr Gly Ser
1               5

<210> SEQ ID NO 1317
<211> LENGTH: 14
<212> TYPE: PRT
<213> ORGANISM: Neisseria meningitidis

<400> SEQUENCE: 1317

Trp Gln Asn Asp Lys Leu Pro Ser Ala Asn Lys Leu Val Ala
1               5                   10

<210> SEQ ID NO 1318

<400> SEQUENCE: 1318

000
```

<210> SEQ ID NO 1319
<211> LENGTH: 9
<212> TYPE: PRT
<213> ORGANISM: Neisseria meningitidis

<400> SEQUENCE: 1319

Gln Ile Ala Asp Asn Thr Thr Leu Arg
1               5

<210> SEQ ID NO 1320
<211> LENGTH: 9
<212> TYPE: PRT
<213> ORGANISM: Neisseria meningitidis

<400> SEQUENCE: 1320

Leu Val Lys Arg Gly Asn Ile Asn Trp
1               5

<210> SEQ ID NO 1321
<211> LENGTH: 13
<212> TYPE: PRT
<213> ORGANISM: Neisseria meningitidis

<400> SEQUENCE: 1321

Lys Thr Leu Glu Asp Asn Ala Glu Leu Lys Pro Leu Ala
1               5                   10

<210> SEQ ID NO 1322

<400> SEQUENCE: 1322

000

<210> SEQ ID NO 1323
<211> LENGTH: 5
<212> TYPE: PRT
<213> ORGANISM: Neisseria meningitidis

<400> SEQUENCE: 1323

Ala Gly Ser Gly Thr
1               5

<210> SEQ ID NO 1324
<211> LENGTH: 8
<212> TYPE: PRT
<213> ORGANISM: Neisseria meningitidis

<400> SEQUENCE: 1324

Glu Pro Ala Asn Arg Ile Ser Ala
1               5

<210> SEQ ID NO 1325
<211> LENGTH: 9
<212> TYPE: PRT
<213> ORGANISM: Neisseria meningitidis

<400> SEQUENCE: 1325

Leu Ser Ile Lys Thr Gly Gly Lys Leu
1               5

<210> SEQ ID NO 1326
<211> LENGTH: 11
<212> TYPE: PRT
<213> ORGANISM: Neisseria meningitidis

```
<400> SEQUENCE: 1326

Leu Ser Ala Lys Gly Gly Asn Ala Gly Ala Pro
1               5                   10

<210> SEQ ID NO 1327
<211> LENGTH: 9
<212> TYPE: PRT
<213> ORGANISM: Neisseria meningitidis

<400> SEQUENCE: 1327

Ser Ser Leu Glu Ala Lys Gly Asn Ile
1               5

<210> SEQ ID NO 1328
<211> LENGTH: 18
<212> TYPE: PRT
<213> ORGANISM: Neisseria meningitidis

<400> SEQUENCE: 1328

Val Thr Gly Glu Thr Asp Leu Arg Gly Ser Lys Ile Thr Ala Gly Lys
1               5                   10                  15

Asn Leu

<210> SEQ ID NO 1329
<211> LENGTH: 7
<212> TYPE: PRT
<213> ORGANISM: Neisseria meningitidis

<400> SEQUENCE: 1329

Thr Lys Gly Lys Leu Asn Ile
1               5

<210> SEQ ID NO 1330
<211> LENGTH: 7
<212> TYPE: PRT
<213> ORGANISM: Neisseria meningitidis

<400> SEQUENCE: 1330

Val Asn Asn Ser Phe Ser Asn
1               5

<210> SEQ ID NO 1331
<211> LENGTH: 18
<212> TYPE: PRT
<213> ORGANISM: Neisseria meningitidis

<400> SEQUENCE: 1331

Pro Thr Gln Lys Ala Ala Glu Leu Asn Gln Lys Ser Lys Glu Leu Glu
1               5                   10                  15

Gln Gln

<210> SEQ ID NO 1332
<211> LENGTH: 13
<212> TYPE: PRT
<213> ORGANISM: Neisseria meningitidis

<400> SEQUENCE: 1332

Gln Leu Lys Lys Ser Ser Pro Lys Ser Lys Leu Ile Pro
1               5                   10
```

<210> SEQ ID NO 1333
<211> LENGTH: 8
<212> TYPE: PRT
<213> ORGANISM: Neisseria meningitidis

<400> SEQUENCE: 1333

Leu Gln Glu Glu Arg Asp Arg Leu
1               5

<210> SEQ ID NO 1334
<211> LENGTH: 16
<212> TYPE: PRT
<213> ORGANISM: Neisseria meningitidis

<400> SEQUENCE: 1334

Ile Asn Lys Glu Val Lys Gly Lys Lys Pro Lys Gly Lys Glu Tyr Leu
1               5                   10                  15

<210> SEQ ID NO 1335
<211> LENGTH: 13
<212> TYPE: PRT
<213> ORGANISM: Neisseria meningitidis

<400> SEQUENCE: 1335

Ile Ser Gly Ser Asp Ile Thr Ala Ser Lys Lys Leu Asn
1               5                   10

<210> SEQ ID NO 1336
<211> LENGTH: 7
<212> TYPE: PRT
<213> ORGANISM: Neisseria meningitidis

<400> SEQUENCE: 1336

Lys Ala Ala Asp Ser Glu Ala
1               5

<210> SEQ ID NO 1337
<211> LENGTH: 34
<212> TYPE: PRT
<213> ORGANISM: Neisseria meningitidis

<400> SEQUENCE: 1337

Gly Ile Thr Asp Gln Tyr Glu Ile Gly Lys Pro Thr Tyr Lys Ser His
1               5                   10                  15

Tyr Asp Lys Ala Ala Leu Asn Lys Pro Ser Arg Leu Thr Gly Arg Thr
            20                  25                  30

Gly Val

<210> SEQ ID NO 1338
<211> LENGTH: 7
<212> TYPE: PRT
<213> ORGANISM: Neisseria meningitidis

<400> SEQUENCE: 1338

Ala Leu Asp Asp Ala Arg Ile
1               5

<210> SEQ ID NO 1339
<211> LENGTH: 20
<212> TYPE: PRT
<213> ORGANISM: Neisseria meningitidis -continued

```
<400> SEQUENCE: 1339

Ser Glu Ile Lys Ala Pro Ser Gly Ser Ile Asp Ile Lys Ala His Ser
1               5                   10                  15

Asp Ile Val Leu
            20

<210> SEQ ID NO 1340
<211> LENGTH: 5
<212> TYPE: PRT
<213> ORGANISM: Neisseria meningitidis

<400> SEQUENCE: 1340

Gly Gln Asn Asp Ala
1               5

<210> SEQ ID NO 1341
<211> LENGTH: 23
<212> TYPE: PRT
<213> ORGANISM: Neisseria meningitidis

<400> SEQUENCE: 1341

Leu Lys Thr Lys Gly Lys Ser Gly Lys Ile Ile Arg Lys Thr Lys Phe
1               5                   10                  15

Thr Ser Thr Arg Asp His Leu
            20

<210> SEQ ID NO 1342
<211> LENGTH: 12
<212> TYPE: PRT
<213> ORGANISM: Neisseria meningitidis

<400> SEQUENCE: 1342

Ala Gly Gly Asn Ile Glu Ala Asn Thr Thr Arg Phe
1               5                   10

<210> SEQ ID NO 1343
<211> LENGTH: 5
<212> TYPE: PRT
<213> ORGANISM: Neisseria meningitidis

<400> SEQUENCE: 1343

Ala Pro Ala Gly Lys
1               5

<210> SEQ ID NO 1344
<211> LENGTH: 27
<212> TYPE: PRT
<213> ORGANISM: Neisseria meningitidis

<400> SEQUENCE: 1344

Ala Gly Glu Glu Leu Gln Leu Leu Ala Glu Glu Gly Ile His Lys His
1               5                   10                  15

Glu Leu Asp Val Gln Lys Ser Arg Arg Phe Ile
            20                  25

<210> SEQ ID NO 1345
<211> LENGTH: 18
<212> TYPE: PRT
<213> ORGANISM: Neisseria meningitidis
```

<400> SEQUENCE: 1345

Lys Val Gly Lys Ser Asn Tyr Ser Lys Asn Glu Leu Asn Glu Thr Lys
1               5                   10                  15
Leu Pro

<210> SEQ ID NO 1346
<211> LENGTH: 12
<212> TYPE: PRT
<213> ORGANISM: Neisseria meningitidis

<400> SEQUENCE: 1346

Ala Ala Thr Arg Ser Gly Trp Asp Thr Val Leu Glu
1               5                   10

<210> SEQ ID NO 1347
<211> LENGTH: 5
<212> TYPE: PRT
<213> ORGANISM: Neisseria meningitidis

<400> SEQUENCE: 1347

Thr Glu Phe Lys Thr
1               5

<210> SEQ ID NO 1348
<211> LENGTH: 4
<212> TYPE: PRT
<213> ORGANISM: Neisseria meningitidis

<400> SEQUENCE: 1348

Gly Ala Asp Ile
1

<210> SEQ ID NO 1349
<211> LENGTH: 9
<212> TYPE: PRT
<213> ORGANISM: Neisseria meningitidis

<400> SEQUENCE: 1349

Val Gly Glu Lys Ala Arg Ala Asp Ala
1               5

<210> SEQ ID NO 1350
<211> LENGTH: 11
<212> TYPE: PRT
<213> ORGANISM: Neisseria meningitidis

<400> SEQUENCE: 1350

Ile Gln Ser Glu Glu Lys Leu Glu Thr Asn Ser
1               5                   10

<210> SEQ ID NO 1351
<211> LENGTH: 11
<212> TYPE: PRT
<213> ORGANISM: Neisseria meningitidis

<400> SEQUENCE: 1351

Val Trp Gln Lys Gln Ala Gly Arg Gly Ser Thr
1               5                   10

<210> SEQ ID NO 1352
<211> LENGTH: 16
<212> TYPE: PRT
<213> ORGANISM: Neisseria meningitidis -continued

```
<400> SEQUENCE: 1352

Leu Lys Leu Pro Ser Phe Glu Ser Pro Thr Pro Pro Lys Leu Thr Ala
1               5                   10                  15

<210> SEQ ID NO 1353
<211> LENGTH: 18
<212> TYPE: PRT
<213> ORGANISM: Neisseria meningitidis

<400> SEQUENCE: 1353

Ile Pro Lys Gly Asn Leu Lys Thr Glu Ile Glu Lys Leu Ala Lys Gln
1               5                   10                  15

Pro Glu

<210> SEQ ID NO 1354
<211> LENGTH: 5
<212> TYPE: PRT
<213> ORGANISM: Neisseria meningitidis

<400> SEQUENCE: 1354

Lys Asn Val Asn Trp
1               5

<210> SEQ ID NO 1355
<211> LENGTH: 13
<212> TYPE: PRT
<213> ORGANISM: Neisseria meningitidis

<400> SEQUENCE: 1355

Ala Tyr Asp Lys Trp Asp Tyr Lys Gln Glu Gly Leu Thr
1               5                   10

<210> SEQ ID NO 1356
<211> LENGTH: 5
<212> TYPE: PRT
<213> ORGANISM: Neisseria meningitidis

<400> SEQUENCE: 1356

Ala Ser Gly Ser Ser
1               5

<210> SEQ ID NO 1357
<211> LENGTH: 20
<212> TYPE: PRT
<213> ORGANISM: Neisseria meningitidis

<400> SEQUENCE: 1357

Asn Asn Lys Gly Asp Val Gly Lys Ala Leu Lys Asp Leu Gly Thr Ser
1               5                   10                  15

Asp Thr Val Lys
            20

<210> SEQ ID NO 1358
<211> LENGTH: 4
<212> TYPE: PRT
<213> ORGANISM: Neisseria meningitidis

<400> SEQUENCE: 1358

Gly Ala Asp Ile
1
```

<210> SEQ ID NO 1359
<211> LENGTH: 17
<212> TYPE: PRT
<213> ORGANISM: Neisseria meningitidis

<400> SEQUENCE: 1359

Leu Asn Ser Lys Val Arg Thr Glu Leu Phe Ser Ser Thr Gly Asn Gln
1               5                   10                  15

Thr

<210> SEQ ID NO 1360
<211> LENGTH: 5
<212> TYPE: PRT
<213> ORGANISM: Neisseria meningitidis

<400> SEQUENCE: 1360

Leu Gly Gly Arg Leu
1               5

<210> SEQ ID NO 1361

<400> SEQUENCE: 1361

000

<210> SEQ ID NO 1362
<211> LENGTH: 11
<212> TYPE: PRT
<213> ORGANISM: Neisseria meningitidis

<400> SEQUENCE: 1362

Val Asn Gly Gly Ser Leu Lys Asp Asn Leu Gly
1               5                   10

<210> SEQ ID NO 1363
<211> LENGTH: 18
<212> TYPE: PRT
<213> ORGANISM: Neisseria meningitidis

<400> SEQUENCE: 1363

Phe Gln Gly Glu Ala Ala Ser Lys Ile Lys Thr Thr Phe Ser Asp Asp
1               5                   10                  15

Tyr Val

<210> SEQ ID NO 1364
<211> LENGTH: 9
<212> TYPE: PRT
<213> ORGANISM: Neisseria meningitidis

<400> SEQUENCE: 1364

Val Gln Gly Lys Cys Lys Asp Gly Ala
1               5

<210> SEQ ID NO 1365

<400> SEQUENCE: 1365

000

<210> SEQ ID NO 1366
<211> LENGTH: 19
<212> TYPE: PRT
<213> ORGANISM: Neisseria meningitidis

```
<400> SEQUENCE: 1366

Ser Met Leu Gly Gly Arg Asn Pro Ala Thr Leu Ser Asp Ala Glu Lys
1               5                   10                  15

His Lys Val

<210> SEQ ID NO 1367
<211> LENGTH: 7
<212> TYPE: PRT
<213> ORGANISM: Neisseria meningitidis

<400> SEQUENCE: 1367

Asn Gly Gly Asp Val Asn Thr
1               5

<210> SEQ ID NO 1368
<211> LENGTH: 23
<212> TYPE: PRT
<213> ORGANISM: Neisseria meningitidis

<400> SEQUENCE: 1368

Leu Asn Phe Asp Ser Thr Pro Thr Asn Ala Lys Lys His Gln Pro Gln
1               5                   10                  15

Lys Pro Asp Lys Thr Ala Leu
            20

<210> SEQ ID NO 1369

<400> SEQUENCE: 1369

000

<210> SEQ ID NO 1370
<211> LENGTH: 8
<212> TYPE: PRT
<213> ORGANISM: Neisseria meningitidis

<400> SEQUENCE: 1370

Thr Asn Pro Gln Asp Lys Asp Ala
1               5

<210> SEQ ID NO 1371
<211> LENGTH: 6
<212> TYPE: PRT
<213> ORGANISM: Neisseria meningitidis

<400> SEQUENCE: 1371

Asn Ile Arg Asn Gly Ile
1               5

<210> SEQ ID NO 1372
<211> LENGTH: 4
<212> TYPE: PRT
<213> ORGANISM: Neisseria meningitidis

<400> SEQUENCE: 1372

Thr Ala Gly Lys
1

<210> SEQ ID NO 1373
<211> LENGTH: 5
<212> TYPE: PRT
<213> ORGANISM: Neisseria meningitidis
```

<400> SEQUENCE: 1373

Ala Asn Pro Ser Gly
1               5

<210> SEQ ID NO 1374
<211> LENGTH: 5
<212> TYPE: PRT
<213> ORGANISM: Neisseria meningitidis

<400> SEQUENCE: 1374

Ala Glu Ala Gly Ala
1               5

<210> SEQ ID NO 1375
<211> LENGTH: 7
<212> TYPE: PRT
<213> ORGANISM: Neisseria meningitidis

<400> SEQUENCE: 1375

Ser Lys Ala Lys Ala Ala Lys
1               5

<210> SEQ ID NO 1376
<211> LENGTH: 19
<212> TYPE: PRT
<213> ORGANISM: Neisseria meningitidis

<400> SEQUENCE: 1376

Gln Thr Val Lys Glu Leu Asp Gly Leu Leu Gln Glu Ser Lys Asn Ile
1               5                   10                  15

Gly Ala Val

<210> SEQ ID NO 1377
<211> LENGTH: 20
<212> TYPE: PRT
<213> ORGANISM: Neisseria meningitidis

<400> SEQUENCE: 1377

Asn Ser Thr Thr Arg Tyr Thr Pro Met Arg Gln Thr Gly Gln Pro Val
1               5                   10                  15

Ser Ala Gly Phe
            20

<210> SEQ ID NO 1378
<211> LENGTH: 7
<212> TYPE: PRT
<213> ORGANISM: Neisseria meningitidis

<400> SEQUENCE: 1378

Pro Ile Ala Asn Asn Arg Ser
1               5

<210> SEQ ID NO 1379
<211> LENGTH: 5
<212> TYPE: PRT
<213> ORGANISM: Neisseria meningitidis

<400> SEQUENCE: 1379

Ser Pro Asn Glu Leu
1               5

<210> SEQ ID NO 1380
<211> LENGTH: 6
<212> TYPE: PRT
<213> ORGANISM: Neisseria meningitidis

<400> SEQUENCE: 1380

Gln Ser Asn Lys Val Val
1               5

<210> SEQ ID NO 1381
<211> LENGTH: 9
<212> TYPE: PRT
<213> ORGANISM: Neisseria meningitidis

<400> SEQUENCE: 1381

Val Ser Met Thr Pro Asp Gly Gln Tyr
1               5

<210> SEQ ID NO 1382
<211> LENGTH: 8
<212> TYPE: PRT
<213> ORGANISM: Neisseria meningitidis

<400> SEQUENCE: 1382

Val Asp Val Gly Lys Val Ile Gly
1               5

<210> SEQ ID NO 1383
<211> LENGTH: 11
<212> TYPE: PRT
<213> ORGANISM: Neisseria meningitidis

<400> SEQUENCE: 1383

Thr Ser Ile Lys Glu Gly Gly Gln Pro Thr Thr
1               5                   10

<210> SEQ ID NO 1384
<211> LENGTH: 8
<212> TYPE: PRT
<213> ORGANISM: Neisseria meningitidis

<400> SEQUENCE: 1384

Val Phe Thr Asp Lys Ser Gly Asn
1               5

<210> SEQ ID NO 1385
<211> LENGTH: 5
<212> TYPE: PRT
<213> ORGANISM: Neisseria meningitidis

<400> SEQUENCE: 1385

Pro Val Lys Gly Asn
1               5

<210> SEQ ID NO 1386

<400> SEQUENCE: 1386

000

<210> SEQ ID NO 1387
<211> LENGTH: 4
<212> TYPE: PRT
<213> ORGANISM: Neisseria meningitidis

```
<400> SEQUENCE: 1387

Lys Lys His Ser
1

<210> SEQ ID NO 1388
<211> LENGTH: 12
<212> TYPE: PRT
<213> ORGANISM: Neisseria meningitidis

<400> SEQUENCE: 1388

Thr Ala Asn Ser Gln Gly Lys Gly Lys Gln Ala Gly
1               5                   10

<210> SEQ ID NO 1389
<211> LENGTH: 13
<212> TYPE: PRT
<213> ORGANISM: Neisseria meningitidis

<400> SEQUENCE: 1389

Thr Ser Gly Asp Leu Cys Gly Lys Leu Lys Thr Thr Leu
1               5                   10

<210> SEQ ID NO 1390
<211> LENGTH: 10
<212> TYPE: PRT
<213> ORGANISM: Neisseria meningitidis

<400> SEQUENCE: 1390

Thr Thr Asp Lys Ser Ala Pro Lys Asn Gln
1               5                   10

<210> SEQ ID NO 1391
<211> LENGTH: 7
<212> TYPE: PRT
<213> ORGANISM: Neisseria meningitidis

<400> SEQUENCE: 1391

Pro Asn Gly Arg Gly Leu Ser
1               5

<210> SEQ ID NO 1392
<211> LENGTH: 6
<212> TYPE: PRT
<213> ORGANISM: Neisseria meningitidis

<400> SEQUENCE: 1392

Asp Val Asp Asn Lys Gly
1               5

<210> SEQ ID NO 1393
<211> LENGTH: 6
<212> TYPE: PRT
<213> ORGANISM: Neisseria meningitidis

<400> SEQUENCE: 1393

Asn Asn Asp Arg Asn Asn
1               5

<210> SEQ ID NO 1394
<211> LENGTH: 8
<212> TYPE: PRT
<213> ORGANISM: Neisseria meningitidis
```

```
<400> SEQUENCE: 1394

Glu Val Arg Gly Thr Ala Ser Lys
1               5

<210> SEQ ID NO 1395
<211> LENGTH: 5
<212> TYPE: PRT
<213> ORGANISM: Neisseria meningitidis

<400> SEQUENCE: 1395

Gly Gln Lys Ala Asp
1               5

<210> SEQ ID NO 1396

<400> SEQUENCE: 1396

000

<210> SEQ ID NO 1397
<211> LENGTH: 7
<212> TYPE: PRT
<213> ORGANISM: Neisseria meningitidis

<400> SEQUENCE: 1397

Gln Ile Gly Lys Asp Gly Ala
1               5

<210> SEQ ID NO 1398
<211> LENGTH: 4
<212> TYPE: PRT
<213> ORGANISM: Neisseria meningitidis

<400> SEQUENCE: 1398

Asp Val Arg Gln
1

<210> SEQ ID NO 1399
<211> LENGTH: 7
<212> TYPE: PRT
<213> ORGANISM: Neisseria meningitidis

<400> SEQUENCE: 1399

Trp Asn Asp Lys Gly Gly Ala
1               5

<210> SEQ ID NO 1400

<400> SEQUENCE: 1400

000

<210> SEQ ID NO 1401
<211> LENGTH: 9
<212> TYPE: PRT
<213> ORGANISM: Neisseria meningitidis

<400> SEQUENCE: 1401

Gly Pro Gln Lys Val Asp Tyr Ala Ser
1               5

<210> SEQ ID NO 1402
<211> LENGTH: 4
<212> TYPE: PRT
<213> ORGANISM: Neisseria meningitidis
```

<400> SEQUENCE: 1402

Glu Ile Ser Ala
1

<210> SEQ ID NO 1403

<400> SEQUENCE: 1403

000

<210> SEQ ID NO 1404
<211> LENGTH: 7
<212> TYPE: PRT
<213> ORGANISM: Neisseria meningitidis

<400> SEQUENCE: 1404

Ala Asn Glu Lys Gly Val Gly
1               5

<210> SEQ ID NO 1405
<211> LENGTH: 4
<212> TYPE: PRT
<213> ORGANISM: Neisseria meningitidis

<400> SEQUENCE: 1405

Glu Ala Ala Lys
1

<210> SEQ ID NO 1406
<211> LENGTH: 9
<212> TYPE: PRT
<213> ORGANISM: Neisseria meningitidis

<400> SEQUENCE: 1406

Gly Arg Ile Glu Asn Ser Gly Arg Ile
1               5

<210> SEQ ID NO 1407
<211> LENGTH: 6
<212> TYPE: PRT
<213> ORGANISM: Neisseria meningitidis

<400> SEQUENCE: 1407

Ala Asp Gly Thr Glu Ala
1               5

<210> SEQ ID NO 1408
<211> LENGTH: 7
<212> TYPE: PRT
<213> ORGANISM: Neisseria meningitidis

<400> SEQUENCE: 1408

Glu Thr Thr Glu Lys Gly Ala
1               5

<210> SEQ ID NO 1409
<211> LENGTH: 7
<212> TYPE: PRT
<213> ORGANISM: Neisseria meningitidis

<400> SEQUENCE: 1409

Gly Arg Ile Glu Ser Lys Gly
1               5

```
<210> SEQ ID NO 1410
<211> LENGTH: 8
<212> TYPE: PRT
<213> ORGANISM: Neisseria meningitidis

<400> SEQUENCE: 1410

Glu Thr Gly Glu Asp Ile Ser Leu
1               5

<210> SEQ ID NO 1411
<211> LENGTH: 6
<212> TYPE: PRT
<213> ORGANISM: Neisseria meningitidis

<400> SEQUENCE: 1411

Asn Gly Ser Arg Pro Ala
1               5

<210> SEQ ID NO 1412
<211> LENGTH: 12
<212> TYPE: PRT
<213> ORGANISM: Neisseria meningitidis

<400> SEQUENCE: 1412

Ile Glu Ser Lys Thr Asn Val Asn Asn Ala Lys Gly
1               5                   10

<210> SEQ ID NO 1413
<211> LENGTH: 14
<212> TYPE: PRT
<213> ORGANISM: Neisseria meningitidis

<400> SEQUENCE: 1413

Leu Ser Ala Asp Gly Arg Thr Val Ile Lys Glu Ala Ser Ile
1               5                   10

<210> SEQ ID NO 1414
<211> LENGTH: 10
<212> TYPE: PRT
<213> ORGANISM: Neisseria meningitidis

<400> SEQUENCE: 1414

Ser Ser Lys Gly Asn Ala Glu Leu Gly Asn
1               5                   10

<210> SEQ ID NO 1415
<211> LENGTH: 5
<212> TYPE: PRT
<213> ORGANISM: Neisseria meningitidis

<400> SEQUENCE: 1415

Thr Arg Ile Thr Gly
1               5

<210> SEQ ID NO 1416
<211> LENGTH: 8
<212> TYPE: PRT
<213> ORGANISM: Neisseria meningitidis

<400> SEQUENCE: 1416

Ile Asp Ala Lys Asp Thr Ala His
1               5
```

<210> SEQ ID NO 1417
<211> LENGTH: 4
<212> TYPE: PRT
<213> ORGANISM: Neisseria meningitidis

<400> SEQUENCE: 1417

Glu Ala Gly Lys
1

<210> SEQ ID NO 1418
<211> LENGTH: 5
<212> TYPE: PRT
<213> ORGANISM: Neisseria meningitidis

<400> SEQUENCE: 1418

Ser Asp Ile Arg Leu
1               5

<210> SEQ ID NO 1419
<211> LENGTH: 6
<212> TYPE: PRT
<213> ORGANISM: Neisseria meningitidis

<400> SEQUENCE: 1419

Ser Ile Lys Gly Gly Lys
1               5

<210> SEQ ID NO 1420
<211> LENGTH: 6
<212> TYPE: PRT
<213> ORGANISM: Neisseria meningitidis

<400> SEQUENCE: 1420

Ala Asp Asp Asn Ile Thr
1               5

<210> SEQ ID NO 1421
<211> LENGTH: 14
<212> TYPE: PRT
<213> ORGANISM: Neisseria meningitidis

<400> SEQUENCE: 1421

Thr Gly Lys Asp Leu Asn Leu Asn Val Asp Lys Asp Leu Ser
1               5                   10

<210> SEQ ID NO 1422
<211> LENGTH: 6
<212> TYPE: PRT
<213> ORGANISM: Neisseria meningitidis

<400> SEQUENCE: 1422

Leu Lys Ser Asp Asn Ala
1               5

<210> SEQ ID NO 1423
<211> LENGTH: 4
<212> TYPE: PRT
<213> ORGANISM: Neisseria meningitidis

<400> SEQUENCE: 1423

Gly Thr Ser Lys
1

```
<210> SEQ ID NO 1424
<211> LENGTH: 10
<212> TYPE: PRT
<213> ORGANISM: Neisseria meningitidis

<400> SEQUENCE: 1424

Leu Thr Ala Ser Lys Asp Met Gly Val Glu
1               5                   10

<210> SEQ ID NO 1425
<211> LENGTH: 6
<212> TYPE: PRT
<213> ORGANISM: Neisseria meningitidis

<400> SEQUENCE: 1425

Asn Leu Arg Thr Asn Ser
1               5

<210> SEQ ID NO 1426

<400> SEQUENCE: 1426

000

<210> SEQ ID NO 1427
<211> LENGTH: 7
<212> TYPE: PRT
<213> ORGANISM: Neisseria meningitidis

<400> SEQUENCE: 1427

Arg Asn Thr Lys Leu Asn Ala
1               5

<210> SEQ ID NO 1428
<211> LENGTH: 4
<212> TYPE: PRT
<213> ORGANISM: Neisseria meningitidis

<400> SEQUENCE: 1428

Lys Ala Leu Glu
1

<210> SEQ ID NO 1429
<211> LENGTH: 7
<212> TYPE: PRT
<213> ORGANISM: Neisseria meningitidis

<400> SEQUENCE: 1429

Ala Lys Ala Asp Val Asn Ala
1               5

<210> SEQ ID NO 1430
<211> LENGTH: 13
<212> TYPE: PRT
<213> ORGANISM: Neisseria meningitidis

<400> SEQUENCE: 1430

Ser Val Gly Lys Gly Arg Leu Lys Ala Asp Asn Thr Asn
1               5                   10

<210> SEQ ID NO 1431

<400> SEQUENCE: 1431

000
```

```
<210> SEQ ID NO 1432
<211> LENGTH: 10
<212> TYPE: PRT
<213> ORGANISM: Neisseria meningitidis

<400> SEQUENCE: 1432

Gly Asp Gly Lys Gln Arg Asn Ser Ile Asn
1               5                   10

<210> SEQ ID NO 1433
<211> LENGTH: 11
<212> TYPE: PRT
<213> ORGANISM: Neisseria meningitidis

<400> SEQUENCE: 1433

Lys Asn Asn Gly Gly Asn Ala Asp Leu Lys Asn
1               5                   10

<210> SEQ ID NO 1434
<211> LENGTH: 4
<212> TYPE: PRT
<213> ORGANISM: Neisseria meningitidis

<400> SEQUENCE: 1434

Ala Lys Ser Gly
1

<210> SEQ ID NO 1435
<211> LENGTH: 7
<212> TYPE: PRT
<213> ORGANISM: Neisseria meningitidis

<400> SEQUENCE: 1435

His Ser Asp Arg Ala Leu Ser
1               5

<210> SEQ ID NO 1436
<211> LENGTH: 9
<212> TYPE: PRT
<213> ORGANISM: Neisseria meningitidis

<400> SEQUENCE: 1436

Glu Asn Thr Lys Leu Glu Ser Thr His
1               5

<210> SEQ ID NO 1437
<211> LENGTH: 7
<212> TYPE: PRT
<213> ORGANISM: Neisseria meningitidis

<400> SEQUENCE: 1437

Ala Gln His Glu Arg Val Thr
1               5

<210> SEQ ID NO 1438
<211> LENGTH: 5
<212> TYPE: PRT
<213> ORGANISM: Neisseria meningitidis

<400> SEQUENCE: 1438

Asp Lys Leu Pro Ser
1               5
```

```
<210> SEQ ID NO 1439

<400> SEQUENCE: 1439

000

<210> SEQ ID NO 1440
<211> LENGTH: 6
<212> TYPE: PRT
<213> ORGANISM: Neisseria meningitidis

<400> SEQUENCE: 1440

Leu Val Lys Arg Gly Asn
1               5

<210> SEQ ID NO 1441
<211> LENGTH: 13
<212> TYPE: PRT
<213> ORGANISM: Neisseria meningitidis

<400> SEQUENCE: 1441

Lys Thr Leu Glu Asp Asn Ala Glu Leu Lys Pro Leu Ala
1               5                   10

<210> SEQ ID NO 1442

<400> SEQUENCE: 1442

000

<210> SEQ ID NO 1443

<400> SEQUENCE: 1443

000

<210> SEQ ID NO 1444
<211> LENGTH: 7
<212> TYPE: PRT
<213> ORGANISM: Neisseria meningitidis

<400> SEQUENCE: 1444

Pro Ala Asn Arg Ile Ser Ala
1               5

<210> SEQ ID NO 1445

<400> SEQUENCE: 1445

000

<210> SEQ ID NO 1446

<400> SEQUENCE: 1446

000

<210> SEQ ID NO 1447
<211> LENGTH: 4
<212> TYPE: PRT
<213> ORGANISM: Neisseria meningitidis

<400> SEQUENCE: 1447

Lys Gly Gly Asn
1
```

<210> SEQ ID NO 1448
<211> LENGTH: 9
<212> TYPE: PRT
<213> ORGANISM: Neisseria meningitidis

<400> SEQUENCE: 1448

Ser Ser Leu Glu Ala Lys Gly Asn Ile
1               5

<210> SEQ ID NO 1449
<211> LENGTH: 14
<212> TYPE: PRT
<213> ORGANISM: Neisseria meningitidis

<400> SEQUENCE: 1449

Val Thr Gly Glu Thr Asp Leu Arg Gly Ser Lys Ile Thr Ala
1               5                   10

<210> SEQ ID NO 1450
<211> LENGTH: 7
<212> TYPE: PRT
<213> ORGANISM: Neisseria meningitidis

<400> SEQUENCE: 1450

Thr Lys Gly Lys Leu Asn Ile
1               5

<210> SEQ ID NO 1451
<211> LENGTH: 14
<212> TYPE: PRT
<213> ORGANISM: Neisseria meningitidis

<400> SEQUENCE: 1451

Lys Ala Ala Glu Leu Asn Gln Lys Ser Lys Glu Leu Glu Gln
1               5                   10

<210> SEQ ID NO 1452
<211> LENGTH: 11
<212> TYPE: PRT
<213> ORGANISM: Neisseria meningitidis

<400> SEQUENCE: 1452

Gln Leu Lys Lys Ser Ser Pro Lys Ser Lys Leu
1               5                   10

<210> SEQ ID NO 1453
<211> LENGTH: 8
<212> TYPE: PRT
<213> ORGANISM: Neisseria meningitidis

<400> SEQUENCE: 1453

Leu Gln Glu Glu Arg Asp Arg Leu
1               5

<210> SEQ ID NO 1454
<211> LENGTH: 16
<212> TYPE: PRT
<213> ORGANISM: Neisseria meningitidis

<400> SEQUENCE: 1454

Ile Asn Lys Glu Val Lys Gly Lys Lys Pro Lys Gly Lys Glu Tyr Leu
1               5                   10                  15

<210> SEQ ID NO 1455

<400> SEQUENCE: 1455

000

<210> SEQ ID NO 1456
<211> LENGTH: 9
<212> TYPE: PRT
<213> ORGANISM: Neisseria meningitidis

<400> SEQUENCE: 1456

Asp Ile Thr Ala Ser Lys Lys Leu Asn
1               5

<210> SEQ ID NO 1457
<211> LENGTH: 7
<212> TYPE: PRT
<213> ORGANISM: Neisseria meningitidis

<400> SEQUENCE: 1457

Lys Ala Ala Asp Ser Glu Ala
1               5

<210> SEQ ID NO 1458
<211> LENGTH: 4
<212> TYPE: PRT
<213> ORGANISM: Neisseria meningitidis

<400> SEQUENCE: 1458

Gly Ile Thr Asp
1

<210> SEQ ID NO 1459
<211> LENGTH: 8
<212> TYPE: PRT
<213> ORGANISM: Neisseria meningitidis

<400> SEQUENCE: 1459

Tyr Glu Ile Gly Lys Pro Thr Tyr
1               5

<210> SEQ ID NO 1460
<211> LENGTH: 16
<212> TYPE: PRT
<213> ORGANISM: Neisseria meningitidis

<400> SEQUENCE: 1460

Ser His Tyr Asp Lys Ala Ala Leu Asn Lys Pro Ser Arg Leu Thr Gly
1               5                   10                  15

<210> SEQ ID NO 1461
<211> LENGTH: 7
<212> TYPE: PRT
<213> ORGANISM: Neisseria meningitidis

<400> SEQUENCE: 1461

Ala Leu Asp Asp Ala Arg Ile
1               5

<210> SEQ ID NO 1462
<211> LENGTH: 16
<212> TYPE: PRT
<213> ORGANISM: Neisseria meningitidis

<400> SEQUENCE: 1462

Ser Glu Ile Lys Ala Pro Ser Gly Ser Ile Asp Ile Lys Ala His Ser
1               5                   10                  15

<210> SEQ ID NO 1463

<400> SEQUENCE: 1463

000

<210> SEQ ID NO 1464
<211> LENGTH: 4
<212> TYPE: PRT
<213> ORGANISM: Neisseria meningitidis

<400> SEQUENCE: 1464

Gly Gln Asn Asp
1

<210> SEQ ID NO 1465
<211> LENGTH: 22
<212> TYPE: PRT
<213> ORGANISM: Neisseria meningitidis

<400> SEQUENCE: 1465

Lys Thr Lys Gly Lys Ser Gly Lys Ile Ile Arg Lys Thr Lys Phe Thr
1               5                   10                  15

Ser Thr Arg Asp His Leu
            20

<210> SEQ ID NO 1466
<211> LENGTH: 7
<212> TYPE: PRT
<213> ORGANISM: Neisseria meningitidis

<400> SEQUENCE: 1466

Gly Asn Ile Glu Ala Asn Thr
1               5

<210> SEQ ID NO 1467
<211> LENGTH: 27
<212> TYPE: PRT
<213> ORGANISM: Neisseria meningitidis

<400> SEQUENCE: 1467

Ala Gly Glu Glu Leu Gln Leu Leu Ala Glu Glu Gly Ile His Lys His
1               5                   10                  15

Glu Leu Asp Val Gln Lys Ser Arg Arg Phe Ile
            20                  25

<210> SEQ ID NO 1468
<211> LENGTH: 18
<212> TYPE: PRT
<213> ORGANISM: Neisseria meningitidis

<400> SEQUENCE: 1468

Lys Val Gly Lys Ser Asn Tyr Ser Lys Asn Glu Leu Asn Glu Thr Lys
1               5                   10                  15

Leu Pro

-continued

<210> SEQ ID NO 1469

<400> SEQUENCE: 1469

000

<210> SEQ ID NO 1470

<400> SEQUENCE: 1470

000

<210> SEQ ID NO 1471
<211> LENGTH: 5
<212> TYPE: PRT
<213> ORGANISM: Neisseria meningitidis

<400> SEQUENCE: 1471

Thr Glu Phe Lys Thr
1               5

<210> SEQ ID NO 1472
<211> LENGTH: 9
<212> TYPE: PRT
<213> ORGANISM: Neisseria meningitidis

<400> SEQUENCE: 1472

Val Gly Glu Lys Ala Arg Ala Asp Ala
1               5

<210> SEQ ID NO 1473
<211> LENGTH: 9
<212> TYPE: PRT
<213> ORGANISM: Neisseria meningitidis

<400> SEQUENCE: 1473

Ile Gln Ser Glu Glu Lys Leu Glu Thr
1               5

<210> SEQ ID NO 1474
<211> LENGTH: 7
<212> TYPE: PRT
<213> ORGANISM: Neisseria meningitidis

<400> SEQUENCE: 1474

Gln Ala Gly Arg Gly Ser Thr
1               5

<210> SEQ ID NO 1475
<211> LENGTH: 6
<212> TYPE: PRT
<213> ORGANISM: Neisseria meningitidis

<400> SEQUENCE: 1475

Glu Ser Pro Thr Pro Pro
1               5

<210> SEQ ID NO 1476

<400> SEQUENCE: 1476

000

<210> SEQ ID NO 1477
<211> LENGTH: 18
<212> TYPE: PRT
<213> ORGANISM: Neisseria meningitidis

<400> SEQUENCE: 1477

Ile Pro Lys Gly Asn Leu Lys Thr Glu Ile Glu Lys Leu Ala Lys Gln
1               5                   10                  15

Pro Glu

<210> SEQ ID NO 1478
<211> LENGTH: 11
<212> TYPE: PRT
<213> ORGANISM: Neisseria meningitidis

<400> SEQUENCE: 1478

Asp Lys Trp Asp Tyr Lys Gln Glu Gly Leu Thr
1               5                   10

<210> SEQ ID NO 1479
<211> LENGTH: 20
<212> TYPE: PRT
<213> ORGANISM: Neisseria meningitidis

<400> SEQUENCE: 1479

Asn Asn Lys Gly Asp Val Gly Lys Ala Leu Lys Asp Leu Gly Thr Ser
1               5                   10                  15

Asp Thr Val Lys
            20

<210> SEQ ID NO 1480
<211> LENGTH: 7
<212> TYPE: PRT
<213> ORGANISM: Neisseria meningitidis

<400> SEQUENCE: 1480

Ser Lys Val Arg Thr Glu Leu
1               5

<210> SEQ ID NO 1481
<211> LENGTH: 8
<212> TYPE: PRT
<213> ORGANISM: Neisseria meningitidis

<400> SEQUENCE: 1481

Gly Ser Leu Lys Asp Asn Leu Gly
1               5

<210> SEQ ID NO 1482
<211> LENGTH: 13
<212> TYPE: PRT
<213> ORGANISM: Neisseria meningitidis

<400> SEQUENCE: 1482

Gln Gly Glu Ala Ala Ser Lys Ile Lys Thr Thr Phe Ser
1               5                   10

<210> SEQ ID NO 1483
<211> LENGTH: 7
<212> TYPE: PRT
<213> ORGANISM: Neisseria meningitidis

<400> SEQUENCE: 1483

Gly Lys Cys Lys Asp Gly Ala
1               5

<210> SEQ ID NO 1484

<400> SEQUENCE: 1484

000

<210> SEQ ID NO 1485
<211> LENGTH: 17
<212> TYPE: PRT
<213> ORGANISM: Neisseria meningitidis

<400> SEQUENCE: 1485

Leu Gly Gly Arg Asn Pro Ala Thr Leu Ser Asp Ala Glu Lys His Lys
1               5                   10                  15

Val

<210> SEQ ID NO 1486
<211> LENGTH: 5
<212> TYPE: PRT
<213> ORGANISM: Neisseria meningitidis

<400> SEQUENCE: 1486

Gly Asp Val Asn Thr
1               5

<210> SEQ ID NO 1487
<211> LENGTH: 19
<212> TYPE: PRT
<213> ORGANISM: Neisseria meningitidis

<400> SEQUENCE: 1487

Ser Thr Pro Thr Asn Ala Lys Lys His Gln Pro Gln Lys Pro Asp Lys
1               5                   10                  15

Thr Ala Leu

<210> SEQ ID NO 1488

<400> SEQUENCE: 1488

000

<210> SEQ ID NO 1489
<211> LENGTH: 7
<212> TYPE: PRT
<213> ORGANISM: Neisseria meningitidis

<400> SEQUENCE: 1489

Asn Pro Gln Asp Lys Asp Ala
1               5

<210> SEQ ID NO 1490

<400> SEQUENCE: 1490

000

<210> SEQ ID NO 1491
<211> LENGTH: 7
<212> TYPE: PRT
<213> ORGANISM: Neisseria meningitidis -continued

```
<400> SEQUENCE: 1491

Ser Lys Ala Lys Ala Ala Lys
1               5

<210> SEQ ID NO 1492
<211> LENGTH: 14
<212> TYPE: PRT
<213> ORGANISM: Neisseria meningitidis

<400> SEQUENCE: 1492

Thr Val Lys Glu Leu Asp Gly Leu Leu Gln Glu Ser Lys Asn
1               5                   10

<210> SEQ ID NO 1493
<211> LENGTH: 4
<212> TYPE: PRT
<213> ORGANISM: Neisseria meningitidis

<400> SEQUENCE: 1493

Arg Gln Thr Gly
1

<210> SEQ ID NO 1494

<400> SEQUENCE: 1494

000

<210> SEQ ID NO 1495

<400> SEQUENCE: 1495

000

<210> SEQ ID NO 1496

<400> SEQUENCE: 1496

000

<210> SEQ ID NO 1497

<400> SEQUENCE: 1497

000

<210> SEQ ID NO 1498

<400> SEQUENCE: 1498

000

<210> SEQ ID NO 1499
<211> LENGTH: 7
<212> TYPE: PRT
<213> ORGANISM: Neisseria meningitidis

<400> SEQUENCE: 1499

Ser Ile Lys Glu Gly Gly Gln
1               5

<210> SEQ ID NO 1500
<211> LENGTH: 6
<212> TYPE: PRT
<213> ORGANISM: Neisseria meningitidis
```

-continued

```
<400> SEQUENCE: 1500

Phe Thr Asp Lys Ser Gly
1               5

<210> SEQ ID NO 1501
<211> LENGTH: 10
<212> TYPE: PRT
<213> ORGANISM: Neisseria meningitidis

<400> SEQUENCE: 1501

Gly Asp Leu Cys Gly Lys Leu Lys Thr Thr
1               5                   10

<210> SEQ ID NO 1502
<211> LENGTH: 7
<212> TYPE: PRT
<213> ORGANISM: Neisseria meningitidis

<400> SEQUENCE: 1502

Lys Leu Asn Gly Ile Val Thr
1               5

<210> SEQ ID NO 1503
<211> LENGTH: 9
<212> TYPE: PRT
<213> ORGANISM: Neisseria meningitidis

<400> SEQUENCE: 1503

Gly Phe Lys Asn Val Gly Arg Gly Ile
1               5

<210> SEQ ID NO 1504

<400> SEQUENCE: 1504

000

<210> SEQ ID NO 1505
<211> LENGTH: 5
<212> TYPE: PRT
<213> ORGANISM: Neisseria meningitidis

<400> SEQUENCE: 1505

Tyr Thr Gly Val Leu
1               5

<210> SEQ ID NO 1506

<400> SEQUENCE: 1506

000

<210> SEQ ID NO 1507
<211> LENGTH: 8
<212> TYPE: PRT
<213> ORGANISM: Neisseria meningitidis

<400> SEQUENCE: 1507

Lys Asn Ala Gly Thr Leu Glu Ala
1               5

<210> SEQ ID NO 1508
<211> LENGTH: 12
<212> TYPE: PRT
<213> ORGANISM: Neisseria meningitidis
```

```
<400> SEQUENCE: 1508

Arg Ile Glu Asn Ser Gly Arg Ile Ala Thr Thr Ala
1               5                   10

<210> SEQ ID NO 1509

<400> SEQUENCE: 1509

000

<210> SEQ ID NO 1510
<211> LENGTH: 7
<212> TYPE: PRT
<213> ORGANISM: Neisseria meningitidis

<400> SEQUENCE: 1510

Ala Thr Thr Val Leu Asn Ala
1               5

<210> SEQ ID NO 1511

<400> SEQUENCE: 1511

000

<210> SEQ ID NO 1512
<211> LENGTH: 9
<212> TYPE: PRT
<213> ORGANISM: Neisseria meningitidis

<400> SEQUENCE: 1512

Thr Ala His Ile Glu Ser Gly Lys Pro
1               5

<210> SEQ ID NO 1513
<211> LENGTH: 4
<212> TYPE: PRT
<213> ORGANISM: Neisseria meningitidis

<400> SEQUENCE: 1513

Lys Gly Gly Lys
1

<210> SEQ ID NO 1514
<211> LENGTH: 5
<212> TYPE: PRT
<213> ORGANISM: Neisseria meningitidis

<400> SEQUENCE: 1514

Asn Leu Asn Thr Pro
1               5

<210> SEQ ID NO 1515

<400> SEQUENCE: 1515

000

<210> SEQ ID NO 1516
<211> LENGTH: 8
<212> TYPE: PRT
<213> ORGANISM: Neisseria meningitidis
```

-continued

```
<400> SEQUENCE: 1516

Asn Ala Ala Lys Ala Leu Glu Thr
1               5

<210> SEQ ID NO 1517
<211> LENGTH: 5
<212> TYPE: PRT
<213> ORGANISM: Neisseria meningitidis

<400> SEQUENCE: 1517

Asp Gly Leu His Ala
1               5

<210> SEQ ID NO 1518
<211> LENGTH: 5
<212> TYPE: PRT
<213> ORGANISM: Neisseria meningitidis

<400> SEQUENCE: 1518

Val Asp Ala Tyr Ala
1               5

<210> SEQ ID NO 1519

<400> SEQUENCE: 1519

000

<210> SEQ ID NO 1520

<400> SEQUENCE: 1520

000

<210> SEQ ID NO 1521

<400> SEQUENCE: 1521

000

<210> SEQ ID NO 1522
<211> LENGTH: 5
<212> TYPE: PRT
<213> ORGANISM: Neisseria meningitidis

<400> SEQUENCE: 1522

Asn Arg Ile Ser Ala
1               5

<210> SEQ ID NO 1523
<211> LENGTH: 9
<212> TYPE: PRT
<213> ORGANISM: Neisseria meningitidis
<220> FEATURE:
<221> NAME/KEY: Variant
<222> LOCATION: 9
<223> OTHER INFORMATION: Xaa is any amino acid

<400> SEQUENCE: 1523

Asn Asn Ser Phe Ser Asn Tyr Phe Xaa
1               5

<210> SEQ ID NO 1524
<211> LENGTH: 7
<212> TYPE: PRT
<213> ORGANISM: Neisseria meningitidis
```

```
<400> SEQUENCE: 1524

Gln Gln Ile Ala Gln Leu Lys
1               5

<210> SEQ ID NO 1525

<400> SEQUENCE: 1525

000

<210> SEQ ID NO 1526
<211> LENGTH: 4
<212> TYPE: PRT
<213> ORGANISM: Neisseria meningitidis

<400> SEQUENCE: 1526

Ala Ser Lys Lys
1

<210> SEQ ID NO 1527
<211> LENGTH: 9
<212> TYPE: PRT
<213> ORGANISM: Neisseria meningitidis

<400> SEQUENCE: 1527

Ile Asp Gly Ile Thr Asp Gln Tyr Glu
1               5

<210> SEQ ID NO 1528
<211> LENGTH: 5
<212> TYPE: PRT
<213> ORGANISM: Neisseria meningitidis

<400> SEQUENCE: 1528

Thr Tyr Lys Ser His
1               5

<210> SEQ ID NO 1529
<211> LENGTH: 8
<212> TYPE: PRT
<213> ORGANISM: Neisseria meningitidis

<400> SEQUENCE: 1529

Ala Leu Asn Lys Pro Ser Arg Leu
1               5

<210> SEQ ID NO 1530
<211> LENGTH: 5
<212> TYPE: PRT
<213> ORGANISM: Neisseria meningitidis

<400> SEQUENCE: 1530

His Ala Ala Ala Ala
1               5

<210> SEQ ID NO 1531
<211> LENGTH: 4
<212> TYPE: PRT
<213> ORGANISM: Neisseria meningitidis
<220> FEATURE:
<221> NAME/KEY: Variant
<222> LOCATION: 2-3
<223> OTHER INFORMATION: Xaa is any amino acid
```

```
<400> SEQUENCE: 1531

Gly Xaa Xaa Ile
1

<210> SEQ ID NO 1532
<211> LENGTH: 7
<212> TYPE: PRT
<213> ORGANISM: Neisseria meningitidis

<400> SEQUENCE: 1532

Ser Gly Trp Asp Thr Val Leu
1               5

<210> SEQ ID NO 1533
<211> LENGTH: 6
<212> TYPE: PRT
<213> ORGANISM: Neisseria meningitidis

<400> SEQUENCE: 1533

Lys Gly Ile Val Asn Arg
1               5

<210> SEQ ID NO 1534
<211> LENGTH: 10
<212> TYPE: PRT
<213> ORGANISM: Neisseria meningitidis

<400> SEQUENCE: 1534

Gly Ser Thr Ile Glu Thr Leu Lys Leu Pro
1               5                   10

<210> SEQ ID NO 1535
<211> LENGTH: 7
<212> TYPE: PRT
<213> ORGANISM: Neisseria meningitidis

<400> SEQUENCE: 1535

Phe Glu Ser Pro Thr Pro Pro
1               5

<210> SEQ ID NO 1536
<211> LENGTH: 9
<212> TYPE: PRT
<213> ORGANISM: Neisseria meningitidis

<400> SEQUENCE: 1536

Leu Ser Ala Pro Gly Gly Tyr Ile Val
1               5

<210> SEQ ID NO 1537
<211> LENGTH: 23
<212> TYPE: PRT
<213> ORGANISM: Neisseria meningitidis

<400> SEQUENCE: 1537

Ile Glu Lys Leu Ser Lys Gln Pro Glu Tyr Ala Tyr Leu Lys Gln Leu
1               5                   10                  15

Gln Val Ala Lys Asn Ile Asn
            20
```

```
<210> SEQ ID NO 1538

<400> SEQUENCE: 1538

000

<210> SEQ ID NO 1539
<211> LENGTH: 6
<212> TYPE: PRT
<213> ORGANISM: Neisseria meningitidis

<400> SEQUENCE: 1539

Phe Ala Ser Leu Ala Ser
1               5

<210> SEQ ID NO 1540
<211> LENGTH: 13
<212> TYPE: PRT
<213> ORGANISM: Neisseria meningitidis

<400> SEQUENCE: 1540

Asp Val Gly Lys Thr Leu Lys Glu Leu Gly Arg Ser Ser
1               5                   10

<210> SEQ ID NO 1541
<211> LENGTH: 9
<212> TYPE: PRT
<213> ORGANISM: Neisseria meningitidis

<400> SEQUENCE: 1541

Gly Val Ala Asp Lys Ile Gly Ala Ser
1               5

<210> SEQ ID NO 1542
<211> LENGTH: 6
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1542

Leu Xaa Asn Val Ser Asp
1               5

<210> SEQ ID NO 1543
<211> LENGTH: 6
<212> TYPE: PRT
<213> ORGANISM: Neisseria meningitidis

<400> SEQUENCE: 1543

Met Asn Lys Gly Leu His
1               5

<210> SEQ ID NO 1544
<211> LENGTH: 7
<212> TYPE: PRT
<213> ORGANISM: Neisseria meningitidis

<400> SEQUENCE: 1544

Phe Ser Lys Lys His Ser Thr
1               5
```

<210> SEQ ID NO 1545
<211> LENGTH: 15
<212> TYPE: PRT
<213> ORGANISM: Neisseria meningitidis

<400> SEQUENCE: 1545

Thr Ala Asn Ser Gln Gly Lys Gly Lys Gln Ala Gly Ser Ser Val
1               5                   10                  15

<210> SEQ ID NO 1546
<211> LENGTH: 15
<212> TYPE: PRT
<213> ORGANISM: Neisseria meningitidis

<400> SEQUENCE: 1546

Leu Lys Thr Ser Gly Asp Leu Cys Gly Lys Leu Lys Thr Ser Leu
1               5                   10                  15

<210> SEQ ID NO 1547
<211> LENGTH: 11
<212> TYPE: PRT
<213> ORGANISM: Neisseria meningitidis
<220> FEATURE:
<221> NAME/KEY: Variant
<222> LOCATION: 11
<223> OTHER INFORMATION: Xaa is any amino acid

<400> SEQUENCE: 1547

Ile Thr Thr Asp Lys Ser Ala Pro Lys Asn Xaa
1               5                   10

<210> SEQ ID NO 1548
<211> LENGTH: 7
<212> TYPE: PRT
<213> ORGANISM: Neisseria meningitidis

<400> SEQUENCE: 1548

Lys Thr Asn Thr Gly Ala Pro
1               5

<210> SEQ ID NO 1549
<211> LENGTH: 36
<212> TYPE: PRT
<213> ORGANISM: Neisseria meningitidis

<400> SEQUENCE: 1549

Gln Thr Pro Asn Gly Arg Gly Leu Ser His Asn Arg Tyr Thr Gln Phe
1               5                   10                  15

Asp Val Asp Asn Lys Gly Ala Val Leu Asn Asn Asp Arg Asn Asn Asn
                20                  25                  30

Pro Phe Leu Val
        35

<210> SEQ ID NO 1550
<211> LENGTH: 10
<212> TYPE: PRT
<213> ORGANISM: Neisseria meningitidis

<400> SEQUENCE: 1550

Glu Val Arg Gly Thr Ala Ser Lys Leu Asn
1               5                   10

```
<210> SEQ ID NO 1551
<211> LENGTH: 8
<212> TYPE: PRT
<213> ORGANISM: Neisseria meningitidis

<400> SEQUENCE: 1551

Val Gly Gly Gln Lys Ala Asp Val
1               5

<210> SEQ ID NO 1552

<400> SEQUENCE: 1552

000

<210> SEQ ID NO 1553
<211> LENGTH: 9
<212> TYPE: PRT
<213> ORGANISM: Neisseria meningitidis

<400> SEQUENCE: 1553

Gly Gly Phe Lys Asn Val Gly Arg Gly
1               5

<210> SEQ ID NO 1554
<211> LENGTH: 8
<212> TYPE: PRT
<213> ORGANISM: Neisseria meningitidis

<400> SEQUENCE: 1554

Pro Gln Ile Gly Lys Asp Gly Ala
1               5

<210> SEQ ID NO 1555
<211> LENGTH: 6
<212> TYPE: PRT
<213> ORGANISM: Neisseria meningitidis

<400> SEQUENCE: 1555

Asp Val Arg Gln Gly Thr
1               5

<210> SEQ ID NO 1556
<211> LENGTH: 10
<212> TYPE: PRT
<213> ORGANISM: Neisseria meningitidis

<400> SEQUENCE: 1556

Gly Trp Asn Asp Lys Gly Gly Ala Asp Tyr
1               5                   10

<210> SEQ ID NO 1557
<211> LENGTH: 7
<212> TYPE: PRT
<213> ORGANISM: Neisseria meningitidis

<400> SEQUENCE: 1557

Lys Leu Gln Gly Lys Asn Leu
1               5

<210> SEQ ID NO 1558
<211> LENGTH: 16
<212> TYPE: PRT
<213> ORGANISM: Neisseria meningitidis
```

-continued

```
<400> SEQUENCE: 1558

Ser Thr Gly Pro Gln Lys Val Asp Tyr Ala Ser Gly Glu Ile Ser Ala
1               5                   10                  15

<210> SEQ ID NO 1559
<211> LENGTH: 9
<212> TYPE: PRT
<213> ORGANISM: Neisseria meningitidis

<400> SEQUENCE: 1559

Thr Ala Ala Gly Thr Lys Pro Thr Ile
1               5

<210> SEQ ID NO 1560
<211> LENGTH: 13
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1560

Ala Xaa Glu Lys Gly Val Gly Val Lys Asn Ala Gly Thr
1               5                   10

<210> SEQ ID NO 1561
<211> LENGTH: 4
<212> TYPE: PRT
<213> ORGANISM: Neisseria meningitidis

<400> SEQUENCE: 1561

Glu Ala Ala Lys
1

<210> SEQ ID NO 1562
<211> LENGTH: 23
<212> TYPE: PRT
<213> ORGANISM: Neisseria meningitidis

<400> SEQUENCE: 1562

Ser Ser Gly Arg Ile Glu Asn Ser Gly Arg Ile Ala Thr Thr Ala Asp
1               5                   10                  15

Gly Thr Glu Ala Ser Pro Thr
            20

<210> SEQ ID NO 1563
<211> LENGTH: 8
<212> TYPE: PRT
<213> ORGANISM: Neisseria meningitidis
<220> FEATURE:
<221> NAME/KEY: Variant
<222> LOCATION: 8
<223> OTHER INFORMATION: Xaa is any amino acid

<400> SEQUENCE: 1563

Glu Thr Thr Glu Lys Gly Ala Xaa
1               5

<210> SEQ ID NO 1564
<211> LENGTH: 10
<212> TYPE: PRT
<213> ORGANISM: Neisseria meningitidis
```

```
<400> SEQUENCE: 1564

Ser Asn Gly Gly Arg Ile Glu Ser Lys Gly
1               5                   10

<210> SEQ ID NO 1565
<211> LENGTH: 11
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 1565

Glu Thr Gly Glu Asp Ile Xaa Leu Arg Asn Gly
1               5                   10

<210> SEQ ID NO 1566
<211> LENGTH: 8
<212> TYPE: PRT
<213> ORGANISM: Neisseria meningitidis

<400> SEQUENCE: 1566

Gln Asn Asn Gly Ser Arg Pro Ala
1               5

<210> SEQ ID NO 1567
<211> LENGTH: 24
<212> TYPE: PRT
<213> ORGANISM: Neisseria meningitidis
<220> FEATURE:
<221> NAME/KEY: Variant
<222> LOCATION: 14
<223> OTHER INFORMATION: Xaa is any amino acid

<400> SEQUENCE: 1567

Ile Glu Ser Lys Thr Asn Val Asn Asn Ala Lys Gly Ser Xaa Asn Leu
1               5                   10                  15

Ser Ala Gly Gly Arg Thr Thr Ile
            20

<210> SEQ ID NO 1568
<211> LENGTH: 6
<212> TYPE: PRT
<213> ORGANISM: Neisseria meningitidis

<400> SEQUENCE: 1568

Asp Ala Thr Ile Gln Ala
1               5

<210> SEQ ID NO 1569
<211> LENGTH: 17
<212> TYPE: PRT
<213> ORGANISM: Neisseria meningitidis
<220> FEATURE:
<221> NAME/KEY: Variant
<222> LOCATION: 8
<223> OTHER INFORMATION: Xaa is any amino acid

<400> SEQUENCE: 1569

Ser Ser Thr Lys Gly Asp Thr Xaa Leu Gly Glu Asn Thr Arg Ile Ile
1               5                   10                  15

Ala
```

<210> SEQ ID NO 1570
<211> LENGTH: 4
<212> TYPE: PRT
<213> ORGANISM: Neisseria meningitidis

<400> SEQUENCE: 1570

Gly Ser Ile Gly
1

<210> SEQ ID NO 1571
<211> LENGTH: 22
<212> TYPE: PRT
<213> ORGANISM: Neisseria meningitidis

<400> SEQUENCE: 1571

Ile Glu Ala Lys Asp Thr Ala His Ile Glu Ser Gly Lys Pro Leu Ser
1               5                   10                  15

Leu Glu Thr Ser Thr Val
            20

<210> SEQ ID NO 1572
<211> LENGTH: 15
<212> TYPE: PRT
<213> ORGANISM: Neisseria meningitidis

<400> SEQUENCE: 1572

Ser Asn Ile Arg Leu Asn Asn Gly Asn Ile Lys Gly Gly Lys Gln
1               5                   10                  15

<210> SEQ ID NO 1573
<211> LENGTH: 16
<212> TYPE: PRT
<213> ORGANISM: Neisseria meningitidis

<400> SEQUENCE: 1573

Ala Asp Asp Asn Ile Thr Ala Lys Thr Thr Asn Leu Asn Thr Pro Gly
1               5                   10                  15

<210> SEQ ID NO 1574
<211> LENGTH: 15
<212> TYPE: PRT
<213> ORGANISM: Neisseria meningitidis

<400> SEQUENCE: 1574

His Thr Gly Lys Asp Leu Asn Leu Asn Val Asp Lys Asp Leu Ser
1               5                   10                  15

<210> SEQ ID NO 1575
<211> LENGTH: 6
<212> TYPE: PRT
<213> ORGANISM: Neisseria meningitidis

<400> SEQUENCE: 1575

Leu Lys Ser Asp Asn Ala
1               5

<210> SEQ ID NO 1576
<211> LENGTH: 15
<212> TYPE: PRT
<213> ORGANISM: Neisseria meningitidis

<400> SEQUENCE: 1576

Thr Gly Thr Ser Lys Thr Leu Thr Ala Ser Lys Asp Met Gly Val
1               5                   10                  15

<210> SEQ ID NO 1577
<211> LENGTH: 9
<212> TYPE: PRT
<213> ORGANISM: Neisseria meningitidis

<400> SEQUENCE: 1577

Thr Asn Leu Arg Thr Asn Ser Gly Asn
1               5

<210> SEQ ID NO 1578
<211> LENGTH: 14
<212> TYPE: PRT
<213> ORGANISM: Neisseria meningitidis

<400> SEQUENCE: 1578

Ala Lys Gly Asn Ile Gln Leu Arg Asn Thr Lys Leu Asn Ala
1               5                   10

<210> SEQ ID NO 1579
<211> LENGTH: 4
<212> TYPE: PRT
<213> ORGANISM: Neisseria meningitidis

<400> SEQUENCE: 1579

Lys Ala Leu Glu
1

<210> SEQ ID NO 1580

<400> SEQUENCE: 1580

000

<210> SEQ ID NO 1581
<211> LENGTH: 5
<212> TYPE: PRT
<213> ORGANISM: Neisseria meningitidis

<400> SEQUENCE: 1581

Ile Val Ser Asp Gly
1               5

<210> SEQ ID NO 1582
<211> LENGTH: 4
<212> TYPE: PRT
<213> ORGANISM: Neisseria meningitidis

<400> SEQUENCE: 1582

Ser Ala Asp Gly
1

<210> SEQ ID NO 1583
<211> LENGTH: 8
<212> TYPE: PRT
<213> ORGANISM: Neisseria meningitidis

<400> SEQUENCE: 1583

Asn Gly Asn Ala Asp Phe Thr Gly
1               5

<210> SEQ ID NO 1584
<211> LENGTH: 7
<212> TYPE: PRT
<213> ORGANISM: Neisseria meningitidis

```
<220> FEATURE:
<221> NAME/KEY: Variant
<222> LOCATION: 6
<223> OTHER INFORMATION: Xaa is any amino acid

<400> SEQUENCE: 1584

Ala Lys Ala Asp Val Xaa Ala
1               5

<210> SEQ ID NO 1585
<211> LENGTH: 21
<212> TYPE: PRT
<213> ORGANISM: Neisseria meningitidis

<400> SEQUENCE: 1585

Ser Val Gly Lys Gly Arg Leu Lys Ala Asp Asn Thr Asn Ile Thr Ser
1               5                   10                  15

Ser Ser Gly Asp Ile
            20

<210> SEQ ID NO 1586
<211> LENGTH: 29
<212> TYPE: PRT
<213> ORGANISM: Neisseria meningitidis

<400> SEQUENCE: 1586

Gln Leu Gly Asp Gly Lys Gln Arg Asn Ser Ile Asn Gly Lys His Ile
1               5                   10                  15

Ser Ile Lys Asn Asn Gly Gly Asn Ala Asp Leu Lys Asn
            20                  25

<210> SEQ ID NO 1587
<211> LENGTH: 4
<212> TYPE: PRT
<213> ORGANISM: Neisseria meningitidis

<400> SEQUENCE: 1587

Ala Lys Ser Gly
1

<210> SEQ ID NO 1588
<211> LENGTH: 18
<212> TYPE: PRT
<213> ORGANISM: Neisseria meningitidis

<400> SEQUENCE: 1588

His Ser Asp Arg Ala Leu Ser Ile Glu Asn Thr Lys Leu Glu Ser Thr
1               5                   10                  15

His Asn

<210> SEQ ID NO 1589
<211> LENGTH: 7
<212> TYPE: PRT
<213> ORGANISM: Neisseria meningitidis

<400> SEQUENCE: 1589

Ala Gln His Glu Arg Val Thr
1               5

<210> SEQ ID NO 1590
<211> LENGTH: 5
<212> TYPE: PRT
<213> ORGANISM: Neisseria meningitidis
```

```
<220> FEATURE:
<221> NAME/KEY: Variant
<222> LOCATION: 3
<223> OTHER INFORMATION: Xaa is any amino acid

<400> SEQUENCE: 1590

Ser Ile Xaa Gly Ser
1               5

<210> SEQ ID NO 1591
<211> LENGTH: 14
<212> TYPE: PRT
<213> ORGANISM: Neisseria meningitidis

<400> SEQUENCE: 1591

Trp Gln Asn Asp Lys Leu Pro Ser Ala Asn Lys Leu Val Ala
1               5                   10

<210> SEQ ID NO 1592
<211> LENGTH: 4
<212> TYPE: PRT
<213> ORGANISM: Neisseria meningitidis

<400> SEQUENCE: 1592

Asn Ala Arg Tyr
1

<210> SEQ ID NO 1593
<211> LENGTH: 9
<212> TYPE: PRT
<213> ORGANISM: Neisseria meningitidis

<400> SEQUENCE: 1593

Gln Ile Ala Asp Asn Thr Thr Leu Arg
1               5

<210> SEQ ID NO 1594
<211> LENGTH: 9
<212> TYPE: PRT
<213> ORGANISM: Neisseria meningitidis

<400> SEQUENCE: 1594

Leu Val Lys Arg Gly Asn Ile Asn Trp
1               5

<210> SEQ ID NO 1595
<211> LENGTH: 13
<212> TYPE: PRT
<213> ORGANISM: Neisseria meningitidis

<400> SEQUENCE: 1595

Lys Thr Leu Glu Asp Asn Ala Glu Leu Lys Pro Leu Ala
1               5                   10

<210> SEQ ID NO 1596

<400> SEQUENCE: 1596

000

<210> SEQ ID NO 1597
<211> LENGTH: 5
<212> TYPE: PRT
<213> ORGANISM: Neisseria meningitidis
```

```
<400> SEQUENCE: 1597

Ala Gly Ser Gly Thr
1               5

<210> SEQ ID NO 1598
<211> LENGTH: 8
<212> TYPE: PRT
<213> ORGANISM: Neisseria meningitidis

<400> SEQUENCE: 1598

Glu Pro Ala Asn Arg Ile Ser Ala
1               5

<210> SEQ ID NO 1599
<211> LENGTH: 9
<212> TYPE: PRT
<213> ORGANISM: Neisseria meningitidis

<400> SEQUENCE: 1599

Leu Ser Ile Lys Thr Gly Gly Lys Leu
1               5

<210> SEQ ID NO 1600
<211> LENGTH: 10
<212> TYPE: PRT
<213> ORGANISM: Neisseria meningitidis

<400> SEQUENCE: 1600

Leu Ser Ala Lys Gly Gly Asn Ala Gly Ala
1               5                   10

<210> SEQ ID NO 1601
<211> LENGTH: 9
<212> TYPE: PRT
<213> ORGANISM: Neisseria meningitidis

<400> SEQUENCE: 1601

Ser Ser Leu Glu Ala Lys Gly Asn Ile
1               5

<210> SEQ ID NO 1602
<211> LENGTH: 14
<212> TYPE: PRT
<213> ORGANISM: Neisseria meningitidis

<400> SEQUENCE: 1602

Thr Asp Leu Arg Gly Ser Lys Ile Thr Ala Gly Lys Asn Leu
1               5                   10

<210> SEQ ID NO 1603
<211> LENGTH: 7
<212> TYPE: PRT
<213> ORGANISM: Neisseria meningitidis

<400> SEQUENCE: 1603

Thr Lys Gly Lys Leu Asn Ile
1               5

<210> SEQ ID NO 1604
<211> LENGTH: 7
<212> TYPE: PRT
<213> ORGANISM: Neisseria meningitidis
```

-continued

```
<400> SEQUENCE: 1604

Val Asn Asn Ser Phe Ser Asn
1               5

<210> SEQ ID NO 1605
<211> LENGTH: 18
<212> TYPE: PRT
<213> ORGANISM: Neisseria meningitidis
<220> FEATURE:
<221> NAME/KEY: Variant
<222> LOCATION: 1 & 5-7
<223> OTHER INFORMATION: Xaa is any amino acid

<400> SEQUENCE: 1605

Xaa Thr Gln Lys Xaa Xaa Xaa Leu Asn Gln Lys Ser Lys Glu Leu Glu
1               5                   10                  15

Gln Gln

<210> SEQ ID NO 1606
<211> LENGTH: 11
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 1606

Gln Leu Lys Lys Ser Ser Xaa Lys Ser Lys Leu
1               5                   10

<210> SEQ ID NO 1607
<211> LENGTH: 8
<212> TYPE: PRT
<213> ORGANISM: Neisseria meningitidis

<400> SEQUENCE: 1607

Leu Gln Glu Glu Arg Asp Arg Leu
1               5

<210> SEQ ID NO 1608
<211> LENGTH: 16
<212> TYPE: PRT
<213> ORGANISM: Neisseria meningitidis

<400> SEQUENCE: 1608

Ile Asn Lys Glu Val Lys Gly Lys Lys Pro Lys Gly Lys Glu Tyr Leu
1               5                   10                  15

<210> SEQ ID NO 1609
<211> LENGTH: 13
<212> TYPE: PRT
<213> ORGANISM: Neisseria meningitidis

<400> SEQUENCE: 1609

Ile Ser Gly Ser Asp Ile Thr Ala Ser Lys Lys Leu Asn
1               5                   10

<210> SEQ ID NO 1610
<211> LENGTH: 7
<212> TYPE: PRT
<213> ORGANISM: Neisseria meningitidis
```

-continued

```
<400> SEQUENCE: 1610

Lys Ala Ala Asp Ser Glu Ala
1               5

<210> SEQ ID NO 1611
<211> LENGTH: 34
<212> TYPE: PRT
<213> ORGANISM: Neisseria meningitidis

<400> SEQUENCE: 1611

Gly Ile Thr Asp Gln Tyr Glu Ile Gly Lys Pro Thr Tyr Lys Ser His
1               5                   10                  15

Tyr Asp Lys Ala Ala Leu Asn Lys Pro Ser Arg Leu Thr Gly Arg Thr
            20                  25                  30

Gly Val

<210> SEQ ID NO 1612
<211> LENGTH: 7
<212> TYPE: PRT
<213> ORGANISM: Neisseria meningitidis

<400> SEQUENCE: 1612

Ala Leu Asp Asp Ala Arg Ile
1               5

<210> SEQ ID NO 1613
<211> LENGTH: 20
<212> TYPE: PRT
<213> ORGANISM: Neisseria meningitidis

<400> SEQUENCE: 1613

Ser Glu Ile Lys Ala Pro Ser Gly Ser Ile Asp Ile Lys Ala His Ser
1               5                   10                  15

Asp Ile Val Leu
            20

<210> SEQ ID NO 1614
<211> LENGTH: 5
<212> TYPE: PRT
<213> ORGANISM: Neisseria meningitidis

<400> SEQUENCE: 1614

Gly Gln Asn Asp Ala
1               5

<210> SEQ ID NO 1615
<211> LENGTH: 20
<212> TYPE: PRT
<213> ORGANISM: Neisseria meningitidis
<220> FEATURE:
<221> NAME/KEY: Variant
<222> LOCATION: 1 & 8-9 & 19-20
<223> OTHER INFORMATION: Xaa is any amino acid

<400> SEQUENCE: 1615

Xaa Thr Lys Gly Lys Ser Gly Xaa Xaa Ile Arg Lys Thr Lys Phe Thr
1               5                   10                  15

Ser Thr Xaa Xaa
            20
```

<210> SEQ ID NO 1616
<211> LENGTH: 12
<212> TYPE: PRT
<213> ORGANISM: Neisseria meningitidis

<400> SEQUENCE: 1616

Ala Gly Gly Asn Ile Glu Ala Asn Thr Thr Arg Phe
1               5                   10

<210> SEQ ID NO 1617
<211> LENGTH: 5
<212> TYPE: PRT
<213> ORGANISM: Neisseria meningitidis

<400> SEQUENCE: 1617

Ala Pro Ala Gly Lys
1               5

<210> SEQ ID NO 1618
<211> LENGTH: 20
<212> TYPE: PRT
<213> ORGANISM: Neisseria meningitidis

<400> SEQUENCE: 1618

Leu Ala Glu Glu Gly Ile His Lys His Glu Leu Asp Val Gln Lys Ser
1               5                   10                  15

Arg Arg Phe Ile
            20

<210> SEQ ID NO 1619
<211> LENGTH: 17
<212> TYPE: PRT
<213> ORGANISM: Neisseria meningitidis
<220> FEATURE:
<221> NAME/KEY: Variant
<222> LOCATION: 3
<223> OTHER INFORMATION: Xaa is any amino acid

<400> SEQUENCE: 1619

Val Gly Xaa Ser Asn Tyr Ser Lys Asn Glu Leu Asn Glu Thr Lys Leu
1               5                   10                  15

Pro

<210> SEQ ID NO 1620
<211> LENGTH: 12
<212> TYPE: PRT
<213> ORGANISM: Neisseria meningitidis

<400> SEQUENCE: 1620

Ala Ala Thr Arg Ser Gly Trp Asp Thr Val Leu Glu
1               5                   10

<210> SEQ ID NO 1621
<211> LENGTH: 5
<212> TYPE: PRT
<213> ORGANISM: Neisseria meningitidis

<400> SEQUENCE: 1621

Thr Glu Phe Lys Thr
1               5

<210> SEQ ID NO 1622
<211> LENGTH: 4
<212> TYPE: PRT
<213> ORGANISM: Neisseria meningitidis

```
<400> SEQUENCE: 1622

Gly Ala Asp Ile
1

<210> SEQ ID NO 1623
<211> LENGTH: 9
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1623

Val Xaa Glu Lys Ala Arg Val Asp Ala
1               5

<210> SEQ ID NO 1624
<211> LENGTH: 11
<212> TYPE: PRT
<213> ORGANISM: Neisseria meningitidis

<400> SEQUENCE: 1624

Ile Gln Ser Glu Glu Lys Leu Glu Thr Asn Ser
1               5                   10

<210> SEQ ID NO 1625
<211> LENGTH: 11
<212> TYPE: PRT
<213> ORGANISM: Neisseria meningitidis

<400> SEQUENCE: 1625

Val Trp Gln Lys Gln Ala Gly Arg Gly Ser Thr
1               5                   10

<210> SEQ ID NO 1626
<211> LENGTH: 16
<212> TYPE: PRT
<213> ORGANISM: Neisseria meningitidis

<400> SEQUENCE: 1626

Leu Lys Leu Pro Ser Phe Glu Ser Pro Thr Pro Pro Lys Leu Ser Ala
1               5                   10                  15

<210> SEQ ID NO 1627
<211> LENGTH: 18
<212> TYPE: PRT
<213> ORGANISM: Neisseria meningitidis

<400> SEQUENCE: 1627

Ile Pro Lys Gly Asn Leu Lys Thr Glu Ile Glu Lys Leu Ser Lys Gln
1               5                   10                  15

Pro Glu

<210> SEQ ID NO 1628
<211> LENGTH: 4
<212> TYPE: PRT
<213> ORGANISM: Neisseria meningitidis

<400> SEQUENCE: 1628

Asn Ile Asn Trp
1
```

```
<210> SEQ ID NO 1629
<211> LENGTH: 13
<212> TYPE: PRT
<213> ORGANISM: Neisseria meningitidis

<400> SEQUENCE: 1629

Ala Tyr Asp Arg Trp Asp Tyr Lys Gln Glu Gly Leu Thr
1               5                   10

<210> SEQ ID NO 1630

<400> SEQUENCE: 1630

000

<210> SEQ ID NO 1631

<400> SEQUENCE: 1631

000

<210> SEQ ID NO 1632
<211> LENGTH: 20
<212> TYPE: PRT
<213> ORGANISM: Neisseria meningitidis

<400> SEQUENCE: 1632

Asn Asn Lys Gly Asp Val Gly Lys Thr Leu Lys Glu Leu Gly Arg Ser
1               5                   10                  15

Ser Thr Val Lys
            20

<210> SEQ ID NO 1633
<211> LENGTH: 6
<212> TYPE: PRT
<213> ORGANISM: Neisseria meningitidis

<400> SEQUENCE: 1633

Val Ala Asp Lys Ile Gly
1               5

<210> SEQ ID NO 1634
<211> LENGTH: 7
<212> TYPE: PRT
<213> ORGANISM: Neisseria meningitidis

<400> SEQUENCE: 1634

Asn Val Ser Asp Lys Gln Trp
1               5

<210> SEQ ID NO 1635
<211> LENGTH: 8
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1635

Asn Xaa Gly Gln Cys Arg Thr Asp
1               5
```

-continued

<210> SEQ ID NO 1636

<400> SEQUENCE: 1636

000

<210> SEQ ID NO 1637
<211> LENGTH: 4
<212> TYPE: PRT
<213> ORGANISM: Neisseria meningitidis

<400> SEQUENCE: 1637

Lys Lys His Ser
1

<210> SEQ ID NO 1638
<211> LENGTH: 12
<212> TYPE: PRT
<213> ORGANISM: Neisseria meningitidis

<400> SEQUENCE: 1638

Thr Ala Asn Ser Gln Gly Lys Gly Lys Gln Ala Gly
1               5                   10

<210> SEQ ID NO 1639
<211> LENGTH: 13
<212> TYPE: PRT
<213> ORGANISM: Neisseria meningitidis

<400> SEQUENCE: 1639

Thr Ser Gly Asp Leu Cys Gly Lys Leu Lys Thr Thr Leu
1               5                   10

<210> SEQ ID NO 1640
<211> LENGTH: 11
<212> TYPE: PRT
<213> ORGANISM: Neisseria meningitidis
<220> FEATURE:
<221> NAME/KEY: Variant
<222> LOCATION: 11
<223> OTHER INFORMATION: Xaa is any amino acid

<400> SEQUENCE: 1640

Ile Thr Thr Asp Lys Ser Ala Pro Lys Asn Xaa
1               5                   10

<210> SEQ ID NO 1641
<211> LENGTH: 7
<212> TYPE: PRT
<213> ORGANISM: Neisseria meningitidis

<400> SEQUENCE: 1641

Pro Asn Gly Arg Gly Leu Ser
1               5

<210> SEQ ID NO 1642
<211> LENGTH: 6
<212> TYPE: PRT
<213> ORGANISM: Neisseria meningitidis

<400> SEQUENCE: 1642

Asp Val Asp Asn Lys Gly
1               5

```
<210> SEQ ID NO 1643
<211> LENGTH: 6
<212> TYPE: PRT
<213> ORGANISM: Neisseria meningitidis

<400> SEQUENCE: 1643

Asn Asn Asp Arg Asn Asn
1               5

<210> SEQ ID NO 1644
<211> LENGTH: 8
<212> TYPE: PRT
<213> ORGANISM: Neisseria meningitidis

<400> SEQUENCE: 1644

Glu Val Arg Gly Thr Ala Ser Lys
1               5

<210> SEQ ID NO 1645
<211> LENGTH: 5
<212> TYPE: PRT
<213> ORGANISM: Neisseria meningitidis

<400> SEQUENCE: 1645

Gly Gln Lys Ala Asp
1               5

<210> SEQ ID NO 1646

<400> SEQUENCE: 1646

000

<210> SEQ ID NO 1647
<211> LENGTH: 7
<212> TYPE: PRT
<213> ORGANISM: Neisseria meningitidis

<400> SEQUENCE: 1647

Gln Ile Gly Lys Asp Gly Ala
1               5

<210> SEQ ID NO 1648
<211> LENGTH: 4
<212> TYPE: PRT
<213> ORGANISM: Neisseria meningitidis

<400> SEQUENCE: 1648

Asp Val Arg Gln
1

<210> SEQ ID NO 1649
<211> LENGTH: 7
<212> TYPE: PRT
<213> ORGANISM: Neisseria meningitidis

<400> SEQUENCE: 1649

Trp Asn Asp Lys Gly Gly Ala
1               5

<210> SEQ ID NO 1650

<400> SEQUENCE: 1650

000
```

```
<210> SEQ ID NO 1651
<211> LENGTH: 9
<212> TYPE: PRT
<213> ORGANISM: Neisseria meningitidis

<400> SEQUENCE: 1651

Gly Pro Gln Lys Val Asp Tyr Ala Ser
1               5

<210> SEQ ID NO 1652
<211> LENGTH: 4
<212> TYPE: PRT
<213> ORGANISM: Neisseria meningitidis

<400> SEQUENCE: 1652

Glu Ile Ser Ala
1

<210> SEQ ID NO 1653

<400> SEQUENCE: 1653

000

<210> SEQ ID NO 1654
<211> LENGTH: 7
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1654

Ala Xaa Glu Lys Gly Val Gly
1               5

<210> SEQ ID NO 1655
<211> LENGTH: 4
<212> TYPE: PRT
<213> ORGANISM: Neisseria meningitidis

<400> SEQUENCE: 1655

Glu Ala Ala Lys
1

<210> SEQ ID NO 1656
<211> LENGTH: 9
<212> TYPE: PRT
<213> ORGANISM: Neisseria meningitidis

<400> SEQUENCE: 1656

Gly Arg Ile Glu Asn Ser Gly Arg Ile
1               5

<210> SEQ ID NO 1657
<211> LENGTH: 6
<212> TYPE: PRT
<213> ORGANISM: Neisseria meningitidis

<400> SEQUENCE: 1657

Ala Asp Gly Thr Glu Ala
1               5
```

```
<210> SEQ ID NO 1658
<211> LENGTH: 7
<212> TYPE: PRT
<213> ORGANISM: Neisseria meningitidis

<400> SEQUENCE: 1658

Glu Thr Thr Glu Lys Gly Ala
1               5

<210> SEQ ID NO 1659
<211> LENGTH: 7
<212> TYPE: PRT
<213> ORGANISM: Neisseria meningitidis

<400> SEQUENCE: 1659

Gly Arg Ile Glu Ser Lys Gly
1               5

<210> SEQ ID NO 1660
<211> LENGTH: 8
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 1660

Glu Thr Gly Glu Asp Ile Xaa Leu
1               5

<210> SEQ ID NO 1661
<211> LENGTH: 6
<212> TYPE: PRT
<213> ORGANISM: Neisseria meningitidis

<400> SEQUENCE: 1661

Asn Gly Ser Arg Pro Ala
1               5

<210> SEQ ID NO 1662
<211> LENGTH: 14
<212> TYPE: PRT
<213> ORGANISM: Neisseria meningitidis
<220> FEATURE:
<221> NAME/KEY: Variant
<222> LOCATION: 14
<223> OTHER INFORMATION: Xaa is any amino acid

<400> SEQUENCE: 1662

Ile Glu Ser Lys Thr Asn Val Asn Asn Ala Lys Gly Ser Xaa
1               5                   10

<210> SEQ ID NO 1663

<400> SEQUENCE: 1663

000

<210> SEQ ID NO 1664

<400> SEQUENCE: 1664

000
```

```
<210> SEQ ID NO 1665
<211> LENGTH: 15
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid

<400> SEQUENCE: 1665

Thr Lys Gly Asp Thr Xaa Leu Gly Glu Asn Thr Arg Ile Ile Ala
1               5                   10                  15

<210> SEQ ID NO 1666
<211> LENGTH: 16
<212> TYPE: PRT
<213> ORGANISM: Neisseria meningitidis

<400> SEQUENCE: 1666

Ile Glu Ala Lys Asp Thr Ala His Ile Glu Ser Gly Lys Pro Leu Ser
1               5                   10                  15

<210> SEQ ID NO 1667
<211> LENGTH: 11
<212> TYPE: PRT
<213> ORGANISM: Neisseria meningitidis

<400> SEQUENCE: 1667

Arg Leu Asn Asn Gly Asn Ile Lys Gly Gly Lys
1               5                   10

<210> SEQ ID NO 1668
<211> LENGTH: 6
<212> TYPE: PRT
<213> ORGANISM: Neisseria meningitidis

<400> SEQUENCE: 1668

Ala Asp Asp Asn Ile Thr
1               5

<210> SEQ ID NO 1669
<211> LENGTH: 14
<212> TYPE: PRT
<213> ORGANISM: Neisseria meningitidis

<400> SEQUENCE: 1669

Thr Gly Lys Asp Leu Asn Leu Asn Val Asp Lys Asp Leu Ser
1               5                   10

<210> SEQ ID NO 1670
<211> LENGTH: 6
<212> TYPE: PRT
<213> ORGANISM: Neisseria meningitidis

<400> SEQUENCE: 1670

Leu Lys Ser Asp Asn Ala
1               5

<210> SEQ ID NO 1671
<211> LENGTH: 4
<212> TYPE: PRT
<213> ORGANISM: Neisseria meningitidis

<400> SEQUENCE: 1671

Gly Thr Ser Lys
1
```

```
<210> SEQ ID NO 1672
<211> LENGTH: 9
<212> TYPE: PRT
<213> ORGANISM: Neisseria meningitidis

<400> SEQUENCE: 1672

Leu Thr Ala Ser Lys Asp Met Gly Val
1               5

<210> SEQ ID NO 1673
<211> LENGTH: 6
<212> TYPE: PRT
<213> ORGANISM: Neisseria meningitidis

<400> SEQUENCE: 1673

Asn Leu Arg Thr Asn Ser
1               5

<210> SEQ ID NO 1674

<400> SEQUENCE: 1674

000

<210> SEQ ID NO 1675
<211> LENGTH: 7
<212> TYPE: PRT
<213> ORGANISM: Neisseria meningitidis

<400> SEQUENCE: 1675

Arg Asn Thr Lys Leu Asn Ala
1               5

<210> SEQ ID NO 1676
<211> LENGTH: 4
<212> TYPE: PRT
<213> ORGANISM: Neisseria meningitidis

<400> SEQUENCE: 1676

Lys Ala Leu Glu
1

<210> SEQ ID NO 1677
<211> LENGTH: 6
<212> TYPE: PRT
<213> ORGANISM: Neisseria meningitidis
<220> FEATURE:
<221> NAME/KEY: Variant
<222> LOCATION: 6
<223> OTHER INFORMATION: Xaa is any amino acid

<400> SEQUENCE: 1677

Ala Lys Ala Asp Val Xaa
1               5

<210> SEQ ID NO 1678
<211> LENGTH: 13
<212> TYPE: PRT
<213> ORGANISM: Neisseria meningitidis

<400> SEQUENCE: 1678

Ser Val Gly Lys Gly Arg Leu Lys Ala Asp Asn Thr Asn
1               5                   10
```

<210> SEQ ID NO 1679

<400> SEQUENCE: 1679

000

<210> SEQ ID NO 1680
<211> LENGTH: 10
<212> TYPE: PRT
<213> ORGANISM: Neisseria meningitidis

<400> SEQUENCE: 1680

Gly Asp Gly Lys Gln Arg Asn Ser Ile Asn
1               5                   10

<210> SEQ ID NO 1681
<211> LENGTH: 11
<212> TYPE: PRT
<213> ORGANISM: Neisseria meningitidis

<400> SEQUENCE: 1681

Lys Asn Asn Gly Gly Asn Ala Asp Leu Lys Asn
1               5                   10

<210> SEQ ID NO 1682
<211> LENGTH: 4
<212> TYPE: PRT
<213> ORGANISM: Neisseria meningitidis

<400> SEQUENCE: 1682

Ala Lys Ser Gly
1

<210> SEQ ID NO 1683
<211> LENGTH: 7
<212> TYPE: PRT
<213> ORGANISM: Neisseria meningitidis

<400> SEQUENCE: 1683

His Ser Asp Arg Ala Leu Ser
1               5

<210> SEQ ID NO 1684
<211> LENGTH: 9
<212> TYPE: PRT
<213> ORGANISM: Neisseria meningitidis

<400> SEQUENCE: 1684

Glu Asn Thr Lys Leu Glu Ser Thr His
1               5

<210> SEQ ID NO 1685
<211> LENGTH: 7
<212> TYPE: PRT
<213> ORGANISM: Neisseria meningitidis

<400> SEQUENCE: 1685

Ala Gln His Glu Arg Val Thr
1               5

<210> SEQ ID NO 1686
<211> LENGTH: 5
<212> TYPE: PRT
<213> ORGANISM: Neisseria meningitidis

```
<400> SEQUENCE: 1686

Asp Lys Leu Pro Ser
1               5

<210> SEQ ID NO 1687

<400> SEQUENCE: 1687

000

<210> SEQ ID NO 1688
<211> LENGTH: 6
<212> TYPE: PRT
<213> ORGANISM: Neisseria meningitidis

<400> SEQUENCE: 1688

Leu Val Lys Arg Gly Asn
1               5

<210> SEQ ID NO 1689
<211> LENGTH: 13
<212> TYPE: PRT
<213> ORGANISM: Neisseria meningitidis

<400> SEQUENCE: 1689

Lys Thr Leu Glu Asp Asn Ala Glu Leu Lys Pro Leu Ala
1               5                   10

<210> SEQ ID NO 1690

<400> SEQUENCE: 1690

000

<210> SEQ ID NO 1691

<400> SEQUENCE: 1691

000

<210> SEQ ID NO 1692
<211> LENGTH: 7
<212> TYPE: PRT
<213> ORGANISM: Neisseria meningitidis

<400> SEQUENCE: 1692

Pro Ala Asn Arg Ile Ser Ala
1               5

<210> SEQ ID NO 1693

<400> SEQUENCE: 1693

000

<210> SEQ ID NO 1694

<400> SEQUENCE: 1694

000

<210> SEQ ID NO 1695
<211> LENGTH: 4
<212> TYPE: PRT
<213> ORGANISM: Neisseria meningitidis
```

```
<400> SEQUENCE: 1695

Lys Gly Gly Asn
1

<210> SEQ ID NO 1696
<211> LENGTH: 9
<212> TYPE: PRT
<213> ORGANISM: Neisseria meningitidis

<400> SEQUENCE: 1696

Ser Ser Leu Glu Ala Lys Gly Asn Ile
1               5

<210> SEQ ID NO 1697
<211> LENGTH: 10
<212> TYPE: PRT
<213> ORGANISM: Neisseria meningitidis

<400> SEQUENCE: 1697

Thr Asp Leu Arg Gly Ser Lys Ile Thr Ala
1               5                   10

<210> SEQ ID NO 1698
<211> LENGTH: 7
<212> TYPE: PRT
<213> ORGANISM: Neisseria meningitidis

<400> SEQUENCE: 1698

Thr Lys Gly Lys Leu Asn Ile
1               5

<210> SEQ ID NO 1699
<211> LENGTH: 15
<212> TYPE: PRT
<213> ORGANISM: Neisseria meningitidis
<220> FEATURE:
<221> NAME/KEY: Variant
<222> LOCATION: 3-5
<223> OTHER INFORMATION: Xaa is any amino acid

<400> SEQUENCE: 1699

Gln Lys Xaa Xaa Xaa Leu Asn Gln Lys Ser Lys Glu Leu Glu Gln
1               5                   10                  15

<210> SEQ ID NO 1700
<211> LENGTH: 11
<212> TYPE: PRT
<213> ORGANISM: Neisseria meningitidis
<220> FEATURE:
<221> NAME/KEY: Variant
<222> LOCATION: 7
<223> OTHER INFORMATION: Xaa is any amino acid

<400> SEQUENCE: 1700

Gln Leu Lys Lys Ser Ser Xaa Lys Ser Lys Leu
1               5                   10

<210> SEQ ID NO 1701
<211> LENGTH: 8
<212> TYPE: PRT
<213> ORGANISM: Neisseria meningitidis

<400> SEQUENCE: 1701

Leu Gln Glu Glu Arg Asp Arg Leu
1               5
```

<210> SEQ ID NO 1702
<211> LENGTH: 16
<212> TYPE: PRT
<213> ORGANISM: Neisseria meningitidis

<400> SEQUENCE: 1702

Ile Asn Lys Glu Val Lys Gly Lys Lys Pro Lys Gly Lys Glu Tyr Leu
1               5                   10                  15

<210> SEQ ID NO 1703

<400> SEQUENCE: 1703

000

<210> SEQ ID NO 1704
<211> LENGTH: 9
<212> TYPE: PRT
<213> ORGANISM: Neisseria meningitidis

<400> SEQUENCE: 1704

Asp Ile Thr Ala Ser Lys Lys Leu Asn
1               5

<210> SEQ ID NO 1705
<211> LENGTH: 7
<212> TYPE: PRT
<213> ORGANISM: Neisseria meningitidis

<400> SEQUENCE: 1705

Lys Ala Ala Asp Ser Glu Ala
1               5

<210> SEQ ID NO 1706
<211> LENGTH: 4
<212> TYPE: PRT
<213> ORGANISM: Neisseria meningitidis

<400> SEQUENCE: 1706

Gly Ile Thr Asp
1

<210> SEQ ID NO 1707
<211> LENGTH: 8
<212> TYPE: PRT
<213> ORGANISM: Neisseria meningitidis

<400> SEQUENCE: 1707

Tyr Glu Ile Gly Lys Pro Thr Tyr
1               5

<210> SEQ ID NO 1708
<211> LENGTH: 16
<212> TYPE: PRT
<213> ORGANISM: Neisseria meningitidis

<400> SEQUENCE: 1708

Ser His Tyr Asp Lys Ala Ala Leu Asn Lys Pro Ser Arg Leu Thr Gly
1               5                   10                  15

<210> SEQ ID NO 1709
<211> LENGTH: 7
<212> TYPE: PRT
<213> ORGANISM: Neisseria meningitidis

```
<400> SEQUENCE: 1709

Ala Leu Asp Asp Ala Arg Ile
1               5

<210> SEQ ID NO 1710
<211> LENGTH: 16
<212> TYPE: PRT
<213> ORGANISM: Neisseria meningitidis

<400> SEQUENCE: 1710

Ser Glu Ile Lys Ala Pro Ser Gly Ser Ile Asp Ile Lys Ala His Ser
1               5                   10                  15

<210> SEQ ID NO 1711

<400> SEQUENCE: 1711

000

<210> SEQ ID NO 1712
<211> LENGTH: 4
<212> TYPE: PRT
<213> ORGANISM: Neisseria meningitidis

<400> SEQUENCE: 1712

Gly Gln Asn Asp
1

<210> SEQ ID NO 1713
<211> LENGTH: 14
<212> TYPE: PRT
<213> ORGANISM: Neisseria meningitidis
<220> FEATURE:
<221> NAME/KEY: Variant
<222> LOCATION: 7-8
<223> OTHER INFORMATION: Xaa is any amino acid

<400> SEQUENCE: 1713

Thr Lys Gly Lys Ser Gly Xaa Xaa Ile Arg Lys Thr Lys Phe
1               5                   10

<210> SEQ ID NO 1714
<211> LENGTH: 7
<212> TYPE: PRT
<213> ORGANISM: Neisseria meningitidis

<400> SEQUENCE: 1714

Gly Asn Ile Glu Ala Asn Thr
1               5

<210> SEQ ID NO 1715
<211> LENGTH: 20
<212> TYPE: PRT
<213> ORGANISM: Neisseria meningitidis

<400> SEQUENCE: 1715

Leu Ala Glu Glu Gly Ile His Lys His Glu Leu Asp Val Gln Lys Ser
1               5                   10                  15

Arg Arg Phe Ile
            20

<210> SEQ ID NO 1716
<211> LENGTH: 13
<212> TYPE: PRT
<213> ORGANISM: Neisseria meningitidis
```

```
<400> SEQUENCE: 1716

Asn Tyr Ser Lys Asn Glu Leu Asn Glu Thr Lys Leu Pro
1               5                   10

<210> SEQ ID NO 1717

<400> SEQUENCE: 1717

000

<210> SEQ ID NO 1718

<400> SEQUENCE: 1718

000

<210> SEQ ID NO 1719
<211> LENGTH: 5
<212> TYPE: PRT
<213> ORGANISM: Neisseria meningitidis

<400> SEQUENCE: 1719

Thr Glu Phe Lys Thr
1               5

<210> SEQ ID NO 1720
<211> LENGTH: 9
<212> TYPE: PRT
<213> ORGANISM: Neisseria meningitidis
<220> FEATURE:
<221> NAME/KEY: Variant
<222> LOCATION: 2
<223> OTHER INFORMATION: Xaa is any amino acid

<400> SEQUENCE: 1720

Val Xaa Glu Lys Ala Arg Val Asp Ala
1               5

<210> SEQ ID NO 1721
<211> LENGTH: 9
<212> TYPE: PRT
<213> ORGANISM: Neisseria meningitidis

<400> SEQUENCE: 1721

Ile Gln Ser Glu Glu Lys Leu Glu Thr
1               5

<210> SEQ ID NO 1722
<211> LENGTH: 7
<212> TYPE: PRT
<213> ORGANISM: Neisseria meningitidis

<400> SEQUENCE: 1722

Gln Ala Gly Arg Gly Ser Thr
1               5

<210> SEQ ID NO 1723
<211> LENGTH: 10
<212> TYPE: PRT
<213> ORGANISM: Neisseria meningitidis

<400> SEQUENCE: 1723

Glu Ser Pro Thr Pro Pro Lys Leu Ser Ala
1               5                   10
```

```
<210> SEQ ID NO 1724
<211> LENGTH: 18
<212> TYPE: PRT
<213> ORGANISM: Neisseria meningitidis

<400> SEQUENCE: 1724

Ile Pro Lys Gly Asn Leu Lys Thr Glu Ile Glu Lys Leu Ser Lys Gln
1               5                   10                  15
Pro Glu

<210> SEQ ID NO 1725
<211> LENGTH: 11
<212> TYPE: PRT
<213> ORGANISM: Neisseria meningitidis

<400> SEQUENCE: 1725

Asp Arg Trp Asp Tyr Lys Gln Glu Gly Leu Thr
1               5                   10

<210> SEQ ID NO 1726

<400> SEQUENCE: 1726

000

<210> SEQ ID NO 1727
<211> LENGTH: 14
<212> TYPE: PRT
<213> ORGANISM: Neisseria meningitidis

<400> SEQUENCE: 1727

Asn Lys Gly Asp Val Gly Lys Thr Leu Lys Glu Leu Gly Arg
1               5                   10

<210> SEQ ID NO 1728

<400> SEQUENCE: 1728

000

<210> SEQ ID NO 1729
<211> LENGTH: 6
<212> TYPE: PRT
<213> ORGANISM: Neisseria meningitidis

<400> SEQUENCE: 1729

Val Ala Asp Lys Ile Gly
1               5

<210> SEQ ID NO 1730

<400> SEQUENCE: 1730

000

<210> SEQ ID NO 1731
<211> LENGTH: 6
<212> TYPE: PRT
<213> ORGANISM: Neisseria meningitidis

<400> SEQUENCE: 1731

Gly Gln Cys Arg Thr Asp
1               5
```

```
<210> SEQ ID NO 1732
<211> LENGTH: 7
<212> TYPE: PRT
<213> ORGANISM: Neisseria meningitidis

<400> SEQUENCE: 1732

Val Leu Ser Lys Asp Ile Phe
1               5

<210> SEQ ID NO 1733

<400> SEQUENCE: 1733

000

<210> SEQ ID NO 1734

<400> SEQUENCE: 1734

000

<210> SEQ ID NO 1735
<211> LENGTH: 7
<212> TYPE: PRT
<213> ORGANISM: Neisseria meningitidis

<400> SEQUENCE: 1735

Gln Ala Val Arg Ala Lys Ala
1               5

<210> SEQ ID NO 1736
<211> LENGTH: 6
<212> TYPE: PRT
<213> ORGANISM: Neisseria meningitidis

<400> SEQUENCE: 1736

Leu Ser Lys Asp Ile Phe
1               5

<210> SEQ ID NO 1737
<211> LENGTH: 4
<212> TYPE: PRT
<213> ORGANISM: Neisseria meningitidis

<400> SEQUENCE: 1737

Gln Thr Ala Asp
1

<210> SEQ ID NO 1738
<211> LENGTH: 9
<212> TYPE: PRT
<213> ORGANISM: Neisseria meningitidis

<400> SEQUENCE: 1738

Gln Ser His Ala Asp Ser Val Arg Leu
1               5

<210> SEQ ID NO 1739
<211> LENGTH: 10
<212> TYPE: PRT
<213> ORGANISM: Neisseria meningitidis

<400> SEQUENCE: 1739

Val Leu Ser Arg Gln Gln Gln Gly Leu Arg
1               5                   10
```

```
<210> SEQ ID NO 1740
<211> LENGTH: 11
<212> TYPE: PRT
<213> ORGANISM: Neisseria meningitidis

<400> SEQUENCE: 1740

Val Asp Asp Arg Leu Leu Leu Arg Lys Cys Arg
1               5                   10

<210> SEQ ID NO 1741
<211> LENGTH: 13
<212> TYPE: PRT
<213> ORGANISM: Neisseria meningitidis

<400> SEQUENCE: 1741

Ser Gln Ala Arg Ala Asp Lys Arg Asp Asn Gly Asn Arg
1               5                   10

<210> SEQ ID NO 1742
<211> LENGTH: 10
<212> TYPE: PRT
<213> ORGANISM: Neisseria meningitidis

<400> SEQUENCE: 1742

Ile His Ser Arg Pro Pro Asp Ala Ser Arg
1               5                   10

<210> SEQ ID NO 1743
<211> LENGTH: 7
<212> TYPE: PRT
<213> ORGANISM: Neisseria meningitidis

<400> SEQUENCE: 1743

Gln Ala Val Arg Ala Lys Ala
1               5

<210> SEQ ID NO 1744

<400> SEQUENCE: 1744

000

<210> SEQ ID NO 1745
<211> LENGTH: 4
<212> TYPE: PRT
<213> ORGANISM: Neisseria meningitidis

<400> SEQUENCE: 1745

Gln Thr Ala Asp
1

<210> SEQ ID NO 1746
<211> LENGTH: 7
<212> TYPE: PRT
<213> ORGANISM: Neisseria meningitidis

<400> SEQUENCE: 1746

Ser His Ala Asp Ser Val Arg
1               5

<210> SEQ ID NO 1747
<211> LENGTH: 4
<212> TYPE: PRT
<213> ORGANISM: Neisseria meningitidis
```

<400> SEQUENCE: 1747

Arg Gln Gln Gln
1

<210> SEQ ID NO 1748
<211> LENGTH: 11
<212> TYPE: PRT
<213> ORGANISM: Neisseria meningitidis

<400> SEQUENCE: 1748

Val Asp Asp Arg Leu Leu Leu Arg Lys Cys Arg
1               5                   10

<210> SEQ ID NO 1749
<211> LENGTH: 13
<212> TYPE: PRT
<213> ORGANISM: Neisseria meningitidis

<400> SEQUENCE: 1749

Ser Gln Ala Arg Ala Asp Lys Arg Asp Asn Gly Asn Arg
1               5                   10

<210> SEQ ID NO 1750
<211> LENGTH: 10
<212> TYPE: PRT
<213> ORGANISM: Neisseria meningitidis

<400> SEQUENCE: 1750

Ile His Ser Arg Pro Pro Asp Ala Ser Arg
1               5                   10

<210> SEQ ID NO 1751

<400> SEQUENCE: 1751

000

<210> SEQ ID NO 1752
<211> LENGTH: 7
<212> TYPE: PRT
<213> ORGANISM: Neisseria meningitidis

<400> SEQUENCE: 1752

Met Ala Lys Ala Val Asn Thr
1               5

<210> SEQ ID NO 1753
<211> LENGTH: 7
<212> TYPE: PRT
<213> ORGANISM: Neisseria meningitidis

<400> SEQUENCE: 1753

Val Leu Ser Lys Asp Ile Phe
1               5

<210> SEQ ID NO 1754

<400> SEQUENCE: 1754

000

<210> SEQ ID NO 1755
<211> LENGTH: 6
<212> TYPE: PRT
<213> ORGANISM: Neisseria meningitidis

```
<400> SEQUENCE: 1755

Leu Ser Lys Asp Ile Phe
1               5

<210> SEQ ID NO 1756
<211> LENGTH: 4
<212> TYPE: PRT
<213> ORGANISM: Neisseria meningitidis

<400> SEQUENCE: 1756

Gln Thr Ala Asp
1

<210> SEQ ID NO 1757
<211> LENGTH: 9
<212> TYPE: PRT
<213> ORGANISM: Neisseria meningitidis

<400> SEQUENCE: 1757

Gln Ser His Ala Asp Gly Val Arg Leu
1               5

<210> SEQ ID NO 1758
<211> LENGTH: 4
<212> TYPE: PRT
<213> ORGANISM: Neisseria meningitidis

<400> SEQUENCE: 1758

Phe Arg Thr Arg
1

<210> SEQ ID NO 1759
<211> LENGTH: 7
<212> TYPE: PRT
<213> ORGANISM: Neisseria meningitidis

<400> SEQUENCE: 1759

Ser Arg Gln Gln Gln Gly Leu
1               5

<210> SEQ ID NO 1760
<211> LENGTH: 11
<212> TYPE: PRT
<213> ORGANISM: Neisseria meningitidis

<400> SEQUENCE: 1760

Asn Asp Arg Leu Leu Leu Arg Lys Ser Arg Leu
1               5                   10

<210> SEQ ID NO 1761
<211> LENGTH: 16
<212> TYPE: PRT
<213> ORGANISM: Neisseria meningitidis

<400> SEQUENCE: 1761

Val Arg His Arg Gln Thr Arg Ala Asp Lys Arg Asp Asp Gly Asn Arg
1               5                   10                  15

<210> SEQ ID NO 1762
<211> LENGTH: 9
<212> TYPE: PRT
<213> ORGANISM: Neisseria meningitidis
```

```
<400> SEQUENCE: 1762

Glu Ile His Ser Arg Pro Pro Asp Val
1               5

<210> SEQ ID NO 1763

<400> SEQUENCE: 1763

000

<210> SEQ ID NO 1764
<211> LENGTH: 4
<212> TYPE: PRT
<213> ORGANISM: Neisseria meningitidis

<400> SEQUENCE: 1764

Gln Thr Ala Asp
1

<210> SEQ ID NO 1765
<211> LENGTH: 7
<212> TYPE: PRT
<213> ORGANISM: Neisseria meningitidis

<400> SEQUENCE: 1765

Ser His Ala Asp Gly Val Arg
1               5

<210> SEQ ID NO 1766
<211> LENGTH: 5
<212> TYPE: PRT
<213> ORGANISM: Neisseria meningitidis

<400> SEQUENCE: 1766

Arg Gln Gln Gln Gly
1               5

<210> SEQ ID NO 1767
<211> LENGTH: 8
<212> TYPE: PRT
<213> ORGANISM: Neisseria meningitidis

<400> SEQUENCE: 1767

Leu Leu Leu Arg Lys Ser Arg Leu
1               5

<210> SEQ ID NO 1768
<211> LENGTH: 16
<212> TYPE: PRT
<213> ORGANISM: Neisseria meningitidis

<400> SEQUENCE: 1768

Val Arg His Arg Gln Thr Arg Ala Asp Lys Arg Asp Asp Gly Asn Arg
1               5                   10                  15

<210> SEQ ID NO 1769
<211> LENGTH: 8
<212> TYPE: PRT
<213> ORGANISM: Neisseria meningitidis

<400> SEQUENCE: 1769

Ile His Ser Arg Pro Pro Asp Val
1               5
```

<210> SEQ ID NO 1770
<211> LENGTH: 736
<212> TYPE: DNA
<213> ORGANISM: Neisseria meningitidis

<400> SEQUENCE: 1770

```
acactgttgt ttgcaacggt tcaggcaagt gctaaccaat gaagagcaag aagaagattt      60
atatttagac cccgtacaac gcactgttgc cgtgttgata gtcaattccg ataaagaagg     120
cacgggagaa aaagaaaaag tagaagaaaa ttcagattgg gcagtatatt tcaacgagaa     180
aggagtacta acagccagag aaatcaccyt caaagccggc gacaacctga aaatcaaaca     240
aaacggcaca aacttcacct actcgctgaa aaaagacctc acagatctga ccagtgttgg     300
aactgaaaaa ttatcgttta gcgcaaacgg caataaagtc aacatcacaa gcgacaccaa     360
aggcttgaat tttgcgaaag aaacggctgg sacgaacggc gacaccacgg ttcatctgaa     420
cggtattggt tcgactttga ccgatacgct gctgaatacc ggagcgacca caaacgtaac     480
caacgacaac gttaccgatg acgagaaaaa acgtgcggca agcgttaaag acgtattaaa     540
cgctggctgg aacattaaag gcgttaaacc cggtacaaca gcttccgata acgttgattt     600
cgtccgcact tacgacacag tcgagttctt gagcgcagat acgaaaacaa cgactgttaa     660
tgtggaaagc aaagacaacg gcaagaaaac cgaagttaaa atcggtgcga agacttctgt     720
tattaaagaa aaagac                                                    736
```

<210> SEQ ID NO 1771
<211> LENGTH: 245
<212> TYPE: PRT
<213> ORGANISM: Neisseria meningitidis
<220> FEATURE:
<221> NAME/KEY: misc_feature
<222> LOCATION: (1)...(245)
<223> OTHER INFORMATION: Xaa is any amino acid

<400> SEQUENCE: 1771

```
Thr Leu Leu Phe Ala Thr Val Gln Ala Ser Ala Asn Gln Glu Glu Gln
              5                  10                  15

Glu Glu Asp Leu Tyr Leu Asp Pro Val Gln Arg Thr Val Ala Val Leu
         20                  25                  30

Ile Val Asn Ser Asp Lys Glu Gly Thr Gly Glu Lys Glu Lys Val Glu
     35                  40                  45

Glu Asn Ser Asp Trp Ala Val Tyr Phe Asn Glu Lys Gly Val Leu Thr
 50                  55                  60

Ala Arg Glu Ile Thr Xaa Lys Ala Gly Asp Asn Leu Lys Ile Lys Gln
65                  70                  75                  80

Asn Gly Thr Asn Phe Thr Tyr Ser Leu Lys Lys Asp Leu Thr Asp Leu
                 85                  90                  95

Thr Ser Val Gly Thr Glu Lys Leu Ser Phe Ser Ala Asn Gly Asn Lys
            100                 105                 110

Val Asn Ile Thr Ser Asp Thr Lys Gly Leu Asn Phe Ala Lys Glu Thr
        115                 120                 125

Ala Gly Thr Asn Gly Asp Thr Thr Val His Leu Asn Gly Ile Gly Ser
    130                 135                 140

Thr Leu Thr Asp Thr Leu Leu Asn Thr Gly Ala Thr Thr Asn Val Thr
145                 150                 155                 160

Asn Asp Asn Val Thr Asp Glu Lys Lys Arg Ala Ala Ser Val Lys
                165                 170                 175
```

| Asp | Val | Leu | Asn | Ala | Gly | Trp | Asn | Ile | Lys | Gly | Val | Lys | Pro | Gly | Thr |
| | | | 180 | | | | | 185 | | | | | 190 | | |

Thr Ala Ser Asp Asn Val Asp Phe Val Arg Thr Tyr Asp Thr Val Glu
        195                 200                 205

Phe Leu Ser Ala Asp Thr Lys Thr Thr Thr Val Asn Val Glu Ser Lys
    210                 215                 220

Asp Asn Gly Lys Lys Thr Glu Val Lys Ile Gly Ala Lys Thr Ser Val
225                 230                 235                 240

Ile Lys Glu Lys Asp
            245

<210> SEQ ID NO 1772
<211> LENGTH: 1776
<212> TYPE: DNA
<213> ORGANISM: Neisseria meningitidis

<400> SEQUENCE: 1772

```
atgaacaaaa taccgcat catttggaat agtgccctca atgcctgggt cgtcgtatcc      60
gagctcacac gcaaccacac caaacgcgcc tccgcaaccg tgaagaccgc cgtattggcg    120
acactgttgt ttgcaacggt tcaggcaagt gctaacaatg aagagcaaga agaagattta    180
tatttagacc ccgtacaacg cactgttgcc gtgttgatag tcaattccga taaagaaggc    240
acgggagaaa aagaaaaagt agaagaaaat tcagattggg cagtatattt caacgagaaa    300
ggagtactaa cagccagaga aatcaccctc aaagccggcg acaacctgaa atcaaaacaa    360
aacggcacaa acttcaccta ctcgctgaaa aaagacctca cagatctgac cagtgttgga    420
actgaaaaat tatcgtttag cgcaaacggc aataaagtca acatcacaag cgacaccaaa    480
ggcttgaatt ttgcgaaaga aacggctggg acgaacggcg acaccacggt tcatctgaac    540
ggtattggtt cgactttgac cgatacgctg ctgaataccg gagcgaccac aaacgtaacc    600
aacgacaacg ttaccgatga cgagaaaaaa cgtgcggcaa gcgttaaaga cgtattaaac    660
gctggctgga acattaaagg cgttaaaccc ggtacaacag cttccgataa cgttgatttc    720
gtccgcactt acgacacagt cgagttcttg agcgcagata cgaaaacaac gactgttaat    780
gtggaaagca agacaacgg caagaaaacc gaagttaaaa tcggtgcgaa gacttctgtt    840
attaagaaa aagacggtaa gttggttact ggtaaagaca aaggcgagaa tggttcttct    900
acagacgaag gcgaaggctt agtgactgca aaagaagtga ttgatgcagt aaacaaggct    960
ggttggagaa tgaaaacaac aaccgctaat ggtcaaacag gtcaagctga caagtttgaa   1020
accgttacat caggcacaaa tgtaaccttt gctagtggta aaggtacaac tgcgactgta   1080
agtaaagatg atcaaggcaa catcactgtt atgtatgatg taaatgtcgg cgatgcccta   1140
aacgtcaatc agctgcaaaa cagcggttgg aatttggatt ccaaagcggt tgcaggttct   1200
tcgggcaaag tcatcagcgg caatgtttcg ccgagcaagg aaagatgga tgaaaccgtc   1260
aacattaatg ccggcaacaa catcgagatt acccgcaacg gtaaaaatat cgacatcgcc   1320
acttcgatga cccccgcagtt ttccagcgtt tcgctcggcg cggggcgga tgcgcccact   1380
ttgagcgtgg atggggacgc attgaatgtc ggcagcaaga aggacaacaa acccgtccgc   1440
attaccaatg tcgccccggg cgttaaagag ggggatgtta caaacgtcgc acaacttaaa   1500
ggcgtggcgc aaaacttgaa caaccgcatc gacaatgtgg acggcaacgc gcgtgcgggc   1560
atcgcccaag cgattgcaac cgcaggtctg gttcaggcgt atttgcccgg caagagtatg   1620
atggcgatcg gcggcggcac ttatcgcggc gaagccggtt acgccatcgg ctactccagt   1680
```

-continued

```
atttccgacg gcggaaattg gattatcaaa ggcacggctt ccggcaattc gcgcggccat    1740
ttcggtgctt ccgcatctgt cggttatcag tggtaa                              1776
```

<210> SEQ ID NO 1773
<211> LENGTH: 591
<212> TYPE: PRT
<213> ORGANISM: Neisseria meningitidis

<400> SEQUENCE: 1773

```
Met Asn Lys Ile Tyr Arg Ile Ile Trp Asn Ser Ala Leu Asn Ala Trp
                 5                  10                  15

Val Val Val Ser Glu Leu Thr Arg Asn His Thr Lys Arg Ala Ser Ala
             20                  25                  30

Thr Val Lys Thr Ala Val Leu Ala Thr Leu Leu Phe Ala Thr Val Gln
         35                  40                  45

Ala Ser Ala Asn Asn Glu Glu Gln Glu Glu Asp Leu Tyr Leu Asp Pro
     50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350
```

```
Gly Lys Gly Thr Thr Ala Thr Val Ser Lys Asp Asp Gln Gly Asn Ile
            355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
        435                 440                 445
Ser Val Ser Leu Gly Ala Gly Ala Asp Ala Pro Thr Leu Ser Val Asp
    450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
        515                 520                 525
Gly Leu Val Gln Ala Tyr Leu Pro Gly Lys Ser Met Met Ala Ile Gly
    530                 535                 540
Gly Gly Thr Tyr Arg Gly Glu Ala Gly Tyr Ala Ile Gly Tyr Ser Ser
545                 550                 555                 560
Ile Ser Asp Gly Gly Asn Trp Ile Ile Lys Gly Thr Ala Ser Gly Asn
                565                 570                 575
Ser Arg Gly His Phe Gly Ala Ser Ala Ser Val Gly Tyr Gln Trp
            580                 585                 590
```

<210> SEQ ID NO 1774
<211> LENGTH: 1779
<212> TYPE: DNA
<213> ORGANISM: Neisseria meningitidis
<220> FEATURE:
<221> NAME/KEY: misc_feature
<222> LOCATION: (1)...(1779)
<223> OTHER INFORMATION: n = A,T,C or G

<400> SEQUENCE: 1774

| | | |
|---|---|---|
| atgaacaaaa tataccgcat catttggaat agtgccctca atgcctgngt cgccgtatcc | 60 |
| gagctcacac gcaaccacac caaacgcgcc tccgcaaccg tgaagaccgc cgtattggcg | 120 |
| acactgttgt ttgcaacggt tcaggcgaat gctaccgatg aagatgaaga agaagagtta | 180 |
| gaatccgtac aacgctctgt cgtagggagc attcaagcca gtatggaagg cagcggcgaa | 240 |
| ttggaaacga tatcattatc aatgactaac gacagcaagg aatttgtaga cccatacata | 300 |
| gtagttaccc tcaaagccgg cgacaacctg aaaatcaaac aaaacaccaa tgaaaacacc | 360 |
| aatgccagta gcttcaccta ctcgctgaaa aagacctca caggcctgat caatgttgan | 420 |
| actgaaaaat tatcgtttgg cgcaaacggc aagaaagtca acatcataag cgacaccaaa | 480 |
| ggcttgaatt tcgcgaaaga aacggctggg acgaacggcg acaccacggt tcatctgaac | 540 |
| ggtatcggtt cgactttgac cgatacgctt gcgggttctt ctgcttctca cgttgatgcg | 600 |
| ggtaaccnaa gtacacatta cactcgtgca gcaagtatta aggatgtgtt gaatgcgggt | 660 |

-continued

```
tggaatatta agggtgttaa annnggctca acaactggtc aatcagaaaa tgtcgatttc      720
gtccgcactt acgacacagt cgagttcttg agcgcagata cgnaaacaac gacngttaat      780
gtggaaagca agacaacgg caagagaacc gaagttaaaa tcggtgcgaa gacttctgtt      840
attaaagaaa aagacggtaa gttggttact ggtaaaggca aggcgagaa tggttcttct       900 acagacgaag gcgaaggctt agtgactgca aaagaagtga ttgatgcagt aaacaaggct     960
ggttggagaa tgaaaacaac aaccgctaat ggtcaaacag gtcaagctga caagtttgaa    1020
accgttacat caggcacaaa tgtaaccttt gctagtggta aggtacaac tgcgactgta     1080 agtaaagatg atcaaggcaa catcactgtt atgtatgatg taaatgtcgg cgatgcccta    1140
aacgtcaatc agctgcaaaa cagcggttgg aatttggatt ccaaagcggt tgcaggttct    1200
tcgggcaaag tcatcagcgg caatgtttcg ccgagcaagg gaaagatgga tgaaaccgtc    1260
aacattaatg ccggcaacaa catcgagatt agccgcaacg gtaaaaatat cgacatcgcc    1320
acttcgatgg cgccgcagtt ttccagcgtt tcgctcggcg cggggggcaga tgcgcccact   1380 ttaagcgtgg atgacgaggg cgcgttgaat gtcggcagca aggatgccaa caaacccgtc    1440
cgcattacca atgtcgcccc gggcgttaaa gangggatg ttacaaacgt cncacaactt     1500
aaaggcgtgg cgcaaaactt gaacaaccgc atcgacaatg tggacggcaa cgcgcgtgcn   1560
ggcatcgccc aagcgattgc aaccgcaggt ctggttcagg cgtatctgcc cggcaagagt   1620
atgatggcga tcggcggcgg cacttatcgc ggcgaagccg gttacgccat cggctactcc    1680
agtatttccg acgcggaaa ttggattatc aaaggcacgg cttccggcaa ttcgcgcggc     1740
catttcggtg cttccgcatc tgtcggttat cagtggtaa                           1779
```

<210> SEQ ID NO 1775
<211> LENGTH: 592
<212> TYPE: PRT
<213> ORGANISM: Neisseria meningitidis
<220> FEATURE:
<221> NAME/KEY: misc_feature
<222> LOCATION: (1)...(592)
<223> OTHER INFORMATION: Xaa is any amino acid

<400> SEQUENCE: 1775

```
Met Asn Lys Ile Tyr Arg Ile Ile Trp Asn Ser Ala Leu Asn Ala Xaa
              5                  10                  15

Val Ala Val Ser Glu Leu Thr Arg Asn His Thr Lys Arg Ala Ser Ala
         20                  25                  30

Thr Val Lys Thr Ala Val Leu Ala Thr Leu Leu Phe Ala Thr Val Gln
     35                  40                  45

Ala Asn Ala Thr Asp Glu Asp Glu Glu Glu Leu Glu Ser Val Gln
 50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                 85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Xaa Thr Glu Lys Leu
    130                 135                 140

Ser Phe Gly Ala Asn Gly Lys Lys Val Asn Ile Ile Ser Asp Thr Lys
145                 150                 155                 160
```

-continued

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Xaa Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Xaa Gly Ser Thr Thr Gly Gln Ser Glu Asn Val Asp Phe
225                 230                 235                 240

Val Arg Thr Tyr Asp Thr Val Glu Phe Leu Ser Ala Asp Thr Xaa Thr
            245                 250                 255

Thr Thr Val Asn Val Glu Ser Lys Asp Asn Gly Lys Arg Thr Glu Val
        260                 265                 270

Lys Ile Gly Ala Lys Thr Ser Val Ile Lys Glu Lys Asp Gly Lys Leu
    275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
            325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
        435                 440                 445

Ser Val Ser Leu Gly Ala Gly Asp Ala Pro Thr Leu Ser Val Asp
    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Xaa Gly Asp Val Thr Asn
            485                 490                 495

Val Xaa Gln Leu Lys Gly Val Ala Gln Asn Leu Asn Asn Arg Ile Asp
        500                 505                 510

Asn Val Asp Gly Asn Ala Arg Ala Gly Ile Ala Gln Ala Ile Ala Thr
    515                 520                 525

Ala Gly Leu Val Gln Ala Tyr Leu Pro Gly Lys Ser Met Met Ala Ile
530                 535                 540

Gly Gly Gly Thr Tyr Arg Gly Glu Ala Gly Tyr Ala Ile Gly Tyr Ser
545                 550                 555                 560

```
Ser Ile Ser Asp Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
            580                 585                 590

<210> SEQ ID NO 1776
<211> LENGTH: 492
<212> TYPE: DNA
<213> ORGANISM: Neisseria meningitidis

<400> SEQUENCE: 1776
atgttacgtt tgactgcttt agccgtatgc accgccctcg ctttgggcgc gtgttcgccg     60
caaaattccg actctgcccc acaagccaaa gaacaggcgg tttccgccgc acaaaccgaa    120
ggcgcgtccg ttaccgtcaa aaccgcgcgc ggcgacgttc aaataccgca aaccccgaa    180 cgcatcgccg tttacgattt gggtatgctc gacaccttga gcaaactggg cgtgaaaacc    240
ggtttgtccg tcgataaaaa ccgcctgccg tatttagagg aatatttcaa aacgacaaaa    300
cctgccggca ctttgttcga gccggattac gaaacgctca cgcttacaa accgcagctc    360 atcatcatcg gcagccgcgc cgccaaggcg tttgacaaat gaacgaaat cgcgccgacc    420 atcgrmwtga ccgccgatac cgccaacctc aaagaaagtg ccaargaggc atcgacgctg    480
gcgcaaatct tc                                                        492

<210> SEQ ID NO 1777
<211> LENGTH: 164
<212> TYPE: PRT
<213> ORGANISM: Neisseria meningitidis
<220> FEATURE:
<221> NAME/KEY: misc_feature
<222> LOCATION: (1)...(164)
<223> OTHER INFORMATION: Xaa is any amino acid

<400> SEQUENCE: 1777

Met Leu Arg Leu Thr Ala Leu Ala Val Cys Thr Ala Leu Ala Leu Gly
            5                   10                  15

Ala Cys Ser Pro Gln Asn Ser Asp Ser Ala Pro Gln Ala Lys Glu Gln
            20                  25                  30

Ala Val Ser Ala Ala Gln Thr Glu Gly Ala Ser Val Thr Val Lys Thr
            35                  40                  45

Ala Arg Gly Asp Val Gln Ile Pro Gln Asn Pro Glu Arg Ile Ala Val
    50                  55                  60

Tyr Asp Leu Gly Met Leu Asp Thr Leu Ser Lys Leu Gly Val Lys Thr
65                  70                  75                  80

Gly Leu Ser Val Asp Lys Asn Arg Leu Pro Tyr Leu Glu Glu Tyr Phe
                85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
            115                 120                 125

Lys Ala Phe Asp Lys Leu Asn Glu Ile Ala Pro Thr Ile Xaa Xaa Thr
            130                 135                 140

Ala Asp Thr Ala Asn Leu Lys Glu Ser Ala Lys Glu Ala Ser Thr Leu
145                 150                 155                 160

Ala Gln Ile Phe
```

<210> SEQ ID NO 1778
<211> LENGTH: 966
<212> TYPE: DNA
<213> ORGANISM: Neisseria meningitidis

<400> SEQUENCE: 1778

```
atgttacgtt tgactgcttt agccgtatgc accgccctcg ctttgggcgc gtgttcgccg      60
caaaattccg actctgcccc acaagccaaa gaacaggcgg tttccgccgc acaaaccgaa     120
ggcgcgtccg ttaccgtcaa aaccgcgcgc ggcgacgttc aaataccgca aaccccgaa      180
cgcatcgccg tttacgattt gggtatgctc gacaccttga gcaaactggg cgtgaaaacc     240
ggtttgtccg tcgataaaaa ccgcctgccg tatttagagg aatatttcaa aacgacaaaa     300
cctgccggca ctttgttcga gccggattac gaaacgctca acgcttacaa accgcagctc     360
atcatcatcg gcagccgcgc cgccaaggcg tttgacaaat gaacgaaat cgcgccgacc      420
atcgaaatga ccgccgatac cgccaacctc aaagaaagtg ccaaagagcg catcgacgcg     480
ctggcgcaaa tcttcggcaa acaggcggaa gccgacaagc tgaaggcgga aatcgacgcg     540
tcttttgaag ccgcgaaaac tgccgcacaa ggtaagggca aggtttggt gattttggtc       600
aacggcggca agatgtcggc tttcggcccg tcttcacgct gggcggctg gctgcacaaa      660
gacatcggcg ttcccgctgt cgatgaatca attaaagaag gcagccacgg tcagcctatc     720
agctttgaat acctgaaaga gaaaaatccc gactggctgt ttgtccttga ccgaagcgcg     780
gccatcggcg aagagggtca ggcggcgaaa gacgtgttgg ataatccgct ggttgccgaa     840
acaaccgctt ggaaaaaagg acaggtcgtg tacctcgttc ctgaaactta tttggcagcc     900
ggtggcgcgc aagagctgct gaatgcaagc aaacaggttg ccgacgcttt taacgcggca     960
aaataa                                                               966
```

<210> SEQ ID NO 1779
<211> LENGTH: 321
<212> TYPE: PRT
<213> ORGANISM: Neisseria meningitidis

<400> SEQUENCE: 1779

```
Met Leu Arg Leu Thr Ala Leu Ala Val Cys Thr Ala Leu Ala Leu Gly
                 5                  10                  15

Ala Cys Ser Pro Gln Asn Ser Asp Ser Ala Pro Gln Ala Lys Glu Gln
             20                  25                  30

Ala Val Ser Ala Ala Gln Thr Glu Gly Ala Ser Val Thr Val Lys Thr
         35                  40                  45

Ala Arg Gly Asp Val Gln Ile Pro Gln Asn Pro Glu Arg Ile Ala Val
     50                  55                  60

Tyr Asp Leu Gly Met Leu Asp Thr Leu Ser Lys Leu Gly Val Lys Thr
 65                  70                  75                  80

Gly Leu Ser Val Asp Lys Asn Arg Leu Pro Tyr Leu Glu Glu Tyr Phe
                 85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
        115                 120                 125

Lys Ala Phe Asp Lys Leu Asn Glu Ile Ala Pro Thr Ile Glu Met Thr
    130                 135                 140

Ala Asp Thr Ala Asn Leu Lys Glu Ser Ala Lys Glu Arg Ile Asp Ala
145                 150                 155                 160
```

-continued

```
Leu Ala Gln Ile Phe Gly Lys Gln Ala Glu Ala Asp Lys Leu Lys Ala
                165                 170                 175
Glu Ile Asp Ala Ser Phe Glu Ala Ala Lys Thr Ala Ala Gln Gly Lys
            180                 185                 190
Gly Lys Gly Leu Val Ile Leu Val Asn Gly Gly Lys Met Ser Ala Phe
        195                 200                 205
Gly Pro Ser Ser Arg Leu Gly Gly Trp Leu His Lys Asp Ile Gly Val
    210                 215                 220
Pro Ala Val Asp Glu Ser Ile Lys Glu Gly Ser His Gly Gln Pro Ile
225                 230                 235                 240
Ser Phe Glu Tyr Leu Lys Glu Lys Asn Pro Asp Trp Leu Phe Val Leu
                245                 250                 255
Asp Arg Ser Ala Ala Ile Gly Glu Glu Gly Gln Ala Ala Lys Asp Val
            260                 265                 270
Leu Asp Asn Pro Leu Val Ala Glu Thr Thr Ala Trp Lys Lys Gly Gln
        275                 280                 285
Val Val Tyr Leu Val Pro Glu Thr Tyr Leu Ala Ala Gly Gly Ala Gln
    290                 295                 300
Glu Leu Leu Asn Ala Ser Lys Gln Val Ala Asp Ala Phe Asn Ala Ala
305                 310                 315                 320
Lys
```

<210> SEQ ID NO 1780
<211> LENGTH: 966
<212> TYPE: DNA
<213> ORGANISM: Neisseria meningitidis

<400> SEQUENCE: 1780

```
atgttacgtt tgactgcttt agccgtatgc accgccctcg ctttgggcgc gtgttcgccg      60
caaaattccg actctgcccc acaagccaaa gaacaggcgg tttccgccgc acaatccgaa     120
ggcgtgtccg ttaccgtcaa acggcgcgc ggcgatgttc aaataccgca aaaccccgaa     180
cgtatcgccg tttacgattt gggtatgctc gacaccttga gcaaactggg cgtgaaaacc     240
ggtttgtccg tcgataaaaa ccgcctgccg tatttagagg aatatttcaa aacgacaaaa     300
cctgccggaa ctttgttcga gccggattac gaaacgctca acgcttacaa accgcagctc     360
atcatcatcg gcagccgcgc agccaaagcg tttgacaaat gaacgaaat cgcgccgacc     420
atcgaaatga ccgccgatac cgccaacctc aaagaaagtg ccaaagagcg tatcgacgcg     480
ctggcgcaaa tcttcggcaa aaaggcgaa gccgacaagc tgaaggcgga aatcgacgcg     540
tcttttgaag ccgcgaaaac tgccgcgcaa ggcaaaggca agggtttggt gattttggtc     600
aacggcggca agatgtccgc cttcggcccg tcttcacgac tgggcggctg gctgcacaaa     660
gacatcggcg ttcccgctgt tgacgaagcc atcaaagaag gcagccacgg tcagcctatc     720
agctttgaat acctgaaaga gaaaaatccc gactggctgt tgtccttga ccgcagcgcg     780
gccatcggcg aagagggtca ggcggcgaaa gacgtgttga caatccgct ggttgccgaa     840
acaaccgctt ggaaaaaagg acaagtcgtt taccttgttc ctgaaactta tttggcagcc     900
ggtggcgcgc aagagctact gaatgcaagc aaacaggttg ccgacgcttt taacgcggca     960
aaataa                                                                966
```

<210> SEQ ID NO 1781
<211> LENGTH: 321
<212> TYPE: PRT
<213> ORGANISM: Neisseria meningitidis

<400> SEQUENCE: 1781

Met Leu Arg Leu Thr Ala Leu Ala Val Cys Thr Ala Leu Ala Leu Gly
1               5                   10                  15

Ala Cys Ser Pro Gln Asn Ser Asp Ser Ala Pro Gln Ala Lys Glu Gln
            20                  25                  30

Ala Val Ser Ala Ala Gln Ser Glu Gly Val Ser Val Thr Val Lys Thr
        35                  40                  45

Ala Arg Gly Asp Val Gln Ile Pro Gln Asn Pro Glu Arg Ile Ala Val
    50                  55                  60

Tyr Asp Leu Gly Met Leu Asp Thr Leu Ser Lys Leu Gly Val Lys Thr
65                  70                  75                  80

Gly Leu Ser Val Asp Lys Asn Arg Leu Pro Tyr Leu Glu Glu Tyr Phe
                85                  90                  95

Lys Thr Thr Lys Pro Ala Gly Thr Leu Phe Glu Pro Asp Tyr Glu Thr
            100                 105                 110

Leu Asn Ala Tyr Lys Pro Gln Leu Ile Ile Ile Gly Ser Arg Ala Ala
        115                 120                 125

Lys Ala Phe Asp Lys Leu Asn Glu Ile Ala Pro Thr Ile Glu Met Thr
    130                 135                 140

Ala Asp Thr Ala Asn Leu Lys Glu Ser Ala Lys Glu Arg Ile Asp Ala
145                 150                 155                 160

Leu Ala Gln Ile Phe Gly Lys Ala Glu Ala Asp Lys Leu Lys Ala
                165                 170                 175

Glu Ile Asp Ala Ser Phe Glu Ala Ala Lys Thr Ala Ala Gln Gly Lys
            180                 185                 190

Gly Lys Gly Leu Val Ile Leu Val Asn Gly Gly Lys Met Ser Ala Phe
        195                 200                 205

Gly Pro Ser Ser Arg Leu Gly Gly Trp Leu His Lys Asp Ile Gly Val
    210                 215                 220

Pro Ala Val Asp Glu Ala Ile Lys Glu Gly Ser His Gly Gln Pro Ile
225                 230                 235                 240

Ser Phe Glu Tyr Leu Lys Glu Lys Asn Pro Asp Trp Leu Phe Val Leu
                245                 250                 255

Asp Arg Ser Ala Ala Ile Gly Glu Glu Gly Gln Ala Ala Lys Asp Val
            260                 265                 270

Leu Asn Asn Pro Leu Val Ala Glu Thr Thr Ala Trp Lys Lys Gly Gln
        275                 280                 285

Val Val Tyr Leu Val Pro Glu Thr Tyr Leu Ala Ala Gly Gly Ala Gln
    290                 295                 300

Glu Leu Leu Asn Ala Ser Lys Gln Val Ala Asp Ala Phe Asn Ala Ala
305                 310                 315                 320

Lys

<210> SEQ ID NO 1782
<211> LENGTH: 375
<212> TYPE: DNA
<213> ORGANISM: Neisseria meningitidis

<400> SEQUENCE: 1782
atgaaacttc tgaccaccgc aatcctgtct tccgcaatcg cgctcagcag tatggctgcc      60
gccgctggca cggacaaccc cactgttgca aaaaaaaccg tcagctacgt ctgccagcaa     120
ggtaaaaaag tcaaagtaac ctacggcttc aacaaacagg gtctgaccac atacgcttcc     180
gccgtcatca acggcaaacg cgtgcaaatg cctgtcaatt tggacaaatc cgacaatgtg     240

```
gaaacattct acggcaaaga aggcggttat gttttgggta ccggcgtgat ggatggcaaa    300
tcctaccgca aacagcccat tatgattacc gcacctgaca accaaatcgt cttcaaagac    360
tgttccccac gttaa                                                     375
```

<210> SEQ ID NO 1783
<211> LENGTH: 124
<212> TYPE: PRT
<213> ORGANISM: Neisseria meningitidis
<400> SEQUENCE: 1783

```
Met Lys Leu Leu Thr Thr Ala Ile Leu Ser Ser Ala Ile Ala Leu Ser
                 5                  10                  15

Ser Met Ala Ala Ala Ala Gly Thr Asp Asn Pro Thr Val Ala Lys Lys
             20                  25                  30

Thr Val Ser Tyr Val Cys Gln Gln Gly Lys Lys Val Lys Val Thr Tyr
         35                  40                  45

Gly Phe Asn Lys Gln Gly Leu Thr Thr Tyr Ala Ser Ala Val Ile Asn
     50                  55                  60

Gly Lys Arg Val Gln Met Pro Val Asn Leu Asp Lys Ser Asp Asn Val
 65                  70                  75                  80

Glu Thr Phe Tyr Gly Lys Glu Gly Tyr Val Leu Gly Thr Gly Val
                 85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
        115                 120
```

<210> SEQ ID NO 1784
<211> LENGTH: 375
<212> TYPE: DNA
<213> ORGANISM: Neisseria meningitidis
<400> SEQUENCE: 1784

```
atgaaacttc tgaccaccgc aatcctgtct tccgcaatcg cgctcagcag tatggctgct    60
gctgccggca cgaacaaccc caccgttgcc aaaaaaaccg tcagctacgt ctgccagcaa    120
ggtaaaaaag tcaaagtaac ctacggcttt aacaaacagg gcctgaccac atacgcttcc    180
gccgtcatca cggcaaacg tgtgcaaatg cctgtcaatt tggacaaatc cgacaatgtg    240
gaaacattct acggcaaaga aggcggttat gttttgggta ccggcgtgat ggatggcaaa    300
tcctatcgca aacagcctat tatgattacc gcacctgaca accaaatcgt cttcaaagac    360
tgttccccac gttaa                                                     375
```

<210> SEQ ID NO 1785
<211> LENGTH: 124
<212> TYPE: PRT
<213> ORGANISM: Neisseria meningitidis
<400> SEQUENCE: 1785

```
Met Lys Leu Leu Thr Thr Ala Ile Leu Ser Ser Ala Ile Ala Leu Ser
                 5                  10                  15

Ser Met Ala Ala Ala Ala Gly Thr Asn Asn Pro Thr Val Ala Lys Lys
             20                  25                  30

Thr Val Ser Tyr Val Cys Gln Gln Gly Lys Lys Val Lys Val Thr Tyr
         35                  40                  45

Gly Phe Asn Lys Gln Gly Leu Thr Thr Tyr Ala Ser Ala Val Ile Asn
     50                  55                  60
```

```
Gly Lys Arg Val Gln Met Pro Val Asn Leu Asp Lys Ser Asp Asn Val
65                  70                  75                  80

Glu Thr Phe Tyr Gly Lys Glu Gly Tyr Val Leu Gly Thr Gly Val
                85                  90                  95

Met Asp Gly Lys Ser Tyr Arg Lys Gln Pro Ile Met Ile Thr Ala Pro
            100                 105                 110

Asp Asn Gln Ile Val Phe Lys Asp Cys Ser Pro Arg
        115                 120
```

<210> SEQ ID NO 1786
<211> LENGTH: 519
<212> TYPE: DNA
<213> ORGANISM: Neisseria meningitidis
<220> FEATURE:
<221> NAME/KEY: misc_feature
<222> LOCATION: (1)...(519)
<223> OTHER INFORMATION: n = A,T,C or G

<400> SEQUENCE: 1786

```
ggcaccgaat tcaaaaccac cctttccgga gccgacatac aggcagggt gggtgaaaaa     60
gcccgagccg atgcgaaaat tatcctaaaa ggcatcgtta accgcatcca aaccgaagaa   120
aagctggaat ccaactcgac cgtatggcaa aagcaggccg gaagcggcag cacggttgaa   180
acgctgaagc taccgagctt tgaagggccg gcactgccta agctgaccgc tcccggcggc   240
tatatcgccg acatccccaa aggcaacctc aaaaccgaaa tcgaaaagct ggccaaacag   300
cccgaatatg cctatctgaa acagcttcag acggtcaagg acgtgaactg gaaccaagta   360
cagctcgctt acgacaaatg ggactataaa caggaaggcc taaccggagc cggagccgca   420
attancgcac tggccgttac cgtggtcacc tcaggcgcag gaaccggagc cgtattggga   480
ttaanacgng tggccgccgc cgcaaccgat gcagcattt                          519
```

<210> SEQ ID NO 1787
<211> LENGTH: 173
<212> TYPE: PRT
<213> ORGANISM: Neisseria meningitidis
<220> FEATURE:
<221> NAME/KEY: misc_feature
<222> LOCATION: (1)...(173)
<223> OTHER INFORMATION: Xaa is any amino acid

<400> SEQUENCE: 1787

```
Gly Thr Glu Phe Lys Thr Thr Leu Ser Gly Ala Asp Ile Gln Ala Gly
                 5                  10                  15

Val Gly Glu Lys Ala Arg Ala Asp Ala Lys Ile Ile Leu Lys Gly Ile
            20                  25                  30

Val Asn Arg Ile Gln Thr Glu Glu Lys Leu Glu Ser Asn Ser Thr Val
        35                  40                  45

Trp Gln Lys Gln Ala Gly Ser Gly Ser Thr Val Glu Thr Leu Lys Leu
    50                  55                  60

Pro Ser Phe Glu Gly Pro Ala Leu Pro Lys Leu Thr Ala Pro Gly Gly
65                  70                  75                  80

Tyr Ile Ala Asp Ile Pro Lys Gly Asn Leu Lys Thr Glu Ile Glu Lys
                85                  90                  95

Leu Ala Lys Gln Pro Glu Tyr Ala Tyr Leu Lys Gln Leu Gln Thr Val
            100                 105                 110

Lys Asp Val Asn Trp Asn Gln Val Gln Leu Ala Tyr Asp Lys Trp Asp
        115                 120                 125
```

```
Tyr Lys Gln Glu Gly Leu Thr Gly Ala Gly Ala Ala Ile Xaa Ala Leu
        130                 135                 140
Ala Val Thr Val Val Thr Ser Gly Ala Gly Thr Gly Ala Val Leu Gly
145                 150                 155                 160
Leu Xaa Arg Val Ala Ala Ala Ala Thr Asp Ala Ala Phe
            165                 170

<210> SEQ ID NO 1788
<211> LENGTH: 1923
<212> TYPE: DNA
<213> ORGANISM: Neisseria meningitidis

<400> SEQUENCE: 1788
```

| | | | | | |
|---|---|---|---|---|---|
| atgcaactgc | tggcagccga | aggcattcac | caacaccaat | tgaatgttca | gaaaagtacc | 60 |
| cgtttcatcg | gcatcaaagt | gggtaaaagc | aattacagca | aaaacgagct | gaacgaaacc | 120 |
| aaactgcccg | tacgcgttat | cgcccaaaca | gccaaaaccc | gttccggctg | ggataccgta | 180 |
| ctcgaaggca | ccgaattcaa | accaccctt | tccggagccg | acatacaggc | aggggtgggt | 240 |
| gaaaaagccc | gagccgatgc | gaaaattatc | ctaaaaggca | tcgttaaccg | catccaaacc | 300 |
| gaagaaaagc | tggaatccaa | ctcgaccgta | tggcaaaagc | aggccggaag | cggcagcacg | 360 |
| gttgaaacgc | tgaagctacc | gagctttgaa | gggccggcac | tgcctaagct | gaccgctccc | 420 |
| ggcggctata | tcgccgacat | ccccaaaggc | aacctcaaaa | ccgaaatcga | aagctggcc | 480 |
| aaacagcccg | aatatgccta | tctgaaacag | cttcagacgg | tcaaggacgt | gaactggaac | 540 |
| caagtacagc | tcgcttacga | caaatgggac | tataaacagg | aaggcctaac | cggagccgga | 600 |
| gccgcaatta | tcgcactggc | cgttaccgtg | gtcacctcag | gcgcaggaac | cggagccgta | 660 |
| ttgggattaa | acggtgcggc | cgccgccgca | accgatgcag | catttgcctc | tttggccagc | 720 |
| caggcttccg | tatcgttcat | caacaacaaa | ggcaatatcg | gtaacaccct | gaaagagctg | 780 |
| ggcagaagca | gcacggtgaa | aaatctgatg | gttgccgtcg | ctaccgcagg | cgtagccgac | 840 |
| aaaatcggtg | cttcggcact | gaacaatgtc | agcgataagc | agtggatcaa | caacctgacc | 900 |
| gtcaacctgg | ccaatgcggg | cagtgccgca | ctgattaata | ccgctgtcaa | cggcggcagc | 960 |
| ctgaaagaca | atctggaagc | gaatatcctt | gcggctttgg | tgaatactgc | gcatggagag | 1020 |
| gcagcaagta | aaatcaaaca | gttggatcag | cactacattg | cccataagat | tgcccatgcc | 1080 |
| atagcgggct | gtgcggcagc | ggcggcgaat | aagggcaagt | gtcaagatgg | tgcgatcggt | 1140 |
| gcggcggtcg | gtgaaatcct | tggcgaaacc | ctactggacg | gcagagaccc | tggcagcctg | 1200 |
| aatgtgaagg | acagggcaaa | aatcattgct | aaggcgaagc | tggcagcagg | ggcggttgcg | 1260 |
| gcgttgagta | aggggatgt | gagtacggcg | gcgaatgcgg | ctgctgtggc | ggtagagaat | 1320 |
| aattctttaa | atgatataca | ggatcgtttg | ttgagtggaa | attatgcttt | atgtatgagt | 1380 |
| gcaggaggag | cagaaagctt | ttgtgagtct | tatcgaccac | tgggcttgcc | acactttgta | 1440 |
| agtgtttcag | gagaaatgaa | attacctaat | aaattcggga | atcgtatggt | taatggaaaa | 1500 |
| ttaattatta | acactagaaa | tggcaatgta | tatttctctg | taggtaaaat | atggagtact | 1560 |
| gtaaaatcaa | caaaatcaaa | tataagtggg | gtatctgtcg | gttgggtttt | aaatgtttcc | 1620 |
| cctaatgatt | atttaaaaga | agcatctatg | aatgatttca | gaaatagtaa | tcaaaataaa | 1680 |
| gcctatgcag | aaatgatttc | ccagactttg | gtaggtgaga | gtgttggtgg | tagtctttgt | 1740 |
| ctgacaagag | cctgcttttc | ggtaagttca | acaatatcta | aatctaaatc | tccttttaaa | 1800 |
| gattcaaaaa | ttattgggga | aatcggtttg | ggaagtggtg | ttgctgcagg | agtagaaaaa | 1860 |

```
acaatataca taggtaacat aaaagatatt gataaattta ttagtgcaaa cataaaaaaa   1920
tag                                                                1923
```

<210> SEQ ID NO 1789
<211> LENGTH: 640
<212> TYPE: PRT
<213> ORGANISM: Neisseria meningitidis

<400> SEQUENCE: 1789

```
Met Gln Leu Leu Ala Ala Glu Gly Ile His Gln His Gln Leu Asn Val
                 5                  10                  15

Gln Lys Ser Thr Arg Phe Ile Gly Ile Lys Val Gly Lys Ser Asn Tyr
             20                  25                  30

Ser Lys Asn Glu Leu Asn Glu Thr Lys Leu Pro Val Arg Val Ile Ala
         35                  40                  45

Gln Thr Ala Lys Thr Arg Ser Gly Trp Asp Thr Val Leu Glu Gly Thr
     50                  55                  60

Glu Phe Lys Thr Thr Leu Ser Gly Ala Asp Ile Gln Ala Gly Val Gly
 65                  70                  75                  80

Glu Lys Ala Arg Ala Asp Ala Lys Ile Ile Leu Lys Gly Ile Val Asn
                 85                  90                  95

Arg Ile Gln Thr Glu Glu Lys Leu Glu Ser Asn Ser Thr Val Trp Gln
            100                 105                 110

Lys Gln Ala Gly Ser Gly Ser Thr Val Glu Thr Leu Lys Leu Pro Ser
        115                 120                 125

Phe Glu Gly Pro Ala Leu Pro Lys Leu Thr Ala Pro Gly Gly Tyr Ile
    130                 135                 140

Ala Asp Ile Pro Lys Gly Asn Leu Lys Thr Glu Ile Glu Lys Leu Ala
145                 150                 155                 160

Lys Gln Pro Glu Tyr Ala Tyr Leu Lys Gln Leu Gln Thr Val Lys Asp
                165                 170                 175

Val Asn Trp Asn Gln Val Gln Leu Ala Tyr Asp Lys Trp Asp Tyr Lys
            180                 185                 190

Gln Glu Gly Leu Thr Gly Ala Gly Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Met Val Ala
            260                 265                 270

Val Ala Thr Ala Gly Val Ala Asp Lys Ile Gly Ala Ser Ala Leu Asn
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320

Leu Lys Asp Asn Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
            340                 345                 350
```

-continued

```
Ile Ala His Lys Ile Ala His Ala Ile Ala Gly Cys Ala Ala Ala Ala
        355                 360                 365
Ala Asn Lys Gly Lys Cys Gln Asp Gly Ala Ile Gly Ala Ala Val Gly
    370                 375                 380
Glu Ile Leu Gly Glu Thr Leu Leu Asp Gly Arg Asp Pro Gly Ser Leu
385                 390                 395                 400
Asn Val Lys Asp Arg Ala Lys Ile Ile Ala Lys Ala Lys Leu Ala Ala
                405                 410                 415
Gly Ala Val Ala Ala Leu Ser Lys Gly Asp Val Ser Thr Ala Ala Asn
            420                 425                 430
Ala Ala Ala Val Ala Val Glu Asn Asn Ser Leu Asn Asp Ile Gln Asp
        435                 440                 445
Arg Leu Leu Ser Gly Asn Tyr Ala Leu Cys Met Ser Ala Gly Gly Ala
    450                 455                 460
Glu Ser Phe Cys Glu Ser Tyr Arg Pro Leu Gly Leu Pro His Phe Val
465                 470                 475                 480
Ser Val Ser Gly Glu Met Lys Leu Pro Asn Lys Phe Gly Asn Arg Met
                485                 490                 495
Val Asn Gly Lys Leu Ile Ile Asn Thr Arg Asn Gly Asn Val Tyr Phe
            500                 505                 510
Ser Val Gly Lys Ile Trp Ser Thr Val Lys Ser Thr Lys Ser Asn Ile
        515                 520                 525
Ser Gly Val Ser Val Gly Trp Val Leu Asn Val Ser Pro Asn Asp Tyr
    530                 535                 540
Leu Lys Glu Ala Ser Met Asn Asp Phe Arg Asn Ser Asn Gln Asn Lys
545                 550                 555                 560
Ala Tyr Ala Glu Met Ile Ser Gln Thr Leu Val Gly Glu Ser Val Gly
                565                 570                 575
Gly Ser Leu Cys Leu Thr Arg Ala Cys Phe Ser Val Ser Ser Thr Ile
            580                 585                 590
Ser Lys Ser Lys Ser Pro Phe Lys Asp Ser Lys Ile Ile Gly Glu Ile
        595                 600                 605
Gly Leu Gly Ser Gly Val Ala Ala Gly Val Glu Lys Thr Ile Tyr Ile
    610                 615                 620
Gly Asn Ile Lys Asp Ile Asp Lys Phe Ile Ser Ala Asn Ile Lys Lys
625                 630                 635                 640
```

<210> SEQ ID NO 1790
<211> LENGTH: 2291
<212> TYPE: DNA
<213> ORGANISM: Neisseria meningitidis
<220> FEATURE:
<221> NAME/KEY: misc_feature
<222> LOCATION: (1)...(1790)
<223> OTHER INFORMATION: n = A,T,C or G

<400> SEQUENCE: 1790

```
ntgcaactgc tggcagaaga aggcatccac aagcacgagt tggatgtcca aaaaagccgc      60
cgctttatcg gcatcaaggt aggtnagagc aattacagta aaaacgaact gaacgaaacc     120
aaattgcctg tccgcgtcgt cgcccaaant gcagccaccc gttcaggctg ggataccgtg     180
ctcgaaggta ccgaattcaa aaccacgctg gccggtgccg acattcaggc aggtgtangc     240
gaaaaagccc gtgtcgatgc gaaaattatc ctcaaaggca ttgtgaaccg tatccagtcg     300
gaagaaaaat tagaaaccaa ctcaaccgta tggcagaaac aggccggacg cggcagcact     360
atcgaaacgc taaaactgcc cagcttcgaa agccctactc cgcccaaatt gtccgcaccc     420
```

```
ggcggntata tcgtcgacat tccgaaaggc aatctgaaaa ccgaaatcga aaagctgtcc      480
aaacagcccg agtatgccta tctgaaacag ctccaagtag cgaaaaacat caactggaat      540
caggtgcagc ttgcttacga cagatgggac tacaaacagg agggcttaac cgaagcaggt      600
gcggcgatta tcgcactggc cgttaccgtg gtcacctcag gcgcaggaac cggagccgta      660
ttgggattaa acggtgcgnc cgccgccgca accgatgcag cattcgcctc tttggccagc      720
caggcttccg tatcgttcat caacaacaaa ggcgatgtcg gcaaaaccct gaaagagctg      780
ggcagaagca gcacggtgaa aaatctggtg gttgccgccg ctaccgcagg cgtagccgac      840
aaaatcggcg cttcggcact gancaatgtc agcgataagc agtggatcaa caacctgacc      900
gtcaacctag ccaatgcggg cagtgccgca ctgattaata ccgctgtcaa cggcggcagc      960
ctgaaagaca ntctggaagc gaatatcctt gcggctttgg tcaataccgc gcatggagaa     1020
gcagccagta aaatcaaaca gttggatcag cactacatag tccacaagat tgcccatgcc     1080
atagcgggct gtgcggcagc ggcggcgaat aagggcaagt gtcaggatgg tgcgataggt     1140
gcggctgtgg gcgagatagt cggggaggct ttgacaaacg gcaaaaatcc tgacactttg     1200
acagctaaag aacgcgaaca gattttggca tacagcaaac tggttgccgg tacggtaagc     1260
ggtgtggtcg gcgcgatgt aaatgcggcg gcgaatgcgg ctgaggtagc ggtgaaaaat     1320
aatcagctta gcgacnaaga gggtagagaa tttgataacg aaatgactgc atgcgccaaa     1380
cagaatantc ctcaactgtg cagaaaaaat actgtaaaaa agtatcaaaa tgttgctgat     1440
aaaagacttg ctgcttcgat tgcaatatgt acggatatat cccgtagtac tgaatgtaga     1500
acaatcagaa acaacatttt gatcgatagt agaagccttc attcatcttg ggaagcaggt     1560
ctaattggta aagatgatga atggtataaa ttattcagca aatcttacac ccaagcagat     1620
ttggctttac agtcttatca tttgaatact gctgctaaat cttggcttca atcgggcaat     1680
acaaagcctt tatccgaatg gatgtccgac caaggttata cacttatttc aggagttaat     1740
cctagattca ttccaatacc aagagggttt gtaaaacaaa atacacctat tactaatgtc     1800
aaatacccgg aaggcatcag tttcgataca aacctanaaa gacatctggc aaatgctgat     1860
ggttttagtc aagaacaggg cattaaagga gcccataacc gcaccaatnt tatggcagaa     1920
ctaaattcac gaggaggang ngtaaaatct gaaacccana ctgatattga aggcattacc     1980
cgaattaaat atgagattcc tacactagac aggacaggta aacctgatgg tggatttaag     2040
gaaatttcaa gtataaaaac tgtttataat cctaaaaant tttnngatga taaaatactt     2100
caaatggctc aanatgctgn ttcacaagga tattcaaaag cctctaaaat tgctcaaaat     2160
gaaagaacta aatcaatatc ggaaagaaaa aatgtcattc aattctcaga aacctttgac     2220
ggaatcaaat ttagannnta tntngatgta aatacaggaa gaattacaaa cattcaccca     2280
gaataattta a                                                           2291
```

<210> SEQ ID NO 1791  
<211> LENGTH: 761  
<212> TYPE: PRT  
<213> ORGANISM: Neisseria meningitidis  
<220> FEATURE:  
<221> NAME/KEY: misc_feature  
<222> LOCATION: (1)...(761)  
<223> OTHER INFORMATION: Xaa is any amino acid

<400> SEQUENCE: 1791

```
Xaa Gln Leu Leu Ala Glu Glu Gly Ile His Lys His Glu Leu Asp Val
                 5                  10                  15
Gln Lys Ser Arg Arg Phe Ile Gly Ile Lys Val Gly Xaa Ser Asn Tyr
             20                  25                  30
Ser Lys Asn Glu Leu Asn Glu Thr Lys Leu Pro Val Arg Val Val Ala
         35                  40                  45
Gln Xaa Ala Ala Thr Arg Ser Gly Trp Asp Thr Val Leu Glu Gly Thr
     50                  55                  60
Glu Phe Lys Thr Thr Leu Ala Gly Ala Asp Ile Gln Ala Gly Val Xaa
 65                  70                  75                  80
Glu Lys Ala Arg Val Asp Ala Lys Ile Ile Leu Lys Gly Ile Val Asn
                 85                  90                  95
Arg Ile Gln Ser Glu Glu Lys Leu Glu Thr Asn Ser Thr Val Trp Gln
            100                 105                 110
Lys Gln Ala Gly Arg Gly Ser Thr Ile Glu Thr Leu Lys Leu Pro Ser
        115                 120                 125
Phe Glu Ser Pro Thr Pro Pro Lys Leu Ser Ala Pro Gly Gly Tyr Ile
    130                 135                 140
Val Asp Ile Pro Lys Gly Asn Leu Lys Thr Glu Ile Glu Lys Leu Ser
145                 150                 155                 160
Lys Gln Pro Glu Tyr Ala Tyr Leu Lys Gln Leu Gln Val Ala Lys Asn
                165                 170                 175
Ile Asn Trp Asn Gln Val Gln Leu Ala Tyr Asp Arg Trp Asp Tyr Lys
            180                 185                 190
Gln Glu Gly Leu Thr Glu Ala Gly Ala Ile Ile Ala Leu Ala Val
        195                 200                 205
Thr Val Val Thr Ser Gly Ala Gly Thr Gly Ala Val Leu Gly Leu Asn
    210                 215                 220
Gly Ala Xaa Ala Ala Ala Thr Asp Ala Ala Phe Ala Ser Leu Ala Ser
225                 230                 235                 240
Gln Ala Ser Val Ser Phe Ile Asn Asn Lys Gly Asp Val Gly Lys Thr
                245                 250                 255
Leu Lys Glu Leu Gly Arg Ser Ser Thr Val Lys Asn Leu Val Val Ala
            260                 265                 270
Ala Ala Thr Ala Gly Val Ala Asp Lys Ile Gly Ala Ser Ala Leu Xaa
        275                 280                 285
Asn Val Ser Asp Lys Gln Trp Ile Asn Asn Leu Thr Val Asn Leu Ala
    290                 295                 300
Asn Ala Gly Ser Ala Ala Leu Ile Asn Thr Ala Val Asn Gly Gly Ser
305                 310                 315                 320
Leu Lys Asp Xaa Leu Glu Ala Asn Ile Leu Ala Ala Leu Val Asn Thr
                325                 330                 335
Ala His Gly Glu Ala Ala Ser Lys Ile Lys Gln Leu Asp Gln His Tyr
            340                 345                 350
Ile Val His Lys Ile Ala His Ala Ile Ala Gly Cys Ala Ala Ala Ala
        355                 360                 365
Ala Asn Lys Gly Lys Cys Gln Asp Gly Ala Ile Gly Ala Ala Val Gly
    370                 375                 380
Glu Ile Val Gly Glu Ala Leu Thr Asn Gly Lys Asn Pro Asp Thr Leu
385                 390                 395                 400
Thr Ala Lys Glu Arg Glu Gln Ile Leu Ala Tyr Ser Lys Leu Val Ala
                405                 410                 415
```

```
Gly Thr Val Ser Gly Val Val Gly Gly Asp Val Asn Ala Ala Ala Asn
            420                 425                 430

Ala Ala Glu Val Ala Val Lys Asn Asn Gln Leu Ser Asp Xaa Glu Gly
            435                 440                 445

Arg Glu Phe Asp Asn Glu Met Thr Ala Cys Ala Lys Gln Asn Xaa Pro
            450                 455                 460

Gln Leu Cys Arg Lys Asn Thr Val Lys Tyr Gln Asn Val Ala Asp
465                 470                 475                 480

Lys Arg Leu Ala Ala Ser Ile Ala Ile Cys Thr Asp Ile Ser Arg Ser
                485                 490                 495

Thr Glu Cys Arg Thr Ile Arg Lys Gln His Leu Ile Asp Ser Arg Ser
            500                 505                 510

Leu His Ser Ser Trp Glu Ala Gly Leu Ile Gly Lys Asp Asp Glu Trp
        515                 520                 525

Tyr Lys Leu Phe Ser Lys Ser Tyr Thr Gln Ala Asp Leu Ala Leu Gln
        530                 535                 540

Ser Tyr His Leu Asn Thr Ala Ala Lys Ser Trp Leu Gln Ser Gly Asn
545                 550                 555                 560

Thr Lys Pro Leu Ser Glu Trp Met Ser Asp Gln Gly Tyr Thr Leu Ile
            565                 570                 575

Ser Gly Val Asn Pro Arg Phe Ile Pro Ile Pro Arg Gly Phe Val Lys
            580                 585                 590

Gln Asn Thr Pro Ile Thr Asn Val Lys Tyr Pro Glu Gly Ile Ser Phe
            595                 600                 605

Asp Thr Asn Leu Xaa Arg His Leu Ala Asn Ala Asp Gly Phe Ser Gln
            610                 615                 620

Glu Gln Gly Ile Lys Gly Ala His Asn Arg Thr Asn Xaa Met Ala Glu
625                 630                 635                 640

Leu Asn Ser Arg Gly Gly Xaa Val Lys Ser Glu Thr Xaa Thr Asp Ile
                645                 650                 655

Glu Gly Ile Thr Arg Ile Lys Tyr Glu Ile Pro Thr Leu Asp Arg Thr
            660                 665                 670

Gly Lys Pro Asp Gly Gly Phe Lys Glu Ile Ser Ser Ile Lys Thr Val
            675                 680                 685

Tyr Asn Pro Lys Xaa Phe Xaa Asp Asp Lys Ile Leu Gln Met Ala Gln
            690                 695                 700

Xaa Ala Xaa Ser Gln Gly Tyr Ser Lys Ala Ser Lys Ile Ala Gln Asn
705                 710                 715                 720

Glu Arg Thr Lys Ser Ile Ser Glu Arg Lys Asn Val Ile Gln Phe Ser
            725                 730                 735

Glu Thr Phe Asp Gly Ile Lys Phe Arg Xaa Tyr Xaa Asp Val Asn Thr
            740                 745                 750

Gly Arg Ile Thr Asn Ile His Pro Glu
        755                 760

<210> SEQ ID NO 1792
<211> LENGTH: 336
<212> TYPE: DNA
<213> ORGANISM: Neisseria meningitidis

<400> SEQUENCE: 1792
cggatcgttg taggtttgcg gatttcttgc gccgtagtca ccgtagtccc aagtataacc      60
caaggctttg tcttcgcctt tcattccgat aagggatatg acgctttggt cggtatagcc     120
gtcttgggaa cctttgtcca cccaacgcat atctgcctgc ggattctcat tgccgcttct     180
```

```
tggctgctga ttttctgcc ttcgcgtttt tcaacttcgc gcttgagggc ttcggcatat      240
ttgtcggcca acgccatttc tttcggatgc agctgcctat tgttccaatc tacattcgca      300
cccaccacag caccaccact accaccagtt gcatag                                336
```

<210> SEQ ID NO 1793
<211> LENGTH: 111
<212> TYPE: PRT
<213> ORGANISM: Neisseria meningitidis

<400> SEQUENCE: 1793

```
Arg Ile Val Val Gly Leu Arg Ile Ser Cys Ala Val Val Thr Val Val
                 5                  10                  15
Pro Ser Ile Thr Gln Gly Phe Val Phe Ala Phe His Ser Asp Lys Gly
             20                  25                  30
Tyr Asp Ala Leu Val Gly Ile Ala Val Leu Gly Thr Phe Val His Pro
         35                  40                  45
Thr His Ile Cys Leu Arg Ile Leu Ile Ala Ala Ser Trp Leu Leu Ile
     50                  55                  60
Phe Leu Pro Ser Arg Phe Ser Thr Ser Arg Leu Arg Ala Ser Ala Tyr
 65                  70                  75                  80
Leu Ser Ala Asn Ala Ile Ser Phe Gly Cys Ser Cys Leu Leu Phe Gln
                 85                  90                  95
Ser Thr Phe Ala Pro Thr Thr Ala Pro Pro Leu Pro Pro Val Ala
            100                 105                 110
```

<210> SEQ ID NO 1794
<211> LENGTH: 1716
<212> TYPE: DNA
<213> ORGANISM: Neisseria meningitidis
<220> FEATURE:
<221> NAME/KEY: misc_feature
<222> LOCATION: (1)...(1716)
<223> OTHER INFORMATION: n = A,T,C or G

<400> SEQUENCE: 1794

```
aagtttgact ttacctggtt tattccggcg gtaatcaaat accgccggtt gttttttgaa      60
gtattggtgg tgtcggtggt gttgcagctg tttgcgctga ttacgcctct gttttttccaa     120 gtggtgatgg acaaggtgct ggtacatcgg ggattctcta ctttggatgt ggtgtcggtg     180
gctttgttgg tggtgtcgct gtttgagatt tgttgggcg gtttgcggac gtatctgttt      240
gcacatacga cttcacgtat tgatgtggaa ttgggcgcgc gtttgttccg gcatctgctt     300
tccctgcctt tatcctatt cgagcacaga cgagtgggtg atacggtggc tcgggtgcgg     360
gaattggagc agattcgcaa tttcttgacc ggtcaggcgc tgacttcggt gttggatttg     420
gcgttttcgt ttatctttct ggcggtgatg tggtattaca gctccactct gacttgggtg     480
gtattggctt cgttgnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
```

```
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnatttgcgc caaccggacg    1560
gtgctgatta tcgcccaccg tctgtccact gttaaaacgg cacaccggat cattgccatg    1620
gataaaggca ggattgtgga agcgggaaca cagcaggaat tgctggcgaa cgnnaacgga    1680
tattaccgct atctgtatga tttacagaac gggtag                              1716

<210> SEQ ID NO 1795
<211> LENGTH: 571
<212> TYPE: PRT
<213> ORGANISM: Neisseria meningitidis
<220> FEATURE:
<221> NAME/KEY: misc_feature
<222> LOCATION: (1)...(571)
<223> OTHER INFORMATION: Xaa is any Amino Acid

<400> SEQUENCE: 1795

Lys Phe Asp Phe Thr Trp Phe Ile Pro Ala Val Ile Lys Tyr Arg Arg
                 5                  10                  15

Leu Phe Phe Glu Val Leu Val Ser Val Val Leu Gln Leu Phe Ala
             20                  25                  30

Leu Ile Thr Pro Leu Phe Phe Gln Val Val Met Asp Lys Val Leu Val
         35                  40                  45

His Arg Gly Phe Ser Thr Leu Asp Val Val Ser Val Ala Leu Leu Val
     50                  55                  60

Val Ser Leu Phe Glu Ile Val Leu Gly Gly Leu Arg Thr Tyr Leu Phe
65                  70                  75                  80

Ala His Thr Thr Ser Arg Ile Asp Val Glu Leu Gly Ala Arg Leu Phe
                 85                  90                  95

Arg His Leu Leu Ser Leu Pro Leu Ser Tyr Phe Glu His Arg Arg Val
            100                 105                 110

Gly Asp Thr Val Ala Arg Val Arg Glu Leu Glu Gln Ile Arg Asn Phe
        115                 120                 125

Leu Thr Gly Gln Ala Leu Thr Ser Val Leu Asp Leu Ala Phe Ser Phe
    130                 135                 140

Ile Phe Leu Ala Val Met Trp Tyr Tyr Ser Ser Thr Leu Thr Trp Val
145                 150                 155                 160

Val Leu Ala Ser Leu Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220
```

```
Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa

```
gtccgccagc ctattaaacg tttggctatg gcgactttac ccgcattggt atggtgtgat    240
gacggcaacc atttcatttt ggccaaaaca gacggtgagg gtgagcatgc ccaattttg     300
atacaggatt tggttacgaa taagtctgcg gtattgtctt ttgccgaatt ttctaacaga    360
tattcgggca aactgatatt ggttgcttcc cgcgcttcgg tattgggcag tttggcaaag    420
tttgacttta cctggtttat tccggcggta atcaaatacc gccggttgtt ttttgaagta    480
ttggtggtgt cggtggtgtt gcagctgttt gcgctgatta cgcctctgtt tttccaagtg    540
gtgatggaca aggtgctggt acatcgggga ttctctactt tggatgtggt gtcggtggct    600
ttgttggtgg tgtcgctgtt tgagattgtg ttgggcggtt gcggacgta tctgtttgca     660
catacgactt cacgtattga tgtggaattg ggcgcgcgtt tgttccggca tctgctttcc    720
ctgcctttat cctatttcga gcacagacga gtgggtgata cggtggctcg ggtgcgggaa    780
ttggagcaga ttcgcaattt cttgaccggt caggcgctga cttcggtgtt ggatttggcg    840
ttttcgttta tctttctggc ggtgatgtgg tattacagct ccactctgac ttgggtggta    900
ttggcttcgt tgcctgccta tgcgttttgg tcggcattta tcagtccgat actgcggacg    960
cgtctgaacg ataagttcgc gcgcaatgca gacaaccagt cgttttttagt agaaagcatc   1020
actgcggtgg gtacggtaaa ggcgatggcg gtggagccgc agatgacgca gcgttgggac    1080
aatcagttgg cggcttatgt ggcttcggga tttcgggtaa cgaagttggc ggtggtcggc    1140
cagcagggg tgcagctgat tcagaagctg gtgacggtgg cgacgttgtg gattggcgca    1200
cggctggtaa ttgagagcaa gctgacggtg gggcagctga ttgcgtttaa tatgctctcg    1260
ggacaggtgg cggcgcctgt tatccgtttg gcgcagttgt ggcaggattt ccagcaggtg    1320
gggatttcgg tggcgcgttt gggggatatt ctgaatgcgc cgaccgagaa tgcgtcttcg    1380
catttggctt tgcccgatat ccggggggag attacgttcg aacatgtcga tttccgctat    1440
aaggcggacg gcaggctgat tttgcaggat ttgaacctgc ggattcgggc gggggaagtg    1500
ctggggattg tgggacgttc ggggtcgggc aaatccacac tcaccaaatt ggtgcagcgt    1560
ctgtatgtac cggagcaggg acgggtgttg gtggacggca acgatttggc tttggccgct    1620
cctgcctggc tgcggcggca ggtcggcgtg gtcttgcagg agaatgtgct gctcaaccgc    1680
agcatacgcg acaatatcgc gctgacggat acgggtatgc cgctggaacg cattatcgaa    1740
gcagccaaac tggcgggcgc acacgagttt attatggagc tgccggaagg ctacggcacc    1800
gtggtgggcg aacaagggc cggcttgtcg gcgcggacagc ggcagcgtat tgcgattgcc    1860
cgcgcgttaa tcaccaatcc gcgcattctg atttttgatg aagccaccag cgcgctggat    1920
tatgaaagtg aacgagcgat tatgcagaac atgcaggcca tttgcgccaa ccggacggtg    1980
ctgattatcg cccaccgtct gtccactgtt aaaacggcac accggatcat tgccatggat    2040
aaaggcagga ttgtggaagc gggaacacag caggaattgc tggcgaagcc gaacggatat    2100
taccgctatc tgtatgattt acagaacggg tag                                 2133
```

<210> SEQ ID NO 1797
<211> LENGTH: 710
<212> TYPE: PRT
<213> ORGANISM: Neisseria meningitidis

<400> SEQUENCE: 1797

Met Ser Ile Val Ser Ala Pro Leu Pro Ala Leu Ser Ala Leu Ile Ile
                5                   10                  15

Leu Ala His Tyr His Gly Ile Ala Ala Asn Pro Ala Asp Ile Gln His
            20                  25                  30

```
Glu Phe Cys Thr Ser Ala Gln Ser Asp Leu Asn Glu Thr Gln Trp Leu
         35                  40                  45

Leu Ala Ala Lys Ser Leu Gly Leu Lys Ala Lys Val Val Arg Gln Pro
 50                  55                  60

Ile Lys Arg Leu Ala Met Ala Thr Leu Pro Ala Leu Val Trp Cys Asp
 65                  70                  75                  80

Asp Gly Asn His Phe Ile Leu Ala Lys Thr Asp Gly Glu Gly Glu His
                 85                  90                  95

Ala Gln Phe Leu Ile Gln Asp Leu Val Thr Asn Lys Ser Ala Val Leu
            100                 105                 110

Ser Phe Ala Glu Phe Ser Asn Arg Tyr Ser Gly Lys Leu Ile Leu Val
        115                 120                 125

Ala Ser Arg Ala Ser Val Leu Gly Ser Leu Ala Lys Phe Asp Phe Thr
    130                 135                 140

Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
            180                 185                 190

Thr Leu Asp Val Val Ser Val Ala Leu Leu Val Ser Leu Phe Glu
        195                 200                 205

Ile Val Leu Gly Gly Leu Arg Thr Tyr Leu Phe Ala His Thr Thr Ser
    210                 215                 220

Arg Ile Asp Val Glu Leu Gly Ala Arg Leu Phe Arg His Leu Leu Ser
225                 230                 235                 240

Leu Pro Leu Ser Tyr Phe Glu His Arg Arg Val Gly Asp Thr Val Ala
                245                 250                 255

Arg Val Arg Glu Leu Glu Gln Ile Arg Asn Phe Leu Thr Gly Gln Ala
            260                 265                 270

Leu Thr Ser Val Leu Asp Leu Ala Phe Ser Phe Ile Phe Leu Ala Val
        275                 280                 285

Met Trp Tyr Tyr Ser Ser Thr Leu Thr Trp Val Val Leu Ala Ser Leu
    290                 295                 300

Pro Ala Tyr Ala Phe Trp Ser Ala Phe Ile Ser Pro Ile Leu Arg Thr
305                 310                 315                 320

Arg Leu Asn Asp Lys Phe Ala Arg Asn Ala Asp Asn Gln Ser Phe Leu
                325                 330                 335

Val Glu Ser Ile Thr Ala Val Gly Thr Val Lys Ala Met Ala Val Glu
            340                 345                 350

Pro Gln Met Thr Gln Arg Trp Asp Asn Gln Leu Ala Ala Tyr Val Ala
        355                 360                 365

Ser Gly Phe Arg Val Thr Lys Leu Ala Val Val Gly Gln Gln Gly Val
    370                 375                 380

Gln Leu Ile Gln Lys Leu Val Thr Val Ala Thr Leu Trp Ile Gly Ala
385                 390                 395                 400

Arg Leu Val Ile Glu Ser Lys Leu Thr Val Gly Gln Leu Ile Ala Phe
                405                 410                 415

Asn Met Leu Ser Gly Gln Val Ala Ala Pro Val Ile Arg Leu Ala Gln
            420                 425                 430

Leu Trp Gln Asp Phe Gln Gln Val Gly Ile Ser Val Ala Arg Leu Gly
        435                 440                 445
```

-continued

```
Asp Ile Leu Asn Ala Pro Thr Glu Asn Ala Ser Ser His Leu Ala Leu
    450                 455                 460
Pro Asp Ile Arg Gly Glu Ile Thr Phe Glu His Val Asp Phe Arg Tyr
465                 470                 475                 480
Lys Ala Asp Gly Arg Leu Ile Leu Gln Asp Leu Asn Leu Arg Ile Arg
                485                 490                 495
Ala Gly Glu Val Leu Gly Ile Val Gly Arg Ser Gly Ser Gly Lys Ser
            500                 505                 510
Thr Leu Thr Lys Leu Val Gln Arg Leu Tyr Val Pro Glu Gln Gly Arg
        515                 520                 525
Val Leu Val Asp Gly Asn Asp Leu Ala Leu Ala Ala Pro Ala Trp Leu
    530                 535                 540
Arg Arg Gln Val Gly Val Val Leu Gln Glu Asn Val Leu Leu Asn Arg
545                 550                 555                 560
Ser Ile Arg Asp Asn Ile Ala Leu Thr Asp Thr Gly Met Pro Leu Glu
                565                 570                 575
Arg Ile Ile Glu Ala Ala Lys Leu Ala Gly Ala His Glu Phe Ile Met
            580                 585                 590
Glu Leu Pro Glu Gly Tyr Gly Thr Val Val Gly Glu Gln Gly Ala Gly
        595                 600                 605
Leu Ser Gly Gly Gln Arg Gln Arg Ile Ala Ile Ala Arg Ala Leu Ile
    610                 615                 620
Thr Asn Pro Arg Ile Leu Ile Phe Asp Glu Ala Thr Ser Ala Leu Asp
625                 630                 635                 640
Tyr Glu Ser Glu Arg Ala Ile Met Gln Asn Met Gln Ala Ile Cys Ala
                645                 650                 655
Asn Arg Thr Val Leu Ile Ile Ala His Arg Leu Ser Thr Val Lys Thr
            660                 665                 670
Ala His Arg Ile Ile Ala Met Asp Lys Gly Arg Ile Val Glu Ala Gly
        675                 680                 685
Thr Gln Gln Glu Leu Leu Ala Lys Pro Asn Gly Tyr Tyr Arg Tyr Leu
    690                 695                 700
Tyr Asp Leu Gln Asn Gly
705                 710

<210> SEQ ID NO 1798
<211> LENGTH: 2133
<212> TYPE: DNA
<213> ORGANISM: Neisseria meningitidis

<400> SEQUENCE: 1798
atgtctatcg tatccgcacc gctcccgcc ctttccgccc tcatcatcct cgcccattac    60
cacggcattg ccgccaatcc tgccgatata cagcatgaat tttgtacttc cgcacagagc   120
gatttaaatg aaacgcaatg gctgttagcc gccaaatctt tgggattgaa ggcaaaggta   180
gtccgccagc ctattaaacg tttggctatg gcgactttac ccgcattggt atggtgtgat   240
gacggcaacc attttatttt ggctaaaaca gacggtgggg gtgagcatgc ccaatatcta   300
atacaggatt taactacgaa taagtctgcg gtattgtctt ttgccgaatt ttctaacaga   360
tattcgggca aactgatatt ggttgcttcc cgcgcttcgg tattgggcag tttggcaaag   420
tttgactttt cctggtttat tccggcggta atcaaatacc gccggttgtt ttttgaagta   480
ttggtggtgt cggtggtgtt gcagctgttt gcgctgatta cgcctctgtt tttccaagtg   540
gtgatggaca aggtgctggt acatcgggga ttctctactt tggatgtggt gtcggtggct   600
```

```
ttgttggtgg tgtcgctgtt tgagattgtg ttgggcggtt tgcggacgta tctgtttgca    660
catacgactt cacgtattga tgtggaattg ggcgcgcgtt tgttccggca tctgctttcc    720
ctgcctttat cctatttcga gcacagacga gtgggtgata cggtggctcg ggtgcgggaa    780
ttggagcaga ttcgcaattt cttgaccggt caggcgctga cttcggtgtt ggatttggcg    840
ttttcgttta tctttctggc ggtgatgtgg tattacagct ccactctgac ttgggtggta    900
ttggcttcgt tgcctgccta tgcgttttgg tcggcattta tcagtccgat actgcggacg    960
cgtctgaacg ataagttcgc gcgcaatgca gacaaccagt cgttttagt agaaagcatc    1020 actgcggtgg gtacggtaaa ggcgatggcg gtggagccgc agatgacgca gcgttgggac    1080
aatcagttgg cggcttatgt ggcttcggga tttcgggtaa cgaagttggc ggtggtcggc    1140
cagcaggggg tgcagctgat tcagaagctg gtgacggtgg cgacgttgtg gattggcgca    1200
cggctggtaa ttgagagcaa gctgacggtg gggcagctga ttgcgtttaa tatgctctcg    1260
ggacaggtgc cggcgcctgt tatccgtttg gcgcagttgt ggcaggattt ccagcaggtg    1320 gggattcgg tggcgcgttt gggggatatt ctgaatgcgc cgaccgagaa tgcgtcttcg    1380
catttggctt tgcccgatat ccgggggag attacgttcg aacatgtcga tttccgctat    1440
aaggcggacg gcaggctgat tttgcaggat ttgaacctgc ggattcgggc ggggaagtg    1500 ctggggattg tgggacgttc ggggtcgggc aaatccacac tcaccaaatt ggtgcagcgt    1560
ctgtatgtac cggcgcaggg acgggtgttg gtggacggca acgatttggc tttggccgct    1620
cctgcttggc tgcggcggca ggtcggcgtg gtcttgcagg agaatgtgct gctcaaccgc    1680
agcatacgcg acaatatcgc gctgacggat acgggtatgc cgctggaacg cattatcgaa    1740
gcagccaaac tggcgggcgc acacgagttt attatggagc tgccggaagg ctacggcacc    1800
gtggtgggcg aacaaggggc cggcttgtcg ggcggacagc ggcagcgtat tgcgattgcc    1860
cgcgcgttaa tcaccaatcc gcgcattctg atttttgatg aagccaccag cgcgctggat    1920
tatgaaagtg aacgagcgat tatgcagaac atgcaggcca tttgcgccaa ccggacggtg    1980
ctgattatcg cccaccgtct gtccactgtt aaaacggcac accggatcat tgccatggat    2040
aaaggcagga ttgtggaagc gggaacacag caggaattgc tggcgaagcc gaacggatat    2100
taccgctatc tgtatgattt acagaacggg tag                                 2133
```

<210> SEQ ID NO 1799
<211> LENGTH: 710
<212> TYPE: PRT
<213> ORGANISM: Neisseria meningitidis

<400> SEQUENCE: 1799

Met Ser Ile Val Ser Ala Pro Leu Pro Ala Leu Ser Ala Leu Ile Ile
                5                  10                  15

Leu Ala His Tyr His Gly Ile Ala Ala Asn Pro Ala Asp Ile Gln His
            20                  25                  30

Glu Phe Cys Thr Ser Ala Gln Ser Asp Leu Asn Glu Thr Gln Trp Leu
        35                  40                  45

Leu Ala Ala Lys Ser Leu Gly Leu Lys Ala Lys Val Val Arg Gln Pro
    50                  55                  60

Ile Lys Arg Leu Ala Met Ala Thr Leu Pro Ala Leu Val Trp Cys Asp
65                  70                  75                  80

Asp Gly Asn His Phe Ile Leu Ala Lys Thr Asp Gly Gly Gly Glu His
                85                  90                  95

-continued

```
Ala Gln Tyr Leu Ile Gln Asp Leu Thr Thr Asn Lys Ser Ala Val Leu
            100                 105                 110

Ser Phe Ala Glu Phe Ser Asn Arg Tyr Ser Gly Lys Leu Ile Leu Val
            115                 120                 125

Ala Ser Arg Ala Ser Val Leu Gly Ser Leu Ala Lys Phe Asp Phe Thr
            130                 135                 140

Trp Phe Ile Pro Ala Val Ile Lys Tyr Arg Arg Leu Phe Phe Glu Val
145                 150                 155                 160

Leu Val Val Ser Val Val Leu Gln Leu Phe Ala Leu Ile Thr Pro Leu
                165                 170                 175

Phe Phe Gln Val Val Met Asp Lys Val Leu Val His Arg Gly Phe Ser
            180                 185                 190

Thr Leu Asp Val Val Ser Val Ala Leu Leu Val Ser Leu Phe Glu
            195                 200                 205

Ile Val Leu Gly Gly Leu Arg Thr Tyr Leu Phe Ala His Thr Thr Ser
            210                 215                 220

Arg Ile Asp Val Glu Leu Gly Ala Arg Leu Phe Arg His Leu Leu Ser
225                 230                 235                 240

Leu Pro Leu Ser Tyr Phe Glu His Arg Val Gly Asp Thr Val Ala
            245                 250                 255

Arg Val Arg Glu Leu Glu Gln Ile Arg Asn Phe Leu Thr Gly Gln Ala
            260                 265                 270

Leu Thr Ser Val Leu Asp Leu Ala Phe Ser Phe Ile Phe Leu Ala Val
            275                 280                 285

Met Trp Tyr Tyr Ser Ser Thr Leu Thr Trp Val Val Leu Ala Ser Leu
290                 295                 300

Pro Ala Tyr Ala Phe Trp Ser Ala Phe Ile Ser Pro Ile Leu Arg Thr
305                 310                 315                 320

Arg Leu Asn Asp Lys Phe Ala Arg Asn Ala Asp Asn Gln Ser Phe Leu
            325                 330                 335

Val Glu Ser Ile Thr Ala Val Gly Thr Val Lys Ala Met Ala Val Glu
            340                 345                 350

Pro Gln Met Thr Gln Arg Trp Asp Asn Gln Leu Ala Ala Tyr Val Ala
            355                 360                 365

Ser Gly Phe Arg Val Thr Lys Leu Ala Val Val Gly Gln Gln Gly Val
            370                 375                 380

Gln Leu Ile Gln Lys Leu Val Thr Val Ala Thr Leu Trp Ile Gly Ala
385                 390                 395                 400

Arg Leu Val Ile Glu Ser Lys Leu Thr Val Gly Gln Leu Ile Ala Phe
            405                 410                 415

Asn Met Leu Ser Gly Gln Val Ala Ala Pro Val Ile Arg Leu Ala Gln
            420                 425                 430

Leu Trp Gln Asp Phe Gln Gln Val Gly Ile Ser Val Ala Arg Leu Gly
            435                 440                 445

Asp Ile Leu Asn Ala Pro Thr Glu Asn Ala Ser Ser His Leu Ala Leu
            450                 455                 460

Pro Asp Ile Arg Gly Glu Ile Thr Phe Glu His Val Asp Phe Arg Tyr
465                 470                 475                 480

Lys Ala Asp Gly Arg Leu Ile Leu Gln Asp Leu Asn Leu Arg Ile Arg
            485                 490                 495

Ala Gly Glu Val Leu Gly Ile Val Gly Arg Ser Gly Ser Gly Lys Ser
            500                 505                 510
```

-continued

```
Thr Leu Thr Lys Leu Val Gln Arg Leu Tyr Val Pro Ala Gln Gly Arg
            515                 520                 525

Val Leu Val Asp Gly Asn Asp Leu Ala Leu Ala Ala Pro Ala Trp Leu
        530                 535                 540

Arg Arg Gln Val Gly Val Leu Gln Glu Asn Val Leu Leu Asn Arg
545                 550                 555                 560

Ser Ile Arg Asp Asn Ile Ala Leu Thr Asp Thr Gly Met Pro Leu Glu
                565                 570                 575

Arg Ile Ile Glu Ala Ala Lys Leu Ala Gly Ala His Glu Phe Ile Met
            580                 585                 590

Glu Leu Pro Glu Gly Tyr Gly Thr Val Val Gly Glu Gln Gly Ala Gly
        595                 600                 605

Leu Ser Gly Gly Gln Arg Gln Arg Ile Ala Ile Ala Arg Ala Leu Ile
    610                 615                 620

Thr Asn Pro Arg Ile Leu Ile Phe Asp Glu Ala Thr Ser Ala Leu Asp
625                 630                 635                 640

Tyr Glu Ser Glu Arg Ala Ile Met Gln Asn Met Gln Ala Ile Cys Ala
                645                 650                 655

Asn Arg Thr Val Leu Ile Ile Ala His Arg Leu Ser Thr Val Lys Thr
            660                 665                 670

Ala His Arg Ile Ile Ala Met Asp Lys Gly Arg Ile Val Glu Ala Gly
        675                 680                 685

Thr Gln Gln Glu Leu Leu Ala Lys Pro Asn Gly Tyr Tyr Arg Tyr Leu
    690                 695                 700

Tyr Asp Leu Gln Asn Gly
705                 710

<210> SEQ ID NO 1800
<211> LENGTH: 186
<212> TYPE: DNA
<213> ORGANISM: Neisseria meningitidis

<400> SEQUENCE: 1800
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacggggtga acgcccaaak sgacgccgaa     180
atcaga                                                                186

<210> SEQ ID NO 1801
<211> LENGTH: 62
<212> TYPE: PRT
<213> ORGANISM: Neisseria meningitidis
<220> FEATURE:
<221> NAME/KEY: misc_feature
<222> LOCATION: (1)...(62)
<223> OTHER INFORMATION: Xaa is any Amino Acid

<400> SEQUENCE: 1801

Met Lys Tyr Leu Ile Arg Thr Ala Leu Leu Ala Val Ala Ala Ala Gly
                5                  10                  15

Ile Tyr Ala Cys Gln Pro Gln Ser Glu Ala Ala Val Gln Val Lys Ala
            20                  25                  30

Glu Asn Ser Leu Thr Ala Met Arg Leu Ala Val Ala Asp Lys Gln Ala
        35                  40                  45

Glu Ile Asp Gly Leu Asn Ala Gln Xaa Asp Ala Glu Ile Arg
    50                  55                  60
```

```
<210> SEQ ID NO 1802
<211> LENGTH: 261
<212> TYPE: DNA
<213> ORGANISM: Neisseria meningitidis

<400> SEQUENCE: 1802
atgaaatact tgatccgcac cgccttactc gcagtcgcag ccgccggcat ctacgcctgc      60
caaccgcaat ccgaagccgc agtgcaagtc aaggctgaaa acagcctgac cgctatgcgc     120
ttagccgtcg ccgacaaaca ggcagagatt gacgggttga acgcccaaat cgacgccgaa     180
atcagacaac gcgaagccga agaattgaaa gactaccgat ggatacacgg cgacgcggaa     240
gtgccggagc tggaaaaatg a                                               261

<210> SEQ ID NO 1803
<211> LENGTH: 86
<212> TYPE: PRT
<213> ORGANISM: Neisseria meningitidis

<400> SEQUENCE: 1803

Met Lys Tyr Leu Ile Arg Thr Ala Leu Leu Ala Val Ala Ala Ala Gly
              5                   10                  15

Ile Tyr Ala Cys Gln Pro Gln Ser Glu Ala Ala Val Gln Val Lys Ala
          20                  25                  30

Glu Asn Ser Leu Thr Ala Met Arg Leu Ala Val Ala Asp Lys Gln Ala
      35                  40                  45

Glu Ile Asp Gly Leu Asn Ala Gln Ile Asp Ala Glu Ile Arg Gln Arg
  50                  55                  60

Glu Ala Glu Glu Leu Lys Asp Tyr Arg Trp Ile His Gly Asp Ala Glu
65                  70                  75                  80

Val Pro Glu Leu Glu Lys
                  85

<210> SEQ ID NO 1804
<211> LENGTH: 279
<212> TYPE: DNA
<213> ORGANISM: Neisseria meningitidis

<400> SEQUENCE: 1804
atggttatcg gaatattact cgcatcaagc aagcatgctc ttgtcattac tctattgtta      60
aatcccgtct tccatgcatc cagttgcgta tcgcgttsgg caatacggaa taaaatctgc     120
tgttctgctt tggctaaatt tgccaaattg tttattgttt ctttaggagc agcttgctta     180
gccgccttcg ctttcgacaa cgcccccaca ggcgcttccc aagcgttgcc taccgttacc     240
gcacccgtgg cgattcccgc gcccgcttcg gcagcctga                            279

<210> SEQ ID NO 1805
<211> LENGTH: 92
<212> TYPE: PRT
<213> ORGANISM: Neisseria meningitidis
<220> FEATURE:
<221> NAME/KEY: misc_feature
<222> LOCATION: (1)...(92)
<223> OTHER INFORMATION: Xaa is any Amino Acid

<400> SEQUENCE: 1805

Met Val Ile Gly Ile Leu Leu Ala Ser Ser Lys His Ala Leu Val Ile
              5                   10                  15

Thr Leu Leu Leu Asn Pro Val Phe His Ala Ser Ser Cys Val Ser Arg
          20                  25                  30
```

-continued

Xaa Ala Ile Arg Asn Lys Ile Cys Cys Ser Ala Leu Ala Lys Phe Ala
         35                  40                  45

Lys Leu Phe Ile Val Ser Leu Gly Ala Ala Cys Leu Ala Ala Phe Ala
     50                  55                  60

Phe Asp Asn Ala Pro Thr Gly Ala Ser Gln Ala Leu Pro Thr Val Thr
65                  70                  75                  80

Ala Pro Val Ala Ile Pro Ala Pro Ala Ser Ala Ala
                 85                  90

<210> SEQ ID NO 1806
<211> LENGTH: 312
<212> TYPE: DNA
<213> ORGANISM: Neisseria meningitidis

<400> SEQUENCE: 1806
atggcttgta caggtttgat ggttttccg ttaatggtta tcggaatatt acttgcatca      60
agcaagcctg ctcctttcct tactctattg ttaaatcccg tcttccatgc atccagttgc    120
gtatcgcgtt gggcaatacg aataaaatc tgctgttctg ctttggctaa atttgccaaa     180
ttgtttattg tttcttagg agcagcttgc ttagccgcct tcgctttcga caacgccccc     240
acaggcgctt cccaagcgtt gcctaccgtt accgcacccg tggcgattcc cgcgcccgct    300
tcggcagcct ga                                                         312

<210> SEQ ID NO 1807
<211> LENGTH: 103
<212> TYPE: PRT
<213> ORGANISM: Neisseria meningitidis

<400> SEQUENCE: 1807

Met Ala Cys Thr Gly Leu Met Val Phe Pro Leu Met Val Ile Gly Ile
             5                   10                  15

Leu Leu Ala Ser Ser Lys Pro Ala Pro Phe Leu Thr Leu Leu Leu Asn
             20                  25                  30

Pro Val Phe His Ala Ser Ser Cys Val Ser Arg Trp Ala Ile Arg Asn
         35                  40                  45

Lys Ile Cys Cys Ser Ala Leu Ala Lys Phe Ala Lys Leu Phe Ile Val
     50                  55                  60

Ser Leu Gly Ala Ala Cys Leu Ala Ala Phe Ala Phe Asp Asn Ala Pro
65                  70                  75                  80

Thr Gly Ala Ser Gln Ala Leu Pro Thr Val Thr Ala Pro Val Ala Ile
                 85                  90                  95

Pro Ala Pro Ala Ser Ala Ala
             100

<210> SEQ ID NO 1808
<211> LENGTH: 255
<212> TYPE: DNA
<213> ORGANISM: Neisseria meningitidis

<400> SEQUENCE: 1808
atgttcagta tttaaatgt gtttcttcat tgtattctgg cttgtgtagt ctctggtgag      60
acgcctacta tatttggtat ccttgctctt ttttacttat tgtatctttc ttatcttgct    120
gtttttaaga ttttctttc tttttttctta gacagagttt cactccggtc tcccaggctg    180
gagtgcaaat ggcatgaccc tttggctcac tggctcacgg ccacttctgc tattctgccg    240
cctcagcctc caggg                                                      255

<210> SEQ ID NO 1809
<211> LENGTH: 85
<212> TYPE: PRT
<213> ORGANISM: Neisseria meningitidis

<400> SEQUENCE: 1809

Met Phe Ser Ile Leu Asn Val Phe Leu His Cys Ile Leu Ala Cys Val
1               5                   10                  15

Val Ser Gly Glu Thr Pro Thr Ile Phe Gly Ile Leu Ala Leu Phe Tyr
            20                  25                  30

Leu Leu Tyr Leu Ser Tyr Leu Ala Val Phe Lys Ile Phe Phe Ser Phe
        35                  40                  45

Phe Leu Asp Arg Val Ser Leu Arg Ser Pro Arg Leu Glu Cys Lys Trp
50                  55                  60

His Asp Pro Leu Ala His Trp Leu Thr Ala Thr Ser Ala Ile Leu Pro
65                  70                  75                  80

Pro Gln Pro Pro Gly
            85

<210> SEQ ID NO 1810
<211> LENGTH: 237
<212> TYPE: DNA
<213> ORGANISM: Neisseria meningitidis

<400> SEQUENCE: 1810
gtgcggacgt ggttggtttt ttggttgcag cgtttgaaat accgttgtt gctttggatt      60 gcggatatgt tgctgtaccg gttgttgggc ggcgcggaaa tcgaatgcgg ccgttgccct     120
gtgccgccga tgacggattg gcagcatttt tgccggcga tgggaacggt gtcggcttgg     180
gtggcggtga tttgggcata cctgatgatt gaaagtgaaa aaaacggaag atattga       237

<210> SEQ ID NO 1811
<211> LENGTH: 78
<212> TYPE: PRT
<213> ORGANISM: Neisseria meningitidis

<400> SEQUENCE: 1811

Val Arg Thr Trp Leu Val Phe Trp Leu Gln Arg Leu Lys Tyr Pro Leu
1               5                   10                  15

Leu Leu Trp Ile Ala Asp Met Leu Leu Tyr Arg Leu Leu Gly Gly Ala
            20                  25                  30

Glu Ile Glu Cys Gly Arg Cys Pro Val Pro Pro Met Thr Asp Trp Gln
        35                  40                  45

His Phe Leu Pro Ala Met Gly Thr Val Ser Ala Trp Val Ala Val Ile
50                  55                  60

Trp Ala Tyr Leu Met Ile Glu Ser Glu Lys Asn Gly Arg Tyr
65                  70                  75

<210> SEQ ID NO 1812
<211> LENGTH: 237
<212> TYPE: DNA
<213> ORGANISM: Neisseria meningitidis

<400> SEQUENCE: 1812
gtgcggacgt ggttggtttt ttggttgcag cgtttgaaat accgttgtt gctttgtatt      60 gcggatatgc tgctgtaccg gttgttgggc ggcgcggaaa tcgaatgcgg ccgttgccct     120
gtaccgccga tgacggattg gcagcatttt tgccgacga tgggaacggt ggcggcttgg     180
gtggcggtga tttgggcata cctgatgatt gaaagtgaaa aaaacggaag atattga       237

<210> SEQ ID NO 1813
<211> LENGTH: 78
<212> TYPE: PRT
<213> ORGANISM: Neisseria meningitidis

<400> SEQUENCE: 1813

```
Val Arg Thr Trp Leu Val Phe Trp Leu Gln Arg Leu Lys Tyr Pro Leu
                 5                  10                  15
Leu Leu Cys Ile Ala Asp Met Leu Leu Tyr Arg Leu Leu Gly Gly Ala
             20                  25                  30
Glu Ile Glu Cys Gly Arg Cys Pro Val Pro Pro Met Thr Asp Trp Gln
         35                  40                  45
His Phe Leu Pro Thr Met Gly Thr Val Ala Ala Trp Val Ala Val Ile
     50                  55                  60
Trp Ala Tyr Leu Met Ile Glu Ser Glu Lys Asn Gly Arg Tyr
 65                  70                  75
```

<210> SEQ ID NO 1814
<211> LENGTH: 660
<212> TYPE: DNA
<213> ORGANISM: Neisseria meningitidis

<400> SEQUENCE: 1814

| | | | | | |
|---|---|---|---|---|---|
| atgtttcaaa | attttgattt | gggcgtgttc | ctgcttgccg | tcctccccgt | gctgccctcc | 60 |
| attaccgtct | cgcacgtggc | gcgcggctat | acggcgcgct | actggggaga | caacactgcc | 120 |
| gaacaatacg | gcaggctgac | actgaacccc | ctgccccata | tcgatttggt | cggcacaatc | 180 |
| atcgtaccgc | tgcttacttt | gatgttcacg | cccttcctgt | tcggctgggc | gcgtccgatt | 240 |
| cctatcgatt | cgcgcaactt | ccgcaacccg | cgccttgcct | ggcgttgcgt | tgccgcgtcc | 300 |
| ggcccgctgt | cgaatctagc | gatggctgtw | ctgtggggcg | tggttttggt | gctgactccg | 360 |
| tatgtcggcg | gggcgtatca | gatgccgttg | gctcaaatgg | caaactacgg | tattctgatc | 420 |
| aatgcgattc | tgttcgcgct | caacatcatc | cccatcctgc | cttgggacgg | cggcattttc | 480 |
| atcgacacct | tcctgtcggc | gaaatattcg | caagcgttcc | gcaaaatcga | accttatggg | 540 |
| acgtggatta | tcctactgct | gatgctgacc | sgggttttgg | gtgcgtttat | wgcaccgatt | 600 |
| stgcggmtgc | gtgattgcrt | ttgtgcagat | gtwcgtctga | ctggctttca | gacggcataa | 660 |

<210> SEQ ID NO 1815
<211> LENGTH: 219
<212> TYPE: PRT
<213> ORGANISM: Neisseria meningitidis
<220> FEATURE:
<221> NAME/KEY: misc_feature
<222> LOCATION: (1)...(219)
<223> OTHER INFORMATION: Xaa is any Amino Acid

<400> SEQUENCE: 1815

```
Met Phe Gln Asn Phe Asp Leu Gly Val Phe Leu Leu Ala Val Leu Pro
                 5                  10                  15
Val Leu Pro Ser Ile Thr Val Ser His Val Ala Arg Gly Tyr Thr Ala
             20                  25                  30
Arg Tyr Trp Gly Asp Asn Thr Ala Glu Gln Tyr Gly Arg Leu Thr Leu
         35                  40                  45
Asn Pro Leu Pro His Ile Asp Leu Val Gly Thr Ile Ile Val Pro Leu
     50                  55                  60
Leu Thr Leu Met Phe Thr Pro Phe Leu Phe Gly Trp Ala Arg Pro Ile
 65                  70                  75                  80
```

```
Pro Ile Asp Ser Arg Asn Phe Arg Asn Pro Arg Leu Ala Trp Arg Cys
                85                  90                  95
Val Ala Ala Ser Gly Pro Leu Ser Asn Leu Ala Met Ala Val Leu Trp
            100                 105                 110
Gly Val Val Leu Val Leu Thr Pro Tyr Val Gly Gly Ala Tyr Gln Met
        115                 120                 125
Pro Leu Ala Gln Met Ala Asn Tyr Gly Ile Leu Ile Asn Ala Ile Leu
    130                 135                 140
Phe Ala Leu Asn Ile Ile Pro Ile Leu Pro Trp Asp Gly Gly Ile Phe
145                 150                 155                 160
Ile Asp Thr Phe Leu Ser Ala Lys Tyr Ser Gln Ala Phe Arg Lys Ile
                165                 170                 175
Glu Pro Tyr Gly Thr Trp Ile Ile Leu Leu Leu Met Leu Thr Xaa Val
            180                 185                 190
Leu Gly Ala Phe Ile Ala Pro Ile Xaa Arg Xaa Arg Asp Cys Xaa Cys
        195                 200                 205
Ala Asp Val Arg Leu Thr Gly Phe Gln Thr Ala
    210                 215

<210> SEQ ID NO 1816
<211> LENGTH: 639
<212> TYPE: DNA
<213> ORGANISM: Neisseria meningitidis

<400> SEQUENCE: 1816
atgtttcaaa attttgattt gggcgtgttt ctgcttgccg tcctgcccgt gctgctctcc      60
attaccgtca gggaggtggc gcgcggctat acggcgcgct actggggaga caacactgcc     120
gaacaatacg gcaggctgac actgaacccc ctgccccata tcgatttggt cggcacaatc     180
atcgtaccgc tgcttacttt gatgttcacg cccttcctgt tcggctgggc gcgtccgatt     240
cctatcgatt cgcgcaactt ccgcaacccg cgccttgcct ggcgttgcgt tgccgcgtcc     300
ggcccgctgt cgaatctagc gatggctgtt ctgtggggcg tggttttggt gctgactccg     360
tatgtcggcg gggcgtatca gatgccgttg gctcaaatgg caaactacgg tattctgatc     420
aatgcgattc tgttcgcgct caacatcatc cccatcctgc cttgggacgg cggcattttc     480
atcgacacct tcctgtcggc gaaatattcg caagcgttcc gcaaaatcga acctatgggg     540
acgtggatta tcctactgct gatgctgacc ggggttttgg gtgcgtttat tgcaccgatt     600
gtgcggctgg tgattgcgtt tgtgcagatg ttcgtctga                            639

<210> SEQ ID NO 1817
<211> LENGTH: 212
<212> TYPE: PRT
<213> ORGANISM: Neisseria meningitidis

<400> SEQUENCE: 1817

Met Phe Gln Asn Phe Asp Leu Gly Val Phe Leu Leu Ala Val Leu Pro
                5                  10                   15
Val Leu Leu Ser Ile Thr Val Arg Glu Val Ala Arg Gly Tyr Thr Ala
            20                  25                  30
Arg Tyr Trp Gly Asp Asn Thr Ala Glu Gln Tyr Gly Arg Leu Thr Leu
        35                  40                  45
Asn Pro Leu Pro His Ile Asp Leu Val Gly Thr Ile Ile Val Pro Leu
    50                  55                  60
Leu Thr Leu Met Phe Thr Pro Phe Leu Phe Gly Trp Ala Arg Pro Ile
65                  70                  75                  80
```

Pro Ile Asp Ser Arg Asn Phe Arg Asn Pro Arg Leu Ala Trp Arg Cys
                85                  90                  95

Val Ala Ala Ser Gly Pro Leu Ser Asn Leu Ala Met Ala Val Leu Trp
            100                 105                 110

Gly Val Leu Val Leu Thr Pro Tyr Val Gly Gly Ala Tyr Gln Met
        115                 120                 125

Pro Leu Ala Gln Met Ala Asn Tyr Gly Ile Leu Ile Asn Ala Ile Leu
    130                 135                 140

Phe Ala Leu Asn Ile Ile Pro Ile Leu Pro Trp Asp Gly Gly Ile Phe
145                 150                 155                 160

Ile Asp Thr Phe Leu Ser Ala Lys Tyr Ser Gln Ala Phe Arg Lys Ile
                165                 170                 175

Glu Pro Tyr Gly Thr Trp Ile Ile Leu Leu Met Leu Thr Gly Val
            180                 185                 190

Leu Gly Ala Phe Ile Ala Pro Ile Val Arg Leu Val Ile Ala Phe Val
        195                 200                 205

Gln Met Phe Val
    210

<210> SEQ ID NO 1818
<211> LENGTH: 558
<212> TYPE: DNA
<213> ORGANISM: Neisseria meningitidis
<220> FEATURE:
<221> NAME/KEY: misc_feature
<222> LOCATION: (1)...(558)
<223> OTHER INFORMATION: n = A,T,C or G

<400> SEQUENCE: 1818
cgcggctata cagcgcgcta ctggggtgac aacactgccg aacaatacgg caggctgaca      60
ctgaaccccc tgccccatat cgatttggtc ggcacaatca tcgtaccgct gcttactttg     120
atgtttacgc ccttcctgtt cggctgggcg cgtccgattc ctatcgattc gcgcaacttc     180
cgcaacccgc gccttgcctg gcgttgcgtt gccgcgtccg gcccgctgtc gaatctggcg     240
atggctgttc tgtggggcgt ggttttggtg ctgactccgt atgtcggtgg ggcgtatcag     300
atgccgttgg cncaaatggc aaactacnnn attctgatca atgcgattct gtncgcgctc     360
aacatcatcc ccatcctgcc ttgggacggc ggcattttca tcgacacctt cctgtcggcn     420
aaatantcgc aagcgttccg caaaatcgaa ccttatggga cgtggattat ccngctgctt     480
atgctgaccg gggttttggg tgcgtntatt gcaccgattg tgcagctggt gattgcgttt     540
gtgcagatgt tcgtctga                                                    558

<210> SEQ ID NO 1819
<211> LENGTH: 185
<212> TYPE: PRT
<213> ORGANISM: Neisseria meningitidis
<220> FEATURE:
<221> NAME/KEY: misc_feature
<222> LOCATION: (1)...(185)
<223> OTHER INFORMATION: Xaa is any Amino Acid

<400> SEQUENCE: 1819

Arg Gly Tyr Thr Ala Arg Tyr Trp Gly Asp Asn Thr Ala Glu Gln Tyr
                5                   10                  15

Gly Arg Leu Thr Leu Asn Pro Leu Pro His Ile Asp Leu Val Gly Thr
            20                  25                  30

Ile Ile Val Pro Leu Leu Thr Leu Met Phe Thr Pro Phe Leu Phe Gly
        35                  40                  45

Trp Ala Arg Pro Ile Pro Ile Asp Ser Arg Asn Phe Arg Asn Pro Arg
         50                  55                  60

Leu Ala Trp Arg Cys Val Ala Ser Gly Pro Leu Ser Asn Leu Ala
 65                  70                  75                  80

Met Ala Val Leu Trp Gly Val Val Leu Val Thr Pro Tyr Val Gly
                 85                  90                  95

Gly Ala Tyr Gln Met Pro Leu Ala Gln Met Ala Asn Tyr Xaa Ile Leu
             100                 105                 110

Ile Asn Ala Ile Leu Xaa Ala Leu Asn Ile Ile Pro Ile Leu Pro Trp
             115                 120                 125

Asp Gly Gly Ile Phe Ile Asp Thr Phe Leu Ser Ala Lys Xaa Ser Gln
             130                 135                 140

Ala Phe Arg Lys Ile Glu Pro Tyr Gly Thr Trp Ile Ile Xaa Leu Leu
145                 150                 155                 160

Met Leu Thr Gly Val Leu Gly Ala Xaa Ile Ala Pro Ile Val Gln Leu
                 165                 170                 175

Val Ile Ala Phe Val Gln Met Phe Val
             180                 185

<210> SEQ ID NO 1820
<211> LENGTH: 498
<212> TYPE: DNA
<213> ORGANISM: Neisseria meningitidis

<400> SEQUENCE: 1820
atgaacctga tttcacgtta catcatccgt caaatggcgg ttatggcggt ttacgcgctc     60
cttgccttcc tcgctttgta cagcttttt gaaatcctgt acgaaaccgg caacctcggc    120
aaaggcagtt acggcatatg ggaatgctg ggctacaccg ccctcaaaat gcccgccgc    180 gcctacgaac tgattcccct cgccgtcctt atcggcggac tggtctcct cagccagctt    240 gccgccggca cgaactgac cgtcatcaaa gccagcggga tgagcaccaa aaagctgctg    300
ttgattctgt cgcagttcgg ttttattttt gctattgcca ccgtcgcgct cggcgaatgg    360
gttgcgccca cactgagcca aaagccgaa aacatcaaag ccgccgccat caacggcaaa    420
atcagcaccg gcaataccgg cctttggctg aaagaaaaaa acagcgtgat caatgtgcgc    480
gaaatgttgc ccgaccat                                                  498

<210> SEQ ID NO 1821
<211> LENGTH: 166
<212> TYPE: PRT
<213> ORGANISM: Neisseria meningitidis

<400> SEQUENCE: 1821

Met Asn Leu Ile Ser Arg Tyr Ile Ile Arg Gln Met Ala Val Met Ala
                 5                  10                  15

Val Tyr Ala Leu Leu Ala Phe Leu Ala Leu Tyr Ser Phe Phe Glu Ile
             20                  25                  30

Leu Tyr Glu Thr Gly Asn Leu Gly Lys Gly Ser Tyr Gly Ile Trp Glu
         35                  40                  45

Met Leu Gly Tyr Thr Ala Leu Lys Met Pro Ala Arg Ala Tyr Glu Leu
 50                  55                  60

Ile Pro Leu Ala Val Leu Ile Gly Gly Leu Val Ser Leu Ser Gln Leu
 65                  70                  75                  80

Ala Ala Gly Ser Glu Leu Thr Val Ile Lys Ala Ser Gly Met Ser Thr
                 85                  90                  95

```
Lys Lys Leu Leu Leu Ile Leu Ser Gln Phe Gly Phe Ile Phe Ala Ile
                100                 105                 110

Ala Thr Val Ala Leu Gly Glu Trp Val Ala Pro Thr Leu Ser Gln Lys
            115                 120                 125

Ala Glu Asn Ile Lys Ala Ala Ile Asn Gly Lys Ile Ser Thr Gly
        130                 135                 140

Asn Thr Gly Leu Trp Leu Lys Glu Lys Asn Ser Val Ile Asn Val Arg
145                 150                 155                 160

Glu Met Leu Pro Asp His
                165

<210> SEQ ID NO 1822
<211> LENGTH: 980
<212> TYPE: DNA
<213> ORGANISM: Neisseria meningitidis

<400> SEQUENCE: 1822
atgaacctga tttcacgtta catcatccgt caaatggcgg ttatggcggt ttacgcgctc     60
cttgccttcc tcgctttgta cagcttttt gaaatcctgt acgaaaccgg caacctcggc    120
aaaggcagtt acggcatatg ggaaatgctg ggctacaccg ccctcaaaat gcccgcccgc    180
gcctacgaac tgattcccct cgccgtcctt atcggcggac tggtctccct cagccagctt    240
gccgccggca gcgaactgac cgtcatcaaa gccagcggca tgagcaccaa aaagctgctg    300
ttgattctgt cgcagttcgg ttttattttt gctattgcca ccgtcgcgct cggcgaatgg    360
gttgcgccca cactgagcca aaagccgaa aacatcaaag ccgccgccat caacggcaaa    420
atcagcaccg gcaataccgg cctttggctg aagaaaaaa acagcrtkat caatgtgcgc    480
gaaatgttgc cgaccatac gcttttgggc atcaaaattt gggcgcgcaa cgataaaaac    540
gaattggcag aggcagtgga agccgattcc gccgttttga acagcgacgg cagttggcag    600
ttgaaaaaca tccgccgcag cacgcttggc gaagacaaag tcgaggtctc tattgcggct    660
gaagaaaact ggccgatttc cgtcaaacgc aacctgatgg acgtattgct cgtcaaaccc    720
gaccaaatgt ccgtcggcga actgaccacc tacatccgcc acctccaaaa caacagccaa    780
aacacccgaa tctacgccat cgcatggtgg cgcaaattgg tttaccccgc cgcagcctgg    840
gtgatggcgc tcgtcgcctt gcctttacc ccgcaaacca cccgccacgg caatatgggc    900
ttaaaactct tcggcggcat ctgtstcgga ttgctgttcc accttgccgg acggctcttt    960
gggtttacca gccaactcgg                                                980

<210> SEQ ID NO 1823
<211> LENGTH: 326
<212> TYPE: PRT
<213> ORGANISM: Neisseria meningitidis
<220> FEATURE:
<221> NAME/KEY: misc_feature
<222> LOCATION: (1)...(326)
<223> OTHER INFORMATION: Xaa is any Amino Acid

<400> SEQUENCE: 1823

Met Asn Leu Ile Ser Arg Tyr Ile Ile Arg Gln Met Ala Val Met Ala
                5                   10                  15

Val Tyr Ala Leu Leu Ala Phe Leu Ala Leu Tyr Ser Phe Phe Glu Ile
            20                  25                  30

Leu Tyr Glu Thr Gly Asn Leu Gly Lys Gly Ser Tyr Gly Ile Trp Glu
        35                  40                  45
```

-continued

```
Met Leu Gly Tyr Thr Ala Leu Lys Met Pro Ala Arg Ala Tyr Glu Leu
 50                  55                  60

Ile Pro Leu Ala Val Leu Ile Gly Gly Leu Val Ser Leu Ser Gln Leu
 65                  70                  75                  80

Ala Ala Gly Ser Glu Leu Thr Val Ile Lys Ala Ser Gly Met Ser Thr
                 85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
        115                 120                 125

Ala Glu Asn Ile Lys Ala Ala Ile Asn Gly Lys Ile Ser Thr Gly
    130                 135                 140

Asn Thr Gly Leu Trp Leu Lys Glu Lys Asn Ser Xaa Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Glu Asn Trp
    210                 215                 220

Pro Ile Ser Val Lys Arg Asn Leu Met Asp Val Leu Leu Val Lys Pro
225                 230                 235                 240

Asp Gln Met Ser Val Gly Glu Leu Thr Thr Tyr Ile Arg His Leu Gln
                245                 250                 255

Asn Asn Ser Gln Asn Thr Arg Ile Tyr Ala Ile Ala Trp Trp Arg Lys
            260                 265                 270

Leu Val Tyr Pro Ala Ala Ala Trp Val Met Ala Leu Val Ala Phe Ala
        275                 280                 285

Phe Thr Pro Gln Thr Thr Arg His Gly Asn Met Gly Leu Lys Leu Phe
    290                 295                 300

Gly Gly Ile Cys Xaa Gly Leu Leu Phe His Leu Ala Gly Arg Leu Phe
305                 310                 315                 320

Gly Phe Thr Ser Gln Leu
            325
```

<210> SEQ ID NO 1824
<211> LENGTH: 1071
<212> TYPE: DNA
<213> ORGANISM: Neisseria meningitidis
<220> FEATURE:
<221> NAME/KEY: misc_feature
<222> LOCATION: (1)...(1076)
<223> OTHER INFORMATION: n = A,T,C or G

<400> SEQUENCE: 1824

```
atgaacctga tttcacgtta catcatccgt caaatggcgg ttatggcggt ttacgcgctc     60
cttgccttcc tcgctttgta cagctttttt gaaatcctgt acgaaaccgg caacctcggc    120
aaaggcagtt acggcatatg ggaaatgntg ggntacaccg ccctcaaaat gnccgcccgc    180
gcctacgaac tgatgcccct cgccgtcctt atcggcggac tggtctctnt cagccagctt    240
gccgccggca gcgaactgan cgtcatcaaa gccagcggca tgagcaccaa aaagctgctg    300
ttgattctgt cgcagttcgg ttttattttt gctattgcca ccgtcgcgct cggcgaatgg    360
gttgcgccca cactgagcca aaaagccgaa aacatcaaag ccgcggccat caacggcaaa    420
```

-continued

```
atcagtaccg gcaataccgg cctttggctg aaagaaaaaa acagcattat caatgtgcgc     480
gaaatgttgc ccgaccatac cctgctgggc attaaaatct gggcccgcaa cgataaaaac     540
gaactggcag aggcagtgga agccgattcc gccgttttga acagcgacgg cagttggcag     600
ttgaaaaaca tccgccgcag cacgcttggc gaagacaaag tcgaggtctc tattgcggct     660
gaagaaaant ggccgatttc cgtcaaacgc aacctgatgg acgtattgct cgtcaaaccc     720
gaccaaatgt ccgtcggcga actgaccacc tacatccgcc acctccaaan nnacagccaa     780
aacacccgaa tctacgccat cgcatggtgg cgcaaattgg tttaccccgc cgcagcctgg     840
gtgatggcgc tcgtcgcctt tgcctttacc ccgcaaacca cccgccacgg caatatgggc     900
ttaaaantct tcggcggcat ctgtctcgga ttgctgttcc accttgccgg ncggctcttc     960
nggtttacca gccaactcta cggcatcccg cccttcctcg ncggcgcact acctaccata    1020
gccttcgcct tgctcgccgt ttggctgata cgcaaacagg aaaaacgcta a              1071
```

<210> SEQ ID NO 1825
<211> LENGTH: 356
<212> TYPE: PRT
<213> ORGANISM: Neisseria meningitidis
<220> FEATURE:
<221> NAME/KEY: misc_feature
<222> LOCATION: (1)...(356)
<223> OTHER INFORMATION: Xaa is any Amino Acid

<400> SEQUENCE: 1825

```
Met Asn Leu Ile Ser Arg Tyr Ile Ile Arg Gln Met Ala Val Met Ala
                 5                  10                  15

Val Tyr Ala Leu Leu Ala Phe Leu Ala Leu Tyr Ser Phe Phe Glu Ile
            20                  25                  30

Leu Tyr Glu Thr Gly Asn Leu Gly Lys Gly Ser Tyr Gly Ile Trp Glu
        35                  40                  45

Met Xaa Gly Tyr Thr Ala Leu Lys Met Xaa Ala Arg Ala Tyr Glu Leu
    50                  55                  60

Met Pro Leu Ala Val Leu Ile Gly Gly Leu Val Ser Xaa Ser Gln Leu
65                  70                  75                  80

Ala Ala Gly Ser Glu Leu Xaa Val Ile Lys Ala Ser Gly Met Ser Thr
                85                  90                  95

Lys Lys Leu Leu Leu Ile Leu Ser Gln Phe Gly Phe Ile Phe Ala Ile
            100                 105                 110

Ala Thr Val Ala Leu Gly Glu Trp Val Ala Pro Thr Leu Ser Gln Lys
        115                 120                 125

Ala Glu Asn Ile Lys Ala Ala Ala Ile Asn Gly Lys Ile Ser Thr Gly
    130                 135                 140

Asn Thr Gly Leu Trp Leu Lys Glu Lys Asn Ser Ile Ile Asn Val Arg
145                 150                 155                 160

Glu Met Leu Pro Asp His Thr Leu Leu Gly Ile Lys Ile Trp Ala Arg
                165                 170                 175

Asn Asp Lys Asn Glu Leu Ala Glu Ala Val Glu Ala Asp Ser Ala Val
            180                 185                 190

Leu Asn Ser Asp Gly Ser Trp Gln Leu Lys Asn Ile Arg Arg Ser Thr
        195                 200                 205

Leu Gly Glu Asp Lys Val Glu Val Ser Ile Ala Ala Glu Glu Xaa Trp
    210                 215                 220

Pro Ile Ser Val Lys Arg Asn Leu Met Asp Val Leu Leu Val Lys Pro
225                 230                 235                 240
```

```
Asp Gln Met Ser Val Gly Glu Leu Thr Thr Tyr Ile Arg His Leu Gln
                245                 250                 255
Xaa Xaa Ser Gln Asn Thr Arg Ile Tyr Ala Ile Ala Trp Trp Arg Lys
            260                 265                 270
Leu Val Tyr Pro Ala Ala Ala Trp Val Met Ala Leu Val Ala Phe Ala
        275                 280                 285
Phe Thr Pro Gln Thr Thr Arg His Gly Asn Met Gly Leu Lys Xaa Phe
    290                 295                 300
Gly Gly Ile Cys Leu Gly Leu Leu Phe His Leu Ala Gly Arg Leu Phe
305                 310                 315                 320
Xaa Phe Thr Ser Gln Leu Tyr Gly Ile Pro Pro Phe Leu Xaa Gly Ala
                325                 330                 335
Leu Pro Thr Ile Ala Phe Ala Leu Leu Ala Val Trp Leu Ile Arg Lys
                340                 345                 350
Gln Glu Lys Arg
        355
```

<210> SEQ ID NO 1826
<211> LENGTH: 856
<212> TYPE: DNA
<213> ORGANISM: Neisseria meningitidis
<220> FEATURE:
<221> NAME/KEY: misc_feature
<222> LOCATION: (1)...(856)
<223> OTHER INFORMATION: n = A,T,C or G

<400> SEQUENCE: 1826

```
gcagtagccg aaactgccaa cagccagggc aaaggtaaac aggcaggcag ttcggtttct      60
gtttcactga aaacttcagg cgacctttgc ggcaaactca aaaccaccct taaaactttg     120
gtctgctctt tggtttccct gagtatggta ttgcctgccc atgcccaaat taccaccgac     180
aaatcagcac ctaaaaacca gcaggtcgtt atccttaaaa ccaacactgg tgcccccttg     240
gtgaatatcc aaactccgaa tggacgcgga ttgagccaca accgctanta cgcatttgat     300
gttgacaaca aaggggcagt gttaaacaac gaccgtaaca ataatccgtt tgtggtcaaa     360
ggcagtgcgc aattgatttt gaacgaggta cgcggtacgg ctagcaaact caacggcatc     420
gttaccgtag gcggtcaaaa ggccgacgtg attattgcca accccaacgg cattaccgtt     480
aatggcggcg gctttaaaaa tgtcggtcgg ggcatcttaa ctaccggtgc gccccaaatc     540
ggcaaagacg gtgcactgac aggatttgat gtgcgtcaag gcacattgga ccgtagragc     600
agcaggttgg aatgataaag gcggagcmrm ytacaccggg gtacttgctc gtgcagttgc     660
tttgcagggg aaattwmmgg gtaaanaact ggcggtttct accggtcctc agaaagtaga     720
ttacgccagc ggcgaaatca gtgcaggtac ggcagcgggt acgaaaccga ctattgccct     780
tgatactgcc gcactgggcg gtatgtacgc cgacagcatc acactgattg ccaatgaaaa     840
aggcgtaggc gtctaa                                                     856
```

<210> SEQ ID NO 1827
<211> LENGTH: 284
<212> TYPE: PRT
<213> ORGANISM: Neisseria meningitidis
<220> FEATURE:
<221> NAME/KEY: misc_feature
<222> LOCATION: (1)...(284)
<223> OTHER INFORMATION: Xaa is any Amino Acid

<400> SEQUENCE: 1827

```
Ala Val Ala Glu Thr Ala Asn Ser Gln Gly Lys Gly Lys Gln Ala Gly
                  5                   10                  15
Ser Ser Val Ser Val Ser Leu Lys Thr Ser Gly Asp Leu Cys Gly Lys
             20                  25                  30
Leu Lys Thr Thr Leu Lys Thr Leu Val Cys Ser Leu Val Ser Leu Ser
         35                  40                  45
Met Val Leu Pro Ala His Ala Gln Ile Thr Thr Asp Lys Ser Ala Pro
     50                  55                  60
Lys Asn Gln Gln Val Val Ile Leu Lys Thr Asn Thr Gly Ala Pro Leu
 65                  70                  75                  80
Val Asn Ile Gln Thr Pro Asn Gly Arg Gly Leu Ser His Asn Arg Xaa
                 85                  90                  95
Tyr Ala Phe Asp Val Asp Asn Lys Gly Ala Val Leu Asn Asn Asp Arg
            100                 105                 110
Asn Asn Asn Pro Phe Val Val Lys Gly Ser Ala Gln Leu Ile Leu Asn
        115                 120                 125
Glu Val Arg Gly Thr Ala Ser Lys Leu Asn Gly Ile Val Thr Val Gly
    130                 135                 140
Gly Gln Lys Ala Asp Val Ile Ile Ala Asn Pro Asn Gly Ile Thr Val
145                 150                 155                 160
Asn Gly Gly Gly Phe Lys Asn Val Gly Arg Gly Ile Leu Thr Thr Gly
                165                 170                 175
Ala Pro Gln Ile Gly Lys Asp Gly Ala Leu Thr Gly Phe Asp Val Val
            180                 185                 190
Lys Ala His Trp Thr Val Xaa Ala Ala Gly Trp Asn Asp Lys Gly Gly
        195                 200                 205
Ala Xaa Tyr Thr Gly Val Leu Ala Arg Ala Val Ala Leu Gln Gly Lys
    210                 215                 220
Xaa Xaa Gly Lys Xaa Leu Ala Val Ser Thr Gly Pro Gln Lys Val Asp
225                 230                 235                 240
Tyr Ala Ser Gly Glu Ile Ser Ala Gly Thr Ala Gly Thr Lys Pro
                245                 250                 255
Thr Ile Ala Leu Asp Thr Ala Ala Leu Gly Gly Met Tyr Ala Asp Ser
            260                 265                 270
Ile Thr Leu Ile Ala Asn Glu Lys Gly Val Gly Val
        275                 280
```

<210> SEQ ID NO 1828
<211> LENGTH: 5937
<212> TYPE: DNA
<213> ORGANISM: Neisseria meningitidis

<400> SEQUENCE: 1828

```
atgaataaag gtttacatcg cattatcttt agtaaaaagc acagcaccat ggttgcagta      60
gccgaaactg ccaacagcca gggcaaaggt aaacaggcag gcagttcggt tctgtttca     120
ctgaaaactt caggcgacct tgcggcaaa ctcaaaacca cccttaaaac tttggtctgc     180
tctttggttt ccctgagtat ggtattgcct gcccatgccc aaattaccac cgacaaatca     240
gcacctaaaa accagcaggt cgttatcctt aaaaccaaca ctggtgcccc cttggtgaat     300
atccaaactc cgaatggacg cggattgagc cacaaccgct atacgcagtt tgatgttgac     360
aacaaagggg cagtgttaaa caacgaccgt aacaataatc cgtttgtggt caaaggcagt     420
gcgcaattga ttttgaacga ggtacgcggt acggctagca aactcaacgg catcgttacc     480
```

-continued

```
gtaggcggtc aaaaggccga cgtgattatt gccaacccca acggcattac cgttaatggc      540
ggcggcttta aaaatgtcgg tcggggcatc ttaactaccg gtgcgcccca aatcggcaaa      600
gacggtgcac tgacaggatt tgatgtgcgt caaggcacat tgaccgtagg agcagcaggt      660
tggaatgata aaggcggagc cgactacacc ggggtacttg ctcgtgcagt tgctttgcag      720
gggaaattac agggtaaaaa cctggcggtt tctaccggtc ctcagaaagt agattacgcc      780
agcggcgaaa tcagtgcagg tacggcagcg ggtacgaaac cgactattgc ccttgatact      840
gccgcactgg gcggtatgta cgccgacagc atcacactga ttgccaatga aaaaggcgta      900
ggcgtcaaaa atgccggcac actcgaagcg gccaagcaat tgattgtgac ttcgtcaggc      960
cgcattgaaa acagcggccg catcgccacc actgccgacg gcaccgaagc ttaccgact     1020
tatctctcca tcgaaaccac cgaaaaagga gcggcaggca catttatctc caatggtggt     1080
cggatcgaga gcaaaggctt attggttatt gagacgggag aagatatcag cttgcgtaac     1140
ggagccgtgg tgcagaataa cggcagtcgc ccagctacca cggtattaaa tgctggtcat     1200
aatttggtga ttgagagcaa aactaatgtg aacaatgcca aaggcccggc tactctgtcg     1260
gccgacggcc gtaccgtcat caaggaggcc agtattcaga ctggcactac cgtatacagt     1320
tccagcaaag gcaacgccga attaggcaat aacacacgca ttaccggggc agatgttacc     1380
gtattatcca acggcaccat cagcagttcc gccgtaatag atgccaaaga caccgcacac     1440
atcgaagcag gcaaaccgct ttctttggaa gcttcaacag ttacctccga tatccgctta     1500
aacggaggca gtatcaaggg cggcaagcag cttgctttac tggcagacga taacattact     1560
gccaaaacta ccaatctgaa tactcccggc aatctgtatg ttcatacagg taaagatctg     1620
aatttgaatg ttgataaaga tttgtctgcc gccagcatcc atttgaaatc ggataacgct     1680
gcccatatta ccggcaccag taaaaccctc actgcctcaa aagacatggg tgtggaggca     1740
ggctcgctga atgttaccaa taccaatctg cgtaccaact cgggtaatct gcacattcag     1800
gcagccaaag gcaatattca gcttcgcaat accaagctga acgcagccaa ggctctcgaa     1860
accaccgcat tgcagggcaa tatcgtttca gacggccttc atgctgtttc tgcagacggt     1920
catgtatcct tattggccaa cggtaatgcc gactttaccg gtcacaatac cctgacagcc     1980
aaggccgatg tcaatgcagg atcggttggt aaaggccgtc tgaaagcaga caataccaat     2040
atcacttcat cttcaggaga tattacgttg gttgccggca acggtattca gcttggtgac     2100
ggaaaacaac gcaattcaat caacggaaaa cacatcagca tcaaaaacaa cggtggtaat     2160
gccgacttaa aaaaccttaa cgtccatgcc aaaagcgggg cattgaacat tcattccgac     2220
cgggcattga gcatagaaaa taccaagctg gagtctaccc ataatacgca tcttaatgca     2280
caacacgagc gggtaacgct caaccaagta gatgcctacg cacaccgtca tctaagcatt     2340
accggcagcc agatttggca aaacgacaaa ctgccttctg ccaacaagct ggtggctaac     2400
ggtgtattgg cactcaatgc gcgctattcc caaattgccg acaacaccac gctgagagcg     2460
ggtgcaatca accttactgc cggtaccgcc ctagtcaagc gcggcaacat caattggagt     2520
accgtttcga ccaaaacttt ggaagataat gccgaattaa aaccattggc cggacggctg     2580
aatattgaag caggtagcgg cacattaacc atcgaacctg ccaaccgcat cagtgcgcat     2640
accgacctga gcatcaaaac aggcggaaaa ttgctgttgt ctgcaaaagg aggaaatgca     2700
ggtgcgccta gtgctcaagt ttcctcattg gaagcaaaag gcaatatccg tctggttaca     2760
ggagaaacag atttaagagg ttctaaaaatt acagccggta aaaacttggt tgtcgccacc     2820
accaaaggca agttgaatat cgaagccgta aacaactcat tcagcaatta ttttcctaca     2880
```

```
caaaaagcgg ctgaactcaa ccaaaaatcc aaagaattgg aacagcagat tgcgcagttg    2940
aaaaaaagct cgcctaaaag caagctgatt ccaaccctgc aagaagaacg cgaccgtctc    3000
gctttctata ttcaagccat caacaaggaa gttaaaggta aaaaacccaa aggcaaagaa    3060
tacctgcaag ccaagctttc tgcacaaaat attgacttga tttccgcaca aggcatcgaa    3120
atcagcggtt ccgatattac cgcttccaaa aaactgaacc ttcacgccgc aggcgtattg    3180
ccaaaggcag cagattcaga ggcggctgct attctgattg acggcataac cgaccaatat    3240
gaaattggca agcccaccta caagagtcac tacgacaaag ctgctctgaa caagccttca    3300
cgtttgaccg gacgtacagg ggtaagtatt catgcagctg cggcactcga tgatgcacgt    3360
attattatcg gtgcatccga aatcaaagct ccctcaggca gcatagacat caaagcccat    3420
agtgatattg tactggaggc tggacaaaac gatgcctata ccttcttaaa aaccaaaggt    3480
aaaagcggca aaatcatcag aaaaaccaag tttaccagca cccgcgacca cctgattatg    3540
ccagcccccg tcgagctgac cgccaacggc ataacgcttc aggcaggcgg caacatcgaa    3600
gctaatacca cccgcttcaa tgcccctgca ggtaaagtta ccctggttgc gggtgaagag    3660
ctgcaactgc tggcagaaga aggcatccac aagcacgagt tggatgtcca aaaaagccgc    3720
cgctttatcg gcatcaaggt aggcaagagc aattacagta aaaacgaact gaacgaaacc    3780
aaattgcctg tccgcgtcgt cgcccaaact gcagccaccc gttcaggctg ggataccgtg    3840
ctcgaaggta ccgaattcaa aaccacgctg gccggtgcgg acattcaggc aggtgtaggc    3900
gaaaaagccc gtgccgatgc gaaaattatc ctcaaaggca ttgtgaaccg tatccagtcg    3960
gaagaaaaat tagaaaccaa ctcaaccgta tggcagaaac aggccggacg cggcagcact    4020
atcgaaacgc tgaaactgcc cagcttcgaa agccctactc cgcccaaact gaccgccccc    4080
ggtggctata tcgtcgacat tccgaaaggc aatttgaaaa ccgaaatcga aagctggcc     4140
aaacagcccg agtatgccta tctgaaacag ctccaagtag cgaaaaacgt caactggaac    4200
caggtgcaac tggcttacga taaatgggac tataagcagg aaggcttaac cagagccggt    4260
gcagcgattg ttaccataat cgtaaccgca ctgacttatg gatacggcgc aaccgcagcg    4320
ggcggtgtag ccgcttcagg aagtagtaca gccgcagctg ccggaacagc cgccacaacg    4380
acagcagcag ctactaccgt ttctacagcg actgccatgc aaaccgctgc tttagcctcc    4440
ttgtatagcc aagcagctgt atccatcatc aataataaag gtgatgtcgg caaagcgttg    4500
aaagatctcg gcaccagtga tacggtcaag cagattgtca cttctgccct gacggcgggt    4560
gcattaaatc agatgggcgc agatattgcc caattgaaca gcaaggtaag aaccgaactg    4620
ttcagcagta cgggcaatca aactattgcc aaccttggag gcagactggc taccaatctc    4680
agtaatgcag gtatctcagc tggtatcaat accgccgtca acggcggcag cctgaaagac    4740
aacttaggca atgccgcatt aggagcattg gttaatagct tccaaggaga agccgccagc    4800
aaaatcaaaa caaccttcag cgacgattat gttgccaaac agttcgccca cgctttggct    4860
gggtgtgtta gcggattggt acaaggaaaa tgtaaagacg gggcaattgg cgcagcagtt    4920
ggggaaatcg tagccgactc catgcttggc ggcagaaacc ctgctacact cagcgatgcg    4980
gaaaagcata aggttatcag ttactcgaag attattgccg gcagcgtggc ggcactcaac    5040
ggcggcgatg tgaatactgc ggcgaatgcg gctgaggtgg cggtagtgaa taatgctttg    5100
aattttgaca gtaccccctac caatgcgaaa aagcatcaac cgcagaagcc cgacaaaacc    5160
gcactggaaa aaattatcca aggtattatg cctgcacatg cagcaggtgc gatgactaat    5220
ccgcaggata aggatgctgc catttggata agcaatatcc gtaatggcat cacaggcccg    5280
```

```
attgtgatta ccagctatgg ggtttatgct gcaggttgga cagctccgct gatcggtaca    5340
gcgggtaaat tagctatcag cacctgcatg gctaatcctt ctggttgtac tgtcatggtc    5400
actcaggctg ccgaagcggg cgcgggaatc gccacgggtg cggtaacggt aggcaacgct    5460
tgggaagcgc ctgtgggggc gttgtcgaaa gcgaaggcgg ccaagcaggc tataccaacc    5520
cagacagtta agaacttga tggcttacta caagaatcaa aaatataagg tgctgtaaat    5580
acacgaatta atatagcgaa tagtactact cgatatacac caatgagaca acgggacaa    5640 ccggtatctg ctggctttga gcatgttctt gaggggcact tccataggcc tattgcgaat    5700
aaccgttcag tttttaccat ctccccaaat gaattgaagg ttatacttca agtaataaa    5760 gtagtttctt ctcccgtatc gatgactcct gatggccaat atatgcggac tgtcgatgta    5820
ggaaaagtta ttggtactac ttctattaaa gaaggtggaa acccacaac tacaattaaa    5880 gtatttacag ataagtcagg aaatttgatt actacatacc cagtaaaagg aaactaa     5937
```

<210> SEQ ID NO 1829
<211> LENGTH: 1978
<212> TYPE: PRT
<213> ORGANISM: Neisseria meningitidis

<400> SEQUENCE: 1829

```
Met Asn Lys Gly Leu His Arg Ile Ile Phe Ser Lys Lys His Ser Thr
              5                  10                  15

Met Val Ala Val Ala Glu Thr Ala Asn Ser Gln Gly Lys Gly Lys Gln
         20                  25                  30

Ala Gly Ser Ser Val Ser Val Ser Leu Lys Thr Ser Gly Asp Leu Cys
     35                  40                  45

Gly Lys Leu Lys Thr Thr Leu Lys Thr Leu Val Cys Ser Leu Val Ser
 50                  55                  60

Leu Ser Met Val Leu Pro Ala His Ala Gln Ile Thr Thr Asp Lys Ser
 65                  70                  75                  80

Ala Pro Lys Asn Gln Gln Val Val Ile Leu Lys Thr Asn Thr Gly Ala
                 85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Val Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Thr Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255
```

-continued

```
Val Asp Tyr Ala Ser Gly Glu Ile Ser Ala Gly Thr Ala Ala Gly Thr
            260                 265                 270

Lys Pro Thr Ile Ala Leu Asp Thr Ala Leu Gly Gly Met Tyr Ala
        275                 280                 285

Asp Ser Ile Thr Leu Ile Ala Asn Glu Lys Gly Val Gly Val Lys Asn
        290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
            325                 330                 335

Ala Ser Pro Thr Tyr Leu Ser Ile Glu Thr Thr Glu Lys Gly Ala Ala
        340                 345                 350

Gly Thr Phe Ile Ser Asn Gly Gly Arg Ile Glu Ser Lys Gly Leu Leu
        355                 360                 365

Val Ile Glu Thr Gly Glu Asp Ile Ser Leu Arg Asn Gly Ala Val Val
        370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Pro
            405                 410                 415

Ala Thr Leu Ser Ala Asp Gly Arg Thr Val Ile Lys Glu Ala Ser Ile
        420                 425                 430

Gln Thr Gly Thr Thr Val Tyr Ser Ser Lys Gly Asn Ala Glu Leu
        435                 440                 445

Gly Asn Asn Thr Arg Ile Thr Gly Ala Asp Val Thr Val Leu Ser Asn
450                 455                 460

Gly Thr Ile Ser Ser Ser Ala Val Ile Asp Ala Lys Asp Thr Ala His
465                 470                 475                 480

Ile Glu Ala Gly Lys Pro Leu Ser Leu Glu Ala Ser Thr Val Thr Ser
            485                 490                 495

Asp Ile Arg Leu Asn Gly Gly Ser Ile Lys Gly Gly Lys Gln Leu Ala
        500                 505                 510

Leu Leu Ala Asp Asp Asn Ile Thr Ala Lys Thr Thr Asn Leu Asn Thr
        515                 520                 525

Pro Gly Asn Leu Tyr Val His Thr Gly Lys Asp Leu Asn Leu Asn Val
        530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
            565                 570                 575

Gly Val Glu Ala Gly Ser Leu Asn Val Thr Asn Thr Asn Leu Arg Thr
        580                 585                 590

Asn Ser Gly Asn Leu His Ile Gln Ala Ala Lys Gly Asn Ile Gln Leu
        595                 600                 605

Arg Asn Thr Lys Leu Asn Ala Ala Lys Ala Leu Glu Thr Thr Ala Leu
        610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
            645                 650                 655

Thr Leu Thr Ala Lys Ala Asp Val Asn Ala Gly Ser Val Gly Lys Gly
        660                 665                 670
```

-continued

```
Arg Leu Lys Ala Asp Asn Thr Asn Ile Thr Ser Ser Ser Gly Asp Ile
            675                 680                 685

Thr Leu Val Ala Gly Asn Gly Ile Gln Leu Gly Asp Gly Lys Gln Arg
            690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
            725                 730                 735

Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Thr Gly Ser Gln
            770                 775                 780

Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
            805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
            885                 890                 895

Gly Gly Asn Ala Gly Ala Pro Ser Ala Gln Val Ser Ser Leu Glu Ala
            900                 905                 910

Lys Gly Asn Ile Arg Leu Val Thr Gly Glu Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
            965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
            995                1000                1005

Lys Glu Val Lys Gly Lys Pro Lys Gly Lys Glu Tyr Leu Gln Ala
            1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ala Ile Leu
            1060                1065                1070

Ile Asp Gly Ile Thr Asp Gln Tyr Glu Ile Gly Lys Pro Thr Tyr Lys
            1075                1080                1085
```

```
Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
                1140                1145                1150

Tyr Thr Phe Leu Lys Thr Lys Gly Lys Ser Gly Lys Ile Ile Arg Lys
                1155                1160                1165

Thr Lys Phe Thr Ser Thr Arg Asp His Leu Ile Met Pro Ala Pro Val
                1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
                1205                1210                1215

Ala Gly Glu Glu Leu Gln Leu Leu Ala Glu Glu Gly Ile His Lys His
                1220                1225                1230

Glu Leu Asp Val Gln Lys Ser Arg Arg Phe Ile Gly Ile Lys Val Gly
                1235                1240                1245

Lys Ser Asn Tyr Ser Lys Asn Glu Leu Asn Glu Thr Lys Leu Pro Val
                1250                1255                1260

Arg Val Val Ala Gln Thr Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
                1285                1290                1295

Ala Gly Val Gly Glu Lys Ala Arg Ala Asp Ala Lys Ile Ile Leu Lys
                1300                1305                1310

Gly Ile Val Asn Arg Ile Gln Ser Glu Glu Lys Leu Glu Thr Asn Ser
                1315                1320                1325

Thr Val Trp Gln Lys Gln Ala Gly Arg Gly Ser Thr Ile Glu Thr Leu
                1330                1335                1340

Lys Leu Pro Ser Phe Glu Ser Pro Thr Pro Lys Leu Thr Ala Pro
1345                1350                1355                1360

Gly Gly Tyr Ile Val Asp Ile Pro Lys Gly Asn Leu Lys Thr Glu Ile
                1365                1370                1375

Glu Lys Leu Ala Lys Gln Pro Glu Tyr Ala Tyr Leu Lys Gln Leu Gln
                1380                1385                1390

Val Ala Lys Asn Val Asn Trp Asn Gln Val Gln Leu Ala Tyr Asp Lys
                1395                1400                1405

Trp Asp Tyr Lys Gln Glu Gly Leu Thr Arg Ala Gly Ala Ala Ile Val
                1410                1415                1420

Thr Ile Ile Val Thr Ala Leu Thr Tyr Tyr Gly Ala Thr Ala Ala
1425                1430                1435                1440

Gly Gly Val Ala Ala Ser Gly Ser Ser Thr Ala Ala Ala Gly Thr
                1445                1450                1455

Ala Ala Thr Thr Thr Ala Ala Ala Thr Thr Val Ser Thr Ala Thr Ala
                1460                1465                1470

Met Gln Thr Ala Ala Leu Ala Ser Leu Tyr Ser Gln Ala Ala Val Ser
                1475                1480                1485

Ile Ile Asn Asn Lys Gly Asp Val Gly Lys Ala Leu Lys Asp Leu Gly
                1490                1495                1500
```

```
                    -continued

Thr Ser Asp Thr Val Lys Gln Ile Val Thr Ser Ala Leu Thr Ala Gly
1505                1510                1515                1520

Ala Leu Asn Gln Met Gly Ala Asp Ile Ala Gln Leu Asn Ser Lys Val
                1525                1530                1535

Arg Thr Glu Leu Phe Ser Ser Thr Gly Asn Gln Thr Ile Ala Asn Leu
            1540                1545                1550

Gly Gly Arg Leu Ala Thr Asn Leu Ser Asn Ala Gly Ile Ser Ala Gly
        1555                1560                1565

Ile Asn Thr Ala Val Asn Gly Gly Ser Leu Lys Asp Asn Leu Gly Asn
    1570                1575                1580

Ala Ala Leu Gly Ala Leu Val Asn Ser Phe Gln Gly Glu Ala Ala Ser
1585                1590                1595                1600

Lys Ile Lys Thr Thr Phe Ser Asp Asp Tyr Val Ala Lys Gln Phe Ala
                1605                1610                1615

His Ala Leu Ala Gly Cys Val Ser Gly Leu Val Gln Gly Lys Cys Lys
            1620                1625                1630

Asp Gly Ala Ile Gly Ala Ala Val Gly Glu Ile Val Ala Asp Ser Met
        1635                1640                1645

Leu Gly Gly Arg Asn Pro Ala Thr Leu Ser Asp Ala Glu Lys His Lys
    1650                1655                1660

Val Ile Ser Tyr Ser Lys Ile Ile Ala Gly Ser Val Ala Ala Leu Asn
1665                1670                1675                1680

Gly Gly Asp Val Asn Thr Ala Ala Asn Ala Ala Glu Val Ala Val Val
                1685                1690                1695

Asn Asn Ala Leu Asn Phe Asp Ser Thr Pro Thr Asn Ala Lys Lys His
            1700                1705                1710

Gln Pro Gln Lys Pro Asp Lys Thr Ala Leu Glu Lys Ile Ile Gln Gly
        1715                1720                1725

Ile Met Pro Ala His Ala Ala Gly Ala Met Thr Asn Pro Gln Asp Lys
    1730                1735                1740

Asp Ala Ala Ile Trp Ile Ser Asn Ile Arg Asn Gly Ile Thr Gly Pro
1745                1750                1755                1760

Ile Val Ile Thr Ser Tyr Gly Val Tyr Ala Ala Gly Trp Thr Ala Pro
                1765                1770                1775

Leu Ile Gly Thr Ala Gly Lys Leu Ala Ile Ser Thr Cys Met Ala Asn
            1780                1785                1790

Pro Ser Gly Cys Thr Val Met Val Thr Gln Ala Ala Glu Ala Gly Ala
        1795                1800                1805

Gly Ile Ala Thr Gly Ala Val Thr Val Gly Asn Ala Trp Glu Ala Pro
    1810                1815                1820

Val Gly Ala Leu Ser Lys Ala Lys Ala Ala Lys Gln Ala Ile Pro Thr
1825                1830                1835                1840

Gln Thr Val Lys Glu Leu Asp Gly Leu Leu Gln Glu Ser Lys Asn Ile
                1845                1850                1855

Gly Ala Val Asn Thr Arg Ile Asn Ile Ala Asn Ser Thr Thr Arg Tyr
            1860                1865                1870

Thr Pro Met Arg Gln Thr Gly Gln Pro Val Ser Ala Gly Phe Glu His
        1875                1880                1885

Val Leu Glu Gly His Phe His Arg Pro Ile Ala Asn Asn Arg Ser Val
    1890                1895                1900

Phe Thr Ile Ser Pro Asn Glu Leu Lys Val Ile Leu Gln Ser Asn Lys
1905                1910                1915                1920
```

```
Val Val Ser Ser Pro Val Ser Met Thr Pro Asp Gly Gln Tyr Met Arg
        1925                1930                1935

Thr Val Asp Val Gly Lys Val Ile Gly Thr Thr Ser Ile Lys Glu Gly
        1940                1945                1950

Gly Gln Pro Thr Thr Thr Ile Lys Val Phe Thr Asp Lys Ser Gly Asn
        1955                1960                1965

Leu Ile Thr Thr Tyr Pro Val Lys Gly Asn
    1970                1975

<210> SEQ ID NO 1830
<211> LENGTH: 4599
<212> TYPE: DNA
<213> ORGANISM: Neisseria meningitidis
<220> FEATURE:
<221> NAME/KEY: misc_feature
<222> LOCATION: (1)...(4599)
<223> OTHER INFORMATION: n = A,T,C or G

<400> SEQUENCE: 1830
atgaataaag gtttacatcg cattatcttt agtaaaaagc acagcaccat ggttgcagta     60
gccgaaactg ccaacagcca gggcaaaggt aaacaggcag gcagttcggt ttctgtttca    120
ctgaaaactt caggcgacct ttgcggcaaa ctcaaaacca cccttaaaac cttggtctgc    180
tctttggttt ccctgagtat ggnattncnn nncnntnccc aaattaccac cgacaaatca    240
gcacctaaaa accancaggt cgttatcctt aaaaccaaca ctggtgcccc cttggtgaat    300
atccaaactc cgaatggacg cggattgagc acaaccgct atacgcagtt tgatgttgac    360
aacaaagggg cagtgttaaa caacgaccgt aacaataatc cgtttctggt caaaggcagt    420
gcgcaattga ttttgaacga ggtacgcggt acggctagca aactcaacgg catcgttacc    480
gtaggcggtc aaaaggccga cgtgattatt gccaacccca acggcattac cgttaatggc    540
ggcggcttta aaaatgtcgg tcggggcatc ttaactatcg gtgcgcccca atcggcaaa    600 gacggtgcac tgacaggatt tgatgtgcgt caaggcacat tgaccgtagg agcagcaggt    660
tggaatgata aaggcggagc cgactacacc ggggtacttg ctcgtgcagt tgctttgcag    720
gggaaattac agggtaaaaa cctggcggtt tctaccggtc ctcagaaagt agattacgcc    780
agcggcgaaa tcagtgcagg tacggcagcg ggtacgaaac cgactattgc ccttgatact    840
gccgcactgg gcggtatgta cgccgacagc atcacactga ttgccantga aaaaggcgta    900
ggcgtcaaaa atgccggcac actcgaagcg gccaagcaat tgattgtgac ttcgtcaggc    960
cgcattgaaa acagcggccg catcgccacc actgccgacg gcaccgaagc ttcaccgact   1020
tatctnncna tcgaaaccac cgaaaaagga gcnncaggca catttatctc caatggtggt   1080
cggatcgaga gcaaaggctt attggttatt gagacgggag aagatatcan cttgcgtaac   1140
ggagccgtgg tgcagaataa cggcagtcgc ccagctacca cggtattaaa tgctggtcat   1200
aatttggtga ttgagagtaa aactaatgtg aacaatgcca aaggctcgnc taatctgtcg   1260
gccggcggtc gtactacgat caatgatgct actattcaag cgggcagttc cgtgtacagc   1320
tccaccaaag gcgatactga nttgggtgaa ataccccgta ttattgctga aaacgtaacc   1380
gtattatcta acggtagtat tggcagtgct gctgtaattg aggctaaaga cactgcacac   1440
attgaatcgg gcaaaccgct ttcttttagaa acctcgaccg ttgcctccaa catccgtttg   1500
aacaacggta acattaaagg cggaaagcag cttgctttac tggcagacga taacattact   1560
gccaaaacta ccaatctgaa tactcccggc aatctgtatg ttcatacagg taagatctg   1620 aatttgaatg ttgataaaga tttgtctgcc gccagcatcc atttgaaatc ggataacgct   1680
```

```
gcccatatta ccggcaccag taaaaccctc actgcctcaa aagacatggg tgtggaggca   1740
ggcttgctga atgttaccaa taccaatctg cgtaccaact cgggtaatct gcacattcag   1800
gcagccaaag gcaatattca gcttcgcaat accaagctga acgcagccaa ggctctcgaa   1860
accaccgcat tgcagggcaa tatcgtttca gacggccttc atgctgtttc tgcagacggt   1920
catgtatcct tattggccaa cggtaatgcc gactttaccg gtcacaatac cctgacagcc   1980
aaggccgatg tcnatgcagg atcggttggt aaaggccgtc tgaaagcaga caataccaat   2040
atcacttcat cttcaggaga tattacgttg gttgccgnnn ncggtattca gcttggtgac   2100
ggaaaacaac gcaattcaat caacggaaaa cacatcagca tcaaaaacaa cggtggtaat   2160
gccgacttaa aaaaccttaa cgtccatgcc aaaagcgggg cattgaacat tcattccgac   2220
cgggcattga gcatagaaaa tacnaagctg gagtctaccc ataatacgca tcttaatgca   2280
caacacgagc gggtaacgct caaccaagta gatgcctacg cacaccgtca tctaagcatt   2340
ancggcagcc agatttggca aaacgacaaa ctgccttctg ccaacaagct ggtggctaac   2400
ggtgtattgg cantcaatgc gcgctattcc caaattgccg acaacaccac gctgagagcg   2460
ggtgcaatca accttactgc cggtaccgcc ctagtcaagc gcggcaacat caattggagt   2520
accgtttcga ccaagacttt ggaagataat gccgaattaa aaccattggc cggacggctg   2580
aatattgaag caggtagcgg cacattaacc atcgaacctg ccaaccgcat cagtgcgcat   2640
accgacctga gcatcaaaac aggcggaaaa ttgctgttgt ctgcaaaagg aggaaatgca   2700
ggtgcgcnta gtgctcaagt ttcctcattg gaagcaaaag gcaatatccg tctggttaca   2760
ggagnaacag atttaagagg ttctaaaatt acagccggta aaaacttggt tgtcgccacc   2820
accaaaggca agttgaatat cgaagccgta acaactcat tcagcaatta ttttcntaca   2880
caaaaagngn nngnnctcaa ccaaaaatcc aaagaattgg aacagcagat tgcgcagttg   2940
aaaaaaagct cgcntaaaag caagctgatt ccaaccctgc aagaagaacg cgaccgtctc   3000
gctttctata ttcaagccat caacaaggaa gttaaaggta aaaacccaa aggcaaagaa   3060
tacctgcaag ccaagctttc tgcacaaaat attgacttga tttccgcaca aggcatcgaa   3120
atcagcggtt ccgatattac cgcttccaaa aaactgaacc ttcacgccgc aggcgtattg   3180
ccaaaggcag cagattcaga gcggctgct attctgattg acggcataac cgaccaatat   3240
gaaattggca agcccaccta aagagtcac tacgacaaag ctgctctgaa caagccttca   3300
cgtttgaccg gacgtacggg ggtaagtatt catgcagctg cggcactcga tgatgcacgt   3360
attattatcg gtgcatccga aatcaaagct ccctcaggca gcatagacat caaagcccat   3420
agtgatattg tactggaggc tggacaaaac gatgcctata ccttcttana accaaaggt   3480
aaaagcggca naatnatcag aaaaacnaag tttaccagca ccngcganca cctgattatg   3540
ccagcccng tcgagctgac cgccaacggt atcacgcttc aggcaggcgg caacatcgaa   3600
gctaatacca cccgcttcaa tgcccctgca ggtaaagtta ccctggttgc gggtgaanag   3660
ntgcaactgc tggcagaaga aggcatccac aagcacgagt tggatgtcca aaaaagccgc   3720
cgctttatcg gcatcaaggt aggtnagagc aattacagta aaaacgaact gaacgaaacc   3780
aaattgcctg tccgcgtcgt cgcccaaant gcagccaccc gttcaggctg ggataccgtg   3840
ctcgaaggta ccgaattcaa aaccacgctg gccggtgccg acattcaggc aggtgtangc   3900
gaaaaagccc gtgtcgatgc gaaaattatc ctcaaaggca ttgtgaaccg tatccagtcg   3960
gaagaaaaat tagaaaccaa ctcaaccgta tggcagaaac aggccggacg cggcagcact   4020
atcgaaacgc taaaactgcc cagcttcgaa agccctactc cgcccaaatt gtccgcaccc   4080
```

-continued

```
ggcggntata tcgtcgacat tccgaaaggc aatctgaaaa ccgaaatcga aaagctgtcc    4140
aaacagcccg agtatgccta tctgaaacag ctccaagtag cgaaaaacat caactggaat    4200
caggtgcagc ttgcttacga cagatgggac tacaaacagg agggcttaac cgaagcaggt    4260
gcggcgatta tcgcactggc cgttaccgtg gtcacctcag gcgcaggaac cggagccgta    4320
ttgggattaa acggtgcgnc cgccgccgca accgatgcag cattcgcctc tttggccagc    4380
caggcttccg tatcgttcat caacaacaaa ggcgatgtcg gcaaaaccct gaaagagctg    4440
ggcagaagca gcacggtgaa aaatctggtg gttgccgccg ctaccgcagg cgtagccgac    4500
aaaatcggcg cttcggcact gancaatgtc agcgataagc agtggatcaa caacctgacc    4560
gtcaacctag ccaatgncgg gcagtgccgc actgattaa                          4599
```

<210> SEQ ID NO 1831
<211> LENGTH: 1532
<212> TYPE: PRT
<213> ORGANISM: Neisseria meningitidis
<220> FEATURE:
<221> NAME/KEY: misc_feature
<222> LOCATION: (1)...(1532)
<223> OTHER INFORMATION: Xaa is any Amino Acid

<400> SEQUENCE: 1831

```
Met Asn Lys Gly Leu His Arg Ile Ile Phe Ser Lys Lys His Ser Thr
              5                  10                  15

Met Val Ala Val Ala Glu Thr Ala Asn Ser Gln Gly Lys Gly Lys Gln
             20                  25                  30

Ala Gly Ser Ser Val Ser Val Ser Leu Lys Thr Ser Gly Asp Leu Cys
         35                  40                  45

Gly Lys Leu Lys Thr Thr Leu Lys Thr Leu Val Cys Ser Leu Val Ser
     50                  55                  60

Leu Ser Met Xaa Xaa Xaa Xaa Xaa Gln Ile Thr Thr Asp Lys Ser
 65                  70                  75                  80

Ala Pro Lys Asn Xaa Gln Val Val Ile Leu Lys Thr Asn Thr Gly Ala
                 85                  90                  95

Pro Leu Val Asn Ile Gln Thr Pro Asn Gly Arg Gly Leu Ser His Asn
            100                 105                 110

Arg Tyr Thr Gln Phe Asp Val Asp Asn Lys Gly Ala Val Leu Asn Asn
        115                 120                 125

Asp Arg Asn Asn Asn Pro Phe Leu Val Lys Gly Ser Ala Gln Leu Ile
    130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
            180                 185                 190

Ile Gly Ala Pro Gln Ile Gly Lys Asp Gly Ala Leu Thr Gly Phe Asp
        195                 200                 205

Val Arg Gln Gly Thr Leu Thr Val Gly Ala Ala Gly Trp Asn Asp Lys
    210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255
```

-continued

```
Val Asp Tyr Ala Ser Gly Glu Ile Ser Ala Gly Thr Ala Ala Gly Thr
            260                 265                 270

Lys Pro Thr Ile Ala Leu Asp Thr Ala Ala Leu Gly Gly Met Tyr Ala
        275                 280                 285

Asp Ser Ile Thr Leu Ile Ala Xaa Glu Lys Gly Val Gly Val Lys Asn
        290                 295                 300

Ala Gly Thr Leu Glu Ala Ala Lys Gln Leu Ile Val Thr Ser Ser Gly
305                 310                 315                 320

Arg Ile Glu Asn Ser Gly Arg Ile Ala Thr Thr Ala Asp Gly Thr Glu
                325                 330                 335

Ala Ser Pro Thr Tyr Leu Xaa Ile Glu Thr Thr Glu Lys Gly Ala Xaa
            340                 345                 350

Gly Thr Phe Ile Ser Asn Gly Gly Arg Ile Glu Ser Lys Gly Leu Leu
                355                 360                 365

Val Ile Glu Thr Gly Glu Asp Ile Xaa Leu Arg Asn Gly Ala Val Val
        370                 375                 380

Gln Asn Asn Gly Ser Arg Pro Ala Thr Thr Val Leu Asn Ala Gly His
385                 390                 395                 400

Asn Leu Val Ile Glu Ser Lys Thr Asn Val Asn Asn Ala Lys Gly Ser
                405                 410                 415

Xaa Asn Leu Ser Ala Gly Gly Arg Thr Thr Ile Asn Asp Ala Thr Ile
        420                 425                 430

Gln Ala Gly Ser Ser Val Tyr Ser Ser Thr Lys Gly Asp Thr Xaa Leu
            435                 440                 445

Gly Glu Asn Thr Arg Ile Ile Ala Glu Asn Val Thr Val Leu Ser Asn
        450                 455                 460

Gly Ser Ile Gly Ser Ala Ala Val Ile Glu Ala Lys Asp Thr Ala His
465                 470                 475                 480

Ile Glu Ser Gly Lys Pro Leu Ser Leu Glu Thr Ser Thr Val Ala Ser
                485                 490                 495

Asn Ile Arg Leu Asn Asn Gly Asn Ile Lys Gly Gly Lys Gln Leu Ala
        500                 505                 510

Leu Leu Ala Asp Asp Asn Ile Thr Ala Lys Thr Thr Asn Leu Asn Thr
            515                 520                 525

Pro Gly Asn Leu Tyr Val His Thr Gly Lys Asp Leu Asn Leu Asn Val
        530                 535                 540

Asp Lys Asp Leu Ser Ala Ala Ser Ile His Leu Lys Ser Asp Asn Ala
545                 550                 555                 560

Ala His Ile Thr Gly Thr Ser Lys Thr Leu Thr Ala Ser Lys Asp Met
                565                 570                 575

Gly Val Glu Ala Gly Leu Leu Asn Val Thr Asn Thr Asn Leu Arg Thr
        580                 585                 590

Asn Ser Gly Asn Leu His Ile Gln Ala Ala Lys Gly Asn Ile Gln Leu
            595                 600                 605

Arg Asn Thr Lys Leu Asn Ala Ala Lys Ala Leu Glu Thr Thr Ala Leu
        610                 615                 620

Gln Gly Asn Ile Val Ser Asp Gly Leu His Ala Val Ser Ala Asp Gly
625                 630                 635                 640

His Val Ser Leu Leu Ala Asn Gly Asn Ala Asp Phe Thr Gly His Asn
                645                 650                 655

Thr Leu Thr Ala Lys Ala Asp Val Xaa Ala Gly Ser Val Gly Lys Gly
        660                 665                 670
```

-continued

```
Arg Leu Lys Ala Asp Asn Thr Asn Ile Thr Ser Ser Ser Gly Asp Ile
            675                 680                 685

Thr Leu Val Ala Xaa Xaa Gly Ile Gln Leu Gly Asp Gly Lys Gln Arg
            690                 695                 700

Asn Ser Ile Asn Gly Lys His Ile Ser Ile Lys Asn Asn Gly Gly Asn
705                 710                 715                 720

Ala Asp Leu Lys Asn Leu Asn Val His Ala Lys Ser Gly Ala Leu Asn
            725                 730                 735

Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Xaa Gly Ser Gln
            770                 775                 780

Ile Trp Gln Asn Asp Lys Leu Pro Ser Ala Asn Lys Leu Val Ala Asn
785                 790                 795                 800

Gly Val Leu Ala Xaa Asn Ala Arg Tyr Ser Gln Ile Ala Asp Asn Thr
            805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
            835                 840                 845

Asp Asn Ala Glu Leu Lys Pro Leu Ala Gly Arg Leu Asn Ile Glu Ala
850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
            885                 890                 895

Gly Gly Asn Ala Gly Ala Xaa Ser Ala Gln Val Ser Ser Leu Glu Ala
            900                 905                 910

Lys Gly Asn Ile Arg Leu Val Thr Gly Xaa Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Asn Ser Phe Ser Asn Tyr Phe Xaa Thr
945                 950                 955                 960

Gln Lys Xaa Xaa Xaa Leu Asn Gln Lys Ser Lys Glu Leu Glu Gln Gln
            965                 970                 975

Ile Ala Gln Leu Lys Lys Ser Ser Xaa Lys Ser Lys Leu Ile Pro Thr
            980                 985                 990

Leu Gln Glu Glu Arg Asp Arg Leu Ala Phe Tyr Ile Gln Ala Ile Asn
            995                1000                1005

Lys Glu Val Lys Gly Lys Pro Lys Gly Lys Glu Tyr Leu Gln Ala
            1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ile Leu
            1060                1065                1070

Ile Asp Gly Ile Thr Asp Gln Tyr Glu Ile Gly Lys Pro Thr Tyr Lys
            1075                1080                1085
```

```
Ser His Tyr Asp Lys Ala Ala Leu Asn Lys Pro Ser Arg Leu Thr Gly
    1090                1095                1100

Arg Thr Gly Val Ser Ile His Ala Ala Ala Leu Asp Asp Ala Arg
1105                1110                1115                1120

Ile Ile Ile Gly Ala Ser Glu Ile Lys Ala Pro Ser Gly Ser Ile Asp
                1125                1130                1135

Ile Lys Ala His Ser Asp Ile Val Leu Glu Ala Gly Gln Asn Asp Ala
                1140                1145                1150

Tyr Thr Phe Leu Xaa Thr Lys Gly Lys Ser Gly Xaa Xaa Ile Arg Lys
                1155                1160                1165

Thr Lys Phe Thr Ser Thr Xaa Xaa His Leu Ile Met Pro Ala Pro Val
    1170                1175                1180

Glu Leu Thr Ala Asn Gly Ile Thr Leu Gln Ala Gly Gly Asn Ile Glu
1185                1190                1195                1200

Ala Asn Thr Thr Arg Phe Asn Ala Pro Ala Gly Lys Val Thr Leu Val
                1205                1210                1215

Ala Gly Glu Xaa Xaa Gln Leu Leu Ala Glu Glu Gly Ile His Lys His
                1220                1225                1230

Glu Leu Asp Val Gln Lys Ser Arg Arg Phe Ile Gly Ile Lys Val Gly
    1235                1240                1245

Xaa Ser Asn Tyr Ser Lys Asn Glu Leu Asn Glu Thr Lys Leu Pro Val
1250                1255                1260

Arg Val Val Ala Gln Xaa Ala Ala Thr Arg Ser Gly Trp Asp Thr Val
1265                1270                1275                1280

Leu Glu Gly Thr Glu Phe Lys Thr Thr Leu Ala Gly Ala Asp Ile Gln
                1285                1290                1295

Ala Gly Val Xaa Glu Lys Ala Arg Val Asp Ala Lys Ile Ile Leu Lys
                1300                1305                1310

Gly Ile Val Asn Arg Ile Gln Ser Glu Glu Lys Leu Glu Thr Asn Ser
                1315                1320                1325

Thr Val Trp Gln Lys Gln Ala Gly Arg Gly Ser Thr Ile Glu Thr Leu
    1330                1335                1340

Lys Leu Pro Ser Phe Glu Ser Pro Thr Pro Lys Leu Ser Ala Pro
1345                1350                1355                1360

Gly Gly Tyr Ile Val Asp Ile Pro Lys Gly Asn Leu Lys Thr Glu Ile
                1365                1370                1375

Glu Lys Leu Ser Lys Gln Pro Glu Tyr Ala Tyr Leu Lys Gln Leu Gln
                1380                1385                1390

Val Ala Lys Asn Ile Asn Trp Asn Gln Val Gln Leu Ala Tyr Asp Arg
                1395                1400                1405

Trp Asp Tyr Lys Gln Glu Gly Leu Thr Glu Ala Gly Ala Ala Ile Ile
    1410                1415                1420

Ala Leu Ala Val Thr Val Val Thr Ser Gly Ala Gly Thr Gly Ala Val
1425                1430                1435                1440

Leu Gly Leu Asn Gly Ala Xaa Ala Ala Ala Thr Asp Ala Ala Phe Ala
                1445                1450                1455

Ser Leu Ala Ser Gln Ala Ser Val Ser Phe Ile Asn Asn Lys Gly Asp
                1460                1465                1470

Val Gly Lys Thr Leu Lys Glu Leu Gly Arg Ser Ser Thr Val Lys Asn
    1475                1480                1485

Leu Val Val Ala Ala Ala Thr Ala Gly Val Ala Asp Lys Ile Gly Ala
    1490                1495                1500
```

```
Ser Ala Leu Xaa Asn Val Ser Asp Lys Gln Trp Ile Asn Asn Leu Thr
1505                1510                1515                1520

Val Asn Leu Ala Asn Xaa Gly Gln Cys Arg Thr Asp
            1525                1530
```

<210> SEQ ID NO 1832
<211> LENGTH: 1782
<212> TYPE: DNA
<213> ORGANISM: Neisseria meningitidis
<220> FEATURE:
<221> NAME/KEY: misc_feature
<222> LOCATION: (1)...(1782)
<223> OTHER INFORMATION: n = A,T,C or G

<400> SEQUENCE: 1832

```
cgcttcattc atgatgaagc agtcggcagc aacatcggcg gcggcaaaat gattgttgca      60
gccgggcagg atatcaatgt acgcggcana agccttattt ctgataaggg cattgtttta     120
aaagcaggac acgacatcga tatttctact gcccataatc gctataccgg caatgaatac     180
cacgagagca waaawtcagg cgtcatgggt actggcggat tgggctttac tatcggtaac     240
cggaaaacta ccgatgacac tgatcgtacc aatattgtsc atacaggcag cattataggc     300
agcctgaatg agacaccgt tacagttgca ggaaaccgct accgacaaac cggcagtacc      360
gtctccagcc cgaggggcg caataccgtc acagccaaaw gcatagatgt agagttcgca      420
aacaaccggt atgccactga ctacgcccat acccagggaa caaaaggcc ttaccgtcgc      480
cctcaatgtc ccggttgtcc aagctgcaca aaacttcata caagcagccc aaaatgtggg     540
caaaagtaaa ataaacgcg ttaatgccat ggctgcagcc aatgctgcat ggcagagtta      600
tcaagcaacc caacaaatgc aacaatttgc tccaagcagc agtgcgggac aaggtcaaaa     660
ctacaatcaa agccccagta tcagtgtgtc cattacntac ggcgaacaga aaagtcgtaa     720
cgagcaaaaa agacattaca ccgaagcggc agcaagtcaa attatcggca aagggcaaac     780
cacacttgcg gcaacaggaa gtggggagca gtccaatatc aatattacag gttccgatgt     840
catcggccat gcaggtactc cnctcattgc cgacaaccat atcagactcc aatctgccaa     900
acaggacggc agcgagcaaa gcaaaaacaa agcagtggt tggaatgcag gcgtacgtnn      960
caaaataggc aacggcatca ggtttggaat taccgccgga ggaaatatcg gtaaaggtaa    1020
agagcaaggg ggaagtacta cccaccgcca cacccatgtc ggcagcacaa ccggcaaaac    1080
taccatccga agcggcgggg gataccaccc tcaaaggtgt gcagctcatc ggcaaaggca    1140
tacaggcaga tacgcgcaac ctgcatatag aaagtgttca agatactgaa acctatcaga    1200
gcaaacagca aaacggcaat gtccaagttt actgtcggtt acggattcag tgcaagcggc    1260
agttaccgcc aaagcaaagt caaagcagac catgcctccg taaccgggca aagcggtatt    1320
tatgccggag aagacggcta tcaaatyaaa gtyagagaca cacagacct yaagggcggt     1380
atcatcacgt ctagccaaag cgcagaagat aagggcaaaa accttttttca gacggccacc   1440
cttactgcca gcgacattca aaaccacagc cgctacgaag cagaagcttc ggcataggc     1500
ggcagtttcg acctgaacgg cggctggac ggcacggtta ccgacaaaca aggcaggcct    1560
accgacagga taagcccggc agccggctac ggcagcgacg gagacagcaa aaacagcacc    1620
acccgcagcg gcgtcaacac ccacaacata cacatcaccg acgaagcggg acaacttgcc    1680
cgaacaggca ggactgcaaa agaaaccgaa gcgcgtatct acaccggcat cgacaccgaa    1740
actgcggatc aacactcagg ccatctgaaa acagcttcg ac                        1782
```

-continued

```
<210> SEQ ID NO 1833
<211> LENGTH: 593
<212> TYPE: PRT
<213> ORGANISM: Neisseria meningitidis
<220> FEATURE:
<221> NAME/KEY: misc_feature
<222> LOCATION: (1)...(593)
<223> OTHER INFORMATION: Xaa is any Amino Acid

<400> SEQUENCE: 1833
```

Arg Phe Ile His Asp Glu Ala Val Gly Ser Asn Ile Gly Gly Gly Lys
                  5                  10                  15

Met Ile Val Ala Ala Gly Gln Asp Ile Asn Val Arg Gly Xaa Ser Leu
             20                  25                  30

Ile Ser Asp Lys Gly Ile Val Leu Lys Ala Gly His Asp Ile Asp Ile
         35                  40                  45

Ser Thr Ala His Asn Arg Tyr Thr Gly Asn Glu Tyr His Glu Ser Xaa
     50                  55                  60

Xaa Ser Gly Val Met Gly Thr Gly Gly Leu Gly Phe Thr Ile Gly Asn
 65                  70                  75                  80

Arg Lys Thr Thr Asp Asp Thr Asp Arg Thr Asn Ile Val His Thr Gly
                 85                  90                  95

Ser Ile Ile Gly Ser Leu Asn Gly Asp Thr Val Thr Val Ala Gly Asn
            100                 105                 110

Arg Tyr Arg Gln Thr Gly Ser Thr Val Ser Ser Pro Glu Gly Arg Asn
        115                 120                 125

Thr Val Thr Ala Lys Xaa Ile Asp Val Glu Phe Ala Asn Asn Arg Tyr
    130                 135                 140

Ala Thr Asp Tyr Ala His Thr Gln Glu Gln Lys Gly Leu Thr Val Ala
145                 150                 155                 160

Leu Asn Val Pro Val Val Gln Ala Ala Gln Asn Phe Ile Gln Ala Ala
                165                 170                 175

Gln Asn Val Gly Lys Ser Lys Asn Lys Arg Val Asn Ala Met Ala Ala
            180                 185                 190

Ala Asn Ala Ala Trp Gln Ser Tyr Gln Ala Thr Gln Gln Met Gln Gln
        195                 200                 205

Phe Ala Pro Ser Ser Ser Ala Gly Gln Gly Gln Asn Tyr Asn Gln Ser
    210                 215                 220

Pro Ser Ile Ser Val Ser Ile Xaa Tyr Gly Glu Gln Lys Ser Arg Asn
225                 230                 235                 240

Glu Gln Lys Arg His Tyr Thr Glu Ala Ala Ser Gln Ile Ile Gly
                245                 250                 255

Lys Gly Gln Thr Thr Leu Ala Thr Gly Ser Gly Glu Gln Ser Asn
            260                 265                 270

Ile Asn Ile Thr Gly Ser Asp Val Ile Gly His Ala Gly Thr Xaa Leu
        275                 280                 285

Ile Ala Asp Asn His Ile Arg Leu Gln Ser Ala Lys Gln Asp Gly Ser
    290                 295                 300

Glu Gln Ser Lys Asn Lys Ser Ser Gly Trp Asn Ala Gly Val Arg Xaa
305                 310                 315                 320

Lys Ile Gly Asn Gly Ile Arg Phe Gly Ile Thr Ala Gly Gly Asn Ile
                325                 330                 335

Gly Lys Gly Lys Glu Gln Gly Gly Ser Thr Thr His Arg His Thr His
            340                 345                 350

Val Gly Ser Thr Thr Gly Lys Thr Thr Ile Arg Ser Gly Gly Asp Thr
        355                 360                 365

-continued

Thr Leu Lys Gly Val Gln Leu Ile Gly Lys Gly Ile Gln Ala Asp Thr
    370                 375                 380

Arg Asn Leu His Ile Glu Ser Val Gln Asp Thr Glu Thr Tyr Gln Ser
385                 390                 395                 400

Lys Gln Gln Asn Gly Asn Val Gln Val Thr Val Gly Tyr Gly Phe Ser
                405                 410                 415

Ala Ser Gly Ser Tyr Arg Gln Ser Lys Val Lys Ala Asp His Ala Ser
            420                 425                 430

Val Thr Gly Gln Ser Gly Ile Tyr Ala Gly Glu Asp Gly Tyr Gln Ile
        435                 440                 445

Lys Val Arg Asp Asn Thr Asp Leu Lys Gly Gly Ile Ile Thr Ser Ser
    450                 455                 460

Gln Ser Ala Glu Asp Lys Gly Lys Asn Leu Phe Gln Thr Ala Thr Leu
465                 470                 475                 480

Thr Ala Ser Asp Ile Gln Asn His Ser Arg Tyr Glu Gly Arg Ser Phe
                485                 490                 495

Gly Ile Gly Gly Ser Phe Asp Leu Asn Gly Gly Trp Asp Gly Thr Val
            500                 505                 510

Thr Asp Lys Gln Gly Arg Pro Thr Asp Arg Ile Ser Pro Ala Ala Gly
        515                 520                 525

Tyr Gly Ser Asp Gly Asp Ser Lys Asn Ser Thr Thr Arg Ser Gly Val
    530                 535                 540

Asn Thr His Asn Ile His Ile Thr Asp Glu Ala Gly Gln Leu Ala Arg
545                 550                 555                 560

Thr Gly Arg Thr Ala Lys Glu Thr Glu Ala Arg Ile Tyr Thr Gly Ile
                565                 570                 575

Asp Thr Glu Thr Ala Asp Gln His Ser Gly His Leu Lys Asn Ser Phe
            580                 585                 590

Asp

<210> SEQ ID NO 1834
<211> LENGTH: 390
<212> TYPE: DNA
<213> ORGANISM: Neisseria meningitidis

<400> SEQUENCE: 1834
acgaccggca gcctcggcgg catactggcc ggcggcggca cttcccttgc cgcaccgtat     60
ttggacaaag cggcggaaaa cctcggtccg gcgggcaaag cggcggtcaa cgcactgggc    120
ggtgcggcca tcggctatgc aactggtggt agtggtggtg ctgtggtggg tgcgaatgta    180
gattggaaca ataggcagct gcatccgaaa gaaatggcgt tggccgacaa atatgccgaa    240
gccctcaagc gcgaagttga aaacgcgaa ggcagaaaaa tcagcagcca agaagcggca    300
atgagaatcc gcaggcagat atgcgttggg tggacaaagg ttcccaagac ggctataccg    360
accaaagcgt catatccctt atcggaatga                                     390

<210> SEQ ID NO 1835
<211> LENGTH: 129
<212> TYPE: PRT
<213> ORGANISM: Neisseria meningitidis

<400> SEQUENCE: 1835

Thr Thr Gly Ser Leu Gly Gly Ile Leu Ala Gly Gly Gly Thr Ser Leu
                5                   10                  15

Ala Ala Pro Tyr Leu Asp Lys Ala Ala Glu Asn Leu Gly Pro Ala Gly
            20                  25                  30

```
Lys Ala Ala Val Asn Ala Leu Gly Gly Ala Ala Ile Gly Tyr Ala Thr
         35                  40                  45

Gly Gly Ser Gly Gly Ala Val Val Gly Ala Asn Val Asp Trp Asn Asn
     50                  55                  60

Arg Gln Leu His Pro Lys Glu Met Ala Leu Ala Asp Lys Tyr Ala Glu
 65                  70                  75                  80

Ala Leu Lys Arg Glu Val Glu Lys Arg Glu Gly Arg Lys Ile Ser Ser
                 85                  90                  95

Gln Glu Ala Ala Met Arg Ile Arg Arg Gln Ile Cys Val Gly Trp Thr
            100                 105                 110

Lys Val Pro Lys Thr Ala Ile Pro Thr Lys Ala Ser Tyr Pro Leu Ser
        115                 120                 125

Glu

<210> SEQ ID NO 1836
<211> LENGTH: 960
<212> TYPE: DNA
<213> ORGANISM: Neisseria meningitidis

<400> SEQUENCE: 1836
caatgccgtc tgaaaagctc acaattttac agacggcatt tgttatgcaa gtacatatac      60
agattcccta tactgcccc agrkgcgtgc gtggctgaag acccccccta cgcttgctat      120
ttgraacagc tccaagtcac caaagacgtc aactggaacc aggtacwact ggcgtacgac     180
aaatgggact ataaacagga aggcttaacc ggagccggag cagcgattat tgcgctggct     240
gttaccgtgg ttactgcggg cgcgggagcc ggagccgcac tgggcttaaa cggcgcggcc     300
gcagcggcaa ccgatgccgc attcgcctcg ctggccagcc aggcttccgt atcgctcatc     360
aacaacaaag gcaatatcgg taacaccctg aaagagctgg gcagaagcag cacggtgaaa     420
aatctgatgg ttgccgtcgc taccgcaggc gtagccgaca aaatcggtgc ttcggcactg     480
aacaatgtca gcgataagca gtggatcaac aacctgaccg tcaacctggc caatgcgggc     540
agtgccgcac tgattaatac cgctgtcaac ggcggcagcc tgaaagacaa tctggaagcg     600
aatatccttg cggctttggt gaatactgcg catggagaag cagccagtaa aatcaaacag     660
ttggatcagc actacattac ccacaagatt gcccatgcca tagcgggctg tgcggctgcg     720
gcggcgaata agggcaagtg tcaggatggt gcgataggtg cggctgtggg cgagatagtc     780
ggggaggctt tgacaaacgg caaaaatcct gacactttga cagctaaaga acgcgaacag     840
attttggcat acagcaaact ggttgccggt acggtaagcg tgtggtcgg cggcgatgta      900
aatgcgcgg cgaatgcggc tgaggtagcg gtgaaaaata tcagcttag cgacaaatga       960

<210> SEQ ID NO 1837
<211> LENGTH: 319
<212> TYPE: PRT
<213> ORGANISM: Neisseria meningitidis
<220> FEATURE:
<221> NAME/KEY: misc_feature
<222> LOCATION: (1)...(319)
<223> OTHER INFORMATION: Xaa is any Amino Acid

<400> SEQUENCE: 1837

Gln Cys Arg Leu Lys Ser Ser Gln Phe Tyr Arg Arg His Leu Leu Cys
                  5                  10                  15

Lys Tyr Ile Tyr Arg Phe Pro Ile Tyr Cys Pro Xaa Ala Cys Val Ala
             20                  25                  30
```

Glu Asp Thr Pro Tyr Ala Cys Tyr Leu Xaa Gln Leu Gln Val Thr Lys
         35                  40                  45

Asp Val Asn Trp Asn Gln Val Xaa Leu Ala Tyr Asp Lys Trp Asp Tyr
         50                  55                  60

Lys Gln Glu Gly Leu Thr Gly Ala Gly Ala Ala Ile Ile Ala Leu Ala
 65                  70                  75                  80

Val Thr Val Val Thr Ala Gly Ala Gly Ala Gly Ala Ala Leu Gly Leu
                 85                  90                  95

Asn Gly Ala Ala Ala Ala Ala Thr Asp Ala Ala Phe Ala Ser Leu Ala
                100                 105                 110

Ser Gln Ala Ser Val Ser Leu Ile Asn Asn Lys Gly Asn Ile Gly Asn
            115                 120                 125

Thr Leu Lys Glu Leu Gly Arg Ser Ser Thr Val Lys Asn Leu Met Val
        130                 135                 140

Ala Val Ala Thr Ala Gly Val Ala Asp Lys Ile Gly Ala Ser Ala Leu
145                 150                 155                 160

Asn Asn Val Ser Asp Lys Gln Trp Ile Asn Asn Leu Thr Val Asn Leu
                165                 170                 175

Ala Asn Ala Gly Ser Ala Ala Leu Ile Asn Thr Ala Val Asn Gly Gly
                180                 185                 190

Ser Leu Lys Asp Asn Leu Glu Ala Asn Ile Leu Ala Ala Leu Val Asn
            195                 200                 205

Thr Ala His Gly Glu Ala Ala Ser Lys Ile Lys Gln Leu Asp Gln His
        210                 215                 220

Tyr Ile Thr His Lys Ile Ala His Ala Ile Ala Gly Cys Ala Ala Ala
225                 230                 235                 240

Ala Ala Asn Lys Gly Lys Cys Gln Asp Gly Ala Ile Gly Ala Ala Val
                245                 250                 255

Gly Glu Ile Val Gly Glu Ala Leu Thr Asn Gly Lys Asn Pro Asp Thr
                260                 265                 270

Leu Thr Ala Lys Glu Arg Glu Gln Ile Leu Ala Tyr Ser Lys Leu Val
            275                 280                 285

Ala Gly Thr Val Ser Gly Val Val Gly Gly Asp Val Asn Ala Ala Ala
        290                 295                 300

Asn Ala Ala Glu Val Ala Val Lys Asn Asn Gln Leu Ser Asp Lys
305                 310                 315

<210> SEQ ID NO 1838
<211> LENGTH: 1860
<212> TYPE: DNA
<213> ORGANISM: Neisseria meningitidis

<400> SEQUENCE: 1838
atgcaagtaa atattcagat tccctatata ctgcccagat gcgtgcgtgc tgaagacacc    60
ccctacgctt gctatttgaa acagctccaa gtcaccaaag acgtcaactg gaaccaggta   120
caactggcgt acgacaaatg ggactataaa caggaaggct taaccggagc cggagcagcg   180
attattgcgc tggctgttac cgtggttact gcgggcgcgg gagccggagc cgcactgggc   240
ttaaacggcg cggccgcagc ggcaaccgat gccgcattcg cctcgctggc cagccaggct   300
tccgtatcgc tcatcaacaa caaaggcaat atcggtaaca ccctgaaaga gctgggcaga   360
agcagcacgg tgaaaaatct gatggttgcc gtcgctaccg caggcgtagc cgacaaaatc   420
ggtgcttcgg cactgaacaa tgtcagcgat aagcagtgga tcaacaacct gaccgtcaac   480
ctggccaatg cgggcagtgc cgcactgatt aataccgctg tcaacggcgg cagcctgaaa   540

-continued

```
gacaatctgg aagcgaatat ccttgcggct ttggtgaata ctgcgcatgg agaagcagcc    600
agtaaaatca aacagttgga tcagcactac attacccaca agattgccca tgccatagcg    660
ggctgtgcgg ctgcggcggc gaataagggc aagtgtcagg atggtgcgat aggtgcggct    720
gtgggcgaga tagtcgggga ggctttgaca acggcaaaa atcctgacac tttgacagct    780
aaagaacgcg aacagatttt ggcatacagc aaactggttg ccggtacggt aagcggtgtg    840
gtcggcggcg atgtaaatgc ggcggcgaat gcggctgagg tagcggtgaa aaataatcag    900
cttagcgaca agagggtag agaatttgat aacgaaatga ctgcatgcgc caaacagaat    960
aatcctcaac tgtgcagaaa aaatactgta aaaagtatc aaaatgttgc tgataaaaga   1020
cttgctgctt cgattgcaat atgtacggat atatcccgta gtactgaatg tagaacaatc   1080
agaaacaac atttgatcga tagtagaagc cttcattcat cttgggaagc aggtctaatt   1140
ggtaaagatg atgaatggta taaattattc agcaaatctt acacccaagc agatttggct   1200
ttacagtctt atcatttgaa tactgctgct aaatcttggc ttcaatcggg caatacaaag   1260
cctttatccg aatggatgtc cgaccaaggt tatacactta tttcaggagt taatcctaga   1320
ttcattccaa taccaagagg gtttgtaaaa caaaatacac ctattactaa tgtcaaatac   1380
ccggaaggca tcagtttcga tacaaaccta aaaagacatc tggcaaatgc tgatggtttt   1440
agtcaaaaac agggcattaa aggagcccat aaccgcacca ttttatggc agaactaaat   1500
tcacgaggag gacgcgtaaa atctgaaacc caaactgata ttgaaggcat tacccgaatt   1560
aaatatgaga ttcctacact agacaggaca ggtaaacctg atggtggatt taaggaaatt   1620
tcaagtataa aaactgttta atcctaaa aaattttctg atgataaaat acttcaaatg   1680
gctcaaaatg ctgcttcaca aggatattca aaagcctcta aaattgctca aaatgaaga   1740
actaaatcaa tatcggaaag aaaaaatgtc attcaattct cagaaacctt tgacggaatc   1800
aaatttagat catattttga tgtaaataca ggaagaatta caaacattca cccagaataa   1860
```

```
<210> SEQ ID NO 1839
<211> LENGTH: 619
<212> TYPE: PRT
<213> ORGANISM: Neisseria meningitidis

<400> SEQUENCE: 1839
```

```
Met Gln Val Asn Ile Gln Ile Pro Tyr Ile Leu Pro Arg Cys Val Arg
                5                  10                  15

Ala Glu Asp Thr Pro Tyr Ala Cys Tyr Leu Lys Gln Leu Gln Val Thr
           20                  25                  30

Lys Asp Val Asn Trp Asn Gln Val Gln Leu Ala Tyr Asp Lys Trp Asp
       35                  40                  45

Tyr Lys Gln Glu Gly Leu Thr Gly Ala Gly Ala Ala Ile Ile Ala Leu
   50                  55                  60

Ala Val Thr Val Thr Ala Gly Ala Gly Ala Gly Ala Ala Leu Gly
65                  70                  75                  80

Leu Asn Gly Ala Ala Ala Ala Thr Asp Ala Ala Phe Ala Ser Leu
               85                  90                  95

Ala Ser Gln Ala Ser Val Ser Leu Ile Asn Asn Lys Gly Asn Ile Gly
          100                 105                 110

Asn Thr Leu Lys Glu Leu Gly Arg Ser Ser Thr Val Lys Asn Leu Met
      115                 120                 125

Val Ala Val Ala Thr Ala Gly Val Ala Asp Lys Ile Gly Ala Ser Ala
  130                 135                 140
```

-continued

```
Leu Asn Asn Val Ser Asp Lys Gln Trp Ile Asn Asn Leu Thr Val Asn
145                 150                 155                 160

Leu Ala Asn Ala Gly Ser Ala Ala Leu Ile Asn Thr Ala Val Asn Gly
                165                 170                 175

Gly Ser Leu Lys Asp Asn Leu Glu Ala Asn Ile Leu Ala Ala Leu Val
            180                 185                 190

Asn Thr Ala His Gly Glu Ala Ala Ser Lys Ile Lys Gln Leu Asp Gln
        195                 200                 205

His Tyr Ile Thr His Lys Ile Ala His Ala Ile Ala Gly Cys Ala Ala
    210                 215                 220

Ala Ala Ala Asn Lys Gly Lys Cys Gln Asp Gly Ala Ile Gly Ala Ala
225                 230                 235                 240

Val Gly Glu Ile Val Gly Glu Ala Leu Thr Asn Gly Lys Asn Pro Asp
                245                 250                 255

Thr Leu Thr Ala Lys Glu Arg Glu Gln Ile Leu Ala Tyr Ser Lys Leu
            260                 265                 270

Val Ala Gly Thr Val Ser Gly Val Gly Gly Asp Val Asn Ala Ala
        275                 280                 285

Ala Asn Ala Ala Glu Val Ala Val Lys Asn Asn Gln Leu Ser Asp Lys
290                 295                 300

Glu Gly Arg Glu Phe Asp Asn Glu Met Thr Ala Cys Ala Lys Gln Asn
305                 310                 315                 320

Asn Pro Gln Leu Cys Arg Lys Asn Thr Val Lys Lys Tyr Gln Asn Val
                325                 330                 335

Ala Asp Lys Arg Leu Ala Ala Ser Ile Ala Ile Cys Thr Asp Ile Ser
            340                 345                 350

Arg Ser Thr Glu Cys Arg Thr Ile Arg Lys Gln His Leu Ile Asp Ser
        355                 360                 365

Arg Ser Leu His Ser Ser Trp Glu Ala Gly Leu Ile Gly Lys Asp Asp
    370                 375                 380

Glu Trp Tyr Lys Leu Phe Ser Lys Ser Tyr Thr Gln Ala Asp Leu Ala
385                 390                 395                 400

Leu Gln Ser Tyr His Leu Asn Thr Ala Ala Lys Ser Trp Leu Gln Ser
                405                 410                 415

Gly Asn Thr Lys Pro Leu Ser Glu Trp Met Ser Asp Gln Gly Tyr Thr
            420                 425                 430

Leu Ile Ser Gly Val Asn Pro Arg Phe Ile Pro Ile Pro Arg Gly Phe
        435                 440                 445

Val Lys Gln Asn Thr Pro Ile Thr Asn Val Lys Tyr Pro Glu Gly Ile
    450                 455                 460

Ser Phe Asp Thr Asn Leu Lys Arg His Leu Ala Asn Ala Asp Gly Phe
465                 470                 475                 480

Ser Gln Lys Gln Gly Ile Lys Gly Ala His Asn Arg Thr Asn Phe Met
                485                 490                 495

Ala Glu Leu Asn Ser Arg Gly Gly Arg Val Lys Ser Glu Thr Gln Thr
            500                 505                 510

Asp Ile Glu Gly Ile Thr Arg Ile Lys Tyr Glu Ile Pro Thr Leu Asp
        515                 520                 525

Arg Thr Gly Lys Pro Asp Gly Gly Phe Lys Glu Ile Ser Ser Ile Lys
    530                 535                 540

Thr Val Tyr Asn Pro Lys Lys Phe Ser Asp Asp Lys Ile Leu Gln Met
545                 550                 555                 560
```

Ala Gln Asn Ala Ala Ser Gln Gly Tyr Ser Lys Ala Ser Lys Ile Ala
                565                 570                 575

Gln Asn Glu Arg Thr Lys Ser Ile Ser Glu Arg Lys Asn Val Ile Gln
            580                 585                 590

Phe Ser Glu Thr Phe Asp Gly Ile Lys Phe Arg Ser Tyr Phe Asp Val
        595                 600                 605

Asn Thr Gly Arg Ile Thr Asn Ile His Pro Glu
    610                 615

<210> SEQ ID NO 1840
<211> LENGTH: 1788
<212> TYPE: DNA
<213> ORGANISM: Neisseria meningitidis
<220> FEATURE:
<221> NAME/KEY: misc_feature
<222> LOCATION: (1)...(1788)
<223> OTHER INFORMATION: n = A,T,C or G

<400> SEQUENCE: 1840

| | |
|---|---:|
| tatctgaaac agctccaagt agcgaaaaac atcaactgga atcaggtgca gcttgcttac | 60 |
| gacagatggg actacaaaca ggagggctta accgaagcag gtgcggcgat tatcgcactg | 120 |
| gccgttaccg tggtcacctc aggcgcagga accggagccg tattgggatt aaacggtgcg | 180 |
| nccgccgccg caaccgatgc agcattcgcc tctttggcca gccaggcttc cgtatcgttc | 240 |
| atcaacaaca aggcgatgt cggcaaaacc ctgaaagagc tgggcagaag cagcacggtg | 300 |
| aaaaatctgg tggttgccgc cgctaccgca ggcgtagccg acaaaatcgg cgcttcggca | 360 |
| ctgancaatg tcagcgataa gcagtggatc aacaacctga ccgtcaacct agccaatgcg | 420 |
| ggcagtgccg cactgattaa taccgctgtc aacggcggca gcctgaaaga cantctggaa | 480 |
| gcgaatatcc ttgcggcttt ggtcaatacc gcgcatggag aagcagccag taaaatcaaa | 540 |
| cagttggatc agcactacat agtccacaag attgcccatg ccatagcggg ctgtgcggca | 600 |
| gcggcggcga ataagggcaa gtgtcaggat ggtgcgatag gtgcggctgt gggcgagata | 660 |
| gtcggggagg cttttgacaaa cggcaaaaat cctgacactt tgacagctaa gaacgcgaa | 720 |
| cagattttgg catacagcaa actggttgcc ggtacgtaa gcggtgtggt cggcggcgat | 780 |
| gtaaatgcgg cggcgaatgc ggctgaggta gcgtgaaaa ataatcagct tagcgacnaa | 840 |
| gagggtagag aatttgataa cgaaatgact gcatgcgcca acagaatan tcctcaactg | 900 |
| tgcagaaaaa atactgtaaa aaagtatcaa aatgttgctg ataaaagact tgctgcttcg | 960 |
| attgcaatat gtacggatat atcccgtagt actgaatgta gaacaatcag aaaacaacat | 1020 |
| ttgatcgata gtagaagcct tcattcatct tgggaagcag gtctaattgg taaagatgat | 1080 |
| gaatggtata aattattcag caaatcttac acccaagcag atttggcttt acagtcttat | 1140 |
| catttgaata ctgctgctaa atcttggctt caatcgggca atacaaagcc tttatccgaa | 1200 |
| tggatgtccg accaaggtta tacttatt tcaggagtta atcctagatt cattccaata | 1260 |
| ccaagagggt ttgtaaaaca aaatacacct attactaatg tcaaataccc ggaaggcatc | 1320 |
| agtttcgata caaacctana aagacatctg gcaaatgctg atggttttag tcaagaacag | 1380 |
| ggcattaaag gagcccataa ccgcaccaat nttatggcag aactaaattc acgaggagga | 1440 |
| ngngtaaaat ctgaaaccca nactgatatt gaaggcatta cccgaattaa atatgagatt | 1500 |
| cctacactag acaggacagg taaacctgat ggtggattta ggaaatttc aagtataaaa | 1560 |
| actgtttata atcctaaaaa nttttnngat gataaaatac ttcaaatggc tcaanatgct | 1620 |
| gnttcacaag gatattcaaa agcctctaaa attgctcaaa atgaaagaac taaatcaata | 1680 | tcggaaagaa aaaatgtcat tcaattctca gaaacctttg acggaatcaa atttagannn    1740 tatntngatg taaatacagg aagaattaca aacattcacc cagaataa                 1788

<210> SEQ ID NO 1841
<211> LENGTH: 595
<212> TYPE: PRT
<213> ORGANISM: Neisseria meningitidis
<220> FEATURE:
<221> NAME/KEY: misc_feature
<222> LOCATION: (1)...(595)
<223> OTHER INFORMATION: Xaa is any Amino Acid

<400> SEQUENCE: 1841

Tyr Leu Lys Gln Leu Gln Val Ala Lys Asn Ile Asn Trp Asn Gln Val
                 5                  10                  15

Gln Leu Ala Tyr Asp Arg Trp Asp Tyr Lys Gln Glu Gly Leu Thr Glu
            20                  25                  30

Ala Gly Ala Ala Ile Ile Ala Leu Ala Val Thr Val Thr Ser Gly
        35                  40                  45

Ala Gly Thr Gly Ala Val Leu Gly Leu Asn Gly Ala Xaa Ala Ala Ala
    50                  55                  60

Thr Asp Ala Ala Phe Ala Ser Leu Ala Ser Gln Ala Ser Val Ser Phe
65                  70                  75                  80

Ile Asn Asn Lys Gly Asp Val Gly Lys Thr Leu Lys Glu Leu Gly Arg
                85                  90                  95

Ser Ser Thr Val Lys Asn Leu Val Val Ala Ala Ala Thr Ala Gly Val
            100                 105                 110

Ala Asp Lys Ile Gly Ala Ser Ala Leu Xaa Asn Val Ser Asp Lys Gln
        115                 120                 125

Trp Ile Asn Asn Leu Thr Val Asn Leu Ala Asn Ala Gly Ser Ala Ala
    130                 135                 140

Leu Ile Asn Thr Ala Val Asn Gly Gly Ser Leu Lys Asp Xaa Leu Glu
145                 150                 155                 160

Ala Asn Ile Leu Ala Ala Leu Val Asn Thr Ala His Gly Glu Ala Ala
                165                 170                 175

Ser Lys Ile Lys Gln Leu Asp Gln His Tyr Ile Val His Lys Ile Ala
            180                 185                 190

His Ala Ile Ala Gly Cys Ala Ala Ala Ala Asn Lys Gly Lys Cys
        195                 200                 205

Gln Asp Gly Ala Ile Gly Ala Ala Val Gly Glu Ile Val Gly Glu Ala
    210                 215                 220

Leu Thr Asn Gly Lys Asn Pro Asp Thr Leu Thr Ala Lys Glu Arg Glu
225                 230                 235                 240

Gln Ile Leu Ala Tyr Ser Lys Leu Val Ala Gly Thr Val Ser Gly Val
                245                 250                 255

Val Gly Gly Asp Val Asn Ala Ala Asn Ala Ala Glu Val Ala Val
            260                 265                 270

Lys Asn Asn Gln Leu Ser Asp Xaa Glu Gly Arg Glu Phe Asp Asn Glu
        275                 280                 285

Met Thr Ala Cys Ala Lys Gln Asn Xaa Pro Gln Leu Cys Arg Lys Asn
    290                 295                 300

Thr Val Lys Lys Tyr Gln Asn Val Ala Asp Lys Arg Leu Ala Ala Ser
305                 310                 315                 320

Ile Ala Ile Cys Thr Asp Ile Ser Arg Ser Thr Glu Cys Arg Thr Ile
                325                 330                 335

```
Arg Lys Gln His Leu Ile Asp Ser Arg Ser Leu His Ser Ser Trp Glu
                340                 345                 350

Ala Gly Leu Ile Gly Lys Asp Asp Glu Trp Tyr Lys Leu Phe Ser Lys
                355                 360                 365

Ser Tyr Thr Gln Ala Asp Leu Ala Leu Gln Ser Tyr His Leu Asn Thr
            370                 375                 380

Ala Ala Lys Ser Trp Leu Gln Ser Gly Asn Thr Lys Pro Leu Ser Glu
385                 390                 395                 400

Trp Met Ser Asp Gln Gly Tyr Thr Leu Ile Ser Gly Val Asn Pro Arg
                405                 410                 415

Phe Ile Pro Ile Pro Arg Gly Phe Val Lys Gln Asn Thr Pro Ile Thr
                420                 425                 430

Asn Val Lys Tyr Pro Glu Gly Ile Ser Phe Asp Thr Asn Leu Xaa Arg
                435                 440                 445

His Leu Ala Asn Ala Asp Gly Phe Ser Gln Glu Gln Gly Ile Lys Gly
            450                 455                 460

Ala His Asn Arg Thr Asn Xaa Met Ala Glu Leu Asn Ser Arg Gly Gly
465                 470                 475                 480

Xaa Val Lys Ser Glu Thr Xaa Thr Asp Ile Glu Gly Ile Thr Arg Ile
                485                 490                 495

Lys Tyr Glu Ile Pro Thr Leu Asp Arg Thr Gly Lys Pro Asp Gly Gly
                500                 505                 510

Phe Lys Glu Ile Ser Ser Ile Lys Thr Val Tyr Asn Pro Lys Xaa Phe
            515                 520                 525

Xaa Asp Asp Lys Ile Leu Gln Met Ala Gln Xaa Ala Xaa Ser Gln Gly
530                 535                 540

Tyr Ser Lys Ala Ser Lys Ile Ala Gln Asn Glu Arg Thr Lys Ser Ile
545                 550                 555                 560

Ser Glu Arg Lys Asn Val Ile Gln Phe Ser Glu Thr Phe Asp Gly Ile
                565                 570                 575

Lys Phe Arg Xaa Tyr Xaa Asp Val Asn Thr Gly Arg Ile Thr Asn Ile
                580                 585                 590

His Pro Glu
        595

<210> SEQ ID NO 1842
<211> LENGTH: 453
<212> TYPE: DNA
<213> ORGANISM: Neisseria meningitidis

<400> SEQUENCE: 1842
atggcaatca ttacattgta ttattctgtc aatggtattt taaatgtatg tgcaaaagca      60
aaaaatattc aagtagttgc caataataag aatatggttc tttttgggtt tttggsmrgc     120
atcatcggcg gttcaaccaa tgccatgtct cccatattgt taatatttt gcttagcgaa      180 acagaaaata aaaatcgtat cgtaaaatca agcaatctat gctatctttt ggcgaaaatt     240
gttcaaatat atatgctaag agaccagtat tggttattaa ataagagtga atacgdttta     300
atatttttac tgtccgtatt gtctgttatt ggattgtatg ttggaattcg gttaaggact     360
aagattagcc caaattttt taaaatgtta attttattg ttttattggt attggctctg      420
aaaatcgggc attcgggttt aatcaaactt taa                                  453
```

<210> SEQ ID NO 1843
<211> LENGTH: 150
<212> TYPE: PRT
<213> ORGANISM: Neisseria meningitidis
<220> FEATURE:
<221> NAME/KEY: misc_feature
<222> LOCATION: (1)...(150)
<223> OTHER INFORMATION: Xaa is any Amino Acid

<400> SEQUENCE: 1843

Met Ala Ile Ile Thr Leu Tyr Tyr Ser Val Asn Gly Ile Leu Asn Val
                5                   10                  15
Cys Ala Lys Ala Lys Asn Ile Gln Val Val Ala Asn Asn Lys Asn Met
            20                  25                  30
Val Leu Phe Gly Phe Leu Xaa Xaa Ile Ile Gly Gly Ser Thr Asn Ala
        35                  40                  45
Met Ser Pro Ile Leu Leu Ile Phe Leu Leu Ser Glu Thr Glu Asn Lys
    50                  55                  60
Asn Arg Ile Val Lys Ser Ser Asn Leu Cys Tyr Leu Leu Ala Lys Ile
65                  70                  75                  80
Val Gln Ile Tyr Met Leu Arg Asp Gln Tyr Trp Leu Leu Asn Lys Ser
                85                  90                  95
Glu Tyr Xaa Leu Ile Phe Leu Leu Ser Val Leu Ser Val Ile Gly Leu
            100                 105                 110
Tyr Val Gly Ile Arg Leu Arg Thr Lys Ile Ser Pro Asn Phe Phe Lys
        115                 120                 125
Met Leu Ile Phe Ile Val Leu Leu Val Leu Ala Leu Lys Ile Gly His
    130                 135                 140
Ser Gly Leu Ile Lys Leu
145                 150

<210> SEQ ID NO 1844
<211> LENGTH: 768
<212> TYPE: DNA
<213> ORGANISM: Neisseria meningitidis

<400> SEQUENCE: 1844
atgcaagaaa taatgcaatc tatcgttttt gttgctgccg caatactgca cggaattaca        60
ggcatgggat ttccgatgct cggtacaacc gcattggctt ttatcatgcc attgtctaag       120
gttgttgcct ggtggcatt accaagcctg ttaatgagct tgttggttct atgcagcaat        180
aacaaaaagg gttttttggca agagattgtt tattatttaa aaacctataa attgcttgct      240
atcggcagcg tcgttggcag cattttgggg gtgaagttgc ttttgatact ccagtgtct        300 tggctgcttt tactgatggc aatcattaca ttgtattatt ctgtcaatgg tatttttaaat     360 gtatgtgcaa aagcaaaaaa tattcaagta gttgccaata taagaatat ggttcttttt        420 gggttttttgg caggcatcat cggcggttca accaatgcca tgtctcccat attgttaata      480
tttttgctta gcgaaacaga aaataaaaat cgtatcgtaa aatcaagcaa tctatgctat       540
cttttggcga aaattgttca atatatatg ctaagagacc agtattggtt attaaataag        600
agtgaatacg gttaatatatt tttactgtcc gtattgtctg ttattggatt gtatgttgga      660
attcggttaa ggactaagat tagcccaaat tttttttaaaa tgttaatttt tattgtttta     720
ttggtattgg ctctgaaaat cgggcattcg ggtttaatca aacttttaa                   768

<210> SEQ ID NO 1845
<211> LENGTH: 255
<212> TYPE: PRT
<213> ORGANISM: Neisseria meningitidis

<400> SEQUENCE: 1845

Met Gln Glu Ile Met Gln Ser Ile Val Phe Val Ala Ala Ile Leu
                 5                  10                  15

His Gly Ile Thr Gly Met Gly Phe Pro Met Leu Gly Thr Thr Ala Leu
            20                  25                  30

Ala Phe Ile Met Pro Leu Ser Lys Val Val Ala Leu Val Ala Leu Pro
        35                  40                  45

Ser Leu Leu Met Ser Leu Leu Val Leu Cys Ser Asn Asn Lys Lys Gly
    50                  55                  60

Phe Trp Gln Glu Ile Val Tyr Tyr Leu Lys Thr Tyr Lys Leu Leu Ala
65                  70                  75                  80

Ile Gly Ser Val Val Gly Ser Ile Leu Gly Val Lys Leu Leu Ile
                85                  90                  95

Leu Pro Val Ser Trp Leu Leu Leu Met Ala Ile Ile Thr Leu Tyr
            100                 105                 110

Tyr Ser Val Asn Gly Ile Leu Asn Val Cys Ala Lys Ala Lys Asn Ile
        115                 120                 125

Gln Val Val Ala Asn Asn Lys Asn Met Val Leu Phe Gly Phe Leu Ala
    130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Val Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
    210                 215                 220

Thr Lys Ile Ser Pro Asn Phe Phe Lys Met Leu Ile Phe Ile Val Leu
225                 230                 235                 240

Leu Val Leu Ala Leu Lys Ile Gly His Ser Gly Leu Ile Lys Leu
                245                 250                 255

<210> SEQ ID NO 1846
<211> LENGTH: 768
<212> TYPE: DNA
<213> ORGANISM: Neisseria meningitidis

<400> SEQUENCE: 1846
atgcaagaaa taatgcaatc tatcgttttt gttgctgccg caatactgca cggaattaca      60
ggcatgggat ttccgatgct cggtacaacc gcattggctt ttatcatgcc attgtctaag     120
gttgttgcct tggtggcatt accaagcctg ttaatgagct tgttggttct atgcagcaat     180
aacaaaaagg ttttttggca agagattgtt tattatttaa aaacctataa attgcttgct     240
atcggcagcg tcgttggcag cattttgggg gtgaagttgc ttttgatact tccagtgtct     300
tggctgcttt tactgatggc aatcattaca ttgtattatt ctgtcaatgg tattttaaat     360
gtatgtgcaa aagcaaaaaa tattcaagta gttgccaata taagaatat ggttcttttt     420 gggttttttgg caggcatcat cggcggttca accaatgcca tgtctcccat attgttaata     480

```
tttttgctta gcgaaacaga gaataaaaat cgtatcgcaa atcaagcaa tctatgctat    540 cttttggcaa aaattgttca aatatatatg ctaagagacc agtattggtt attaaataag    600
agtgaatacg gtttaatatt tttactgtcc gtattgtctg ttattggatt gtatgttgga    660
attcggttaa ggactaagat tagcccaaat ttttttaaaa tgttaatttt tattgtttta    720
ttggtattgg ctctgaaaat cgggtattca ggtttaatca aactttaa                 768
```

<210> SEQ ID NO 1847
<211> LENGTH: 255
<212> TYPE: PRT
<213> ORGANISM: Neisseria meningitidis

<400> SEQUENCE: 1847

```
Met Gln Glu Ile Met Gln Ser Ile Val Phe Val Ala Ala Ala Ile Leu
                 5                  10                  15

His Gly Ile Thr Gly Met Gly Phe Pro Met Leu Gly Thr Thr Ala Leu
            20                  25                  30

Ala Phe Ile Met Pro Leu Ser Lys Val Val Ala Leu Val Ala Leu Pro
        35                  40                  45

Ser Leu Leu Met Ser Leu Leu Val Leu Cys Ser Asn Asn Lys Lys Gly
    50                  55                  60

Phe Trp Gln Glu Ile Val Tyr Tyr Leu Lys Thr Tyr Lys Leu Leu Ala
65                  70                  75                  80

Ile Gly Ser Val Val Gly Ser Ile Leu Gly Val Lys Leu Leu Ile
                85                  90                  95

Leu Pro Val Ser Trp Leu Leu Leu Met Ala Ile Ile Thr Leu Tyr
            100                 105                 110

Tyr Ser Val Asn Gly Ile Leu Asn Val Cys Ala Lys Ala Lys Asn Ile
        115                 120                 125

Gln Val Val Ala Asn Asn Lys Asn Met Val Leu Phe Gly Phe Leu Ala
    130                 135                 140

Gly Ile Ile Gly Gly Ser Thr Asn Ala Met Ser Pro Ile Leu Leu Ile
145                 150                 155                 160

Phe Leu Leu Ser Glu Thr Glu Asn Lys Asn Arg Ile Ala Lys Ser Ser
                165                 170                 175

Asn Leu Cys Tyr Leu Leu Ala Lys Ile Val Gln Ile Tyr Met Leu Arg
            180                 185                 190

Asp Gln Tyr Trp Leu Leu Asn Lys Ser Glu Tyr Gly Leu Ile Phe Leu
        195                 200                 205

Leu Ser Val Leu Ser Val Ile Gly Leu Tyr Val Gly Ile Arg Leu Arg
    210                 215                 220

Thr Lys Ile Ser Pro Asn Phe Phe Lys Met Leu Ile Phe Ile Val Leu
225                 230                 235                 240

Leu Val Leu Ala Leu Lys Ile Gly Tyr Ser Gly Leu Ile Lys Leu
                245                 250                 255
```

<210> SEQ ID NO 1848
<211> LENGTH: 516
<212> TYPE: DNA
<213> ORGANISM: Neisseria meningitidis

<400> SEQUENCE: 1848

```
atgagacata tgaaaataca aaattattta ctagtattta agtttttaca tatagccttg    60
atagtaatta atatagtgtt tggttatttt gttttctat ttgatttttt tgcgttttg    120 tttttgcaa acgtctttct tgctgtaaat ttattatttt tagaaaaaaa cataaaaaac    180
```

-continued

```
aaattattgt ttttattgcc gatttctatt attatatgga tggtaattca tattagtatg    240
ataaatataa aattttataa atttgagcat caaataaagg aacaaaatat atcctcgatt    300
actggggtga taaaaccaca tgatagttat aattatgttt atgactcaaa tggatatgct    360
aaattaaaag ataatcatag atatggtagg gtaattagag aaacacctta tattgatgta    420
gttgcatctg atgttaaaaa taaatccata agattaagct tggtttgtgg tattcattca    480
tatgctccat gtgccaattt tataaaattt gtcagg                              516
```

<210> SEQ ID NO 1849
<211> LENGTH: 172
<212> TYPE: PRT
<213> ORGANISM: Neisseria meningitidis

<400> SEQUENCE: 1849

```
Met Arg His Met Lys Ile Gln Asn Tyr Leu Leu Val Phe Ile Val Leu
                 5                  10                  15

His Ile Ala Leu Ile Val Ile Asn Ile Val Phe Gly Tyr Phe Val Phe
            20                  25                  30

Leu Phe Asp Phe Phe Ala Phe Leu Phe Phe Ala Asn Val Phe Leu Ala
        35                  40                  45

Val Asn Leu Leu Phe Leu Glu Lys Asn Ile Lys Asn Lys Leu Leu Phe
    50                  55                  60

Leu Leu Pro Ile Ser Ile Ile Trp Met Val Ile His Ile Ser Met
65                  70                  75                  80

Ile Asn Ile Lys Phe Tyr Lys Phe Glu His Gln Ile Lys Glu Gln Asn
                85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Val Arg
                165                 170
```

<210> SEQ ID NO 1850
<211> LENGTH: 729
<212> TYPE: DNA
<213> ORGANISM: Neisseria meningitidis

<400> SEQUENCE: 1850

```
atgagacata tgaaaaataa aaattattta ctagtattta gttttaca tatagccttg     60 atagtaatta atatagtgtt tggttatttt gttttctat ttgattttt tgcgttttg    120 tttttgcaa acgtctttct tgctgtaaat ttattatttt tagaaaaaa cataaaaaac    180 aaattattgt ttttattgcc gatttctatt attatatgga tggtaattca tattagtatg    240
ataaatataa aattttataa atttgagcat caaataaagg aacaaaatat atcctcgatt    300
actggggtga taaaaccaca tgatagttat aattatgttt atgactcaaa tggatatgct    360
aaattaaaag ataatcatag atatggtagg gtaattagag aaacacctta tattgatgta    420
gttgcatctg atgttaaaaa taaatccata agattaagct tggtttgtgg tattcattca    480
tatgctccat gtgccaattt tataaaattt gcaaaaaaac ctgttaaaat ttatttttat    540
```

```
aatcaacctc aaggagattt tatagataat gtaatatttg aaattaatga tggaaacaaa    600
agtttgtact tgttagataa gtataaaaca ttttttctta ttgaaaacag tgtttgtatc    660
gtattaatta ttttatattt aaaatttaat ttgcttttat ataggactta cttcaatgag    720
ttggaatag                                                           729
```

<210> SEQ ID NO 1851
<211> LENGTH: 242
<212> TYPE: PRT
<213> ORGANISM: Neisseria meningitidis

<400> SEQUENCE: 1851

```
Met Arg His Met Lys Asn Lys Asn Tyr Leu Leu Val Phe Ile Val Leu
                 5                  10                  15

His Ile Ala Leu Ile Val Ile Asn Ile Val Phe Gly Tyr Phe Val Phe
             20                  25                  30

Leu Phe Asp Phe Phe Ala Phe Leu Phe Phe Ala Asn Val Phe Leu Ala
         35                  40                  45

Val Asn Leu Leu Phe Leu Glu Lys Asn Ile Lys Asn Lys Leu Leu Phe
     50                  55                  60

Leu Leu Pro Ile Ser Ile Ile Trp Met Val Ile His Ile Ser Met
 65                  70                  75                  80

Ile Asn Ile Lys Phe Tyr Lys Phe Glu His Gln Ile Lys Glu Gln Asn
                 85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Asn Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Tyr Arg Thr Tyr Phe Asn Glu
225                 230                 235                 240

Leu Glu
```

<210> SEQ ID NO 1852
<211> LENGTH: 729
<212> TYPE: DNA
<213> ORGANISM: Neisseria meningitidis

<400> SEQUENCE: 1852

```
atgagacata tgaaaaataa aaattattta ctagtattta gttttaca tataaccttg    60 atagtaatta atatagtgtt tggttatttt gtttttctat ttgattttt tgcgttttg   120 tttttgcaa acgtctttct tgctgtaaat ttattttt tagaaaaaaa cataaaaaac   180
aaattattgt ttttattgcc gatttctatt attatatgga tggtaattca tattagtatg   240
```

-continued

```
ataaatataa aatttttataa atttgagcat caaataaagg aacaaaatat atcctcgatt    300
actggggtga taaaaccaca tgatagttat aattatgttt atgactcaaa tggatatgct    360
aaattaaaag ataatcatag atatggtagg gtaattagag aaacaccta tattgatgta    420 gttgcatctg atgttaaaaa taaatccata agattaagct tggtttgtgg tattcattca    480
tatgctccat gtgccaattt tataaaattt gcaaaaaaac ctgttaaaat ttatttttat    540
aatcaacctc aaggagattt tatagataat gtaatatttg aaattaatga tggaaaaaaa    600
agtttgtact tgttagataa gtataaaaca ttttttctta ttgaaaacag tgtttgtatc    660
gtattaatta ttttatattt aaaatttaat ttgcttttat ataggactta cttcaatgag    720
ttggaatag                                                           729
```

<210> SEQ ID NO 1853
<211> LENGTH: 242
<212> TYPE: PRT
<213> ORGANISM: Neisseria meningitidis

<400> SEQUENCE: 1853

Met Arg His Met Lys Asn Lys Asn Tyr Leu Leu Val Phe Ile Val Leu
                5                  10                  15

His Ile Thr Leu Ile Val Ile Asn Ile Val Phe Gly Tyr Phe Val Phe
            20                  25                  30

Leu Phe Asp Phe Phe Ala Phe Leu Phe Phe Ala Asn Val Phe Leu Ala
        35                  40                  45

Val Asn Leu Leu Phe Leu Glu Lys Asn Ile Lys Asn Lys Leu Leu Phe
    50                  55                  60

Leu Leu Pro Ile Ser Ile Ile Trp Met Val Ile His Ile Ser Met
65                  70                  75                  80

Ile Asn Ile Lys Phe Tyr Lys Phe Glu His Gln Ile Lys Glu Gln Asn
                85                  90                  95

Ile Ser Ser Ile Thr Gly Val Ile Lys Pro His Asp Ser Tyr Asn Tyr
            100                 105                 110

Val Tyr Asp Ser Asn Gly Tyr Ala Lys Leu Lys Asp Asn His Arg Tyr
        115                 120                 125

Gly Arg Val Ile Arg Glu Thr Pro Tyr Ile Asp Val Val Ala Ser Asp
    130                 135                 140

Val Lys Asn Lys Ser Ile Arg Leu Ser Leu Val Cys Gly Ile His Ser
145                 150                 155                 160

Tyr Ala Pro Cys Ala Asn Phe Ile Lys Phe Ala Lys Lys Pro Val Lys
                165                 170                 175

Ile Tyr Phe Tyr Asn Gln Pro Gln Gly Asp Phe Ile Asp Asn Val Ile
            180                 185                 190

Phe Glu Ile Asn Asp Gly Lys Lys Ser Leu Tyr Leu Leu Asp Lys Tyr
        195                 200                 205

Lys Thr Phe Phe Leu Ile Glu Asn Ser Val Cys Ile Val Leu Ile Ile
    210                 215                 220

Leu Tyr Leu Lys Phe Asn Leu Leu Tyr Arg Thr Tyr Phe Asn Glu
225                 230                 235                 240

Leu Glu

<210> SEQ ID NO 1854
<211> LENGTH: 552
<212> TYPE: DNA
<213> ORGANISM: Neisseria meningitidis

<400> SEQUENCE: 1854

```
accccccaaca gcgtgaccgt cttgccgtct ttcggcggat tcgggcgtac cggcgcgacc    60
atcaatgcag caggcggggt cggcatgact gccttttcga caaccttaat ttccgtagcc   120
gagggcgcgg ttgtagagct gcaggccgtg agagccaaag ccgtcaatgc aaccgccgct   180
tgcattttta cggtcttgag taaggacatt ttcgatttcc ttttatttt ccgttttcag    240
acggctgact tccgcctgta ttttcgccaa agccatgccg acagcgtgcg ccttgacttc   300
atatttaaaa gcttccgcgc gtgccagttc cagttcgcgc gcatagtttt gagccgacaa   360
cagcagggct gcgccttgt cgcgctccat cttgtcgatg accgcctgca gcttcgcaaa    420
tgccgacttg tagccttgat ggtgcgacac agccaagccc gtgccgacaa gcgcgataat   480
ggcaatcggt tgccagtaat tcgccagcag tttcacgaga ttcattctcg acctcctgac   540
gcttcacgct ga                                                       552
```

<210> SEQ ID NO 1855
<211> LENGTH: 183
<212> TYPE: PRT
<213> ORGANISM: Neisseria meningitidis

<400> SEQUENCE: 1855

```
Thr Pro Asn Ser Val Thr Val Leu Pro Ser Phe Gly Gly Phe Gly Arg
              5                  10                  15
Thr Gly Ala Thr Ile Asn Ala Ala Gly Gly Val Gly Met Thr Ala Phe
         20                  25                  30
Ser Thr Thr Leu Ile Ser Val Ala Glu Gly Ala Val Val Glu Leu Gln
     35                  40                  45
Ala Val Arg Ala Lys Ala Val Asn Ala Thr Ala Ala Cys Ile Phe Thr
 50                  55                  60
Val Leu Ser Lys Asp Ile Phe Asp Phe Leu Phe Ile Phe Arg Phe Gln
 65                  70                  75                  80
Thr Ala Asp Phe Arg Leu Tyr Phe Arg Gln Ser His Ala Asp Ser Val
                 85                  90                  95
Arg Leu Asp Phe Ile Phe Lys Ser Phe Arg Ala Cys Gln Phe Gln Phe
            100                 105                 110
Ala Arg Ile Val Leu Ser Arg Gln Gln Gln Gly Leu Arg Leu Val Ala
        115                 120                 125
Leu His Leu Val Asp Asp Arg Leu Gln Leu Arg Lys Cys Arg Leu Val
    130                 135                 140
Ala Leu Met Val Arg His Ser Gln Ala Arg Ala Asp Lys Arg Asp Asn
145                 150                 155                 160
Gly Asn Arg Leu Pro Val Ile Arg Gln Gln Phe His Glu Ile His Ser
                165                 170                 175
Arg Pro Pro Asp Ala Ser Arg
            180
```

<210> SEQ ID NO 1856
<211> LENGTH: 468
<212> TYPE: DNA
<213> ORGANISM: Neisseria meningitidis

<400> SEQUENCE: 1856

```
atgactgcct ttcgacaac cttaatttcc gtagccgagg gcgcggttgt agagctgcag     60
gccgtgagag ccaaagccgt caatgcaacc gccgcttgca ttttacggt cttgagtaag    120
gacattttcg atttcctttt tattttccgt ttcagacgg ctgacttccg cctgtttttt    180
```

```
cgccaaagcc atgccgacag cgtgcgcctt gacttcatat ttttagctt ccgcgcgtgc     240 cagttccagt tcgcgcgcat agttttgagc cgacaacag agggcttgcg ccttgtcgcg     300
ctccatcttg tcgatgaccg cctgctgctt cgcaaatgcc gacttgtagc cttgatggtg    360
cgacacagcc aagcccgtgc cgacaagcgc gataatggca atcggttgcc agttattcgc    420
cagcagtttc acgagattca ttctcgacct cctgacgctt cacgctga                 468
```

```
<210> SEQ ID NO 1857
<211> LENGTH: 155
<212> TYPE: PRT
<213> ORGANISM: Neisseria meningitidis

<400> SEQUENCE: 1857

Met Thr Ala Phe Ser Thr Thr Leu Ile Ser Val Ala Glu Gly Ala Val
                5                  10                  15
Val Glu Leu Gln Ala Val Arg Ala Lys Ala Val Asn Ala Thr Ala Ala
            20                  25                  30
Cys Ile Phe Thr Val Leu Ser Lys Asp Ile Phe Asp Phe Leu Phe Ile
        35                  40                  45
Phe Arg Phe Gln Thr Ala Asp Phe Arg Leu Phe Arg Gln Ser His
    50                  55                  60
Ala Asp Ser Val Arg Leu Asp Phe Ile Phe Ser Phe Arg Ala Cys
65                  70                  75                  80
Gln Phe Gln Phe Ala Arg Ile Val Leu Ser Arg Gln Gln Gly Leu
                85                  90                  95
Arg Leu Val Ala Leu His Leu Val Asp Asp Arg Leu Leu Arg Lys
            100                 105                 110
Cys Arg Leu Val Ala Leu Met Val Arg His Ser Gln Ala Arg Ala Asp
        115                 120                 125
Lys Arg Asp Asn Gly Asn Arg Leu Pro Val Ile Arg Gln Gln Phe His
    130                 135                 140
Glu Ile His Ser Arg Pro Pro Asp Ala Ser Arg
145                 150                 155
```

```
<210> SEQ ID NO 1858
<211> LENGTH: 462
<212> TYPE: DNA
<213> ORGANISM: Neisseria meningitidis

<400> SEQUENCE: 1858
atgaccgcct tttcgacaac cttaatttcc gtagccgagg gcgcgcttgt agagctgcaa    60
gccgtgatgg ccaaagccgt caatacaacc gccgcctgca tttttacggt cttgagtaag   120
gacattttcg atttcctttt tatttccgt tttcagacgg ctgacttccg cctgtttttt    180
cgccaaagcc atgccgacgg cgtgcgcctt gacttcatat ttttagctt ccgcacgcgc    240 ctgttccagt tcgcgggcgt agttttgagc cgacaacag agggcttgcg ccttgtcgcg    300 cttcatttc tcaatgaccg cctgctgctt cgcaaaagcc gacttgtagc cttgatggtg    360
cgacaccgcc aaacccgtgc cgacaagcgc gatgatggca atcggttgcc agttattcgc    420
cagcagtttc acgagattca ttctcgacct cctgacgttt ga                       462
```

```
<210> SEQ ID NO 1859
<211> LENGTH: 153
<212> TYPE: PRT
<213> ORGANISM: Neisseria meningitidis
```

-continued

```
<400> SEQUENCE: 1859

Met Thr Ala Phe Ser Thr Thr Leu Ile Ser Val Ala Glu Gly Ala Leu
                 5                  10                  15

Val Glu Leu Gln Ala Val Met Ala Lys Ala Val Asn Thr Thr Ala Ala
             20                  25                  30

Cys Ile Phe Thr Val Leu Ser Lys Asp Ile Phe Asp Phe Leu Phe Ile
             35                  40                  45

Phe Arg Phe Gln Thr Ala Asp Phe Arg Leu Phe Phe Arg Gln Ser His
         50                  55                  60

Ala Asp Gly Val Arg Leu Asp Phe Ile Phe Phe Ser Phe Arg Thr Arg
65                      70                  75                  80

Leu Phe Gln Phe Ala Gly Val Val Leu Ser Arg Gln Gln Gln Gly Leu
                 85                  90                  95

Arg Leu Val Ala Leu His Phe Leu Asn Asp Arg Leu Leu Leu Arg Lys
             100                 105                 110

Ser Arg Leu Val Ala Leu Met Val Arg His Arg Gln Thr Arg Ala Asp
         115                 120                 125

Lys Arg Asp Asp Gly Asn Arg Leu Pro Val Ile Arg Gln Gln Phe His
     130                 135                 140

Glu Ile His Ser Arg Pro Pro Asp Val
145                 150
```

ANTIGENIC MENINGOCOCCAL PEPTIDES

All documents cited herein are incorporated by reference in their entirety. In particular, the contents of international patent application WO99/36544 are fully incorporated herein.

FIELD OF THE INVENTION

This invention relates to antigenic peptide sequences from the bacterium *Neisseria meningitidis*.

BACKGROUND

*Neisseria meningitidis* is a non-motile, Gram-negative *diplococcus* that is pathogenic in humans.

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries.

The meningococcal vaccine currently in use is a tetravalent polysaccharide vaccine composed of serogroups A, C, Y and W135. Meningococcus B remains a problem, however. The polysaccharide approach cannot be used because the menb capsular polysaccharide is a polymer of α(2-8)-linked N-acetyl neuraminic acid that is also present in mammalian tissue. One approach to a menB vaccine uses mixtures of outer membrane proteins (OMPs) To overcome the antigenic variability, multivalent vaccines containing up to nine different porins have been constructed [e.g. Poolman J T (1992) *Infect. Agents Dis.* 4:13-28]. Additional proteins to be used in outer membrane vaccines have been the opa and opc proteins, but none of these approaches have been able to overcome the antigenic variability [e.g. Ala'Aldeen & Borriello (1996) *Vaccine* 14(1):49-53].

THE INVENTION

The invention provides fragments of the proteins disclosed in international patent application WO99/36544, wherein the fragments comprise at least one antigenic determinant.

Thus, if the length of any particular protein sequence disclosed in WO99/36544 is x amino acids (see Table II), the present invention provides fragments of at most x−1 amino acids of that protein. The fragment may be shorter than this (e.g. x−2, x−3, x−4, ... ), and is preferably 100 amino acids or less (e.g. 90 amino acids, 80 amino acids etc.). The fragment may be as short as 3 amino acids, but is preferably longer (e.g. up to 6, 7, 8, 9, 10, 12, 15, 20, 25, 30, 35, 40, 50, 75, or 100 amino acids).

Preferred fragments comprise the meningococcal peptide sequences disclosed in Table I, or sub-sequences thereof. The fragments may be longer than those given in Table I e.g. where a fragment in Table I runs from amino acid residue p to residue q of a protein, the invention also relates to fragments from residue (p−1), (p−2), or (p−3) to residue (q+1), (q+2), or (q+3).

The invention also provides polypeptides that are homologous (i.e. have sequence identity) to these fragments. Depending on the particular fragment, the degree of sequence identity is preferably greater than 50% (e.g. 60%, 70%, 80%, 90%, 95%, 99% or more). These homologous polypeptides include mutants and allelic variants of the fragments. Identity between the two sequences is preferably determined by the Smith-Waterman homology search algorithm as implemented in the MPSRCH program (Oxford Molecular), using an affine gap search with parameters gap open penalty=12 and gap extension penalty=1.

The invention also provides proteins comprising one or more of the above-defined fragments.

The invention is subject to the proviso that it does not include within its scope proteins comprising any of the 45 protein sequences disclosed in WO99/36544 (i.e. the even SEQ IDs: 2, 4, 6, 8, 10, ..., 86, 88, 90 of WO99/36544).

The proteins of the invention can, of course, be prepared by various means (e.g. recombinant expression, purification from cell culture, chemical synthesis etc.) and in various forms (e.g. native, C-terminal and/or N-terminal fusions etc.). They are preferably prepared in substantially pure form (i.e. substantially free from other Neisserial or host cell proteins). Short proteins are preferably produced using chemical peptide synthesis.

According to a further aspect, the invention provides antibodies which recognise the fragments of the invention, with the proviso that the invention does not include within its scope antibodies which recognise one of 45 complete protein sequences in WO99/36544. The antibodies may be polyclonal or, preferably, monoclonal, and may be produced by any suitable means.

The invention also provides proteins comprising peptide sequences recognised by these antibodies. These peptide sequences will, of course, include fragments of the meningococcal proteins in WO99/36544, but will also include peptides that mimic the antigenic structure of the meningococcal peptides when bound to immunoglobulin.

According to a further aspect, the invention provides nucleic acid encoding the fragments and proteins of the invention, with the proviso that the invention does not include within its scope nucleic acid encoding one of the 45 protein sequences in WO99/36544.

In addition, the invention provides nucleic acid comprising sequences homologous (i.e. having sequence identity) to these sequences. Furthermore, the invention provides nucleic acid which can hybridise to these sequences, preferably under "high stringency" conditions (e.g. 65° C. in a 0.1×SSC, 0.5% SDS solution).

It should also be appreciated that the invention provides nucleic acid comprising sequences complementary to those described above (e.g. for antisense or probing purposes).

Nucleic acid according to the invention can, of course, be prepared in many ways (e.g. by chemical synthesis, from genomic or cDNA libraries, from the organism itself etc.) and can take various forms (e.g. single stranded, double stranded, vectors, probes etc.). In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (e.g. expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (e.g. as vaccines or as immunogenic compositions) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially strain A or strain B.

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

A summary of standard techniques and procedures which may be employed in order to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature e.g. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional to X, such as X+Y.

The term "antigenic determinant" includes B-cell epitopes and T-cell epitopes.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a meningococcal sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

Expression Systems

The meningococcal nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed*]. Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell, 2nd ed.*]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA". In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Viak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038 (1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Repir*, 11 (2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet*, 202:179-185, 1985. The genetic material may also be transferred into the plant cell by using polyethylene glycol, Krens, et al., *Nature*, 296, 72-74, 1982. Another method of introduction of nucleic acid segments is high velocity ballistic penetration by small particles with the nucleic acid either within the matrix of small beads or particles, or on the surface, Klein, et al., *Nature*, 327, 70-73, 1987 and Knudsen and Muller, 1991, *Planta*, 185:330-336 teaching particle bombardment of barley endosperm to create transgenic barley. Yet another method of introduction would be fusion of protoplasts with other entities, either mini-cells, cells, lysosomes or other fusible lipid-surfaced bodies, Fraley, et al., *Proc. Natl. Acad. Sci. USA*, 79, 1859-1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Pelunia, Digitalis, Majorana, Cichorium, Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EP-A-0267851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad. Sci. USA*

79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids". In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation", in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0284044), glucose-6-phosphate isomerase, glyceraldehyde-3-phosphate-dehydrogenase (GAP or GAPDH), enolase, glucokinase, hexokinase, phosphofructokinase, 3-phosphoglycerate mutase, and pyruvate kinase (PyK) (EP-A-0329203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. EP-A-0 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (e.g. WO88/ 024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCl/1 [Brake et al. (1984) *Proc. Natl. Acad. Sci USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying meningococcal proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (e.g. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g. see WO98/20734), needles, and gene guns or hypospreys. Dosage treatment may be a single dose schedule or a multiple dose schedule.

Vaccines

Vaccines according to the invention may either be prophylactic (i.e. to prevent infection) or therapeutic (i.e. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ adjuvant (Chiron Corporation, Emeryville, Calif.; WO 90/14837; Chapter 10 in *Vaccine design: the subunit and adjuvant approach*, eds. Powell & Newman, Plenum Press 1995), containing 5% Squalene, 0.5% TWEEN 80 surfactant (Uniqema, New Castle, Del.), and 0.5% SPAN 85 surfactant (Uniqema) (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80 surfactant (Uniqema), 5% pluronic-blocked polymer L121, and thr-MDP (see below) either microfluidized into a submicron emulsion or vortexed to generate a larger particle size emulsion, and (c) RIBI adjuvant system (RAS), (Corixa Corporation, Seattle, Wash.) containing 2% Squalene, 0.2% Tween 80, and one or more bacterial cell wall components from the group consisting of monophosphorylipid A (MPL), trehalose dimycolate (TDM), and cell wall skeleton (CWS), preferably DETOX adjuvant (MPL+CWS) (Corixa Corporation); (3) saponin adjuvants, such as STIMULON adjuvant (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc; and (6) other substances that act as immunostimulating agents to enhance the effectiveness of the composition. Alum and MF59™ adjuvant (Chiron Corporation) are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MLP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [e.g. Robinson & Torres (1997) *Seminars in Immunology* 9:271-283; Donnelly et al. (1997) *Annu Rev Immunol* 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplit (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses e.g. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (e.g. HT1080 cells) or mink parent cell lines, which eliminates inactivation in human serum.

Preferred retroviruses for the construction of retroviral gene therapy vectors include Avian Leukosis Virus, Bovine Leukemia Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19: 19-25), Abelson (ATCC No. VR-999), Friend (ATCC No. VR-245), Graffi, Gross (ATCC No. VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") at 10801 University Boulevard, Manassas, Va. 20110-2209 or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC at 10801 University Boulevard, Manassas, Va. 20110-2209 or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g. see WO98/20734), needles, and gene guns or hyposprays. Dosage treatment may be a single dose schedule or a multiple dose schedule.

Methods for the ex vivo delivery and reimplantation of transformed cells into a subject are known in the art and described in e.g. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta*. 1097:1-17; Straubinger (1983) *Meth. Enzymol*. 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem*. 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, e.g. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See e.g. Straubinger (1983) *Meth. Immunol*. 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun*. 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem*. (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C & E, over time these lipoproteins lose A and acquire C & E apoproteins. VLDL comprises A, B, C & E apoproteins, LDL comprises apoprotein B; HDL comprises apoproteins A, C, & E.

The amino acid of these apoproteins are known and are described in, for example, Breslow (1985) *Annu Rev. Biochem* 54:699; Law (1986) *Adv. Exp Med. Biol*. 151:162;

Chen (1986) J Biol Chem 261:12918; Kane (1980) Proc Natl Acad Sci USA 77:2465; and Utermann (1984) Hum Genet 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in Zuckermann et al. WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Meningogoccal antigens of the invention can be used in immunoassays to detect antibody levels (or, conversely, antimeningococcal antibodies can be used to detect antigen levels). Immunoassays based on well defined, recombinant antigens can be developed to replace invasive diagnostics methods. Antibodies to meningococcal proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10} Ci)+0.4[\%(G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the meningococcal nucleotide sequences of the invention (including both sense and antisense strands). Though many different nucleotide sequences will encode the amino acid sequence, the native meningococcal sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the meningococcal sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional meningococcal sequence may also be helpful as a label to detect the formed duplex. For example, a non-complementary nucleotide sequence may be attached to the 5' end of the probe, with the remainder of the probe sequence being complementary to a meningococcal sequence. Alternatively, non-complementary bases or longer sequences can be interspersed into the probe, provided that the probe sequence has sufficient complementarity with the a meningococcal sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Nat. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated e.g. backbone modifications, such as phosphorothioates or methylphosphonates, can be used to increase in vivo half-life, alter RNA affinity, increase nuclease resistance etc. [e.g. see Agrawal & Iyer (1995) *Curr Opin Biotechnol* 6:12-19; Agrawal (1996) *TIBTECH* 14:376-387]; analogues such as peptide nucleic acids may also be used [e.g. see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acids. The assay is described in: Mullis et al. [*Meth. Enzymol.* (1987) 155: 335-350]; U.S. Pat. Nos. 4,683, 195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired meningococcal sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the meningococcal sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

Examples of Preferred Fragments

The protein sequences disclosed in WO99/36544 have been subjected to computer analysis to predict antigenic peptide fragments within the full-length proteins. Three algorithms have been used in this analysis:

AMPHI This program has been used to predict T-cell epitopes [Gao et al. (1989) *J. Immunol.* 143:3007; Roberts et al. (1996) *AIDS Res Hum Retrovir* 12:593; Quakyi et al. (1992) *Scand J Immunol* suppl. 11:9] and is available in the Protean package of DNASTAR, Inc. (1228 South Park Street, Madison, Wis. 53715 USA).

ANTIGENIC INDEX as disclosed by Jameson & Wolf (1988) The antigenic index: a novel algorithm for predicting antigenic determinants. *CABIOS* 4:181:186.

HYDROPHILICITY as disclosed by Hopp & Woods (1981) Prediction of protein antigenic determinants from amino acid sequences. *PNAS USA* 78:3824-3828

Table I indicates preferred fragments of the proteins disclosed in WO99/36544. The three algorithms often identify the same fragments (e.g. ORF38-1—the fragments from residue 37-42 and 143-146 are both identified twice). Such multiply-identified fragments are particularly preferred. The algorithms often identify overlapping fragments (e.g. ORF40-1—AMPHI identifies residues 161-165, and Hydrophilicity identified residues 163-175). The invention explicitly includes fragments resulting from a combination of these overlapping fragments (e.g. the fragment from residue 161 to residue 175 in the case of ORF40-1). Fragments separated by a single amino acid are also often identified (e.g. ORF40-1 Antigenic Index 423-426 and 428-438). The invention also includes fragments spanning the two extremes of such "adjacent" fragments (e.g. 423-438 for ORF40-1).

TABLE I 1769 fragments of the proteins disclosed in WO99/36544

| Fragment# (SEQ ID NO) | WO99/36544 ORF | Algorithm | Amino Acids |
|---|---|---|---|
| 1. | 38-1 | AMPHI | 6-14 |
| 2. | 38-1 | AMPHI | 57-59 |
| 3. | 38-1 | AMPHI | 67-76 |
| 4. | 38-1 | AMPHI | 92-100 |
| 5. | 38-1 | AMPHI | 127-137 |
| 6. | 38-1 | AMPHI | 149-166 |
| 7. | 38-1 | AMPHI | 210-215 |
| 8. | 38-1 | AMPHI | 231-236 |
| 9. | 38-1 | AMPHI | 270-272 |
| 10. | 38-1 | AMPHI | 303-320 |
| 11. | 38-1 | Antigenic Index | 16-34 |
| 12. | 38-1 | Antigenic Index | 37-42 |
| 13. | 38-1 | Antigenic Index | 46-64 |
| 14. | 38-1 | Antigenic Index | 72-91 |
| 15. | 38-1 | Antigenic Index | 94-112 |
| 16. | 38-1 | Antigenic Index | 114-117 |
| 17. | 38-1 | Antigenic Index | 124-136 |
| 18. | 38-1 | Antigenic Index | 143-146 |
| 19. | 38-1 | Antigenic Index | 148-160 |
| 20. | 38-1 | Antigenic Index | 167-195 |
| 21. | 38-1 | Antigenic Index | 201-216 |
| 22. | 38-1 | Antigenic Index | 218-240 |
| 23. | 38-1 | Antigenic Index | 244-252 |
| 24. | 38-1 | Antigenic Index | 257-278 |
| 25. | 38-1 | Antigenic Index | 282-290 |
| 26. | 38-1 | Antigenic Index | 308-314 |
| 27. | 38-1 | Hydrophilicity | 21-34 |
| 28. | 38-1 | Hydrophilicity | 37-42 |
| 29. | 38-1 | Hydrophilicity | 47-55 |
| 30. | 38-1 | Hydrophilicity | 57-61 |
| 31. | 38-1 | Hydrophilicity | 72-74 |
| 32. | 38-1 | Hydrophilicity | 76-78 |
| 33. | 38-1 | Hydrophilicity | 82-91 |
| 34. | 38-1 | Hydrophilicity | 94-101 |
| 35. | 38-1 | Hydrophilicity | 108-112 |
| 36. | 38-1 | Hydrophilicity | 126-136 |
| 37. | 38-1 | Hydrophilicity | 143-146 |
| 38. | 38-1 | Hydrophilicity | 148-160 |
| 39. | 38-1 | Hydrophilicity | 167-195 |
| 40. | 38-1 | Hydrophilicity | 221-223 |
| 41. | 38-1 | Hydrophilicity | 226-236 |
| 42. | 38-1 | Hydrophilicity | 244-250 |
| 43. | 38-1 | Hydrophilicity | 257-274 |
| 44. | 38-1 | Hydrophilicity | 282-286 |
| 45. | 38-1 | Hydrophilicity | 311-314 |
| 46. | 38a | AMPHI | 6-14 |
| 47. | 38a | AMPHI | 57-59 |
| 48. | 38a | AMPHI | 67-76 |
| 49. | 38a | AMPHI | 92-100 |
| 50. | 38a | AMPHI | 127-137 |
| 51. | 38a | AMPHI | 149-166 |
| 52. | 38a | AMPHI | 210-215 |
| 53. | 38a | AMPHI | 223-225 |
| 54. | 38a | AMPHI | 231-236 |
| 55. | 38a | AMPHI | 270-272 |
| 56. | 38a | AMPHI | 303-320 |
| 57. | 38a | Antigenic Index | 16-34 |
| 58. | 38a | Antigenic Index | 37-42 |
| 59. | 38a | Antigenic Index | 46-64 |
| 60. | 38a | Antigenic Index | 72-91 |
| 61. | 38a | Antigenic Index | 94-112 |
| 62. | 38a | Antigenic Index | 114-117 |
| 63. | 38a | Antigenic Index | 124-136 |
| 64. | 38a | Antigenic Index | 143-146 |
| 65. | 38a | Antigenic Index | 148-160 |
| 66. | 38a | Antigenic Index | 165-195 |
| 67. | 38a | Antigenic Index | 201-216 |
| 68. | 38a | Antigenic Index | 218-240 |
| 69. | 38a | Antigenic Index | 244-252 |
| 70. | 38a | Antigenic Index | 257-278 |
| 71. | 38a | Antigenic Index | 282-290 |
| 72. | 38a | Antigenic Index | 308-314 |
| 73. | 38a | Hydrophilicity | 21-34 |
| 74. | 38a | Hydrophilicity | 37-42 |
| 75. | 38a | Hydrophilicity | 47-55 |
| 76. | 38a | Hydrophilicity | 57-61 |
| 77. | 38a | Hydrophilicity | 72-74 |
| 78. | 38a | Hydrophilicity | 76-78 |
| 79. | 38a | Hydrophilicity | 82-91 |
| 80. | 38a | Hydrophilicity | 94-101 |
| 81. | 38a | Hydrophilicity | 108-112 |
| 82. | 38a | Hydrophilicity | 126-136 |
| 83. | 38a | Hydrophilicity | 143-146 |
| 84. | 38a | Hydrophilicity | 148-160 |
| 85. | 38a | Hydrophilicity | 165-195 |
| 86. | 38a | Hydrophilicity | 221-223 |
| 87. | 38a | Hydrophilicity | 226-236 |
| 88. | 38a | Hydrophilicity | 244-250 |
| 89. | 38a | Hydrophilicity | 257-273 |
| 90. | 38a | Hydrophilicity | 282-286 |
| 91. | 38a | Hydrophilicity | 311-314 |
| 92. | 39-1 | AMPHI | 6-13 |
| 93. | 39-1 | AMPHI | 21-24 |
| 94. | 39-1 | AMPHI | 37-40 |
| 95. | 39-1 | AMPHI | 60-75 |
| 96. | 39-1 | AMPHI | 118-122 |
| 97. | 39-1 | AMPHI | 134-139 |
| 98. | 39-1 | AMPHI | 165-183 |
| 99. | 39-1 | AMPHI | 192-195 |
| 100. | 39-1 | AMPHI | 233-241 |
| 101. | 39-1 | AMPHI | 247-267 |
| 102. | 39-1 | AMPHI | 273-275 |
| 103. | 39-1 | AMPHI | 299-308 |
| 104. | 39-1 | AMPHI | 310-319 |
| 105. | 39-1 | AMPHI | 322-330 |
| 106. | 39-1 | AMPHI | 338-347 |
| 107. | 39-1 | AMPHI | 358-364 |
| 108. | 39-1 | AMPHI | 366-368 |
| 109. | 39-1 | AMPHI | 376-378 |
| 110. | 39-1 | AMPHI | 385-392 |
| 111. | 39-1 | AMPHI | 413-416 |

TABLE I-continued

1769 fragments of the proteins disclosed in WO99/36544

| Fragment# (SEQ ID NO) | WO99/36544 ORF | Algorithm | Amino Acids |
|---|---|---|---|
| 112. | 39-1 | AMPHI | 421-424 |
| 113. | 39-1 | AMPHI | 429-438 |
| 114. | 39-1 | AMPHI | 445-454 |
| 115. | 39-1 | AMPHI | 456-458 |
| 116. | 39-1 | AMPHI | 498-500 |
| 117. | 39-1 | AMPHI | 512-519 |
| 118. | 39-1 | AMPHI | 576-587 |
| 119. | 39-1 | AMPHI | 589-600 |
| 120. | 39-1 | AMPHI | 650-652 |
| 121. | 39-1 | AMPHI | 670-674 |
| 122. | 39-1 | Antigenic Index | 26-32 |
| 123. | 39-1 | Antigenic Index | 35-45 |
| 124. | 39-1 | Antigenic Index | 54-69 |
| 125. | 39-1 | Antigenic Index | 79-84 |
| 126. | 39-1 | Antigenic Index | 88-96 |
| 127. | 39-1 | Antigenic Index | 105-110 |
| 128. | 39-1 | Antigenic Index | 117-124 |
| 129. | 39-1 | Antigenic Index | 152-154 |
| 130. | 39-1 | Antigenic Index | 190-192 |
| 131. | 39-1 | Antigenic Index | 222-231 |
| 132. | 39-1 | Antigenic Index | 246-265 |
| 133. | 39-1 | Antigenic Index | 292-295 |
| 134. | 39-1 | Antigenic Index | 318-335 |
| 135. | 39-1 | Antigenic Index | 353-362 |
| 136. | 39-1 | Antigenic Index | 370-372 |
| 137. | 39-1 | Antigenic Index | 402-404 |
| 138. | 39-1 | Antigenic Index | 406-408 |
| 139. | 39-1 | Antigenic Index | 419-421 |
| 140. | 39-1 | Antigenic Index | 446-449 |
| 141. | 39-1 | Antigenic Index | 453-460 |
| 142. | 39-1 | Antigenic Index | 465-469 |
| 143. | 39-1 | Antigenic Index | 476-487 |
| 144. | 39-1 | Antigenic Index | 491-499 |
| 145. | 39-1 | Antigenic Index | 505-514 |
| 146. | 39-1 | Antigenic Index | 522-536 |
| 147. | 39-1 | Antigenic Index | 557-567 |
| 148. | 39-1 | Antigenic Index | 569-575 |
| 149. | 39-1 | Antigenic Index | 577-580 |
| 150. | 39-1 | Antigenic Index | 593-599 |
| 151. | 39-1 | Antigenic Index | 603-619 |
| 152. | 39-1 | Antigenic Index | 626-628 |
| 153. | 39-1 | Antigenic Index | 634-637 |
| 154. | 39-1 | Antigenic Index | 639-647 |
| 155. | 39-1 | Antigenic Index | 655-658 |
| 156. | 39-1 | Antigenic Index | 672-674 |
| 157. | 39-1 | Antigenic Index | 677-686 |
| 158. | 39-1 | Antigenic Index | 688-691 |
| 159. | 39-1 | Antigenic Index | 693-699 |
| 160. | 39-1 | Antigenic Index | 707-710 |
| 161. | 39-1 | Hydrophilicity | 28-32 |
| 162. | 39-1 | Hydrophilicity | 38-44 |
| 163. | 39-1 | Hydrophilicity | 54-69 |
| 164. | 39-1 | Hydrophilicity | 80-83 |
| 165. | 39-1 | Hydrophilicity | 89-96 |
| 166. | 39-1 | Hydrophilicity | 117-119 |
| 167. | 39-1 | Hydrophilicity | 121-123 |
| 168. | 39-1 | Hydrophilicity | 152-154 |
| 169. | 39-1 | Hydrophilicity | 224-231 |
| 170. | 39-1 | Hydrophilicity | 247-265 |
| 171. | 39-1 | Hydrophilicity | 318-332 |
| 172. | 39-1 | Hydrophilicity | 357-361 |
| 173. | 39-1 | Hydrophilicity | 402-404 |
| 174. | 39-1 | Hydrophilicity | 406-408 |
| 175. | 39-1 | Hydrophilicity | 446-449 |
| 176. | 39-1 | Hydrophilicity | 454-459 |
| 177. | 39-1 | Hydrophilicity | 465-469 |
| 178. | 39-1 | Hydrophilicity | 476-487 |
| 179. | 39-1 | Hydrophilicity | 491-499 |
| 180. | 39-1 | Hydrophilicity | 506-514 |
| 181. | 39-1 | Hydrophilicity | 525-535 |
| 182. | 39-1 | Hydrophilicity | 560-567 |
| 183. | 39-1 | Hydrophilicity | 573-575 |
| 184. | 39-1 | Hydrophilicity | 577-580 |
| 185. | 39-1 | Hydrophilicity | 594-596 |
| 186. | 39-1 | Hydrophilicity | 605-607 |
| 187. | 39-1 | Hydrophilicity | 611-619 |
| 188. | 39-1 | Hydrophilicity | 634-637 |
| 189. | 39-1 | Hydrophilicity | 639-647 |
| 190. | 39-1 | Hydrophilicity | 672-674 |
| 191. | 39-1 | Hydrophilicity | 677-686 |
| 192. | 39-1 | Hydrophilicity | 688-690 |
| 193. | 39-1 | Hydrophilicity | 693-695 |
| 194. | 39a | AMPHI | 6-13 |
| 195. | 39a | AMPHI | 21-24 |
| 196. | 39a | AMPHI | 37-40 |
| 197. | 39a | AMPHI | 60-75 |
| 198. | 39a | AMPHI | 118-122 |
| 199. | 39a | AMPHI | 134-139 |
| 200. | 39a | AMPHI | 165-183 |
| 201. | 39a | AMPHI | 192-195 |
| 202. | 39a | AMPHI | 233-241 |
| 203. | 39a | AMPHI | 247-267 |
| 204. | 39a | AMPHI | 273-275 |
| 205. | 39a | AMPHI | 299-308 |
| 206. | 39a | AMPHI | 310-319 |
| 207. | 39a | AMPHI | 322-330 |
| 208. | 39a | AMPHI | 338-347 |
| 209. | 39a | AMPHI | 358-364 |
| 210. | 39a | AMPHI | 366-368 |
| 211. | 39a | AMPHI | 376-378 |
| 212. | 39a | AMPHI | 385-392 |
| 213. | 39a | AMPHI | 413-416 |
| 214. | 39a | AMPHI | 421-424 |
| 215. | 39a | AMPHI | 429-438 |
| 216. | 39a | AMPHI | 445-454 |
| 217. | 39a | AMPHI | 456-458 |
| 218. | 39a | AMPHI | 498-500 |
| 219. | 39a | AMPHI | 512-520 |
| 220. | 39a | AMPHI | 576-587 |
| 221. | 39a | AMPHI | 589-600 |
| 222. | 39a | AMPHI | 650-652 |
| 223. | 39a | AMPHI | 670-674 |
| 224. | 39a | Antigenic Index | 26-32 |
| 225. | 39a | Antigenic Index | 35-45 |
| 226. | 39a | Antigenic Index | 54-69 |
| 227. | 39a | Antigenic Index | 79-84 |
| 228. | 39a | Antigenic Index | 89-96 |
| 229. | 39a | Antigenic Index | 103-110 |
| 230. | 39a | Antigenic Index | 117-124 |
| 231. | 39a | Antigenic Index | 152-154 |
| 232. | 39a | Antigenic Index | 190-192 |
| 233. | 39a | Antigenic Index | 222-231 |
| 234. | 39a | Antigenic Index | 246-265 |
| 235. | 39a | Antigenic Index | 292-295 |
| 236. | 39a | Antigenic Index | 318-335 |
| 237. | 39a | Antigenic Index | 353-362 |
| 238. | 39a | Antigenic Index | 370-372 |
| 239. | 39a | Antigenic Index | 402-404 |
| 240. | 39a | Antigenic Index | 406-408 |
| 241. | 39a | Antigenic Index | 419-421 |
| 242. | 39a | Antigenic Index | 446-449 |
| 243. | 39a | Antigenic Index | 453-460 |
| 244. | 39a | Antigenic Index | 465-469 |
| 245. | 39a | Antigenic Index | 476-487 |
| 246. | 39a | Antigenic Index | 491-499 |
| 247. | 39a | Antigenic Index | 505-514 |
| 248. | 39a | Antigenic Index | 529-535 |
| 249. | 39a | Antigenic Index | 557-567 |
| 250. | 39a | Antigenic Index | 569-575 |
| 251. | 39a | Antigenic Index | 577-580 |
| 252. | 39a | Antigenic Index | 593-599 |
| 253. | 39a | Antigenic Index | 603-619 |
| 254. | 39a | Antigenic Index | 626-628 |
| 255. | 39a | Antigenic Index | 634-637 |
| 256. | 39a | Antigenic Index | 639-647 |
| 257. | 39a | Antigenic Index | 655-658 |
| 258. | 39a | Antigenic Index | 672-674 |
| 259. | 39a | Antigenic Index | 677-686 |

TABLE I-continued

1769 fragments of the proteins disclosed in WO99/36544

| Fragment# (SEQ ID NO) | WO99/36544 ORF | Algorithm | Amino Acids |
|---|---|---|---|
| 260. | 39a | Antigenic Index | 688-691 |
| 261. | 39a | Antigenic Index | 693-699 |
| 262. | 39a | Antigenic Index | 707-710 |
| 263. | 39a | Hydrophilicity | 28-32 |
| 264. | 39a | Hydrophilicity | 38-44 |
| 265. | 39a | Hydrophilicity | 54-69 |
| 266. | 39a | Hydrophilicity | 80-83 |
| 267. | 39a | Hydrophilicity | 89-95 |
| 268. | 39a | Hydrophilicity | 105-108 |
| 269. | 39a | Hydrophilicity | 117-119 |
| 270. | 39a | Hydrophilicity | 121-123 |
| 271. | 39a | Hydrophilicity | 152-154 |
| 272. | 39a | Hydrophilicity | 224-231 |
| 273. | 39a | Hydrophilicity | 247-265 |
| 274. | 39a | Hydrophilicity | 318-332 |
| 275. | 39a | Hydrophilicity | 357-361 |
| 276. | 39a | Hydrophilicity | 402-404 |
| 277. | 39a | Hydrophilicity | 406-408 |
| 278. | 39a | Hydrophilicity | 446-449 |
| 279. | 39a | Hydrophilicity | 454-459 |
| 280. | 39a | Hydrophilicity | 465-469 |
| 281. | 39a | Hydrophilicity | 476-487 |
| 282. | 39a | Hydrophilicity | 491-499 |
| 283. | 39a | Hydrophilicity | 506-514 |
| 284. | 39a | Hydrophilicity | 529-535 |
| 285. | 39a | Hydrophilicity | 560-567 |
| 286. | 39a | Hydrophilicity | 573-575 |
| 287. | 39a | Hydrophilicity | 577-580 |
| 288. | 39a | Hydrophilicity | 594-596 |
| 289. | 39a | Hydrophilicity | 605-607 |
| 290. | 39a | Hydrophilicity | 611-619 |
| 291. | 39a | Hydrophilicity | 634-637 |
| 292. | 39a | Hydrophilicity | 639-647 |
| 293. | 39a | Hydrophilicity | 672-674 |
| 294. | 39a | Hydrophilicity | 677-686 |
| 295. | 39a | Hydrophilicity | 688-690 |
| 296. | 39a | Hydrophilicity | 693-695 |
| 297. | 40-1 | AMPHI | 6-14 |
| 298. | 40-1 | AMPHI | 16-19 |
| 299. | 40-1 | AMPHI | 22-27 |
| 300. | 40-1 | AMPHI | 30-33 |
| 301. | 40-1 | AMPHI | 41-44 |
| 302. | 40-1 | AMPHI | 62-68 |
| 303. | 40-1 | AMPHI | 129-139 |
| 304. | 40-1 | AMPHI | 161-165 |
| 305. | 40-1 | AMPHI | 181-191 |
| 306. | 40-1 | AMPHI | 199-202 |
| 307. | 40-1 | AMPHI | 215-220 |
| 308. | 40-1 | AMPHI | 237-249 |
| 309. | 40-1 | AMPHI | 298-302 |
| 310. | 40-1 | AMPHI | 313-318 |
| 311. | 40-1 | AMPHI | 335-342 |
| 312. | 40-1 | AMPHI | 376-383 |
| 313. | 40-1 | AMPHI | 399-402 |
| 314. | 40-1 | AMPHI | 426-428 |
| 315. | 40-1 | AMPHI | 430-433 |
| 316. | 40-1 | AMPHI | 435-437 |
| 317. | 40-1 | AMPHI | 479-482 |
| 318. | 40-1 | AMPHI | 491-511 |
| 319. | 40-1 | AMPHI | 523-525 |
| 320. | 40-1 | AMPHI | 560-563 |
| 321. | 40-1 | Antigenic Index | 21-32 |
| 322. | 40-1 | Antigenic Index | 49-61 |
| 323. | 40-1 | Antigenic Index | 64-66 |
| 324. | 40-1 | Antigenic Index | 74-92 |
| 325. | 40-1 | Antigenic Index | 98-123 |
| 326. | 40-1 | Antigenic Index | 129-135 |
| 327. | 40-1 | Antigenic Index | 138-176 |
| 328. | 40-1 | Antigenic Index | 193-195 |
| 329. | 40-1 | Antigenic Index | 199-219 |
| 330. | 40-1 | Antigenic Index | 226-240 |
| 331. | 40-1 | Antigenic Index | 242-245 |
| 332. | 40-1 | Antigenic Index | 251-257 |
| 333. | 40-1 | Antigenic Index | 261-276 |
| 334. | 40-1 | Antigenic Index | 279-306 |
| 335. | 40-1 | Antigenic Index | 308-346 |
| 336. | 40-1 | Antigenic Index | 352-367 |
| 337. | 40-1 | Antigenic Index | 375-378 |
| 338. | 40-1 | Antigenic Index | 384-406 |
| 339. | 40-1 | Antigenic Index | 408-420 |
| 340. | 40-1 | Antigenic Index | 423-426 |
| 341. | 40-1 | Antigenic Index | 428-438 |
| 342. | 40-1 | Antigenic Index | 453-459 |
| 343. | 40-1 | Antigenic Index | 462-481 |
| 344. | 40-1 | Antigenic Index | 485-494 |
| 345. | 40-1 | Antigenic Index | 506-518 |
| 346. | 40-1 | Antigenic Index | 535-539 |
| 347. | 40-1 | Antigenic Index | 544-552 |
| 348. | 40-1 | Antigenic Index | 559-566 |
| 349. | 40-1 | Antigenic Index | 571-582 |
| 350. | 40-1 | Hydrophilicity | 21-32 |
| 351. | 40-1 | Hydrophilicity | 51-61 |
| 352. | 40-1 | Hydrophilicity | 64-66 |
| 353. | 40-1 | Hydrophilicity | 75-92 |
| 354. | 40-1 | Hydrophilicity | 100-122 |
| 355. | 40-1 | Hydrophilicity | 129-135 |
| 356. | 40-1 | Hydrophilicity | 140-145 |
| 357. | 40-1 | Hydrophilicity | 149-152 |
| 358. | 40-1 | Hydrophilicity | 157-161 |
| 359. | 40-1 | Hydrophilicity | 163-175 |
| 360. | 40-1 | Hydrophilicity | 199-201 |
| 361. | 40-1 | Hydrophilicity | 203-219 |
| 362. | 40-1 | Hydrophilicity | 227-240 |
| 363. | 40-1 | Hydrophilicity | 251-257 |
| 364. | 40-1 | Hydrophilicity | 261-276 |
| 365. | 40-1 | Hydrophilicity | 279-306 |
| 366. | 40-1 | Hydrophilicity | 308-318 |
| 367. | 40-1 | Hydrophilicity | 320-328 |
| 368. | 40-1 | Hydrophilicity | 334-341 |
| 369. | 40-1 | Hydrophilicity | 354-356 |
| 370. | 40-1 | Hydrophilicity | 359-366 |
| 371. | 40-1 | Hydrophilicity | 392-398 |
| 372. | 40-1 | Hydrophilicity | 400-405 |
| 373. | 40-1 | Hydrophilicity | 410-420 |
| 374. | 40-1 | Hydrophilicity | 429-438 |
| 375. | 40-1 | Hydrophilicity | 463-467 |
| 376. | 40-1 | Hydrophilicity | 471-480 |
| 377. | 40-1 | Hydrophilicity | 487-493 |
| 378. | 40-1 | Hydrophilicity | 506-518 |
| 379. | 40-1 | Hydrophilicity | 547-552 |
| 380. | 40-1 | Hydrophilicity | 575-579 |
| 381. | 40a | AMPHI | 6-10 |
| 382. | 40a | AMPHI | 19-27 |
| 383. | 40a | AMPHI | 30-33 |
| 384. | 40a | AMPHI | 41-44 |
| 385. | 40a | AMPHI | 61-72 |
| 386. | 40a | AMPHI | 78-81 |
| 387. | 40a | AMPHI | 92-94 |
| 388. | 40a | AMPHI | 128-130 |
| 389. | 40a | AMPHI | 132-134 |
| 390. | 40a | AMPHI | 161-165 |
| 391. | 40a | AMPHI | 181-193 |
| 392. | 40a | AMPHI | 197-199 |
| 393. | 40a | AMPHI | 204-211 |
| 394. | 40a | AMPHI | 213-218 |
| 395. | 40a | AMPHI | 227-229 |
| 396. | 40a | AMPHI | 237-249 |
| 397. | 40a | AMPHI | 298-302 |
| 398. | 40a | AMPHI | 313-318 |
| 399. | 40a | AMPHI | 335-342 |
| 400. | 40a | AMPHI | 376-383 |
| 401. | 40a | AMPHI | 399-402 |
| 402. | 40a | AMPHI | 426-428 |
| 403. | 40a | AMPHI | 435-437 |
| 404. | 40a | AMPHI | 475-483 |
| 405. | 40a | AMPHI | 492-512 |
| 406. | 40a | AMPHI | 524-526 |
| 407. | 40a | AMPHI | 561-564 |

TABLE I-continued

1769 fragments of the proteins disclosed in WO99/36544

| Fragment# (SEQ ID NO) | WO99/36544 ORF | Algorithm | Amino Acids |
|---|---|---|---|
| 408. | 40a | Antigenic Index | 21-34 |
| 409. | 40a | Antigenic Index | 50-64 |
| 410. | 40a | Antigenic Index | 75-83 |
| 411. | 40a | Antigenic Index | 88-97 |
| 412. | 40a | Antigenic Index | 105-122 |
| 413. | 40a | Antigenic Index | 129-134 |
| 414. | 40a | Antigenic Index | 140-176 |
| 415. | 40a | Antigenic Index | 190-207 |
| 416. | 40a | Antigenic Index | 211-217 |
| 417. | 40a | Antigenic Index | 224-240 |
| 418. | 40a | Antigenic Index | 242-245 |
| 419. | 40a | Antigenic Index | 250-255 |
| 420. | 40a | Antigenic Index | 260-276 |
| 421. | 40a | Antigenic Index | 279-306 |
| 422. | 40a | Antigenic Index | 308-346 |
| 423. | 40a | Antigenic Index | 352-367 |
| 424. | 40a | Antigenic Index | 375-378 |
| 425. | 40a | Antigenic Index | 384-406 |
| 426. | 40a | Antigenic Index | 408-420 |
| 427. | 40a | Antigenic Index | 423-438 |
| 428. | 40a | Antigenic Index | 453-468 |
| 429. | 40a | Antigenic Index | 471-481 |
| 430. | 40a | Antigenic Index | 487-493 |
| 431. | 40a | Antigenic Index | 507-519 |
| 432. | 40a | Antigenic Index | 536-540 |
| 433. | 40a | Antigenic Index | 545-553 |
| 434. | 40a | Antigenic Index | 560-567 |
| 435. | 40a | Antigenic Index | 572-583 |
| 436. | 40a | Hydrophilicity | 21-34 |
| 437. | 40a | Hydrophilicity | 50-64 |
| 438. | 40a | Hydrophilicity | 75-83 |
| 439. | 40a | Hydrophilicity | 88-96 |
| 440. | 40a | Hydrophilicity | 105-121 |
| 441. | 40a | Hydrophilicity | 129-134 |
| 442. | 40a | Hydrophilicity | 140-145 |
| 443. | 40a | Hydrophilicity | 148-155 |
| 444. | 40a | Hydrophilicity | 157-161 |
| 445. | 40a | Hydrophilicity | 163-175 |
| 446. | 40a | Hydrophilicity | 196-202 |
| 447. | 40a | Hydrophilicity | 211-217 |
| 448. | 40a | Hydrophilicity | 225-230 |
| 449. | 40a | Hydrophilicity | 232-240 |
| 450. | 40a | Hydrophilicity | 253-255 |
| 451. | 40a | Hydrophilicity | 261-276 |
| 452. | 40a | Hydrophilicity | 279-306 |
| 453. | 40a | Hydrophilicity | 308-318 |
| 454. | 40a | Hydrophilicity | 320-328 |
| 455. | 40a | Hydrophilicity | 334-341 |
| 456. | 40a | Hydrophilicity | 354-356 |
| 457. | 40a | Hydrophilicity | 359-366 |
| 458. | 40a | Hydrophilicity | 392-398 |
| 459. | 40a | Hydrophilicity | 400-405 |
| 460. | 40a | Hydrophilicity | 410-420 |
| 461. | 40a | Hydrophilicity | 428-438 |
| 462. | 40a | Hydrophilicity | 462-468 |
| 463. | 40a | Hydrophilicity | 472-481 |
| 464. | 40a | Hydrophilicity | 489-493 |
| 465. | 40a | Hydrophilicity | 507-519 |
| 466. | 40a | Hydrophilicity | 548-553 |
| 467. | 40a | Hydrophilicity | 576-580 |
| 468. | 41-1 | AMPHI | 30-36 |
| 469. | 41-1 | AMPHI | 93-98 |
| 470. | 41-1 | AMPHI | 111-122 |
| 471. | 41-1 | AMPHI | 126-129 |
| 472. | 41-1 | AMPHI | 136-143 |
| 473. | 41-1 | AMPHI | 145-150 |
| 474. | 41-1 | AMPHI | 156-158 |
| 475. | 41-1 | AMPHI | 186-195 |
| 476. | 41-1 | AMPHI | 201-208 |
| 477. | 41-1 | AMPHI | 213-223 |
| 478. | 41-1 | AMPHI | 236-247 |
| 479. | 41-1 | AMPHI | 250-255 |
| 480. | 41-1 | AMPHI | 273-282 |
| 481. | 41-1 | AMPHI | 303-309 |
| 482. | 41-1 | AMPHI | 311-314 |
| 483. | 41-1 | AMPHI | 329-338 |
| 484. | 41-1 | AMPHI | 344-362 |
| 485. | 41-1 | AMPHI | 372-377 |
| 486. | 41-1 | AMPHI | 385-392 |
| 487. | 41-1 | AMPHI | 409-412 |
| 488. | 41-1 | AMPHI | 419-426 |
| 489. | 41-1 | AMPHI | 458-463 |
| 490. | 41-1 | AMPHI | 470-474 |
| 491. | 41-1 | AMPHI | 486-489 |
| 492. | 41-1 | AMPHI | 512-518 |
| 493. | 41-1 | AMPHI | 527-551 |
| 494. | 41-1 | AMPHI | 564-579 |
| 495. | 41-1 | AMPHI | 593-597 |
| 496. | 41-1 | Antigenic Index | 13-22 |
| 497. | 41-1 | Antigenic Index | 30-38 |
| 498. | 41-1 | Antigenic Index | 43-55 |
| 499. | 41-1 | Antigenic Index | 73-75 |
| 500. | 41-1 | Antigenic Index | 87-89 |
| 501. | 41-1 | Antigenic Index | 105-112 |
| 502. | 41-1 | Antigenic Index | 114-124 |
| 503. | 41-1 | Antigenic Index | 136-141 |
| 504. | 41-1 | Antigenic Index | 147-153 |
| 505. | 41-1 | Antigenic Index | 163-166 |
| 506. | 41-1 | Antigenic Index | 174-184 |
| 507. | 41-1 | Antigenic Index | 195-207 |
| 508. | 41-1 | Antigenic Index | 226-236 |
| 509. | 41-1 | Antigenic Index | 244-246 |
| 510. | 41-1 | Antigenic Index | 249-265 |
| 511. | 41-1 | Antigenic Index | 281-287 |
| 512. | 41-1 | Antigenic Index | 294-313 |
| 513. | 41-1 | Antigenic Index | 317-342 |
| 514. | 41-1 | Antigenic Index | 350-375 |
| 515. | 41-1 | Antigenic Index | 379-386 |
| 516. | 41-1 | Antigenic Index | 390-396 |
| 517. | 41-1 | Antigenic Index | 413-422 |
| 518. | 41-1 | Antigenic Index | 425-430 |
| 519. | 41-1 | Antigenic Index | 436-440 |
| 520. | 41-1 | Antigenic Index | 446-465 |
| 521. | 41-1 | Antigenic Index | 468-495 |
| 522. | 41-1 | Antigenic Index | 498-518 |
| 523. | 41-1 | Antigenic Index | 520-522 |
| 524. | 41-1 | Antigenic Index | 525-542 |
| 525. | 41-1 | Antigenic Index | 547-558 |
| 526. | 41-1 | Antigenic Index | 565-590 |
| 527. | 41-1 | Antigenic Index | 595-602 |
| 528. | 41-1 | Antigenic Index | 608-619 |
| 529. | 41-1 | Hydrophilicity | 14-21 |
| 530. | 41-1 | Hydrophilicity | 30-33 |
| 531. | 41-1 | Hydrophilicity | 45-55 |
| 532. | 41-1 | Hydrophilicity | 87-89 |
| 533. | 41-1 | Hydrophilicity | 106-111 |
| 534. | 41-1 | Hydrophilicity | 114-120 |
| 535. | 41-1 | Hydrophilicity | 122-124 |
| 536. | 41-1 | Hydrophilicity | 136-141 |
| 537. | 41-1 | Hydrophilicity | 148-150 |
| 538. | 41-1 | Hydrophilicity | 177-184 |
| 539. | 41-1 | Hydrophilicity | 195-207 |
| 540. | 41-1 | Hydrophilicity | 226-234 |
| 541. | 41-1 | Hydrophilicity | 249-265 |
| 542. | 41-1 | Hydrophilicity | 285-287 |
| 543. | 41-1 | Hydrophilicity | 294-297 |
| 544. | 41-1 | Hydrophilicity | 299-313 |
| 545. | 41-1 | Hydrophilicity | 317-321 |
| 546. | 41-1 | Hydrophilicity | 323-342 |
| 547. | 41-1 | Hydrophilicity | 350-371 |
| 548. | 41-1 | Hydrophilicity | 379-386 |
| 549. | 41-1 | Hydrophilicity | 417-422 |
| 550. | 41-1 | Hydrophilicity | 425-427 |
| 551. | 41-1 | Hydrophilicity | 447-449 |
| 552. | 41-1 | Hydrophilicity | 459-462 |
| 553. | 41-1 | Hydrophilicity | 468-475 |
| 554. | 41-1 | Hydrophilicity | 479-482 |
| 555. | 41-1 | Hydrophilicity | 484-491 |

TABLE I-continued

1769 fragments of the proteins disclosed in WO99/36544

| Fragment# (SEQ ID NO) | WO99/36544 ORF | Algorithm | Amino Acids |
|---|---|---|---|
| 556. | 41-1 | Hydrophilicity | 499-518 |
| 557. | 41-1 | Hydrophilicity | 520-522 |
| 558. | 41-1 | Hydrophilicity | 526-542 |
| 559. | 41-1 | Hydrophilicity | 550-558 |
| 560. | 41-1 | Hydrophilicity | 568-590 |
| 561. | 41-1 | Hydrophilicity | 595-598 |
| 562. | 41-1 | Hydrophilicity | 617-619 |
| 563. | 41a | AMPHI | 6-12 |
| 564. | 41a | AMPHI | 32-34 |
| 565. | 41a | AMPHI | 69-74 |
| 566. | 41a | AMPHI | 86-98 |
| 567. | 41a | AMPHI | 111-119 |
| 568. | 41a | AMPHI | 121-126 |
| 569. | 41a | AMPHI | 132-134 |
| 570. | 41a | AMPHI | 155-160 |
| 571. | 41a | AMPHI | 162-171 |
| 572. | 41a | AMPHI | 177-184 |
| 573. | 41a | AMPHI | 189-199 |
| 574. | 41a | AMPHI | 212-223 |
| 575. | 41a | AMPHI | 226-231 |
| 576. | 41a | AMPHI | 249-258 |
| 577. | 41a | AMPHI | 287-290 |
| 578. | 41a | AMPHI | 305-314 |
| 579. | 41a | AMPHI | 320-338 |
| 580. | 41a | AMPHI | 348-353 |
| 581. | 41a | AMPHI | 361-368 |
| 582. | 41a | AMPHI | 385-388 |
| 583. | 41a | AMPHI | 395-402 |
| 584. | 41a | AMPHI | 434-439 |
| 585. | 41a | AMPHI | 446-450 |
| 586. | 41a | AMPHI | 462-467 |
| 587. | 41a | AMPHI | 470-475 |
| 588. | 41a | AMPHI | 488-494 |
| 589. | 41a | AMPHI | 503-525 |
| 590. | 41a | AMPHI | 540-555 |
| 591. | 41a | AMPHI | 569-573 |
| 592. | 41a | AMPHI | 578-594 |
| 593. | 41a | Antigenic Index | 10-13 |
| 594. | 41a | Antigenic Index | 19-31 |
| 595. | 41a | Antigenic Index | 48-50 |
| 596. | 41a | Antigenic Index | 63-65 |
| 597. | 41a | Antigenic Index | 82-101 |
| 598. | 41a | Antigenic Index | 112-117 |
| 599. | 41a | Antigenic Index | 123-129 |
| 600. | 41a | Antigenic Index | 139-142 |
| 601. | 41a | Antigenic Index | 150-160 |
| 602. | 41a | Antigenic Index | 171-183 |
| 603. | 41a | Antigenic Index | 202-212 |
| 604. | 41a | Antigenic Index | 220-222 |
| 605. | 41a | Antigenic Index | 225-241 |
| 606. | 41a | Antigenic Index | 257-263 |
| 607. | 41a | Antigenic Index | 270-289 |
| 608. | 41a | Antigenic Index | 293-318 |
| 609. | 41a | Antigenic Index | 326-351 |
| 610. | 41a | Antigenic Index | 355-362 |
| 611. | 41a | Antigenic Index | 366-372 |
| 612. | 41a | Antigenic Index | 389-398 |
| 613. | 41a | Antigenic Index | 401-406 |
| 614. | 41a | Antigenic Index | 412-416 |
| 615. | 41a | Antigenic Index | 422-441 |
| 616. | 41a | Antigenic Index | 444-446 |
| 617. | 41a | Antigenic Index | 451-471 |
| 618. | 41a | Antigenic Index | 475-494 |
| 619. | 41a | Antigenic Index | 496-498 |
| 620. | 41a | Antigenic Index | 501-518 |
| 621. | 41a | Antigenic Index | 523-534 |
| 622. | 41a | Antigenic Index | 540-566 |
| 623. | 41a | Antigenic Index | 571-578 |
| 624. | 41a | Antigenic Index | 582-595 |
| 625. | 41a | Hydrophilicity | 21-31 |
| 626. | 41a | Hydrophilicity | 63-65 |
| 627. | 41a | Hydrophilicity | 83-96 |
| 628. | 41a | Hydrophilicity | 98-100 |
| 629. | 41a | Hydrophilicity | 112-117 |
| 630. | 41a | Hydrophilicity | 124-126 |
| 631. | 41a | Hydrophilicity | 153-160 |
| 632. | 41a | Hydrophilicity | 171-183 |
| 633. | 41a | Hydrophilicity | 202-210 |
| 634. | 41a | Hydrophilicity | 220-222 |
| 635. | 41a | Hydrophilicity | 225-241 |
| 636. | 41a | Hydrophilicity | 261-263 |
| 637. | 41a | Hydrophilicity | 270-273 |
| 638. | 41a | Hydrophilicity | 275-289 |
| 639. | 41a | Hydrophilicity | 293-297 |
| 640. | 41a | Hydrophilicity | 299-318 |
| 641. | 41a | Hydrophilicity | 326-347 |
| 642. | 41a | Hydrophilicity | 355-362 |
| 643. | 41a | Hydrophilicity | 393-398 |
| 644. | 41a | Hydrophilicity | 401-403 |
| 645. | 41a | Hydrophilicity | 423-425 |
| 646. | 41a | Hydrophilicity | 435-438 |
| 647. | 41a | Hydrophilicity | 454-458 |
| 648. | 41a | Hydrophilicity | 460-471 |
| 649. | 41a | Hydrophilicity | 475-494 |
| 650. | 41a | Hydrophilicity | 496-498 |
| 651. | 41a | Hydrophilicity | 502-518 |
| 652. | 41a | Hydrophilicity | 527-534 |
| 653. | 41a | Hydrophilicity | 544-566 |
| 654. | 41a. | Hydrophilicity | 571-574 |
| 655. | 41a | Hydrophilicity | 593-595 |
| 656. | 44-1 | AMPHI | 57-60 |
| 657. | 44-1 | AMPHI | 76-79 |
| 658. | 44-1 | Antigenic Index | 22-34 |
| 659. | 44-1 | Antigenic Index | 38-46 |
| 660. | 44-1 | Antigenic Index | 50-55 |
| 661. | 44-1 | Antigenic Index | 64-70 |
| 662. | 44-1 | Antigenic Index | 72-80 |
| 663. | 44-1 | Antigenic Index | 83-89 |
| 664. | 44-1 | Antigenic Index | 96-106 |
| 665. | 44-1 | Antigenic Index | 110-124 |
| 666. | 44-1 | Hydrophilicity | 22-34 |
| 667. | 44-1 | Hydrophilicity | 40-46 |
| 668. | 44-1 | Hydrophilicity | 64-69 |
| 669. | 44-1 | Hydrophilicity | 73-80 |
| 670. | 44-1 | Hydrophilicity | 84-89 |
| 671. | 44-1 | Hydrophilicity | 97-106 |
| 672. | 44.1 | Hydrophilicity | 120-124 |
| 673. | 44a | AMPHI | 57-60 |
| 674. | 44a | AMPHI | 76-79 |
| 675. | 44a | Antigenic Index | 23-34 |
| 676. | 44a | Antigenic Index | 38-46 |
| 677. | 44a | Antigenic Index | 50-55 |
| 678. | 44a | Antigenic Index | 64-70 |
| 679. | 44a | Antigenic Index | 72-80 |
| 680. | 44a | Antigenic Index | 83-89 |
| 681. | 44a | Antigenic Index | 96-106 |
| 682. | 44a | Antigenic Index | 110-124 |
| 683. | 44a | Hydrophilicity | 28-34 |
| 684. | 44a | Hydrophilicity | 40-46 |
| 685. | 44a | Hydrophilicity | 64-69 |
| 686. | 44a | Hydrophilicity | 73-80 |
| 687. | 44a | Hydrophilicity | 84-89 |
| 688. | 44a | Hydrophilicity | 97-106 |
| 689. | 44a | Hydrophilicity | 120-124 |
| 690. | 49-1 | AMPHI | 16-21 |
| 691. | 49-1 | AMPHI | 44-48 |
| 692. | 49-1 | AMPHI | 56-61 |
| 693. | 49-1 | AMPHI | 92-97 |
| 694. | 49-1 | AMPHI | 118-127 |
| 695. | 49-1 | AMPHI | 130-149 |
| 696. | 49-1 | AMPHI | 156-178 |
| 697. | 49-1 | AMPHI | 235-240 |
| 698. | 49-1 | AMPHI | 253-264 |
| 699. | 49-1 | AMPHI | 268-271 |
| 700. | 49-1 | AMPHI | 278-285 |
| 701. | 49-1 | AMPHI | 287-292 |
| 702. | 49-1 | AMPHI | 298-300 |
| 703. | 49-1 | AMPHI | 328-337 |

TABLE I-continued

1769 fragments of the proteins disclosed in WO99/36544

| Fragment# (SEQ ID NO) | WO99/36544 ORF | Algorithm | Amino Acids |
|---|---|---|---|
| 704. | 49-1 | AMPHI | 343-350 |
| 705. | 49-1 | AMPHI | 355-365 |
| 706. | 49-1 | AMPHI | 378-389 |
| 707. | 49-1 | AMPHI | 422-424 |
| 708. | 49-1 | AMPHI | 442-450 |
| 709. | 49-1 | AMPHI | 464-481 |
| 710. | 49-1 | AMPHI | 486-496 |
| 711. | 49-1 | AMPHI | 514-521 |
| 712. | 49-1 | AMPHI | 548-551 |
| 713. | 49-1 | AMPHI | 553-557 |
| 714. | 49-1 | AMPHI | 562-568 |
| 715. | 49-1 | AMPHI | 573-575 |
| 716. | 49-1 | AMPHI | 588-590 |
| 717. | 49-1 | AMPHI | 603-605 |
| 718. | 49-1 | AMPHI | 614-618 |
| 719. | 49-1 | Antigenic Index | 15-21 |
| 720. | 49-1 | Antigenic Index | 26-43 |
| 721. | 49-1 | Antigenic Index | 50-59 |
| 722. | 49-1 | Antigenic Index | 61-75 |
| 723. | 49-1 | Antigenic Index | 79-87 |
| 724. | 49-1 | Antigenic Index | 98-108 |
| 725. | 49-1 | Antigenic Index | 110-120 |
| 726. | 49-1 | Antigenic Index | 122-139 |
| 727. | 49-1 | Antigenic Index | 147-164 |
| 728. | 49-1 | Antigenic Index | 171-179 |
| 729. | 49-1 | Antigenic Index | 185-197 |
| 730. | 49-1 | Antigenic Index | 214-216 |
| 731. | 49-1 | Antigenic Index | 229-231 |
| 732. | 49-1 | Antigenic Index | 248-266 |
| 733. | 49-1 | Antigenic Index | 278-283 |
| 734. | 49-1 | Antigenic Index | 289-295 |
| 735. | 49-1 | Antigenic Index | 316-326 |
| 736. | 49-1 | Antigenic Index | 337-349 |
| 737. | 49-1 | Antigenic Index | 368-378 |
| 738. | 49-1 | Antigenic Index | 386-388 |
| 739. | 49-1 | Antigenic Index | 390-410 |
| 740. | 49-1 | Antigenic Index | 412-414 |
| 741. | 49-1 | Antigenic Index | 423-429 |
| 742. | 49-1 | Antigenic Index | 438-454 |
| 743. | 49-1 | Antigenic Index | 462-475 |
| 744. | 49-1 | Antigenic Index | 482-500 |
| 745. | 49-1 | Antigenic Index | 503-509 |
| 746. | 49-1 | Antigenic Index | 521-528 |
| 747. | 49-1 | Antigenic Index | 540-562 |
| 748. | 49-1 | Antigenic Index | 572-579 |
| 749. | 49-1 | Antigenic Index | 590-606 |
| 750. | 49-1 | Antigenic Index | 610-612 |
| 751. | 49-1 | Antigenic Index | 617-619 |
| 752. | 49-1 | Antigenic Index | 626-634 |
| 753. | 49-1 | Antigenic Index | 637-640 |
| 754. | 49-1 | Hydrophilicity | 18-21 |
| 755. | 49-1 | Hydrophilicity | 26-29 |
| 756. | 49-1 | Hydrophilicity | 31-43 |
| 757. | 49-1 | Hydrophilicity | 51-57 |
| 758. | 49-1 | Hydrophilicity | 64-68 |
| 759. | 49-1 | Hydrophilicity | 79-87 |
| 760. | 49-1 | Hydrophilicity | 98-107 |
| 761. | 49-1 | Hydrophilicity | 122-125 |
| 762. | 49-1 | Hydrophilicity | 147-164 |
| 763. | 49-1 | Hydrophilicity | 172-175 |
| 764. | 49-1 | Hydrophilicity | 187-197 |
| 765. | 49-1 | Hydrophilicity | 229-231 |
| 766. | 49-1 | Hydrophilicity | 256-262 |
| 767. | 49-1 | Hydrophilicity | 264-266 |
| 768. | 49-1 | Hydrophilicity | 278-283 |
| 769. | 49-1 | Hydrophilicity | 290-292 |
| 770. | 49-1 | Hydrophilicity | 319-326 |
| 771. | 49-1 | Hydrophilicity | 337-349 |
| 772. | 49-1 | Hydrophilicity | 368-376 |
| 773. | 49-1 | Hydrophilicity | 386-388 |
| 774. | 49-1 | Hydrophilicity | 390-410 |
| 775. | 49-1 | Hydrophilicity | 412-414 |
| 776. | 49-1 | Hydrophilicity | 423-429 |
| 777. | 49-1 | Hydrophilicity | 441-451 |
| 778. | 49-1 | Hydrophilicity | 466-472 |
| 779. | 49-1 | Hydrophilicity | 484-490 |
| 780. | 49-1 | Hydrophilicity | 492-494 |
| 781. | 49-1 | Hydrophilicity | 496-498 |
| 782. | 49-1 | Hydrophilicity | 522-528 |
| 783. | 49-1 | Hydrophilicity | 543-562 |
| 784. | 49-1 | Hydrophilicity | 591-606 |
| 785. | 49-1 | Hydrophilicity | 617-619 |
| 786. | 49-1 | Hydrophilicity | 626-632 |
| 787. | 49-1 | Hydrophilicity | 637-640 |
| 788. | 49a | AMPHI | 55-61 |
| 789. | 49a | AMPHI | 92-97 |
| 790. | 49a | AMPHI | 118-127 |
| 791. | 49a | AMPHI | 129-135 |
| 792. | 49a | AMPHI | 137-145 |
| 793. | 49a | AMPHI | 156-178 |
| 794. | 49a | AMPHI | 198-200 |
| 795. | 49a | AMPHI | 235-240 |
| 796. | 49a | AMPHI | 252-264 |
| 797. | 49a | AMPHI | 277-285 |
| 798. | 49a | AMPHI | 287-292 |
| 799. | 49a | AMPHI | 298-300 |
| 800. | 49a | AMPHI | 321-326 |
| 801. | 49a | AMPHI | 328-337 |
| 802. | 49a | AMPHI | 343-350 |
| 803. | 49a | AMPHI | 355-365 |
| 804. | 49a | AMPHI | 378-389 |
| 805. | 49a | AMPHI | 392-397 |
| 806. | 49a | AMPHI | 415-424 |
| 807. | 49a | AMPHI | 453-456 |
| 808. | 49a | AMPHI | 471-480 |
| 809. | 49a | AMPHI | 486-504 |
| 810. | 49a | AMPHI | 514-519 |
| 811. | 49a | AMPHI | 527-534 |
| 812. | 49a | AMPHI | 551-554 |
| 813. | 49a | AMPHI | 561-568 |
| 814. | 49a | AMPHI | 600-605 |
| 815. | 49a | AMPHI | 612-616 |
| 816. | 49a | AMPHI | 628-633 |
| 817. | 49a | AMPHI | 636-641 |
| 818. | 49a | AMPHI | 654-660 |
| 819. | 49a | AMPHI | 669-691 |
| 820. | 49a | AMPHI | 706-721 |
| 821. | 49a | AMPHI | 735-739 |
| 822. | 49a | AMPHI | 744-760 |
| 823. | 49a | Antigenic Index | 4-23 |
| 824. | 49a | Antigenic Index | 27-43 |
| 825. | 49a | Antigenic Index | 51-62 |
| 826. | 49a | Antigenic Index | 64-68 |
| 827. | 49a | Antigenic Index | 72-75 |
| 828. | 49a | Antigenic Index | 79-87 |
| 829. | 49a | Antigenic Index | 98-108 |
| 830. | 49a | Antigenic Index | 110-120 |
| 831. | 49a | Antigenic Index | 124-139 |
| 832. | 49a | Antigenic Index | 147-164 |
| 833. | 49a | Antigenic Index | 176-179 |
| 834. | 49a | Antigenic Index | 185-197 |
| 835. | 49a | Antigenic Index | 214-216 |
| 836. | 49a | Antigenic Index | 229-231 |
| 837. | 49a | Antigenic Index | 248-267 |
| 838. | 49a | Antigenic Index | 278-283 |
| 839. | 49a | Antigenic Index | 289-295 |
| 840. | 49a | Antigenic Index | 305-308 |
| 841. | 49a | Antigenic Index | 316-326 |
| 842. | 49a | Antigenic Index | 337-349 |
| 843. | 49a | Antigenic Index | 368-378 |
| 844. | 49a | Antigenic Index | 386-388 |
| 845. | 49a | Antigenic Index | 391-407 |
| 846. | 49a | Antigenic Index | 423-429 |
| 847. | 49a | Antigenic Index | 436-455 |
| 848. | 49a | Antigenic Index | 459-484 |
| 849. | 49a | Antigenic Index | 492-517 |
| 850. | 49a | Antigenic Index | 521-528 |
| 851. | 49a | Antigenic Index | 532-539 |

TABLE I-continued 1769 fragments of the proteins disclosed in WO99/36544

| Fragment# (SEQ ID NO) | WO99/36544 ORF | Algorithm | Amino Acids |
|---|---|---|---|
| 852. | 49a | Antigenic Index | 555-564 |
| 853. | 49a | Antigenic Index | 567-572 |
| 854. | 49a | Antigenic Index | 578-582 |
| 855. | 49a | Antigenic Index | 588-607 |
| 856. | 49a | Antigenic Index | 610-612 |
| 857. | 49a | Antigenic Index | 617-637 |
| 858. | 49a | Antigenic Index | 641-660 |
| 859. | 49a | Antigenic Index | 662-664 |
| 860. | 49a | Antigenic Index | 667-684 |
| 861. | 49a | Antigenic Index | 689-700 |
| 862. | 49a | Antigenic Index | 706-732 |
| 863. | 49a | Antigenic Index | 737-744 |
| 864. | 49a | Antigenic Index | 748-761 |
| 865. | 49a | Hydrophilicity | 4-23 |
| 866. | 49a | Hydrophilicity | 31-43 |
| 867. | 49a | Hydrophilicity | 51-53 |
| 868. | 49a | Hydrophilicity | 55-57 |
| 869. | 49a | Hydrophilicity | 64-68 |
| 870. | 49a | Hydrophilicity | 79-87 |
| 871. | 49a | Hydrophilicity | 98-106 |
| 872. | 49a | Hydrophilicity | 114-120 |
| 873. | 49a | Hydrophilicity | 130-139 |
| 874. | 49a | Hydrophilicity | 147-164 |
| 875. | 49a | Hydrophilicity | 187-197 |
| 876. | 49a | Hydrophilicity | 229-231 |
| 877. | 49a | Hydrophilicity | 249-262 |
| 878. | 49a | Hydrophilicity | 264-266 |
| 879. | 49a | Hydrophilicity | 278-283 |
| 880. | 49a | Hydrophilicity | 290-292 |
| 881. | 49a | Hydrophilicity | 319-326 |
| 882. | 49a | Hydrophilicity | 337-349 |
| 883. | 49a | Hydrophilicity | 368-376 |
| 884. | 49a | Hydrophilicity | 386-388 |
| 885. | 49a | Hydrophilicity | 391-407 |
| 886. | 49a | Hydrophilicity | 427-429 |
| 887. | 49a | Hydrophilicity | 436-439 |
| 888. | 49a | Hydrophilicity | 441-455 |
| 889. | 49a | Hydrophilicity | 459-463 |
| 890. | 49a | Hydrophilicity | 465-484 |
| 891. | 49a | Hydrophilicity | 492-513 |
| 892. | 49a | Hydrophilicity | 521-528 |
| 893. | 49a | Hydrophilicity | 559-564 |
| 894. | 49a | Hydrophilicity | 567-569 |
| 895. | 49a | Hydrophilicity | 589-591 |
| 896. | 49a | Hydrophilicity | 601-604 |
| 897. | 49a | Hydrophilicity | 620-624 |
| 898. | 49a | Hydrophilicity | 626-637 |
| 899. | 49a | Hydrophilicity | 641-660 |
| 900. | 49a | Hydrophilicity | 662-664 |
| 901. | 49a | Hydrophilicity | 668-684 |
| 902. | 49a | Hydrophilicity | 693-700 |
| 903. | 49a | Hydrophilicity | 710-732 |
| 904. | 49a | Hydrophilicity | 737-740 |
| 905. | 49a | Hydrophilicity | 759-761 |
| 906. | 51-1 | AMPHI | 15-21 |
| 907. | 51-1 | AMPHI | 40-54 |
| 908. | 51-1 | AMPHI | 75-86 |
| 909. | 51-1 | AMPHI | 108-110 |
| 910. | 51-1 | AMPHI | 112-124 |
| 911. | 51-1 | AMPHI | 141-148 |
| 912. | 51-1 | AMPHI | 184-189 |
| 913. | 51-1 | AMPHI | 211-216 |
| 914. | 51-1 | Antigenic Index | 58-65 |
| 915. | 51-1 | Antigenic Index | 123-127 |
| 916. | 51-1 | Antigenic Index | 132-137 |
| 917. | 51-1 | Antigenic Index | 149-153 |
| 918. | 51-1 | Antigenic Index | 165-177 |
| 919. | 51-1 | Antigenic Index | 198-204 |
| 920. | 51-1 | Antigenic Index | 222-231 |
| 921. | 51-1 | Hydrophilicity | 60-65 |
| 922. | 51-1 | Hydrophilicity | 123-127 |
| 923. | 51-1 | Hydrophilicity | 132-135 |
| 924. | 51-1 | Hydrophilicity | 165-174 |
| 925. | 51-1 | Hydrophilicity | 200-203 |
| 926. | 51-1 | Hydrophilicity | 222-227 |
| 927. | 51a | AMPHI | 15-21 |
| 928. | 51a | AMPHI | 40-54 |
| 929. | 51a | AMPHI | 75-86 |
| 930. | 51a | AMPHI | 108-110 |
| 931. | 51a | AMPHI | 112-124 |
| 932. | 51a | AMPHI | 141-148 |
| 933. | 51a | AMPHI | 184-189 |
| 934. | 51a | AMPHI | 211-216 |
| 935. | 51a | Hydrophilicity | 60-65 |
| 936. | 51a | Hydrophilicity | 123-127 |
| 937. | 51a | Hydrophilicity | 132-135 |
| 938. | 51a | Hydrophilicity | 165-174 |
| 939. | 51a | Hydrophilicity | 200-203 |
| 940. | 51a | Hydrophilicity | 222-227 |
| 941. | 52-1 | AMPHI | 48-50 |
| 942. | 52-1 | AMPHI | 64-73 |
| 943. | 52-1 | Antigenic Index | 19-26 |
| 944. | 52-1 | Antigenic Index | 30-35 |
| 945. | 52-1 | Antigenic Index | 42-52 |
| 946. | 52-1 | Antigenic Index | 57-86 |
| 947. | 52-1 | Hydrophilicity | 22-26 |
| 948. | 52-1 | Hydrophilicity | 30-35 |
| 949. | 52-1 | Hydrophilicity | 42-52 |
| 950. | 52-1 | Hydrophilicity | 57-71 |
| 951. | 52-1 | Hydrophilicity | 78-86 |
| 952. | 69-1 | AMPHI | 25-27 |
| 953. | 69-1 | AMPHI | 46-66 |
| 954. | 69-1 | Antigenic Index | 32-41 |
| 955. | 69-1 | Antigenic Index | 43-45 |
| 956. | 69-1 | Antigenic Index | 71-78 |
| 957. | 69-1 | Hydrophilicity | 32-38 |
| 958. | 69-1 | Hydrophilicity | 71-78 |
| 959. | 69a | AMPHI | 25-27 |
| 960. | 69a | AMPHI | 46-66 |
| 961. | 69a | Antigenic Index | 32-41 |
| 962. | 69a | Antigenic Index | 43-46 |
| 963. | 69a | Antigenic Index | 71-78 |
| 964. | 69a | Hydrophilicity | 32-38 |
| 965. | 69a | Hydrophilicity | 71-78 |
| 966. | 77-1 | AMPHI | 12-16 |
| 967. | 77-1 | AMPHI | 23-33 |
| 968. | 77-1 | AMPHI | 35-42 |
| 969. | 77-1 | AMPHI | 51-57 |
| 970. | 77-1 | AMPHI | 67-70 |
| 971. | 77-1 | AMPHI | 73-79 |
| 972. | 77-1 | AMPHI | 122-124 |
| 973. | 77-1 | AMPHI | 130-134 |
| 974. | 77-1 | AMPHI | 165-178 |
| 975. | 77-1 | AMPHI | 191-211 |
| 976. | 77-1 | Antigenic Index | 22-31 |
| 977. | 77-1 | Antigenic Index | 34-44 |
| 978. | 77-1 | Antigenic Index | 80-94 |
| 979. | 77-1 | Antigenic Index | 101-104 |
| 980. | 77-1 | Antigenic Index | 155-158 |
| 981. | 77-1 | Antigenic Index | 167-181 |
| 982. | 77-1 | Hydrophilicity | 22-28 |
| 983. | 77-1 | Hydrophilicity | 38-44 |
| 984. | 77-1 | Hydrophilicity | 80-92 |
| 985. | 77-1 | Hydrophilicity | 171-178 |
| 986. | 77a | AMPHI | 8-15 |
| 987. | 77a | AMPHI | 24-30 |
| 988. | 77a | AMPHI | 40-43 |
| 989. | 77a | AMPHI | 46-52 |
| 990. | 77a | AMPHI | 95-97 |
| 991. | 77a | AMPHI | 103-107 |
| 992. | 77a | AMPHI | 114-125 |
| 993. | 77a | AMPHI | 144-151 |
| 994. | 77a | AMPHI | 154-156 |
| 995. | 77a | AMPHI | 166-184 |
| 996. | 77a | Antigenic Index | 7-17 |
| 997. | 77a | Antigenic Index | 53-67 |
| 998. | 77a | Antigenic Index | 74-77 |
| 999. | 77a | Antigenic Index | 128-131 |

TABLE I-continued 1769 fragments of the proteins disclosed in WO99/36544

| Fragment# (SEQ ID NO) | WO99/36544 ORF | Algorithm | Amino Acids |
|---|---|---|---|
| 1000. | 77a | Antigenic Index | 140-154 |
| 1001. | 77a | Hydrophilicity | 11-17 |
| 1002. | 77a | Hydrophilicity | 53-65 |
| 1003. | 77a | Hydrophilicity | 141-151 |
| 1004. | 81-1 | AMPHI | 30-40 |
| 1005. | 81-1 | AMPHI | 54-56 |
| 1006. | 81-1 | AMPHI | 60-63 |
| 1007. | 81-1 | AMPHI | 76-93 |
| 1008. | 81-1 | AMPHI | 96-101 |
| 1009. | 81-1 | AMPHI | 104-406 |
| 1010. | 81-1 | AMPHI | 118-126 |
| 1011. | 81-1 | AMPHI | 190-205 |
| 1012. | 81-1 | AMPHI | 230-233 |
| 1013. | 81-1 | AMPHI | 239-242 |
| 1014. | 81-1 | AMPHI | 256-258 |
| 1015. | 81-1 | AMPHI | 264-284 |
| 1016. | 81-1 | AMPHI | 290-297 |
| 1017. | 81-1 | AMPHI | 317-326 |
| 1018. | 81-1 | AMPHI | 388-396 |
| 1019. | 81-1 | AMPHI | 403-414 |
| 1020. | 81-1 | AMPHI | 458-463 |
| 1021. | 81-1 | AMPHI | 476-480 |
| 1022. | 81-1 | Antigenic Index | 1-4 |
| 1023. | 81-1 | Antigenic Index | 35-38 |
| 1024. | 81-1 | Antigenic Index | 86-89 |
| 1025. | 81-1 | Antigenic Index | 95-98 |
| 1026. | 81-1 | Antigenic Index | 100-103 |
| 1027. | 81-1 | Antigenic Index | 128-136 |
| 1028. | 81-1 | Antigenic Index | 154-174 |
| 1029. | 81-1 | Antigenic Index | 197-211 |
| 1030. | 81-1 | Antigenic Index | 220-226 |
| 1031. | 81-1 | Antigenic Index | 232-240 |
| 1032. | 81-1 | Antigenic Index | 244-249 |
| 1033. | 81-1 | Antigenic Index | 251-253 |
| 1034. | 81-1 | Antigenic Index | 255-258 |
| 1035. | 81-1 | Antigenic Index | 276-290 |
| 1036. | 81-1 | Antigenic Index | 292-301 |
| 1037. | 81-1 | Antigenic Index | 307-312 |
| 1038. | 81-1 | Antigenic Index | 318-323 |
| 1039. | 81-1 | Antigenic Index | 334-345 |
| 1040. | 81-1 | Antigenic Index | 352-358 |
| 1041. | 81-1 | Antigenic Index | 364-372 |
| 1042. | 81-1 | Antigenic Index | 376-384 |
| 1043. | 81-1 | Antigenic Index | 387-401 |
| 1044. | 81-1 | Antigenic Index | 409-417 |
| 1045. | 81-1 | Antigenic Index | 423-444 |
| 1046. | 81-1 | Antigenic Index | 452-459 |
| 1047. | 81-1 | Antigenic Index | 486-488 |
| 1048. | 81-1 | Antigenic Index | 490-499 |
| 1049. | 81-1 | Antigenic Index | 507-520 |
| 1050, | 81-1 | Hydrophilicity | 1-4 |
| 1051. | 81-1 | Hydrophilicity | 35-38 |
| 1052. | 81-1 | Hydrophilicity | 95-98 |
| 1053. | 81-1 | Hydrophilicity | 128-136 |
| 1054. | 81-1 | Hydrophilicity | 154-164 |
| 1055. | 81-1 | Hydrophilicity | 166-172 |
| 1056. | 81-1 | Hydrophilicity | 202-209 |
| 1057. | 81-1 | Hydrophilicity | 220-226 |
| 1058. | 81-1 | Hydrophilicity | 234-238 |
| 1059. | 81-1 | Hydrophilicity | 245-249 |
| 1060. | 81-1 | Hydrophilicity | 251-253 |
| 1061. | 81-1 | Hydrophilicity | 284-287 |
| 1062. | 81-1 | Hydrophilicity | 292-299 |
| 1063. | 81-1 | Hydrophilicity | 307-312 |
| 1064. | 81-1 | Hydrophilicity | 321-323 |
| 1065. | 81-1 | Hydrophilicity | 338-345 |
| 1066. | 81-1 | Hydrophilicity | 366-368 |
| 1067. | 81-1 | Hydrophilicity | 378-384 |
| 1068. | 81-1 | Hydrophilicity | 387-401 |
| 1069. | 81-1 | Hydrophilicity | 409-415 |
| 1070. | 81-1 | Hydrophilicity | 453-459 |
| 1071. | 81-1 | Hydrophilicity | 493-499 |
| 1072. | 81-1 | Hydrophilicity | 507-509 |
| 1073. | 81-1 | Hydrophilicity | 512-518 |
| 1074. | 82a | AMPHI | 36-40 |
| 1075. | 82a | AMPHI | 95-111 |
| 1076. | 82a | AMPHI | 117-132 |
| 1077. | 82a | AMPHI | 135-137 |
| 1078. | 82a | AMPHI | 160-174 |
| 1079. | 82a | AMPHI | 183-187 |
| 1080. | 82a | Antigenic Index | 2-8 |
| 1081. | 82a | Antigenic Index | 56-60 |
| 1082. | 82a | Antigenic Index | 90-97 |
| 1083. | 82a | Antigenic Index | 104-111 |
| 1084. | 82a | Antigenic Index | 114-137 |
| 1085. | 82a | Antigenic Index | 141-151 |
| 1086. | 82a | Antigenic Index | 170-175 |
| 1087. | 82a | Antigenic Index | 180-188 |
| 1088. | 82a | Antigenic Index | 194-201 |
| 1089. | 82a | Antigenic Index | 206-209 |
| 1090. | 82a | Antigenic Index | 216-218 |
| 1091. | 82a | Hydrophilicity | 2-8 |
| 1092. | 82a | Hydrophilicity | 56-60 |
| 1093. | 82a | Hydrophilicity | 90-97 |
| 1094. | 82a | Hydrophilicity | 105-108 |
| 1095. | 82a | Hydrophilicity | 120-128 |
| 1096. | 82a | Hydrophilicity | 130-134 |
| 1097. | 82a | Hydrophilicity | 141-151 |
| 1098. | 82a | Hydrophilicity | 170-175 |
| 1099. | 82a | Hydrophilicity | 186-188 |
| 1100. | 82a | Hydrophilicity | 195-201 |
| 1101. | 82a | Hydrophilicity | 206-209 |
| 1102. | 112-1 | AMPHI | 6-8 |
| 1103. | 112-1 | AMPHI | 12-34 |
| 1104. | 112-1 | AMPHI | 45-53 |
| 1105. | 112-1 | AMPHI | 63-65 |
| 1106. | 112-1 | AMPHI | 70-82 |
| 1107. | 112-1 | AMPHI | 84-86 |
| 1108. | 112-1 | AMPHI | 107-109 |
| 1109. | 112-1 | AMPHI | 116-123 |
| 1110. | 112-1 | AMPHI | 183-186 |
| 1111. | 112-1 | AMPHI | 244-246 |
| 1112. | 112-1 | AMPHI | 248-258 |
| 1113. | 112-1 | AMPHI | 280-282 |
| 1114. | 112-1 | AMPHI | 302-313 |
| 1115. | 112-1 | Antigenic Index | 35-44 |
| 1116. | 112-1 | Antigenic Index | 57-61 |
| 1117. | 112-1 | Antigenic Index | 81-84 |
| 1118. | 112-1 | Antigenic Index | 91-98 |
| 1119. | 112-1 | Antigenic Index | 125-133 |
| 1120. | 112-1 | Antigenic Index | 140-147 |
| 1121. | 112-1 | Antigenic Index | 149-159 |
| 1122. | 112-1 | Antigenic Index | 161-165 |
| 1123. | 112-1 | Antigenic Index | 174-190 |
| 1124. | 112-1 | Antigenic Index | 192-200 |
| 1125. | 112-1 | Antigenic Index | 202-216 |
| 1126. | 112-1 | Antigenic Index | 218-224 |
| 1127. | 112-1 | Antigenic Index | 228-232 |
| 1128. | 112-1 | Antigenic Index | 239-244 |
| 1129. | 112-1 | Antigenic Index | 255-263 |
| 1130. | 112-1 | Antigenic Index | 290-300 |
| 1131. | 112-1 | Hydrophilicity | 38-40 |
| 1132. | 112-1 | Hydrophilicity | 57-61 |
| 1133. | 112-1 | Hydrophilicity | 92-98 |
| 1134. | 112-1 | Hydrophilicity | 125-133 |
| 1135. | 112-1 | Hydrophilicity | 141-143 |
| 1136. | 112-1 | Hydrophilicity | 150-159 |
| 1137. | 112-1 | Hydrophilicity | 161-164 |
| 1138. | 112-1 | Hydrophilicity | 175-190 |
| 1139. | 112-1 | Hydrophilicity | 203-216 |
| 1140. | 112-1 | Hydrophilicity | 218-224 |
| 1141. | 112-1 | Hydrophilicity | 228-232 |
| 1142. | 112-1 | Hydrophilicity | 239-244 |
| 1143. | 112-1 | Hydrophilicity | 259-261 |
| 1144. | 112-1 | Hydrophilicity | 293-297 |
| 1145. | 112a | AMPHI | 6-8 |
| 1146. | 112a | AMPHI | 12-34 |
| 1147. | 112a | AMPHI | 47-54 |

TABLE I-continued 1769 fragments of the proteins disclosed in WO99/36544

| Fragment# (SEQ ID NO) | WO99/36544 ORF | Algorithm | Amino Acids |
|---|---|---|---|
| 1148. | 112a | AMPHI | 63-65 |
| 1149. | 112a | AMPHI | 69-72 |
| 1150. | 112a | AMPHI | 84-86 |
| 1151. | 112a | AMPHI | 89-91 |
| 1152. | 112a | AMPHI | 107-109 |
| 1153. | 112a | AMPHI | 116-123 |
| 1154. | 112a | AMPHI | 183-186 |
| 1155. | 112a | AMPHI | 244-246 |
| 1156. | 112a | AMPHI | 248-258 |
| 1157. | 112a | AMPHI | 280-282 |
| 1158. | 112a | AMPHI | 302-310 |
| 1159. | 112a | AMPHI | 321-336 |
| 1160. | 112a | Antigenic Index | 35-44 |
| 1161. | 112a | Antigenic Index | 57-61 |
| 1162. | 112a | Antigenic Index | 81-84 |
| 1163. | 112a | Antigenic Index | 91-98 |
| 1164. | 112a | Antigenic Index | 125-133 |
| 1165. | 112a | Antigenic Index | 140-147 |
| 1166. | 112a | Antigenic Index | 150-158 |
| 1167. | 112a | Antigenic Index | 161-164 |
| 1168. | 112a | Antigenic Index | 174-190 |
| 1169. | 112a | Antigenic Index | 194-200 |
| 1170. | 112a | Antigenic Index | 202-216 |
| 1171. | 112a | Antigenic Index | 218-220 |
| 1172. | 112a | Antigenic Index | 222-224 |
| 1173. | 112a | Antigenic Index | 228-232 |
| 1174. | 112a | Antigenic Index | 239-244 |
| 1175. | 112a | Antigenic Index | 256-263 |
| 1176. | 112a | Antigenic Index | 290-301 |
| 1177. | 112a | Antigenic Index | 351-356 |
| 1178. | 112a | Hydrophilicity | 38-40 |
| 1179. | 112a | Hydrophilicity | 57-61 |
| 1180. | 112a | Hydrophilicity | 93-98 |
| 1181. | 112a | Hydrophilicity | 125-133 |
| 1182. | 112a | Hydrophilicity | 141-143 |
| 1183. | 112a | Hydrophilicity | 150-155 |
| 1184. | 112a | Hydrophilicity | 161-164 |
| 1185. | 112a | Hydrophilicity | 175-190 |
| 1186. | 112a | Hydrophilicity | 203-216 |
| 1187. | 112a | Hydrophilicity | 218-220 |
| 1188. | 112a | Hydrophilicity | 222-224 |
| 1189. | 112a | Hydrophilicity | 228-232 |
| 1190. | 112a | Hydrophilicity | 239-244 |
| 1191. | 112a | Hydrophilicity | 259-261 |
| 1192. | 112a | Hydrophilicity | 293-297 |
| 1193. | 112a | Hydrophilicity | 351-356 |
| 1194. | 114-1 | AMPHI | 45-54 |
| 1195. | 114-1 | AMPHI | 154-160 |
| 1196. | 114-1 | AMPHI | 182-190 |
| 1197. | 114-1 | AMPHI | 224-226 |
| 1198. | 114-1 | AMPHI | 229-233 |
| 1199. | 114-1 | AMPHI | 285-287 |
| 1200. | 114-1 | AMPHI | 303-310 |
| 1201. | 114-1 | AMPHI | 321-332 |
| 1202. | 114-1 | AMPHI | 392-398 |
| 1203. | 114-1 | AMPHI | 413-416 |
| 1204. | 114-1 | AMPHI | 450-452 |
| 1205. | 114-1 | AMPHI | 477-487 |
| 1206. | 114-1 | AMPHI | 506-509 |
| 1207. | 114-1 | AMPHI | 525-529 |
| 1208. | 114-1 | AMPHI | 565-567 |
| 1209. | 114-1 | AMPHI | 614-621 |
| 1210. | 114-1 | AMPHI | 631-635 |
| 1211. | 114-1 | AMPHI | 770-774 |
| 1212. | 114-1 | AMPHI | 810-813 |
| 1213. | 114-1 | AMPHI | 847-849 |
| 1214. | 114-1 | AMPHI | 851-853 |
| 1215. | 114-1 | AMPHI | 875-879 |
| 1216. | 114-1 | AMPHI | 951-956 |
| 1217. | 114-1 | AMPHI | 975-980 |
| 1218. | 114-1 | AMPHI | 1034-1036 |
| 1219. | 114-1 | AMPHI | 1048-1051 |
| 1220. | 114-1 | AMPHI | 1073-1081 |
| 1221. | 114-1 | AMPHI | 1086-1090 |
| 1222. | 114-1 | AMPHI | 1095-1102 |
| 1223. | 114-1 | AMPHI | 1111-1115 |
| 1224. | 114-1 | AMPHI | 1163-1167 |
| 1225. | 114-1 | AMPHI | 1242-1245 |
| 1226. | 114-1 | AMPHI | 1275-1281 |
| 1227. | 114-1 | AMPHI | 1312-1317 |
| 1228. | 114-1 | AMPHI | 1338-1347 |
| 1229. | 114-1 | AMPHI | 1349-1355 |
| 1230. | 114-1 | AMPHI | 1357-1360 |
| 1231. | 114-1 | AMPHI | 1362-1365 |
| 1232. | 114-1 | AMPHI | 1376-1398 |
| 1233. | 114-1 | AMPHI | 1418-1421 |
| 1234. | 114-1 | AMPHI | 1425-1429 |
| 1235. | 114-1 | AMPHI | 1468-1473 |
| 1236. | 114-1 | AMPHI | 1476-1485 |
| 1237. | 114-1 | AMPHI | 1495-1515 |
| 1238. | 114-1 | AMPHI | 1518-1526 |
| 1239. | 114-1 | AMPHI | 1546-1555 |
| 1240. | 114-1 | AMPHI | 1557-1559 |
| 1241. | 114-1 | AMPHI | 1580-1583 |
| 1242. | 114-1 | AMPHI | 1585-1597 |
| 1243. | 114-1 | AMPHI | 1604-1606 |
| 1244. | 114-1 | AMPHI | 1613-1624 |
| 1245. | 114-1 | AMPHI | 1626-1630 |
| 1246. | 114-1 | AMPHI | 1638-1644 |
| 1247. | 114-1 | AMPHI | 1655-1660 |
| 1248. | 114-1 | AMPHI | 1662-1664 |
| 1249. | 114-1 | AMPHI | 1672-1674 |
| 1250. | 114-1 | AMPHI | 1677-1679 |
| 1251. | 114-1 | AMPHI | 1691-1694 |
| 1252. | 114-1 | AMPHI | 1713-1716 |
| 1253. | 114-1 | AMPHI | 1719-1729 |
| 1254. | 114-1 | AMPHI | 1735-1738 |
| 1255. | 114-1 | AMPHI | 1753-1757 |
| 1256. | 114-1 | AMPHI | 1772-1778 |
| 1257. | 114-1 | AMPHI | 1790-1792 |
| 1258. | 114-1 | AMPHI | 1817-1826 |
| 1259. | 114-1 | AMPHI | 1828-1832 |
| 1260. | 114-1 | AMPHI | 1840-1851 |
| 1261. | 114-1 | AMPHI | 1854-1856 |
| 1262. | 114-1 | AMPHI | 1871-1881 |
| 1263. | 114-1 | AMPHI | 1883-1896 |
| 1264. | 114-1 | AMPHI | 1922-1927 |
| 1265. | 114-1 | AMPHI | 1934-1946 |
| 1266. | 114-1 | AMPHI | 1950-1955 |
| 1267. | 114-1 | AMPHI | 1957-1964 |
| 1268. | 114-1 | Antigenic Index | 1-6 |
| 1269. | 114-1 | Antigenic Index | 10-16 |
| 1270. | 114-1 | Antigenic Index | 23-37 |
| 1271. | 114-1 | Antigenic Index | 41-55 |
| 1272. | 114-1 | Antigenic Index | 75-85 |
| 1273. | 114-1 | Antigenic Index | 91-97 |
| 1274. | 114-1 | Antigenic Index | 102-140 |
| 1275. | 114-1 | Antigenic Index | 147-156 |
| 1276. | 114-1 | Antigenic Index | 161-168 |
| 1277. | 114-1 | Antigenic Index | 172-174 |
| 1278. | 114-1 | Antigenic Index | 181-189 |
| 1279. | 114-1 | Antigenic Index | 196-203 |
| 1280. | 114-1 | Antigenic Index | 208-213 |
| 1281. | 114-1 | Antigenic Index | 220-229 |
| 1282. | 114-1 | Antigenic Index | 242-248 |
| 1283. | 114-1 | Antigenic Index | 251-266 |
| 1284. | 114-1 | Antigenic Index | 268-276 |
| 1285. | 114-1 | Antigenic Index | 295-307 |
| 1286. | 114-1 | Antigenic Index | 309-312 |
| 1287. | 114-1 | Antigenic Index | 318-340 |
| 1288. | 114-1 | Antigenic Index | 345-351 |
| 1289. | 114-1 | Antigenic Index | 357-366 |
| 1290. | 114-1 | Antigenic Index | 371-381 |
| 1291. | 114-1 | Antigenic Index | 385-392 |
| 1292. | 114-1 | Antigenic Index | 404-417 |
| 1293. | 114-1 | Antigenic Index | 419-432 |
| 1294. | 114-1 | Antigenic Index | 440-456 |
| 1295. | 114-1 | Antigenic Index | 464-468 |

TABLE I-continued

1769 fragments of the proteins disclosed in WO99/36544

| Fragment# (SEQ ID NO) | WO99/36544 ORF | Algorithm | Amino Acids |
|---|---|---|---|
| 1296. | 114-1 | Antigenic Index | 473-480 |
| 1297. | 114-1 | Antigenic Index | 482-488 |
| 1298. | 114-1 | Antigenic Index | 496-511 |
| 1299. | 114-1 | Antigenic Index | 515-530 |
| 1300. | 114-1 | Antigenic Index | 535-549 |
| 1301. | 114-1 | Antigenic Index | 555-560 |
| 1302. | 114-1 | Antigenic Index | 564-582 |
| 1303. | 114-1 | Antigenic Index | 588-596 |
| 1304. | 114-1 | Antigenic Index | 602-615 |
| 1305. | 114-1 | Antigenic Index | 617-620 |
| 1306. | 114-1 | Antigenic Index | 622-624 |
| 1307. | 114-1 | Antigenic Index | 628-632 |
| 1308. | 114-1 | Antigenic Index | 637-640 |
| 1309. | 114-1 | Antigenic Index | 647-654 |
| 1310. | 114-1 | Antigenic Index | 660-666 |
| 1311. | 114-1 | Antigenic Index | 668-688 |
| 1312. | 114-1 | Antigenic Index | 696-725 |
| 1313. | 114-1 | Antigenic Index | 730-733 |
| 1314. | 114-1 | Antigenic Index | 738-755 |
| 1315. | 114-1 | Antigenic Index | 760-766 |
| 1316. | 114-1 | Antigenic Index | 779-783 |
| 1317. | 114-1 | Antigenic Index | 786-799 |
| 1318. | 114-1 | Antigenic Index | 807-809 |
| 1319. | 114-1 | Antigenic Index | 811-819 |
| 1320. | 114-1 | Antigenic Index | 831-839 |
| 1321. | 114-1 | Antigenic Index | 845-857 |
| 1322. | 114-1 | Antigenic Index | 860-862 |
| 1323. | 114-1 | Antigenic Index | 864-868 |
| 1324. | 114-1 | Antigenic Index | 872-879 |
| 1325. | 114-1 | Antigenic Index | 883-891 |
| 1326. | 114-1 | Antigenic Index | 893-903 |
| 1327. | 114-1 | Antigenic Index | 908-916 |
| 1328. | 114-1 | Antigenic Index | 919-936 |
| 1329. | 114-1 | Antigenic Index | 941-947 |
| 1330. | 114-1 | Antigenic Index | 950-956 |
| 1331. | 114-1 | Antigenic Index | 959-976 |
| 1332. | 114-1 | Antigenic Index | 979-991 |
| 1333. | 114-1 | Antigenic Index | 993-1000 |
| 1334. | 114-1 | Antigenic Index | 1007-1022 |
| 1335. | 114-1 | Antigenic Index | 1041-1053 |
| 1336. | 114-1 | Antigenic Index | 1062-1068 |
| 1337. | 114-1 | Antigenic Index | 1075-1108 |
| 1338. | 114-1 | Antigenic Index | 1115-1121 |
| 1339. | 114-1 | Antigenic Index | 1126-1145 |
| 1340. | 114-1 | Antigenic Index | 1148-1152 |
| 1341. | 114-1 | Antigenic Index | 1156-1178 |
| 1342. | 114-1 | Antigenic Index | 1195-1206 |
| 1343. | 114-1 | Antigenic Index | 1208-1212 |
| 1344. | 114-1 | Antigenic Index | 1217-1243 |
| 1345. | 114-1 | Antigenic Index | 1246-1263 |
| 1346. | 114-1 | Antigenic Index | 1271-1282 |
| 1347. | 114-1 | Antigenic Index | 1284-1288 |
| 1348. | 114-1 | Antigenic Index | 1292-1295 |
| 1349. | 114-1 | Antigenic Index | 1299-1307 |
| 1350. | 114-1 | Antigenic Index | 1318-1328 |
| 1351. | 114-1 | Antigenic Index | 1330-1340 |
| 1352. | 114-1 | Antigenic Index | 1344-1359 |
| 1353. | 114-1 | Antigenic Index | 1367-1384 |
| 1354. | 114-1 | Antigenic Index | 1395-1399 |
| 1355. | 114-1 | Antigenic Index | 1405-1417 |
| 1356. | 114-1 | Antigenic Index | 1445-1449 |
| 1357. | 114-1 | Antigenic Index | 1491-1510 |
| 1358. | 114-1 | Antigenic Index | 1526-1529 |
| 1359. | 114-1 | Antigenic Index | 1532-1548 |
| 1360. | 114-1 | Antigenic Index | 1552-1556 |
| 1361. | 114-1 | Antigenic Index | 1560-1562 |
| 1362. | 114-1 | Antigenic Index | 1573-1583 |
| 1363. | 114-1 | Antigenic Index | 1594-1611 |
| 1364. | 114-1 | Antigenic Index | 1627-1635 |
| 1365. | 114-1 | Antigenic Index | 1643-1645 |
| 1366. | 114-1 | Antigenic Index | 1647-1665 |
| 1367. | 114-1 | Antigenic Index | 1680-1686 |
| 1368. | 114-1 | Antigenic Index | 1700-1722 |
| 1369. | 114-1 | Antigenic Index | 1724-1726 |
| 1370. | 114-1 | Antigenic Index | 1739-1746 |
| 1371. | 114-1 | Antigenic Index | 1752-1757 |
| 1372. | 114-1 | Antigenic Index | 1780-1783 |
| 1373. | 114-1 | Antigenic Index | 1791-1795 |
| 1374. | 114-1 | Antigenic Index | 1804-1808 |
| 1375. | 114-1 | Antigenic Index | 1829-1835 |
| 1376. | 114-1 | Antigenic Index | 1841-1859 |
| 1377. | 114-1 | Antigenic Index | 1867-1886 |
| 1378. | 114-1 | Antigenic Index | 1897-1903 |
| 1379. | 114-1 | Antigenic Index | 1908-1912 |
| 1380. | 114-1 | Antigenic Index | 1917-1922 |
| 1381. | 114-1 | Antigenic Index | 1926-1934 |
| 1382. | 114-1 | Antigenic Index | 1938-1945 |
| 1383. | 114-1 | Antigenic Index | 1947-1957 |
| 1384. | 114-1 | Antigenic Index | 1961-1968 |
| 1385. | 114-1 | Antigenic Index | 1974-1978 |
| 1386. | 114-1 | Hydrophilicity | 4-6 |
| 1387. | 114-1 | Hydrophilicity | 12-15 |
| 1388. | 114-1 | Hydrophilicity | 23-34 |
| 1389. | 114-1 | Hydrophilicity | 43-55 |
| 1390. | 114-1 | Hydrophilicity | 76-85 |
| 1391. | 114-1 | Hydrophilicity | 104-110 |
| 1392. | 114-1 | Hydrophilicity | 118-123 |
| 1393. | 114-1 | Hydrophilicity | 127-132 |
| 1394. | 114-1 | Hydrophilicity | 147-154 |
| 1395. | 114-1 | Hydrophilicity | 163-167 |
| 1396. | 114-1 | Hydrophilicity | 185-187 |
| 1397. | 114-1 | Hydrophilicity | 197-203 |
| 1398. | 114-1 | Hydrophilicity | 208-211 |
| 1399. | 114-1 | Hydrophilicity | 221-227 |
| 1400. | 114-1 | Hydrophilicity | 243-245 |
| 1401. | 114-1 | Hydrophilicity | 253-261 |
| 1402. | 114-1 | Hydrophilicity | 263-266 |
| 1403. | 114-1 | Hydrophilicity | 270-272 |
| 1404. | 114-1 | Hydrophilicity | 295-301 |
| 1405. | 114-1 | Hydrophilicity | 309-312 |
| 1406. | 114-1 | Hydrophilicity | 320-328 |
| 1407. | 114-1 | Hydrophilicity | 332-337 |
| 1408. | 114-1 | Hydrophilicity | 345-351 |
| 1409. | 114-1 | Hydrophilicity | 360-366 |
| 1410. | 114-1 | Hydrophilicity | 371-378 |
| 1411. | 114-1 | Hydrophilicity | 387-392 |
| 1412. | 114-1 | Hydrophilicity | 404-415 |
| 1413. | 114-1 | Hydrophilicity | 419-432 |
| 1414. | 114-1 | Hydrophilicity | 441-450 |
| 1415. | 114-1 | Hydrophilicity | 452-456 |
| 1416. | 114-1 | Hydrophilicity | 473-480 |
| 1417. | 114-1 | Hydrophilicity | 482-485 |
| 1418. | 114-1 | Hydrophilicity | 496-500 |
| 1419. | 114-1 | Hydrophilicity | 504-509 |
| 1420. | 114-1 | Hydrophilicity | 515-520 |
| 1421. | 114-1 | Hydrophilicity | 536-549 |
| 1422. | 114-1 | Hydrophilicity | 555-560 |
| 1423. | 114-1 | Hydrophilicity | 565-568 |
| 1424. | 114-1 | Hydrophilicity | 570-579 |
| 1425. | 114-1 | Hydrophilicity | 589-594 |
| 1426. | 114-1 | Hydrophilicity | 602-604 |
| 1427. | 114-1 | Hydrophilicity | 609-615 |
| 1428. | 114-1 | Hydrophilicity | 617-620 |
| 1429. | 114-1 | Hydrophilicity | 660-666 |
| 1430. | 114-1 | Hydrophilicity | 668-680 |
| 1431. | 114-1 | Hydrophilicity | 684-686 |
| 1432. | 114-1 | Hydrophilicity | 699-708 |
| 1433. | 114-1 | Hydrophilicity | 715-725 |
| 1434. | 114-1 | Hydrophilicity | 730-733 |
| 1435. | 114-1 | Hydrophilicity | 738-744 |
| 1436. | 114-1 | Hydrophilicity | 746-754 |
| 1437. | 114-1 | Hydrophilicity | 760-766 |
| 1438. | 114-1 | Hydrophilicity | 789-793 |
| 1439. | 114-1 | Hydrophilicity | 816-818 |
| 1440. | 114-1 | Hydrophilicity | 831-836 |
| 1441. | 114-1 | Hydrophilicity | 845-857 |
| 1442. | 114-1 | Hydrophilicity | 860-862 |
| 1443. | 114-1 | Hydrophilicity | 864-866 |

TABLE I-continued

1769 fragments of the proteins disclosed in WO99/36544

| Fragment# (SEQ ID NO) | WO99/36544 ORF | Algorithm | Amino Acids |
|---|---|---|---|
| 1444. | 114-1 | Hydrophilicity | 873-879 |
| 1445. | 114-1 | Hydrophilicity | 883-885 |
| 1446. | 114-1 | Hydrophilicity | 887-889 |
| 1447. | 114-1 | Hydrophilicity | 896-899 |
| 1448. | 114-1 | Hydrophilicity | 908-916 |
| 1449. | 114-1 | Hydrophilicity | 919-932 |
| 1450. | 114-1 | Hydrophilicity | 941-947 |
| 1451. | 114-1 | Hydrophilicity | 962-975 |
| 1452. | 114-1 | Hydrophilicity | 979-989 |
| 1453. | 114-1 | Hydrophilicity | 993-1000 |
| 1454. | 114-1 | Hydrophilicity | 1007-1022 |
| 1455. | 114-1 | Hydrophilicity | 1041-1043 |
| 1456. | 114-1 | Hydrophilicity | 1045-1053 |
| 1457. | 114-1 | Hydrophilicity | 1062-1068 |
| 1458. | 114-1 | Hydrophilicity | 1075-1078 |
| 1459. | 114-1 | Hydrophilicity | 1080-1087 |
| 1460. | 114-1 | Hydrophilicity | 1089-1104 |
| 1461. | 114-1 | Hydrophilicity | 1115-1121 |
| 1462. | 114-1 | Hydrophilicity | 1126-1141 |
| 1463. | 114-1 | Hydrophilicity | 1143-1145 |
| 1464. | 114-1 | Hydrophilicity | 1148-1151 |
| 1465. | 114-1 | Hydrophilicity | 1157-1178 |
| 1466. | 114-1 | Hydrophilicity | 1197-1203 |
| 1467. | 114-1 | Hydrophilicity | 1217-1243 |
| 1468. | 114-1 | Hydrophilicity | 1246-1263 |
| 1469. | 114-1 | Hydrophilicity | 1271-1273 |
| 1470. | 114-1 | Hydrophilicity | 1275-1277 |
| 1471. | 114-1 | Hydrophilicity | 1284-1288 |
| 1472. | 114-1 | Hydrophilicity | 1299-1307 |
| 1473. | 114-1 | Hydrophilicity | 1318-1326 |
| 1474. | 114-1 | Hydrophilicity | 1334-1340 |
| 1475. | 114-1 | Hydrophilicity | 1350-1355 |
| 1476. | 114-1 | Hydrophilicity | 1357-1359 |
| 1477. | 114-1 | Hydrophilicity | 1367-1384 |
| 1478. | 114-1 | Hydrophilicity | 1407-1417 |
| 1479. | 114-1 | Hydrophilicity | 1491-1510 |
| 1480. | 114-1 | Hydrophilicity | 1534-1540 |
| 1481. | 114-1 | Hydrophilicity | 1576-1583 |
| 1482. | 114-1 | Hydrophilicity | 1595-1607 |
| 1483. | 114-1 | Hydrophilicity | 1629-1635 |
| 1484. | 114-1 | Hydrophilicity | 1643-1645 |
| 1485. | 114-1 | Hydrophilicity | 1649-1665 |
| 1486. | 114-1 | Hydrophilicity | 1682-1686 |
| 1487. | 114-1 | Hydrophilicity | 1704-1722 |
| 1488. | 114-1 | Hydrophilicity | 1724-1726 |
| 1489. | 114-1 | Hydrophilicity | 1740-1746 |
| 1490. | 114-1 | Hydrophilicity | 1804-1806 |
| 1491. | 114-1 | Hydrophilicity | 1829-1835 |
| 1492. | 114-1 | Hydrophilicity | 1842-1855 |
| 1493. | 114-1 | Hydrophilicity | 1876-1879 |
| 1494. | 114-1 | Hydrophilicity | 1898-1900 |
| 1495. | 114-1 | Hydrophilicity | 1910-1912 |
| 1496. | 114-1 | Hydrophilicity | 1920-1922 |
| 1497. | 114-1 | Hydrophilicity | 1928-1930 |
| 1498. | 114-1 | Hydrophilicity | 1938-1940 |
| 1499. | 114-1 | Hydrophilicity | 1948-1954 |
| 1500. | 114-1 | Hydrophilicity | 1962-1967 |
| 1501. | 114a | AMPHI | 45-54 |
| 1502. | 114a | AMPHI | 154-160 |
| 1503. | 114a | AMPHI | 182-190 |
| 1504. | 114a | AMPHI | 224-226 |
| 1505. | 114a | AMPHI | 229-233 |
| 1506. | 114a | AMPHI | 285-287 |
| 1507. | 114a | AMPHI | 303-310 |
| 1508. | 114a | AMPHI | 321-332 |
| 1509. | 114a | AMPHI | 348-350 |
| 1510. | 114a | AMPHI | 392-398 |
| 1511. | 114a | AMPHI | 414-416 |
| 1512. | 114a | AMPHI | 478-486 |
| 1513. | 114a | AMPHI | 506-509 |
| 1514. | 114a | AMPHI | 525-529 |
| 1515. | 114a | AMPHI | 565-567 |
| 1516. | 114a | AMPHI | 614-621 |
| 1517. | 114a | AMPHI | 631-635 |
| 1518. | 114a | AMPHI | 770-774 |
| 1519. | 114a | AMPHI | 811-813 |
| 1520. | 114a | AMPHI | 847-849 |
| 1521. | 114a | AMPHI | 851-853 |
| 1522. | 114a | AMPHI | 875-879 |
| 1523. | 114a | AMPHI | 951-959 |
| 1524. | 114a | AMPHI | 975-981 |
| 1525. | 114a | AMPHI | 1034-1036 |
| 1526. | 114a | AMPHI | 1048-1051 |
| 1527. | 114a | AMPHI | 1073-1081 |
| 1528. | 114a | AMPHI | 1086-1090 |
| 1529. | 114a | AMPHI | 1095-1102 |
| 1530. | 114a | AMPHI | 1111-1115 |
| 1531. | 114a | AMPHI | 1163-1166 |
| 1532. | 114a | AMPHI | 1275-1281 |
| 1533. | 114a | AMPHI | 1312-1317 |
| 1534. | 114a | AMPHI | 1338-1347 |
| 1535. | 114a | AMPHI | 1349-1355 |
| 1536. | 114a | AMPHI | 1357-1365 |
| 1537. | 114a | AMPHI | 1376-1398 |
| 1538. | 114a | AMPHI | 1418-1420 |
| 1539. | 114a | AMPHI | 1455-1460 |
| 1540. | 114a | AMPHI | 1472-1484 |
| 1541. | 114a | AMPHI | 1497-1505 |
| 1542. | 114a | AMPHI | 1507-1512 |
| 1543. | 114a | Antigenic Index | 1-6 |
| 1544. | 114a | Antigenic Index | 10-16 |
| 1545. | 114a | Antigenic Index | 23-37 |
| 1546. | 114a | Antigenic Index | 41-55 |
| 1547. | 114a | Antigenic Index | 75-85 |
| 1548. | 114a | Antigenic Index | 91-97 |
| 1549. | 114a | Antigenic Index | 102-137 |
| 1550. | 114a | Antigenic Index | 147-156 |
| 1551. | 114a | Antigenic Index | 161-168 |
| 1552. | 114a | Antigenic Index | 172-174 |
| 1553. | 114a | Antigenic Index | 181-189 |
| 1554. | 114a | Antigenic Index | 196-203 |
| 1555. | 114a | Antigenic Index | 208-213 |
| 1556. | 114a | Antigenic Index | 220-229 |
| 1557. | 114a | Antigenic Index | 242-248 |
| 1558. | 114a | Antigenic Index | 251-266 |
| 1559. | 114a | Antigenic Index | 268-276 |
| 1560. | 114a | Antigenic Index | 295-307 |
| 1561. | 114a | Antigenic Index | 309-312 |
| 1562. | 114a | Antigenic Index | 318-340 |
| 1563. | 114a | Antigenic Index | 345-352 |
| 1564. | 114a | Antigenic Index | 357-366 |
| 1565. | 114a | Antigenic Index | 371-381 |
| 1566. | 114a | Antigenic Index | 385-392 |
| 1567. | 114a | Antigenic Index | 404-427 |
| 1568. | 114a | Antigenic Index | 429-434 |
| 1569. | 114a | Antigenic Index | 440-456 |
| 1570. | 114a | Antigenic Index | 465-468 |
| 1571. | 114a | Antigenic Index | 473-494 |
| 1572. | 114a | Antigenic Index | 496-510 |
| 1573. | 114a | Antigenic Index | 515-530 |
| 1574. | 114a | Antigenic Index | 535-549 |
| 1575. | 114a | Antigenic Index | 555-560 |
| 1576. | 114a | Antigenic Index | 564-578 |
| 1577. | 114a | Antigenic Index | 5 88-596 |
| 1578. | 114a | Antigenic Index | 602-615 |
| 1579. | 114a | Antigenic Index | 617-620 |
| 1580. | 114a | Antigenic Index | 622-624 |
| 1581. | 114a | Antigenic Index | 628-632 |
| 1582. | 114a | Antigenic Index | 637-640 |
| 1583. | 114a | Antigenic Index | 647-654 |
| 1584. | 114a | Antigenic Index | 660-666 |
| 1585. | 114a | Antigenic Index | 668-688 |
| 1586. | 114a | Antigenic Index | 697-725 |
| 1587. | 114a | Antigenic Index | 730-733 |
| 1588. | 114a | Antigenic Index | 738-755 |
| 1589. | 114a | Antigenic Index | 760-766 |
| 1590. | 114a | Antigenic Index | 779-783 |
| 1591. | 114a | Antigenic Index | 786-799 |

TABLE I-continued 1769 fragments of the proteins disclosed in WO99/36544

| Fragment# (SEQ ID NO) | WO99/36544 ORF | Algorithm | Amino Acids |
|---|---|---|---|
| 1592. | 114a | Antigenic Index | 806-809 |
| 1593. | 114a | Antigenic Index | 811-819 |
| 1594. | 114a | Antigenic Index | 831-839 |
| 1595. | 114a | Antigenic Index | 845-857 |
| 1596. | 114a | Antigenic Index | 860-862 |
| 1597. | 114a | Antigenic Index | 864-868 |
| 1598. | 114a | Antigenic Index | 872-879 |
| 1599. | 114a | Antigenic Index | 883-891 |
| 1600. | 114a | Antigenic Index | 893-902 |
| 1601. | 114a | Antigenic Index | 908-916 |
| 1602. | 114a | Antigenic Index | 923-936 |
| 1603. | 114a | Antigenic Index | 941-947 |
| 1604. | 114a | Antigenic Index | 950-956 |
| 1605. | 114a | Antigenic Index | 959-976 |
| 1606. | 114a | Antigenic Index | 979-989 |
| 1607. | 114a | Antigenic Index | 993-1000 |
| 1608. | 114a | Antigenic Index | 1007-1022 |
| 1609. | 114a | Antigenic Index | 1041-1053 |
| 1610. | 114a | Antigenic Index | 1062-1068 |
| 1611. | 114a | Antigenic Index | 1075-1108 |
| 1612. | 114a | Antigenic Index | 1115-1121 |
| 1613. | 114a | Antigenic Index | 1126-1145 |
| 1614. | 114a | Antigenic Index | 1148-1152 |
| 1615. | 114a | Antigenic Index | 1157-1176 |
| 1616. | 114a | Antigenic Index | 1195-1206 |
| 1617. | 114a | Antigenic Index | 1208-1212 |
| 1618. | 114a | Antigenic Index | 1224-1243 |
| 1619. | 114a | Antigenic Index | 1247-1263 |
| 1620. | 114a | Antigenic Index | 1271-1282 |
| 1621. | 114a | Antigenic Index | 1284-1288 |
| 1622. | 114a | Antigenic Index | 1292-1295 |
| 1623. | 114a | Antigenic Index | 1299-1307 |
| 1624. | 114a | Antigenic Index | 1318-1328 |
| 1625. | 114a | Antigenic Index | 1330-1340 |
| 1626. | 114a | Antigenic Index | 1344-1359 |
| 1627. | 114a | Antigenic Index | 1367-1384 |
| 1628. | 114a | Antigenic Index | 1396-1399 |
| 1629. | 114a | Antigenic Index | 1405-1417 |
| 1630. | 114a | Antigenic Index | 1434-1436 |
| 1631. | 114a | Antigenic Index | 1449-1451 |
| 1632. | 114a | Antigenic Index | 1468-1487 |
| 1633. | 114a | Antigenic Index | 1498-1503 |
| 1634. | 114a | Antigenic Index | 1509-1515 |
| 1635. | 114a | Antigenic Index | 1525-1532 |
| 1636. | 114a | Hydrophilicity | 4-6 |
| 1637. | 114a | Hydrophilicity | 12-15 |
| 1638. | 114a | Hydrophilicity | 23-34 |
| 1639. | 114a | Hydrophilicity | 43-55 |
| 1640. | 114a | Hydrophilicity | 75-85 |
| 1641. | 114a | Hydrophilicity | 104-110 |
| 1642. | 114a | Hydrophilicity | 118-123 |
| 1643. | 114a | Hydrophilicity | 127-132 |
| 1644. | 114a | Hydrophilicity | 147-154 |
| 1645. | 114a | Hydrophilicity | 163-167 |
| 1646. | 114a | Hydrophilicity | 185-187 |
| 1647. | 114a | Hydrophilicity | 197-203 |
| 1648. | 114a | Hydrophilicity | 208-211 |
| 1649. | 114a | Hydrophilicity | 221-227 |
| 1650. | 114a | Hydrophilicity | 243-245 |
| 1651. | 114a | Hydrophilicity | 253-261 |
| 1652. | 114a | Hydrophilicity | 263-266 |
| 1653. | 114a | Hydrophilicity | 270-272 |
| 1654. | 114a | Hydrophilicity | 295-301 |
| 1655. | 114a | Hydrophilicity | 309-312 |
| 1656. | 114a | Hydrophilicity | 320-328 |
| 1657. | 114a | Hydrophilicity | 332-337 |
| 1658. | 114a | Hydrophilicity | 345-351 |
| 1659. | 114a | Hydrophilicity | 360-366 |
| 1660. | 114a | Hydrophilicity | 371-378 |
| 1661. | 114a | Hydrophilicity | 387-392 |
| 1662. | 114a | Hydrophilicity | 404-417 |
| 1663. | 114a | Hydrophilicity | 421-423 |
| 1664. | 114a | Hydrophilicity | 425-427 |
| 1665. | 114a | Hydrophilicity | 442-456 |
| 1666. | 114a | Hydrophilicity | 473-488 |
| 1667. | 114a | Hydrophilicity | 499-509 |
| 1668. | 114a | Hydrophilicity | 515-520 |
| 1669. | 114a | Hydrophilicity | 536-549 |
| 1670. | 114a | Hydrophilicity | 555-560 |
| 1671. | 114a | Hydrophilicity | 565-568 |
| 1672. | 114a | Hydrophilicity | 570-578 |
| 1673. | 114a | Hydrophilicity | 589-594 |
| 1674. | 114a | Hydrophilicity | 602-604 |
| 1675. | 114a | Hydrophilicity | 609-615 |
| 1676. | 114a | Hydrophilicity | 617-620 |
| 1677. | 114a | Hydrophilicity | 660-665 |
| 1678. | 114a | Hydrophilicity | 668-680 |
| 1679. | 114a | Hydrophilicity | 684-686 |
| 1680. | 114a | Hydrophilicity | 699-708 |
| 1681. | 114a | Hydrophilicity | 715-725 |
| 1682. | 114a | Hydrophilicity | 730-733 |
| 1683. | 114a | Hydrophilicity | 738-744 |
| 1684. | 114a | Hydrophilicity | 746-754 |
| 1685. | 114a | Hydrophilicity | 760-766 |
| 1686. | 114a | Hydrophilicity | 789-793 |
| 1687. | 114a | Hydrophilicity | 816-818 |
| 1688. | 114a | Hydrophilicity | 831-836 |
| 1689. | 114a | Hydrophilicity | 845-857 |
| 1690. | 114a | Hydrophilicity | 860-862 |
| 1691. | 114a | Hydrophilicity | 864-866 |
| 1692. | 114a | Hydrophilicity | 873-879 |
| 1693. | 114a | Hydrophilicity | 883-885 |
| 1694. | 114a | Hydrophilicity | 887-889 |
| 1695. | 114a | Hydrophilicity | 896-899 |
| 1696. | 114a | Hydrophilicity | 908-916 |
| 1697. | 114a | Hydrophilicity | 923-932 |
| 1698. | 114a | Hydrophilicity | 941-947 |
| 1699. | 114a | Hydrophilicity | 961-975 |
| 1700. | 114a | Hydrophilicity | 979-989 |
| 1701. | 114a | Hydrophilicity | 993-1000 |
| 1702. | 114a | Hydrophilicity | 1007-1022 |
| 1703. | 114a | Hydrophilicity | 1041-1043 |
| 1704. | 114a | Hydrophilicity | 1045-1053 |
| 1705. | 114a | Hydrophilicity | 1062-1068 |
| 1706. | 114a | Hydrophilicity | 1075-1078 |
| 1707. | 114a | Hydrophilicity | 1080-1087 |
| 1708. | 114a | Hydrophilicity | 1089-1104 |
| 1709. | 114a | Hydrophilicity | 1115-1121 |
| 1710. | 114a | Hydrophilicity | 1126-1141 |
| 1711. | 114a | Hydrophilicity | 1143-1145 |
| 1712. | 114a | Hydrophilicity | 1148-1151 |
| 1713. | 114a | Hydrophilicity | 1158-1171 |
| 1714. | 114a | Hydrophilicity | 1197-1203 |
| 1715. | 114a | Hydrophilicity | 1224-1243 |
| 1716. | 114a | Hydrophilicity | 1251-1263 |
| 1717. | 114a | Hydrophilicity | 1271-1273 |
| 1718. | 114a | Hydrophilicity | 1275-1277 |
| 1719. | 114a | Hydrophilicity | 1284-1288 |
| 1720. | 114a | Hydrophilicity | 1299-1307 |
| 1721. | 114a | Hydrophilicity | 1318-1326 |
| 1722. | 114a | Hydrophilicity | 1334-1340 |
| 1723. | 114a | Hydrophilicity | 1350-1359 |
| 1724. | 114a | Hydrophilicity | 1367-1384 |
| 1725. | 114a | Hydrophilicity | 1407-1417 |
| 1726. | 114a | Hydrophilicity | 1449-1451 |
| 1727. | 114a | Hydrophilicity | 1469-1482 |
| 1728. | 114a | Hydrophilicity | 1484-1486 |
| 1729. | 114a | Hydrophilicity | 1498-1503 |
| 1730. | 114a | Hydrophilicity | 1510-1512 |
| 1731. | 114a | Hydrophilicity | 1527-1532 |
| 1732. | 124-1 | AMPHI | 37-43 |
| 1733. | 124-1 | AMPHI | 94-96 |
| 1734. | 124-1 | AMPHI | 113-115 |
| 1735. | 124-1 | Antigenic Index | 20-26 |
| 1736. | 124-1 | Antigenic Index | 38-43 |
| 1737. | 124-1 | Antigenic Index | 52-55 |
| 1738. | 124-1 | Antigenic Index | 62-70 |
| 1739. | 124-1 | Antigenic Index | 88-97 |

TABLE I-continued 1769 fragments of the proteins disclosed in WO99/36544

| Fragment# (SEQ ID NO) | WO99/36544 ORF | Algorithm | Amino Acids |
|---|---|---|---|
| 1740. | 124-1 | Antigenic Index | 104-114 |
| 1741. | 124-1 | Antigenic Index | 123-135 |
| 1742. | 124-1 | Antigenic Index | 146-155 |
| 1743. | 124-1 | Hydrophilicity | 20-26 |
| 1744. | 124-1 | Hydrophilicity | 41-43 |
| 1745. | 124-1 | Hydrophilicity | 52-55 |
| 1746. | 124-1 | Hydrophilicity | 63-69 |
| 1747. | 124-1 | Hydrophilicity | 91-94 |
| 1748. | 124-1 | Hydrophilicity | 104-114 |
| 1749. | 124-1 | Hydrophilicity | 123-135 |
| 1750. | 124-1 | Hydrophilicity | 146-155 |
| 1751. | 124a | AMPHI | 19-21 |
| 1752. | 124a | AMPHI | 23-29 |
| 1753. | 124a | AMPHI | 37-43 |
| 1754. | 124a | AMPHI | 94-96 |
| 1755. | 124a | Antigenic Index | 38-43 |
| 1756. | 124a | Antigenic Index | 52-55 |
| 1757. | 124a | Antigenic Index | 62-70 |
| 1758. | 124a | Antigenic Index | 77-80 |
| 1759. | 124a | Antigenic Index | 90-96 |
| 1760. | 124a | Antigenic Index | 105-115 |
| 1761. | 124a | Antigenic Index | 120-135 |
| 1762. | 124a | Antigenic Index | 145-153 |
| 1763. | 124a | Hydrophilicity | 41-43 |
| 1764. | 124a | Hydrophilicity | 52-55 |
| 1765. | 124a | Hydrophilicity | 63-69 |
| 1766. | 124a | Hydrophilicity | 91-95 |
| 1767. | 124a | Hydrophilicity | 108-115 |
| 1768. | 124a | Hydrophilicity | 120-135 |
| 1769. | 124a | Hydrophilicity | 146-153 |

Key:
fragment#1 of the present application is amino acids 6-14 of ORF38-1 disclosed in WO99/36544, fragment#2 of the present application is amino acids 57-59 of ORF38-1 disclosed in WO99/36544 etc.

It will be understood that the invention is described above by way of example only and modifications may be made whilst remaining within the scope and spirit of the invention.

TABLE II

The present invention does not include within its scope proteins comprising any of the 45 protein sequences disclosed in WO99/36544. As stated above, if the length of any particular protein sequence disclosed in WO99/36544 is x amino acids, the antigenic fragment of the present invention has at most x − 1 amino acids of that protein. For each of the 45 protein sequences given in WO99/36544, the value of x is given, for reference, in the following table:

| SEQ ID NO: | x |
|---|---|
| 2 | 245 |
| 4 | 591 |
| 6 | 592 |
| 8 | 164 |
| 10 | 321 |
| 12 | 321 |
| 14 | 124 |
| 16 | 124 |
| 18 | 173 |
| 20 | 640 |
| 22 | 761 |
| 24 | 111 |
| 26 | 571 |
| 28 | 710 |
| 30 | 710 |
| 32 | 62 |
| 34 | 86 |
| 36 | 92 |
| 38 | 103 |
| 40 | 85 |
| 42 | 78 |
| 44 | 78 |
| 46 | 219 |
| 48 | 212 |
| 50 | 185 |
| 52 | 166 |
| 54 | 326 |
| 56 | 356 |
| 58 | 284 |
| 60 | 1978 |
| 62 | 1532 |
| 64 | 593 |
| 66 | 129 |
| 68 | 319 |
| 70 | 619 |
| 72 | 595 |
| 74 | 150 |
| 76 | 255 |
| 78 | 255 |
| 80 | 172 |
| 82 | 242 |
| 84 | 242 |
| 86 | 183 |
| 88 | 155 |
| 90 | 153 |

The invention claimed is:

1. A purified polypeptide having a length of 100 amino acids or less comprising the amino acid sequence of SEQ ID NO:1331.

2. A composition comprising the polypeptide of claim 1 and a pharmaceutically acceptable vehicle.

3. The polypeptide of claim 1, wherein the polypeptide has a length of 50 amino acids or less.

4. The polypeptide of claim 1, wherein the polypeptide has a length of 25 amino acids or less.

5. The polypeptide of claim 1, wherein the polypeptide has a length of 20 amino acids or less.

6. A composition comprising the polypeptide of claim 3 and a pharmaceutically acceptable vehicle.

7. A composition comprising the polypeptide of claim 4 and a pharmaceutically acceptable vehicle.

8. A composition comprising the polypeptide of claim 5 and a pharmaceutically acceptable vehicle.

* * * * *